United States Patent
Stegger et al.

(10) Patent No.: US 9,279,160 B2
(45) Date of Patent: Mar. 8, 2016

(54) **DNA-BASED METHODS FOR CLONE-SPECIFIC IDENTIFICATION OF *STAPHYLOCOCCUS AUREUS***

(75) Inventors: Marc Stegger, Brønshøj (DK); Luca Guardabassi, Copenhagen SV (DK); Jodi Lindsay, London (GB)

(73) Assignees: Statens Serum Institut, Copenhagen S (DK); The University of Copenhagen, Copenhagen K (DK); St Georges Hospital Medical School, London (GB)

( * ) Notice: Subject to any disclaimer, the term of this patent is extended or adjusted under 35 U.S.C. 154(b) by 686 days.

(21) Appl. No.: 13/379,499

(22) PCT Filed: Jun. 17, 2010

(86) PCT No.: PCT/DK2010/000093
§ 371 (c)(1),
(2), (4) Date: Dec. 20, 2011

(87) PCT Pub. No.: WO2010/149159
PCT Pub. Date: Dec. 29, 2010

(65) Prior Publication Data
US 2012/0208714 A1    Aug. 16, 2012

(30) Foreign Application Priority Data
Jun. 22, 2009   (DK) .................................. 2009 00767

(51) Int. Cl.
*C12P 19/34*    (2006.01)
*C12Q 1/68*    (2006.01)

(52) U.S. Cl.
CPC ................ *C12Q 1/689* (2013.01); *C12Q 1/686* (2013.01); *C12Q 2561/113* (2013.01)

(58) Field of Classification Search
CPC ... C12Q 1/686; C12Q 1/689; C12Q 2561/113
USPC ............................................. 435/91.2, 91.21
See application file for complete search history.

(56) References Cited

U.S. PATENT DOCUMENTS

2007/0031850 A1*   2/2007   Mounts et al. ..................... 435/6

FOREIGN PATENT DOCUMENTS

| EP | 1770171 | * | 4/2007 |
| EP | 1770171 A1 | | 4/2007 |
| WO | WO2005/05682 A1 | | 6/2005 |

OTHER PUBLICATIONS

Chambers, Methicillin Resistance in *Staphylococci*: Molecular and Biochemical Basis and Clinical Implications, Clin. Microbiol. Rev., Oct. 1997, pp. 781-791, vol. 10, No. 4.
Cockfield, et al., Rapid determination of hospital-acquired meticillin-resistant *Staphylococcus aureus* lineages, J. Med. Microbiol., May 2007, pp. 614-619, vol. 56.
Deborggraeve, et al., Molecular Dipstick Test for Diagnosis of Sleeping Sickness, J. Clin. Microbiol., Aug. 2006, pp. 2884-2889, vol. 44, No. 8.
Enright, et al., Multilocus Sequence Typing for Characterization of Methicillin-Resistant and Methicillin-Susceptible Clones of *Staphylococcus aureus*, J. Clin. Microbiol., Mar. 2000, pp. 1008-1015, vol. 38, No. 3.
European Commission, Commission Decision of Dec. 20, 2007 concerning a financial contribution from the Community towards a survey on the prevalence of *Salmonella* spp. and Methicillin-resistant *S. aureus* in herds of breeding pigs to be carried out in the Member States (2008/55/EC), Official Journal of the European Union, Jan. 17, 2008.
Kalogianni, et al., Dry-reagent disposable dipstick test for visual screening of seven leukemia-related chromosomal translocations, Nucleic Acids Research, Jan. 23, 2007 (online), pp. 1-12, vol. 35, No. 4, e23.
Koreen, et al., *spa* Typing Method for Discriminating among *Staphylococcus aureus* Isolates: Implications for Use of a Single Marker to Detect Genetic Micro- and Macrovariation, J. Clin. Microbiol., Feb. 2004, pp. 792-799, vol. 42, No. 2.
Lewis, et al., Pigs as Source of Methicillin-Resistant *Staphylococcus aureus* CC398 Infections in Humans, Denmark, Emerg. Infect. Dis., Sep. 2008, pp. 1383-1389, vol. 14, No. 9.
Monecke, et al., Assignment of *Staphylococcus aureus* isolates to clonal complexes based on microarray analysis and pattern recognition, FEMS Immunol. Med. Microbiol., May 27, 2008 (online), pp. 237-251, vol. 53.
Moodley, et al., High risk for nasal carriage of methicillin-resistant *Staphylococcus aureus* among Danish veterinary practitioners, Scand., J. Work Environ. Health, Apr. 2008, pp. 151-157, vol. 34, No. 2.
Murchan, et al., Harmonization of Pulsed-Field Gel Electrophoresis Protocols for Epidemiologic Typing of Stains of Methicillin-Resistant *Staphylococcus aureus*: a Single Approach Developed by Consensus in 10 European Laboratories and Its Application for Tracing the Spread of Related Strains, J. Clin. Microbiol., Apr. 2003, pp. 1574-1585, vol. 41, No. 4.

(Continued)

Primary Examiner — Cynthia B Wilder
(74) Attorney, Agent, or Firm — Howson & Howson LLP

(57) ABSTRACT

MRSA CC398 is a clone of *S. aureus* that has recently emerged in pigs and other domestic animals worldwide. As any other MRSA, the clone displays high levels of antibiotic resistance and poses a serious threat to human health because of the risk of antibiotic treatment failure in human patients. We developed a new diagnostic test for identification of MRSA CC398 using a single one-step PCR that is very easily performed within a few hours. The test is based on the principle that clonal differences within *S. aureus* are reflected in the sequence of a gene (sau1hsdS1) located on the chromosome of this bacterial species. Accordingly, such a gene represents an optimal target for *S. aureus* and MRSA identification at the clone level. The test includes detection of the gene conferring methicillin resistance (mecA), therefore allowing rapid discrimination between methicillin-susceptible and methicillin-resistant variants of the clone. A preliminary validation of the test was performed on a collection of CC398 and non-CC398 strains, resulting in 100% sensitivity and 100% specificity. The test can be combined to real-time PCR technology to further reduce simplify the test performance as well as to allow quantification of the target MRSA clone in biological specimens. The invention has important applications related to surveillance and control of MRSA CC398 in humans, animals and food products.

12 Claims, 11 Drawing Sheets

(56) References Cited

OTHER PUBLICATIONS

Poulsen, et al., Detection of methicillin resistance in coagulase-negative staphylococci and in *staphylococci* directly from simulated blood cultures using the EVIGENE MRSA Detection Kit, J. Antimicrobial Chemotherapy, Jan. 14, 2003 (online), pp. 419-421, vol. 51.

Stegger, et al., Rapid PCR Detection of *Staphylococcus aureus* Clonal Complex 398 by Targeting the Restriction-Modification System Carrying *saul-hsdS1*, J. Clin. Microbiol., Feb. 2011, pp. 732-734, vol. 49, No. 2.

van Loo, et al., Emergence of Methicillin-Resistant *Staphylococcus aureus* of Animal Origin in Humans, Emerg. Infect. Dis., Dec. 2007, pp. 1834-1839, vol. 13, No. 12.

Vandenbroucke-Grauls, et al., Letters to the Editor—Specific detection of methicillin-resistant *Staphylococcus* species by multiplex PCR, J. Clin. Microbiol., Jun. 1996, p. 1599, vol. 34, No. 6.

Vannuffel, et al., Specific detection of methicillin-resistant *Staphylococcus* species by multiplex PCR, J. Clin. Microbiol., Nov. 1995, pp. 2864-2867, vol. 33, No. 11.

Voss, et al., Methicillin-resistant *Staphylococcus aureus* in Pig Farming, Emerg. Infect. Dis., Dec. 2005, pp. 1965-1966, vol. 11, No. 12.

Waldron, et al., Saul: a Novel Lineage-Specific Type I Restriction-Modification System That Blocks Horizontal Gene Transfer into *Staphylococcus aureus* and between *S. aureus* Isolates of Different Lineages, J. Bacteriol., Aug. 2006, pp. 5578-5585, vol. 188, No. 15.

Wulf, et al., Prevalence of methicillin-resistant *Staphylococcus aureus* among veterinarians: an international study, Clin. Microbiol. Infect., Nov. 7, 2007 (online), pp. 29-34, vol. 14.

International Search Report from PCT/DK2010/000093 (International Stage of current application, U.S. Appl. No. 13/379,499).

Written Opinion from PCT/DK2010/000093 (International Stage of current application, U.S. Appl. No. 13/379,499).

Belkum, et al., Methicillin -Resistant and -Susceptible *Staphylococcus aureus* Sequence Type 398 in Pigs and Humans, Emerging Infectious Diseases, Mar. 2008, 14(3):479-483.

Monecke, et al., Molecular epidemiology of *Staphylococcus aureus* in asymptomatic carriers, Eur J Clin Microbiol Infect Dis., online May 12, 2009, pp. 1159-1165.

Oct. 5, 2012 Communication (Extended European Search Report) in counterpart European Patent Application No. 10791626.4.

Mar. 27, 2013 Reply, including claim amendments, to Oct. 5, 2012 Communication (and related Oct. 23, 2012 Communication) in counterpart European Patent Application No. 10791626.4.

\* cited by examiner

DNA-BASED METHODS FOR CLONE-SPECIFIC IDENTIFICATION OF STAPHYLOCOCCUS AUREUS

CROSS-REFERENCE TO RELATED APPLICATIONS

This application is a national stage of International Patent Application No. PCT/DK2010/000093, filed Jun. 17, 2010, which claims the benefit of the priority of Danish Patent Application No. PA 2009 00767, filed Jun. 22, 2009, all of which are incorporated by reference herein.

FIELD OF INVENTION

The present invention relates to DNA-based methods for identification, detection and/or typing of *Staphylococcus aureus* strains, clones and/or lineages. Specifically, the present invention relates to DNA-based methods for detection and typing of *S. aureus* clonal complexes based on the sequence of the hsdS gene. More specifically the invention relates to DNA-based methods for detection and/or typing of *S. aureus* CC398 but can be applied to identification of any other CCs. The present invention furthermore relates to a method for simultaneous identification, detection and/or typing of a *Staphylococcus aureus* clonal complex and/or strain and/or lineage and for methicillin-resistant *S. aureus* (MRSA), wherein MRSA is determined by the presence of the mecA gene encoding methicillin resistance, thereby allowing both identification of *S. aureus* at the CC level and discrimination between MRSA and methicillin-susceptible *S. aureus* (MSSA) within any CCs.

BACKGROUND OF THE INVENTION

*Staphylococcus aureus* (*S. aureus*) is one of the most frequent causes of bacterial infections in the world. About 20% of the population is long-term carriers of *S. aureus*. *S. aureus* can cause a range of illnesses from minor skin infections, such as pimples, impetigo, boils, cellulitis folliculitis, furuncles, carbuncles, scalded skin syndrome and abscesses, to life-threatening diseases such as bacteraemia, pneumonia, meningitis, osteomyelitis, endocarditis, toxic shock syndrome (TSS), and septicaemia. Its incidence is from skin, soft tissue, respiratory, bone, joint, endovascular to wound infections. It is still one of the four most common causes of nosocomial infections, often causing postsurgical wound infections.

*S. aureus* may occur as a commensal on human skin; it also occurs in the nose frequently (in about a third of the population) and throat less commonly. Although the occurrence of *S. aureus* or MRSA under these circumstances does not indicate infection, healthy carriage of these bacteria is a major risk factor for infection, which usually manifests when normal barriers such as skin or mucosal lining have been breached. *S. aureus* can spread between individuals through direct contact with infected wounds, skin-to-skin contact, aerosol as well as by contact with contaminated objects such as towels, sheets, clothing, or athletic equipment. It can also colonize domestic animals such as pigs, cattle, dogs, cats and horses, and can cause various animal diseases such as mastitis in dairy cows and bumblefoot in chickens.

MRSA strains harbour the mecA gene, which confers resistance to all beta-lactam antibiotics and is often resistant to alternative antimicrobials (Chambers 1997). MRSA significantly contribute to mortality due to high risk of treatment failure, and results in an economical burden to the society due to prolonged hospitalization and recourse to more expensive antimicrobials. MRSA was originally confined to hospital and health care environments but during the last decade the incidence of community-acquired infections has increased.

Recently, MRSA belonging to a specific genetic lineage called CC398 has emerged in pigs, calves and other animals worldwide. MRSA CC398 colonizes the skin and the mucosal surfaces of healthy animals without any clinical signs. However, the emergence of this MRSA clone in animals represents a major public health problem since animal carriers may contribute to the spread of MRSA among humans. Independent studies in North America (Hanselmann et al. 2006), Holland (Wulf et al. 2006) and Denmark (Moodley et al. 2008; Wulf et al. 2008) have indicated the frequency of MRSA colonization is higher in veterinary staff and pig farmers than in the community. Two case-control studies in the Netherlands (van Loo et al. 2007) and in Denmark (Lewis et al. 2008) have shown that pig farmers are categories at risk for MRSA CC398 infection. Differently from other MRSA lineages, MRSA CC398 is likely to have animal origin and therefore is presently regarded as a zoonosis. It has been reported that the prevalence of MRSA among pig farmers was >760 times higher than that among patients admitted to Dutch hospitals (Voss et al. 2005). Typing of these MRSA indicated that they belonged to CC398 and had been transmitted from pigs to farm workers.

Recently it was established that CC398 accounted for 20% of all MRSA detected in the Netherlands (van Loo et al. 2007), highlighting the need for a fast, simple, inexpensive and reliable typing of this particular MRSA lineage. More generally, molecular typing of MRSA, in particular in hospital-acquired infections, is an important prerequisite for an effective and targeted use of infection control measures aimed at preventing further dissemination within hospitals as well as from the community to hospitals. In doing so, it is necessary to identify genetic markers allowing rapid and reliable MRSA identification at the CC level and easy communication of results between laboratories.

MRSA CC398 and more broadly any MRSA clones are currently identified using a multi-step procedure which includes: i) identification of *S. aureus* at the species level (Bannerman 2003); ii) detection of methicillin resistance by phenotypic and/or genotypic methods; and iii) clone identification using standard methods for *S. aureus* typing, namely pulsed-field gel electrophoresis (PFGE) (Murchan et al. 2003), multi-locus sequence typing (MLST) (Enright et al. 2000) and spa typing (Koreen et al. 2004). There have been attempts to merge the first two steps (Vannuffel et al. 1996). However, prior to the invention, no methods were available to cover all three steps. Recently, an restriction-modification (RM) system of *S. aureus* was described by Waldron et al. (2006). The RM system is composed by five genes: two hsdM (modification) genes, one hsdR (restriction) gene and two hsdS (specificity) genes. The two sau1hsdS genes (sau1hsdS1 and sau1hsdS2) were found to exhibit high sequence variation between isolates belonging to distinct CCs. This finding was subsequently used by Cockfield et al. (2008) to identify six distinct lineages (CC1, CC5, CC8, CC22, CC30 and CC45).

Due to the emerging importance of CC398 in the veterinary sector, the need for rapid methods for MRSA identification at the CC level is no longer limited to human medicine but is now extended to MRSA surveillance in living animals, farm environments and animal food products. In 2007 the EU Commission financed baseline surveys to assess the prevalence of MRSA in breeding pigs (EU Commission 2007). The EU initiative has been accompanied by a number of research and surveillance programs at the national level. This situation has determined a need for a specific method enabling rapid and accurate identification of CC398, including both MRSA and Methicillin-Sensitive *S. aureus* (MSSA) variants belonging to this *S. aureus* lineage. Therefore, the invention described herein below has important diagnostic and epidemiological applications in human medicine as well as in the veterinary sector. The invention represents a useful tool for surveillance and control of MRSA CC398 in humans, animals and food products, and more importantly, can be used for clone identification of any MRSA.

BRIEF DESCRIPTION OF DRAWINGS

FIGS. 3A-3I: Alignment of hsdS sequences. An alignment of a selection of the hsdS1 gene from various *S. aureus* lineages using CLCbio's Genomic Workbench v. 3.2.

SUMMARY OF THE INVENTION

Figure 1:
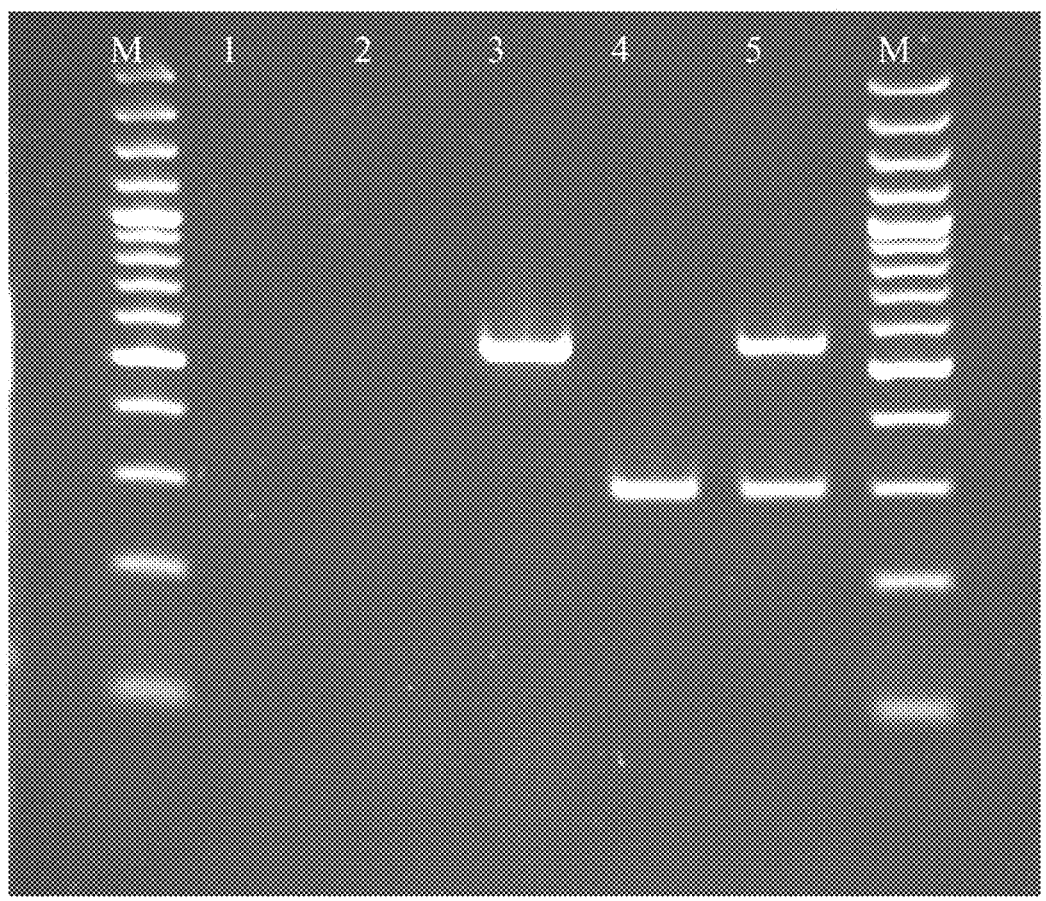
FIG. 1: Example of how the invention enables identification of methicillin-susceptible (MSSA) and methicillin-resistant (MRSA) *S. aureus* CC398. Lane M, DNA marker (100-bp ladder); lane 1, negative control (water); lane 2, non-CC398 methicillin-susceptible *S. aureus* (strain ATCC 6538); lane 3, non-CC398 methicillin-resistant *S. aureus* (strain ATCC 33591); lane 4, CC398 methicillin-sensitive *S. aureus* (SSI 52615); lane 5, CC398 methicillin-resistant *S. aureus* (KVL 288).

The applicants herein describe a rapid and reliable identification method of *S. aureus* types and/or lineages and more specifically for the identification of the clone CC398, even more specifically for the detection of MRSA strains belonging to CC398. The hsdS gene has previously been found to exhibit high sequence variation between isolates belonging to distinct clonal complexes (Waldron D E et al. 2006). These genes are thus suitable for the development methods for the typing of *S. aureus* clonal complexes. Surprisingly the method described herein identifies *S. aureus* CC398 with 100% sensitivity and 100% specificity.

The present invention as described herein relates to methods using amplification primers and/or probes which are specific and sensitive for determining the presence of nucleic acid(s) from a *S. aureus* clonal complex, strain or lineage in any sample suspected of containing said *S. aureus* nucleic acid(s) thereby identifying, detecting and/or typing said *S. aureus* clonal complex, strain or lineage, wherein each of said nucleic acid(s) or variant(s) or part(s) thereof comprises a selected target region hybridizable with said probes or primers; said method comprising the following steps: contacting said sample with said primers, or probes and detecting the presence of amplified products or hybridized probes as an indication of the presence of said specific *S. aureus* clonal complex, strain or lineage thereby identifying, detecting and/or typing said *S. aureus* clonal complex, strain or lineage.

A specific aspect of the invention relates to detection, identification and/or typing of any *S. aureus* clonal complex using at least one or more amplification primers and/or probes which are specific and sensitive for determining the presence of clone-specific nucleic acid(s) from the hsdS gene which is hybridizable with said probes or primers, said method comprising the following steps: contacting a sample with said primers or probes and detecting the presence of amplified products or hybridized probes as an indication of the presence of said specific hsdS gene thereby identifying, detecting and/or typing said *S. aureus* clonal complex.

Another specific aspect of the invention relates to detection, identification and/or typing of any *S. aureus* clonal complex using at least one or more amplification primers and/or probes which are specific and sensitive for determining the presence of clone-specific nucleic acid(s) from the hsdS gene which is hybridizable with said probes or primers, said method comprising the following steps: contacting a sample with said primers or probes and detecting the presence of amplified products or hybridized probes as an indication of the presence of said specific hsdS gene thereby identifying, detecting and/or typing said *S. aureus* clonal complex provided that said clonal complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

Another aspect of the invention relates to a method for the detection, identification and/or typing of a *S. aureus* clonal complex, strain, clone or lineage, in a test sample which comprises the following steps: a) treating said sample with an aqueous solution containing at least one pair of oligonucleotide primers, one of said primers being capable of hybridizing selectively with one of the two complementary strands of said *S. aureus* clone-specific hsdS gene that contains a target sequence, and the other of said primers being capable of hybridizing with the other of said strands so as to form an extension product which contains the target sequence as a template, said at least one primer being chosen from a nucleotide sequence within the clone-specific hsdS gene with regard to said *S. aureus* clonal complex, a sequence complementary thereof, and a variant thereof; b) synthesizing an extension product of each of said primers, said extension product containing the target sequence, and amplifying said target sequence, if any, to a detectable level; and c) detecting the presence and/or amount of said amplified target sequence as an indication of the presence and/or amount of said *S. aureus* clonal complex, in said test sample.

Preferably, the primers are the primers specified in SEQ ID NO: 2 and SEQ ID NO: 6 for the identification, detection and/or typing of *S. aureus* CC398 and the primers specified in SEQ ID NO: 7 and SEQ ID NO: 8 for the detection of the mecA gene.

Another aspect of the invention relates to a method for the detection, identification and/or typing of a *S. aureus* strain or lineage thereby identifying, detecting and/or typing said *S. aureus* strain or lineage, directly from a test sample or from bacterial cultures, which comprises the following steps: a) depositing and fixing on an solid support or leaving in solution the said *S. aureus* nucleic acid(s) of the sample or of a substantially homogeneous population of said *S. aureus* isolated from this sample, or inoculating said sample or said substantially homogeneous population of *S. aureus* isolated from this sample on an solid support, and lysing in situ said inoculated sample or said isolated *S. aureus* to release the said *S. aureus* DNA, said *S. aureus* DNA being made in a substantially single-stranded form; b) contacting said single-stranded DNA with a probe, said probe comprising at least one single-stranded nucleic acid which nucleotide sequence is sequence complementary to a sequence of SEQ ID NO: 1, and a variant thereof, which specifically and ubiquitously anneals with strains or lineages of *S. aureus*, under conditions such that the nucleic acid(s) of said probe can selectively hybridize with said *S. aureus* DNA, whereby a hybridization complex is formed; and c) detecting the presence of said hybridization complex on said solid support or in said solution as an indication of the presence and/or amount of said *S. aureus*, in said test sample.

The present invention as described herein further relates to a method for obtaining hsdS sequences from any *S. aureus* strain or lineage directly from a test sample or a bacterial culture, which comprises the following steps: a) treating said sample with an aqueous solution containing at least one pair of primers having a sequence selected within the nucleotide sequences defined in SEQ ID NOS: 9, 10, 11 and 12 and a variant thereof, one of said primers being capable of hybridizing selectively with one of the two complementary strands of said *S. aureus* hsdS gene that contains a target sequence, and the other of said primers being capable of hybridizing with the other of said strands so as to form an extension product which contains the target sequence as a template; b) synthesizing an extension product of each of said primers, said extension product containing the target sequence, and amplifying said target sequence, if any, to a detectable level; and c) detecting the presence and/or amount of said amplified target sequence; and d) determining the nucleotide sequence of the said amplified target sequence by using any DNA sequencing method.

It is contemplated that said primers may not necessarily be completely within the hsdS gene, but may also hybridize to adjacent regions to said hsdS gene.

Furthermore, the present invention as described herein relates to a solid support coated with a set of probes for detection, identification or typing of any *S. aureus* clonal complex from an extract of its genomic DNA, each probe being able to specifically hybridize with a relevant gene or with a representative fragment thereof susceptible to be present in said genomic DNA to be tested, characterized in that said relevant genes whose presence or absence is to be determined using the set of probes comprise the following genes: a) a clone-specific hsdS gene, for identification, detection and/or typing of said *S. aureus* clonal complex, and b) at least one gene considered as a negative control, said gene being absent in the genome of said *S. aureus* species, and optionally c) a gene for antibiotic resistance. Preferably, the solid support is for detection, identification and/or typing of *S. aureus* CC398.

Yet another aspect of the invention relates to a DNA micro-array for identification and typing of any *S. aureus* clonal complex comprising the solid support of described herein below. Preferably, the DNA micro-array is for detection, identification and/or typing of *S. aureus* CC398.

The present invention as described herein further relates to a kit for typing any *S. aureus* clonal complex comprising the solid support described herein below or the DNA micro-array described herein below. Preferably, the kit is for detection, identification and/or typing of *S. aureus* CC398.

The present invention as described herein further relates to a kit for detection, identification and/or typing any *S. aureus* clonal complex, comprising any suitable combination of clone-specific primers.

The present invention as described herein further relates to a kit for detection, identification and/or typing CC398 *S. aureus* clonal complex, comprising any suitable combination of clone-specific primers selected from the group consisting of SEQ ID NOS: 2 and 6, sequences complementary thereof, and variants thereof.

A further aspect of the invention relates to a kit for detection, identification and/or typing *S. aureus*, comprising
a. means for taking a sample from a subject
b. means for mailing said sample to an institution for detecting, identification and/or typing of any *S. aureus* clonal complex and
c. optionally means for detection of MRSA in said sample and
d. optionally means for detection of CC398

Yet another aspect of the invention relates to a kit for detection, identification and/or typing *S. aureus*, comprising
a. means for taking a sample from a subject
b. means for, at the place where the sample is taken, detecting, identification and/or typing of any *S. aureus* clonal complex and optionally for detection of MRSA in said sample.

The present invention as described herein further relates to a device for the detection, identification and/or typing of any *S. aureus* clonal complex, wherein the device comprises means for measuring the presence of clone-specific hsdS nucleic acid(s). Preferably, the device is for identification and detection, identification and/or typing of CC398 *S. aureus*.

Furthermore, the present invention as described herein relates to a device for the detection, identification and/or typing of any *S. aureus* clonal complex, wherein the device comprises means for measuring the presence of clone-specific hsdS nucleic acid(s) as well as the bacterial resistance gene mecA, for the detection of MRSA. Preferably, the device is for identification and detection, identification and/or typing of CC398 *S. aureus*.

DEFINITIONS

Amplifying: Any process or combination of process steps that increases the number of copies of a templated molecule. Amplification of templated molecules may be carried out by any state of the art method including, but not limited to, a polymerase chain reaction to increase the copy number of each template, and using the templates for synthesising additional copies of the templated molecules comprising a sequence of functional groups resulting from the synthesis of the templated molecule being templated by the template. Any amplification reaction or combination of such reactions known in the art can be used as appropriate as readily recognized by those skilled in the art. Accordingly, templated molecules can be amplified by using the polymerase chain reaction (PCR), ligase chain reaction (LCR), in vivo amplification of cloned DNA, and the like. The amplification method should preferably result in the proportions of the amplified mixture being essentially representative of the proportions of templates of different sequences in a mixture prior to amplification.

Amplification: amplification according to the present invention is the process wherein a plurality of exact copies of a starting molecule is synthesised, without employing knowledge of the exact composition of the starting molecule. Hence a template may be amplified even though the exact composition of said template is unknown. In one preferred embodiment of the present invention amplification of a template comprises the process wherein a template is copied by a nucleic acid polymerase or polymerase homologue, for example a DNA polymerase or an RNA polymerase. For example, templates may be amplified using reverse transcription, the polymerase chain reaction (PCR), ligase chain reaction (LCR), in vivo amplification of cloned DNA, and similar procedures capable of complementing a nucleic acid sequence.

Animal: as used herein may be defined to include human beings, domestic or agricultural animals (cats, dogs, cows, sheep, llama, goat etc) or test species (mouse, rat, rabbit, etc).

Array: In the present context an array means an ordered plurality of molecules. Mostly consisting of a plurality of dsDNA or ssDNA fragments covalently attached to a slide or a similar solid support, said DNA fragments being identified by their two dimensional position in the array.

Beta-lactam antibiotics: are a broad class of antibiotics that include penicillin derivatives, cephalosporins, monobactams, carbapenems, and β-lactamase inhibitors that is, any antibiotic agent that contains a β-lactam nucleus in its molecular structure.

Biological sample: as used herein, is intended to mean a sample obtained from a subject or individual.

Clonal complex (CC): group of isolates that are genetically related based on multilocus sequence typing (MLST). They are grouped into clonal complexes by their similarity to a central allelic profile. Clonal complex and lineage can be used interchangeably herein.

Clonal complex 398/CC398/ST398: S. aureus lineage including strains that belong to MLST type ST398 and variants of this MLST type including but not limited to ST291, ST621, ST752, ST753, ST804, ST813, ST1066, ST1067, ST1112, ST1232 and ST1277. It also quite possibly includes ST140, ST580, ST601, ST727, ST810 and ST1094 as double locus variants of CC398 identified sequence types. It includes but is not limited to S. aureus strains of spa type t011, t034, t108 t567, t899, t1197, t1451, t1939, t1793, t2876, t1255 and t571.

Clone specific primers/probes or Lineage specific primers/probes: as used herein, is intended to mean primers and/or probes that target the unconserved/variable region(s) of the hsdS gene.

Complex: Templated molecule linked to the template that templated the synthesis of the templated molecule. The template can be a complementing template as defined herein that is optionally hybridised or otherwise attached to a corresponding template of linked coding elements.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%.

Complementary DNA (cDNA): Any DNA obtained by means of reverse transcriptase acting on RNA as a substrate. Complementary DNA is also termed copy DNA.

Complementary strand: Double stranded polynucleotide contains two strands that are complementary in sequence and capable of hybridizing to one another.

Dipstick: Devices that can be dipped into a liquid to perform a chemical test or to provide a measure of quantity of the liquid. Alternatively a dry-reagent dipstick (see herein below).

dsDNA: Double stranded DNA.

hsd gene: "host specificity of DNA", a subunit of a type I restriction system. There are three types of subunits hsdR, hsdM and hsdS.

Individual: Any species or subspecies of bird, mammal, fish, amphibian, or reptile. Preferably a human being or a domesticated animal.

Ligation: Enzymatic reaction carried out by the enzyme ligase. Ligase catalysis the covalent bonding between two nucleotides adjacent to each other. The reaction of ligase is facilitated by a complementary strand holding the two nucleotides in close proximity. The reaction is further facilitated if the two nucleotides comprises the 3' and 5' ends of two polynucleotides that is hold in close proximity to each other by a complementary strand leaving no gaps between the two ends. See "Hybrid oligonucleotide tag". Even if that is the situation the reaction cannot occur if there is no phosphate group on the 5' end or no OH group on the 3' end or if either of the ends are blocked in any other way. Ligation can be carried out using any enzyme capable of ligating nucleotides.

Ligase Chain Reaction (LCR): In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA.

Lineage: Clusters or groups of genetically related isolates of S. aureus. Isolates belonging to the same lineage share very similar sequence for the majority of their genome (excluding mobile genetic elements). They can also be identified by MLST that have ST types that cluster using BURST software. They can also be identified by spa typing of t types that cluster using BURP software. For S. aureus, two geographically and temporally distinct isolates can be remarkably similar because they belong to the same lineage.

Linker: Connects two moieties or groups or molecules with each other.

mecA gene: Encodes penicillin-binding protein 2a (PBP2a). The presence of mecA in a bacterium gene confers antibiotic resistance to antibiotics such as Methicillin, Penicillin, and other penicillin-like antibiotics.

Messenger RNA (mRNA): mRNA, a polynucleotide being transcribed only from genes that are actively expressed, where the expressed mRNA codes for a protein.

MRSA: Methicillin-resistant S. aureus. A bacterium displaying high levels of antibiotic resistance. It represents a serious public health concern due to increased mortality associated with treatment failure and increased costs to the healthcare system.

MSSA: Methicillin-Sensitive S. aureus, refers to all of the strains of S. aureus that are susceptible to methicillin.

MLST: Multi-locus sequence typing. A method for discriminating bacterial strains/clones belonging to the same species. The method is based on sequencing of 7 housekeeping genes present in all members of the species.

Nucleic acid: A chain or sequence of nucleotides that convey genetic information. The nucleic acid may for example be DNA, RNA, LNA, HNA, PNA, preferably the nucleic acid is DNA or RNA.

Nucleoside: A base attached to a ribose ring, as in RNA nucleosides, or a deoxyribose ring, as in DNA nucleosides.

Nucleotide: Monomer of RNA or DNA. A nucleotide is a ribose or a deoxyribose ring attached to both a base and a phosphate group. Both mono-, di-, and tri-phosphate nucleosides are referred to as nucleotides.

Oligonucleotide: The term "oligonucleotide" as used herein includes linear oligomers of natural or modified monomers or linkages, including deoxyribonucleotides, ribonucleotides, anomeric forms thereof, peptide nucleic acid monomers (PNAs), locked nucleotide acid monomers (LNA), and the like, capable of specifically binding to a single stranded polynucleotide tag by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'→3' order from left to right and the "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise methylated or non-natural nucleotide analogs. When oligonucleotides are referred to as "double-stranded," it is understood by those of skill in the art that "a pair" of oligonucleotides exist in a hydrogen-bonded, helical configuration typically associated with, for example, DNA. In addition to the 100% complementary form of double-stranded oligonucleotides, the term "double-stranded" as used herein is also meant to refer to those forms which include such structural features as bulges and loops.

PBP: Penicillin-binding proteins are membrane bound DD-peptidases that have evolved from serine proteases. PBP2a is encoded by the MecA gene and determines methicillin resistance.

PCR: The polymerase chain reaction (PCR) is a technique widely used in molecular biology. It derives its name from one of its key components, a DNA polymerase used to amplify a piece of DNA by in vitro enzymatic replication. As PCR progresses, the DNA thus generated is itself used as a template for replication.

PCR reagents: refers to the chemicals, apart from the target nucleic acid sequence, needed to perform the PCR process. These chemicals generally consist of five classes of components: (i) an aqueous buffer, (ii) a water soluble magnesium salt, (iii) at least four deoxyribonucleotide triphosphates (dNTPs), (iv) oligonucleotide primers (normally two primers for each target sequence, the sequences defining the 5' ends of the two complementary strands of the double-stranded target sequence), and (v) a polynucleotide polymerase, preferably a DNA polymerase, more preferably a thermostable DNA polymerase, i.e., a DNA polymerase which can tolerate temperatures between 90[deg.] C. and 100[deg.] C. for a total time of at least 10 min without losing more than about half its activity [0030] The four conventional dNTPs are thymidine triphosphate (dTTP), deoxyadenosine triphosphate (dATP), deoxycitidine triphosphate (dCTP) and deoxyguanosine triphosphate (dGTP). These conventional triphosphates may be supplemented or replaced by dNTPs containing base analogues which Watson-Crick base pair like the conventional four bases, e.g., deoxyuridine triphosphate (dUTP).

RM system: Restriction modification (RM) systems are used by bacteria to protect themselves from foreign DNA.

RNA: ribonucleic acid. Different groups of ribonucleic acids exists: mRNA, tRNA, rRNA and nRNA.

sau1: A chromosomal RM system with widespread distribution in all S. aureus isolates.

Solid support: A material having a rigid or semi-rigid surface. Such materials will preferably take the form of plates or slides, small beads, pellets, disks, capillary tubes or other convenient forms, although other forms may be used. In some embodiments, at least one surface of the solid support will be substantially flat. The solid support may be biological, non-biological, organic, inorganic, or a combination of any of these, existing as particles, strands, precipitates, gels, sheets, tubing, spheres, containers, capillaries, pads, slices, films, plates, slides, etc.

Spa type: Typing method based on the sequence of a single gene called staphylococcal protein A (spa) gene. Is used for classifying different strains and/or lineages of S. aureus. A spa type is composed of various repeats, each of which represents 21 to 30 nucleotides (7-10 codons).

ssDNA: Single stranded DNA.

*Staphylococcus aureus* (*S. aureus*): Is a bacterium, frequently found in the nose and skin of a person.

Strain/isolate: A strain according to the present invention is a bacterial isolate that has initially been derived from a pure culture. A strain can also be derived from a clone. If two isolates belong to a clone it suggests that two isolates have derived from a single isolate recently. Clones may also according to the present invention derived from a strain and includes bacteria that exhibit minor changes in their genome, when compared to the initial isolate. As an example, multiple strains of the same clone can occur in one individual after some time due to a treatment which causes recombination and/or mutation events. Thus, for example, a patient could be infected by several strains that belong to the same clone that have developed from one initial infection with a single strain.

ST type: A classification system of *s. aureus* based on MLST typing of housekeeping genes.

T type: A classification system of *s. aureus* based on spa typing.

Typing: Typing according to the present invention shall mean that said strains or lineages of *S. aureus* are sorted into bacterial groups based on the results of the analysis as performed in the context of the present invention. Detection, identification or typing are used interchangeably herein.

vanA gene: Gene conferring vancomycin resistance.

Zoonosis (or zoonose): Any infectious disease that is able to be transmitted (in some instances, by a vector) from other animals, both wild and domestic, to humans or from humans to animals (the latter is sometimes called reverse zoonosis).

DETAILED DISCLOSURE OF THE INVENTION

The applicants herein describe a method for rapid and reliable identification of *S. aureus* types, clonal complexes, and/or strains and/or lineages and more specifically for the identification of clonal complex CC398.

The present invention also enables a rapid and specific identification of methicillin-resistant (MRSA) and methicillin susceptible (MSSA) variants of *S. aureus* by simultaneous detection of clone-specific gene sequences in the hsd RM system and of a gene for antibiotic resistance, preferably MecA.

One embodiment of the invention relates to methods using amplification primers and/or probes which are specific and sensitive for determining the presence of nucleic acid(s) from a *S. aureus* strain or lineage in any sample suspected of containing said *S. aureus* nucleic acid(s) thereby identifying, detecting and/or typing said *S. aureus* strain or lineage, wherein each of said nucleic acid(s) or variant(s) or part(s) thereof comprises a selected target region hybridizable with said probes or primers; said method comprising the following steps: contacting said sample with said primers, or probes and detecting the presence of amplified products or hybridized probes as an indication of the presence of said specific *S. aureus* strain or lineage thereby identifying, detecting and/or typing said *S. aureus* strain or lineage.

In a more specific embodiment the nucleic acid(s) from a *S. aureus* strain or lineage is a species specific restriction-modification (RM) gene, preferably a hsdS gene, even more preferably a sau1hsdS1 or sau1hsdS2 gene.

Thus in a particular embodiment the invention relates to a method for identifying, detecting and/or typing any *S. aureus* clonal complex using at least one or more amplification primers and/or probes which are specific and sensitive for determining the presence of clone-specific nucleic acid(s) from the hsdS gene which is hybridizable with said probes or primers, said method comprising the following steps: contacting a sample with said primers or probes and detecting the presence of amplified products or hybridized probes as an indication of the presence of said specific hsdS gene thereby identifying, detecting and/or typing said *S. aureus* clonal complex.

Another particular embodiment the invention relates to a method for identifying, detecting and/or typing any *S. aureus* clonal complex using at least one or more amplification primers and/or probes which are specific and sensitive for determining the presence of clone-specific nucleic acid(s) from the hsdS gene which is hybridizable with said probes or primers, said method comprising the following steps: contacting a sample with said primers or probes and detecting the presence of amplified products or hybridized probes as an indication of the presence of said specific hsdS gene thereby identifying, detecting and/or typing said *S. aureus* clonal complex provided that said clonal complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

*S. aureus*

As described herein above *S. aureus* is one of the most frequent causes of bacterial infections in the world. About 20% of the population is long-term carriers of *S. aureus*. *S. aureus* may occur as a commensal on human skin; it also occurs in the nose frequently (in about a third of the population) and throat less commonly.

Methicillin-Resistant *S. aureus* (MRSA)

MRSA is by definition a strain of *S. aureus* that is resistant to a large group of antibiotics called the beta-lactams, which include the penicillins and the cephalosporins (see herein below). MRSA may also be referred to as multidrug-resistant *S. aureus* or oxacillin-resistant *S. aureus* (ORSA).

The organism is often sub-categorized as Community-Associated MRSA (CA-MRSA) or nosocomial infections. Nosocomial infections are also known as Health Care-Associated MRSA (HA-MRSA). Nosocomial infections are infections which are a result of treatment in a hospital or a healthcare service unit, but secondary to the patient's original condition. Infections are considered nosocomial if they first appear 48 hours or more after hospital admission or within 30 days after discharge. This type of infection is also known as a hospital-acquired infection (or more generically healthcare-associated infections).

MRSA is especially troublesome in nosocomial infections. In hospitals, patients with open wounds, invasive devices, and weakened immune systems are at greater risk for infection than the general public. Hospital staff who have not followed proper sanitary procedures may transfer bacteria from patient to patient. Visitors to patients with MRSA infections or MRSA colonization are advised to follow hospital isolation protocol by using the provided gloves, gowns, and masks if indicated. Visitors who do not follow such protocols are capable of spreading the bacteria to cafeterias, bathrooms, and elevators.

Some have defined CA-MRSA by criteria related to patients suffering from an MRSA infection while others have defined CA-MRSA by genetic characteristics of the bacteria themselves. CA-MRSA strains were first reported in the late 1980s; these cases were defined by a lack of exposure to the health care setting. In the next several years, it became clear that CA-MRSA infections were caused by strains of MRSA that differed from the older and better studied healthcare-associated strains. Both Community-Associated MRSA (CA-MRSA) and Health Care-Associated MRSA (HA-MRSA) are encompassed within the scope of the present invention.

Healthy individuals may carry MRSA asymptomatically for periods ranging from a few weeks to many years. Patients with compromised immune systems are at a significantly greater risk of symptomatic secondary infection.

The initial presentation of MRSA is small red bumps that resemble pimples, spider bites, or boils that may be accompanied by fever and occasionally rashes. Within a few days the bumps become larger, painful and eventually open into deep, pus-filled boils. About 75 percent of CA-MRSA infections are localized to skin and soft tissue and usually can be treated effectively. However CA-MRSA strains display enhanced virulence, spreading more rapidly and causing illness much more severe than traditional HA-MRSA infections and they can affect vital organs and lead to widespread infection (sepsis), toxic shock syndrome and necrotizing ("flesh-eating") pneumonia.

Both CA-MRSA and nosocomial MRSA (HA-MRSA) are resistant to traditional anti-staphylococcal beta-lactam antibiotics (see herein below). CA-MRSA has a greater spectrum of antimicrobial susceptibility, including to sulfa drugs, tetracyclines, and clindamycin. HA-MRSA is often resistant even to these antibiotics and often is susceptible only to vancomycin.

Subjects

The subjects referred to herein are single members of a species, herein preferably a mammalian species. Any mammalian species is an object of the present invention, although any of the following species are of particular relevance: mouse, rat, guinea goat, llama, pig, hamster, rabbit, cat, dog, pig, cow, horse, sheep, monkey, and human. The subjects may in the present text also be referred to as patients or individuals.

The *S. aureus* nucleic acid(s), preferably clone-specific nucleic acid(s) from the hsdS gene of the present invention may be derived from strains and/or lineages of any subject, the subject being preferably persons and/or animals. In preferred embodiments the sample of *S. aureus* nucleic acid(s), preferably clone-specific nucleic acid(s) from the hsdS gene may be derived from strains and/or lineages from a person from an at risk population.

At risk populations include but are not limited to:
Persons staying in a health care facility for an extended period of time
Health care workers
Farm workers
Veterinarian staff
Persons involved in sales to farms
Persons involved in the handling of livestock
Slaughterhouse workers
Persons involved in post production of meat including but not limited to butchers in general
People with weak immune systems (AIDS patients, cancer patients, severe asthmatics, etc.)

Diabetics
Athletes participating in contact sports or weight training
Young children
The elderly
Prisoners or anyone living in confined space with other people.
Cystic fibrosis patients In a preferred embodiment the sample of nucleic acid(s) is derived from strains and/or lineages of persons staying in a health care facility for an extended period of time, health care workers, farm workers, veterinarian staff, persons involved in sales to farms and any person involved in the handling of livestock and/or butchery.

In a specific embodiment the sample of nucleic acid(s) is derived from strains and/or lineages of one individual patient or hospital.

In another specific embodiment several lineages and/or hospital isolates are analysed.

S. aureus is not only present in humans. It may be useful to test animals for the presence of S. aureus nucleic acid(s), preferably clone-specific nucleic acid(s) from the hsdS gene and/or for the presence of mecA nucleic acid(s).

Thus, in other embodiments the test sample may be derived from any animal, preferably any domesticated animal. In some embodiment the test sample may be derived from poultry, whereas in other embodiments the test sample may be derived from a mammal, such as a mouse, a rat, a guinea pig, a goat, a llama, a hamster, a rabbit, a cat, a dog, a pig, a cow, a horse, a sheep, a monkey, and a human being. Preferably the mammal is a human being or a domesticated animal.

In some embodiments the mammal may be selected from the group consisting of domesticated animals including but not limited to livestock such as pigs, horses and cows, sheep, goats, whereas in other embodiments the mammal may be selected from the group consisting of pet animals including but not limited to dogs and cats.

Biological Sample

A biological sample is a sample obtained from a subject. As such a biological sample may be a sample selected from the group consisting of tissue, blood, serum, plasma samples, urine, cerebrospinal fluid, synovial fluid, ascites, and saliva.

In specific embodiments of the invention the sample may be a sample selected from the group consisting of swabs from mucosal tissues including but not limited to nasal swabs, throat swabs and mouth swabs. The sample may also be a sample selected from the group consisting of swabs from the skin surface especially from hands, feet, Perineum, face and from any infectious tissue such as boils and sores.

In some specific embodiments the S. aureus nucleic acid(s) of the present invention, preferably clone-specific nucleic acid(s) from the hsdS gene may be derived from meat or any food products and any sample thereof.

Strains and Lineages

According to the present invention the S. aureus strain or lineage may be any S. aureus clonal complex, strain or lineage.

In a particular embodiment of the present invention the S. aureus strain or lineage may be any S. aureus clonal complex, strain or lineage provided that said clonal complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873.

In some embodiments the S. aureus clonal complex, strain or lineage is a MRSA strain or lineage, including but not limited to Community-Associated MRSA (CA-MRSA) or noncomisal MRSA (HA-MRSA).

In some embodiments, when the S. aureus clonal complex, strain or lineage is determined simultaneously with the determination of the presence of an antibiotic gene, preferably mecA, the S. aureus strain or lineage may be any S. aureus strain or lineage.

In a preferred embodiment of the present invention the S. aureus clonal complex, is CC398.

In a preferred embodiment of the present invention the S. aureus clonal complex is MRSA CC398.

In a preferred embodiment of the present invention the S. aureus strain or lineage is any CC398 lineage or strain.

In a preferred embodiment of the present invention the S. aureus strain or lineage is a MRSA CC398 lineage or strain.

Clonal Complex 398/CC398/ST398

CC398 is an S. aureus lineage that includes strains belonging to MLST type ST398 and variants of this MLST type including but not limited to ST291, ST621, ST752, ST753, ST804, ST813, ST1066, ST1067, ST1112, ST1232 and ST1277. It also quite possibly includes ST140, ST580, ST601, ST727, ST810 and ST1094 as double locus variants of CC398 identified sequence types. It includes but is not limited to S. aureus strains of spa type t011, t034, t108 t567, t899, t1197, t1451, t1939, t1793, t2876, t1255 and t571.

CC398 may also include ST140, ST580, ST601, ST727, ST810 and ST1094 as double locus variants of CC398 identified sequence types.

CC398 further includes but is not limited to S. aureus strains of spa type t011, t034, t108 t567, t899, t1197, t1451, t1939, t1793, t2876, t1255 and t571.

Figure 2:
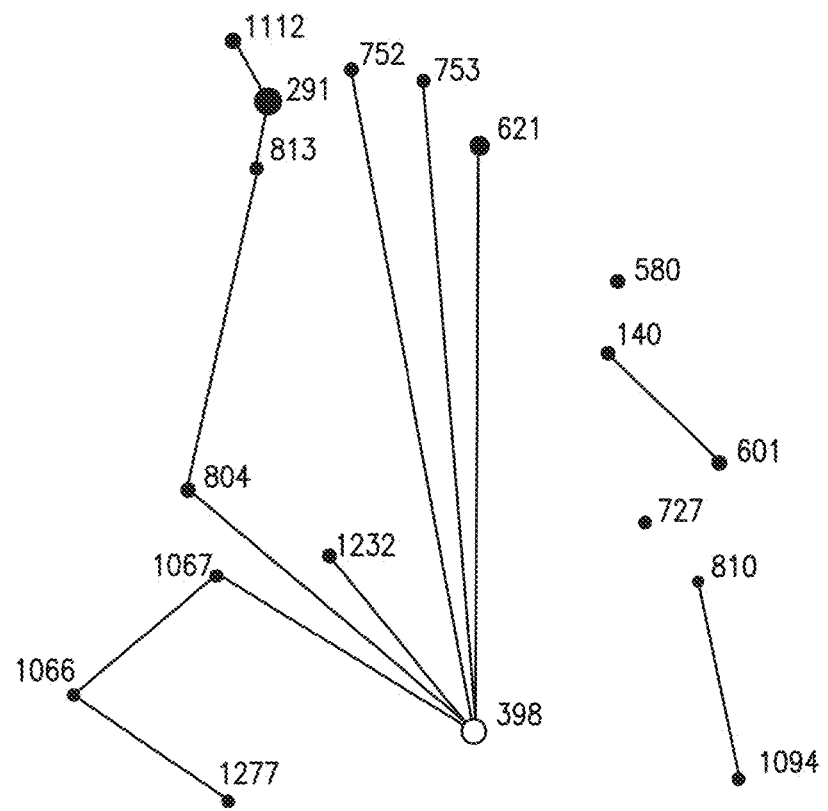
FIG. 2: ST types expected to be linked to CC398. Sequence types (ST) identified to belong or associate to clonal complex 398 by eBURST analysis (www.mlst.net). Linked STs are all directly identified as belonging to CC398 whereas the CC398 unlinked isolates are identified as being double-locus variants of the directly identified STs.
Figure 3A:
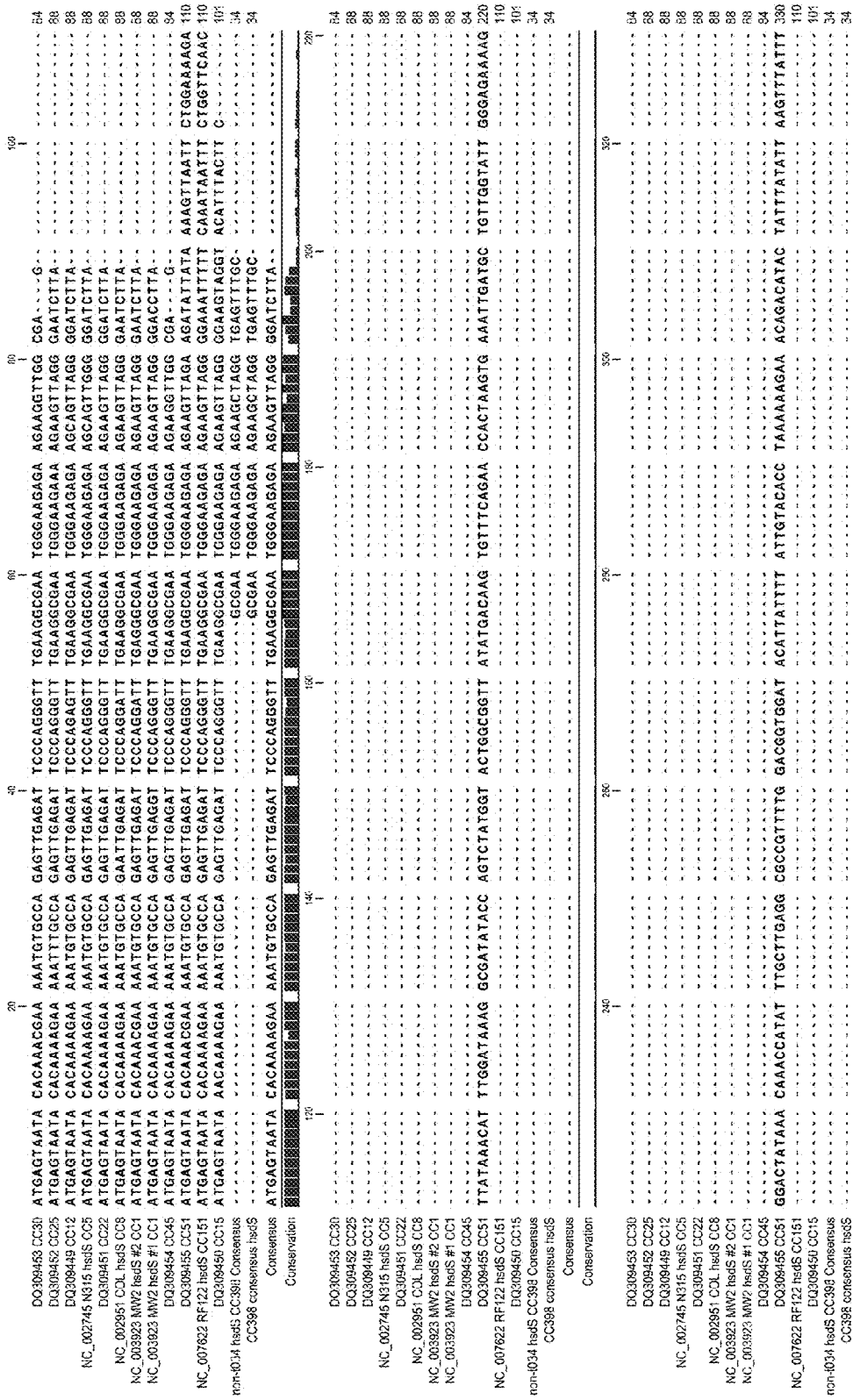
Figure 3B:
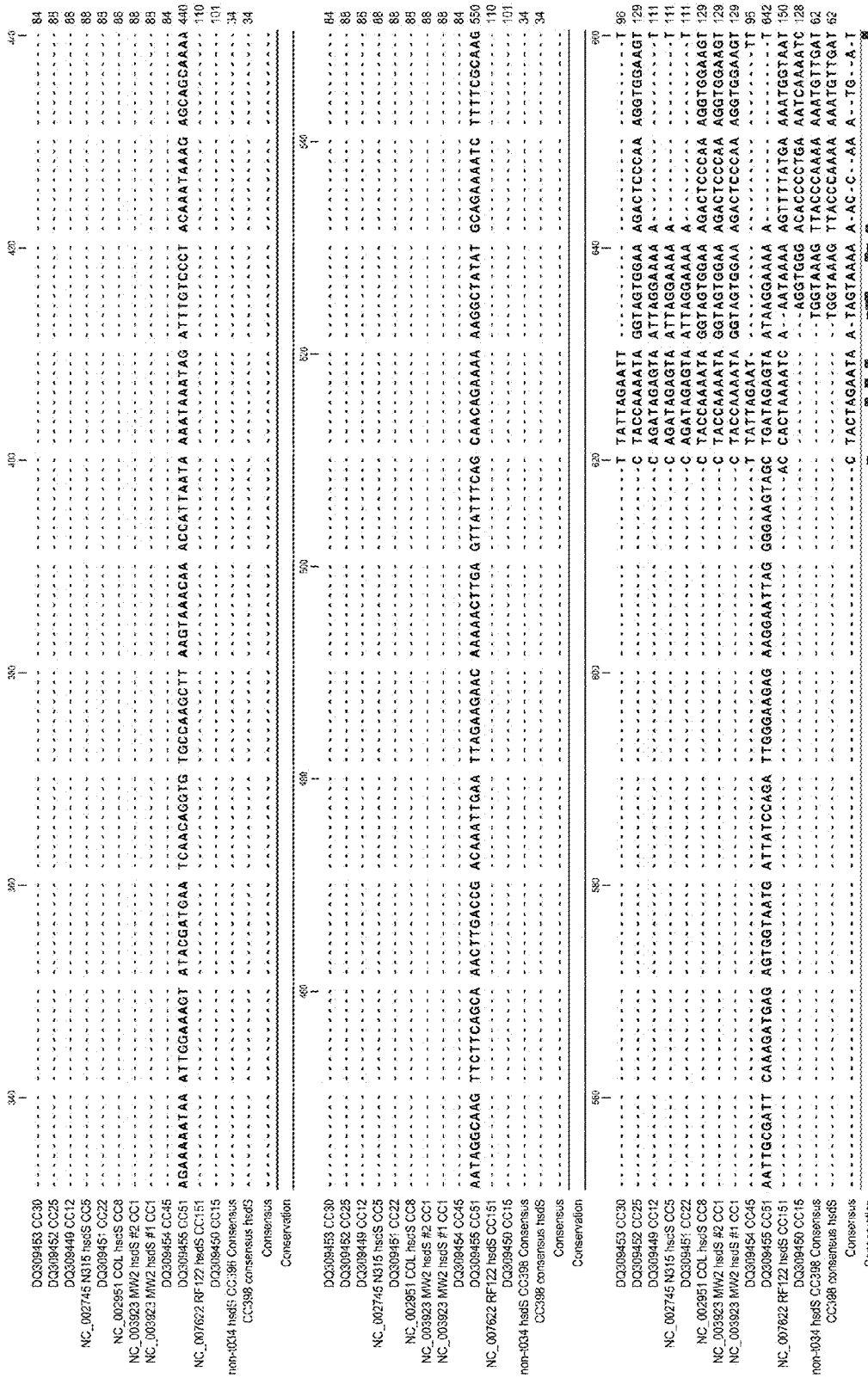
Figure 3C:
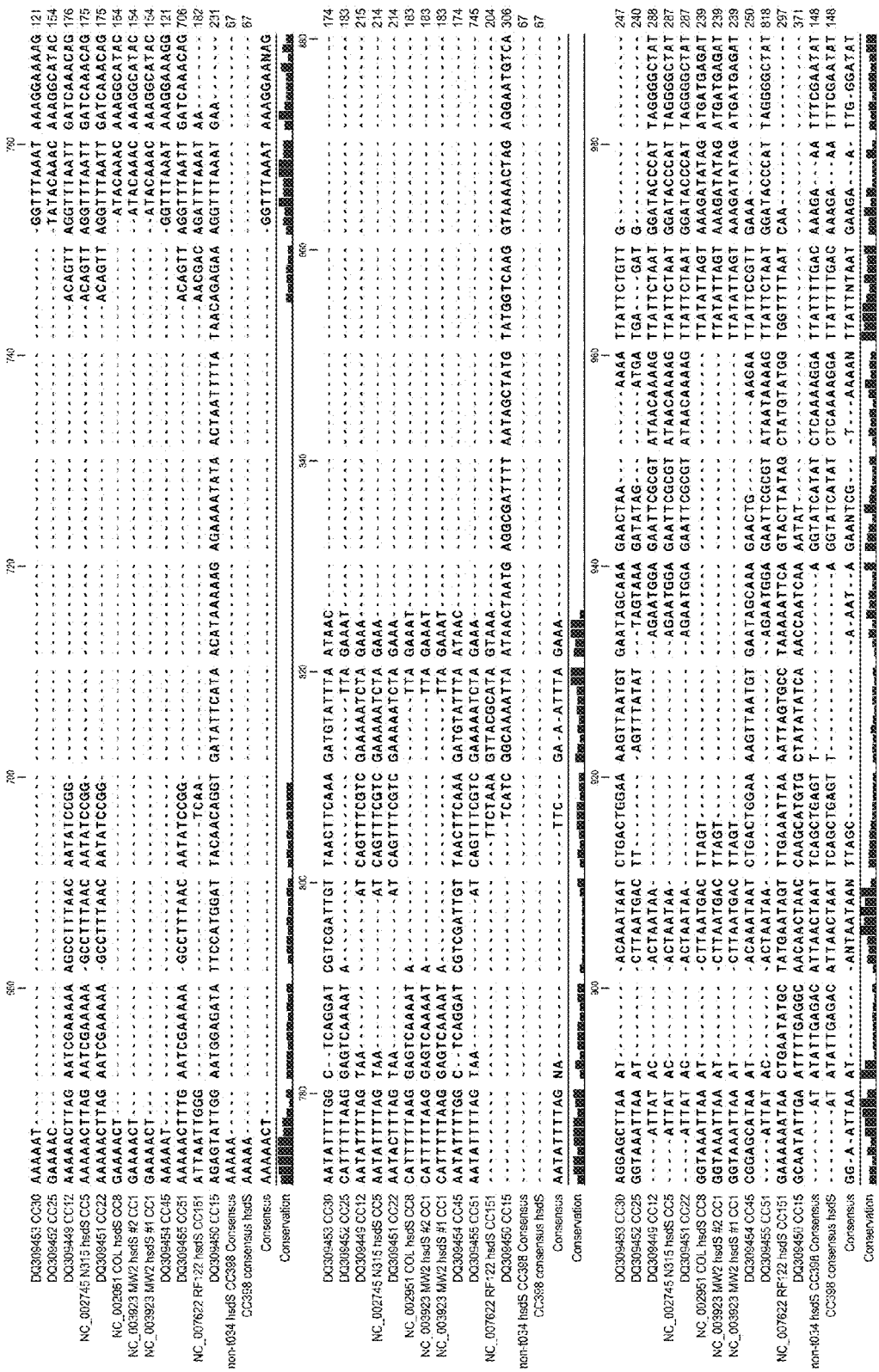
Figure 3D:
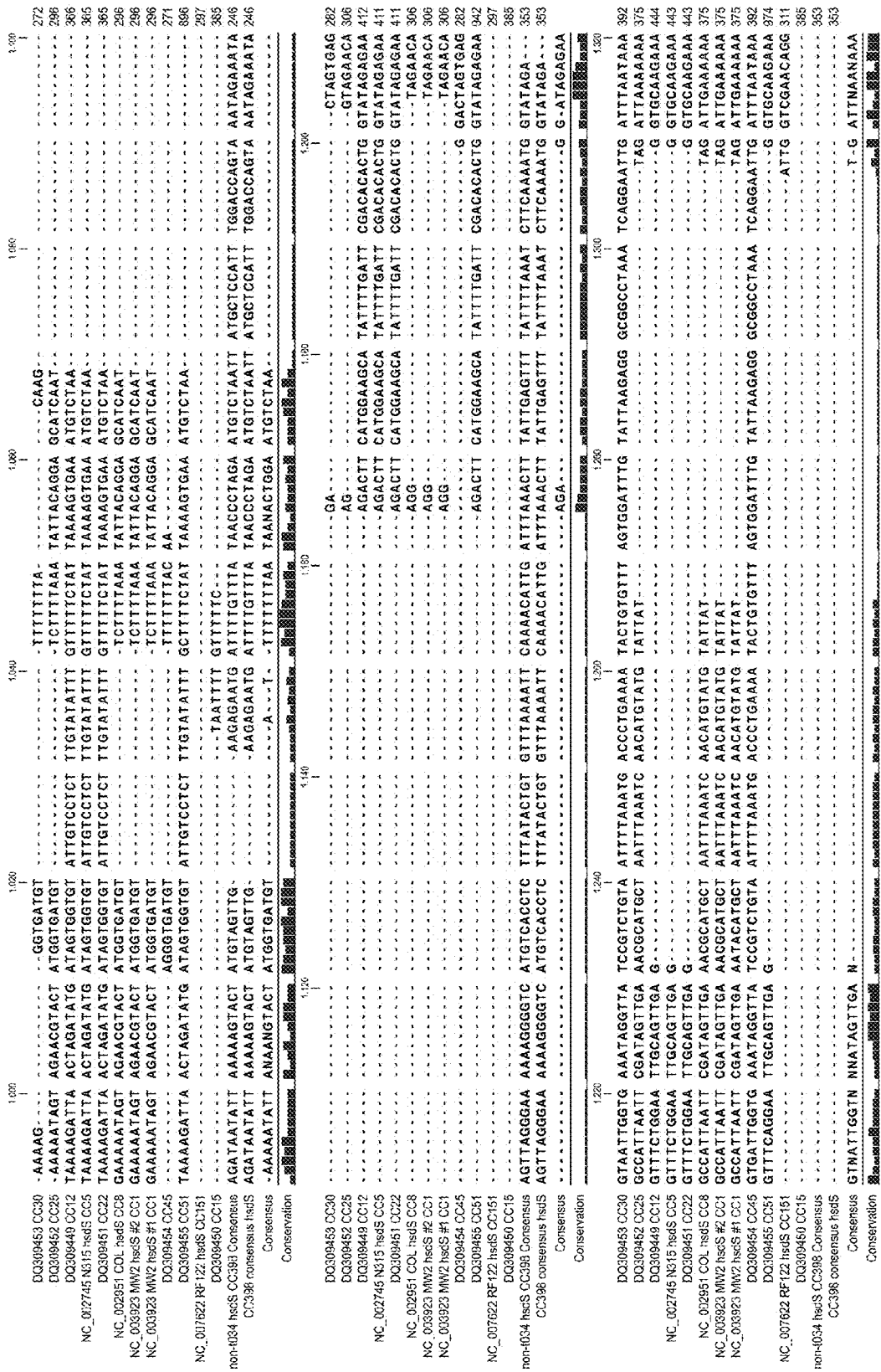
Figure 3E:
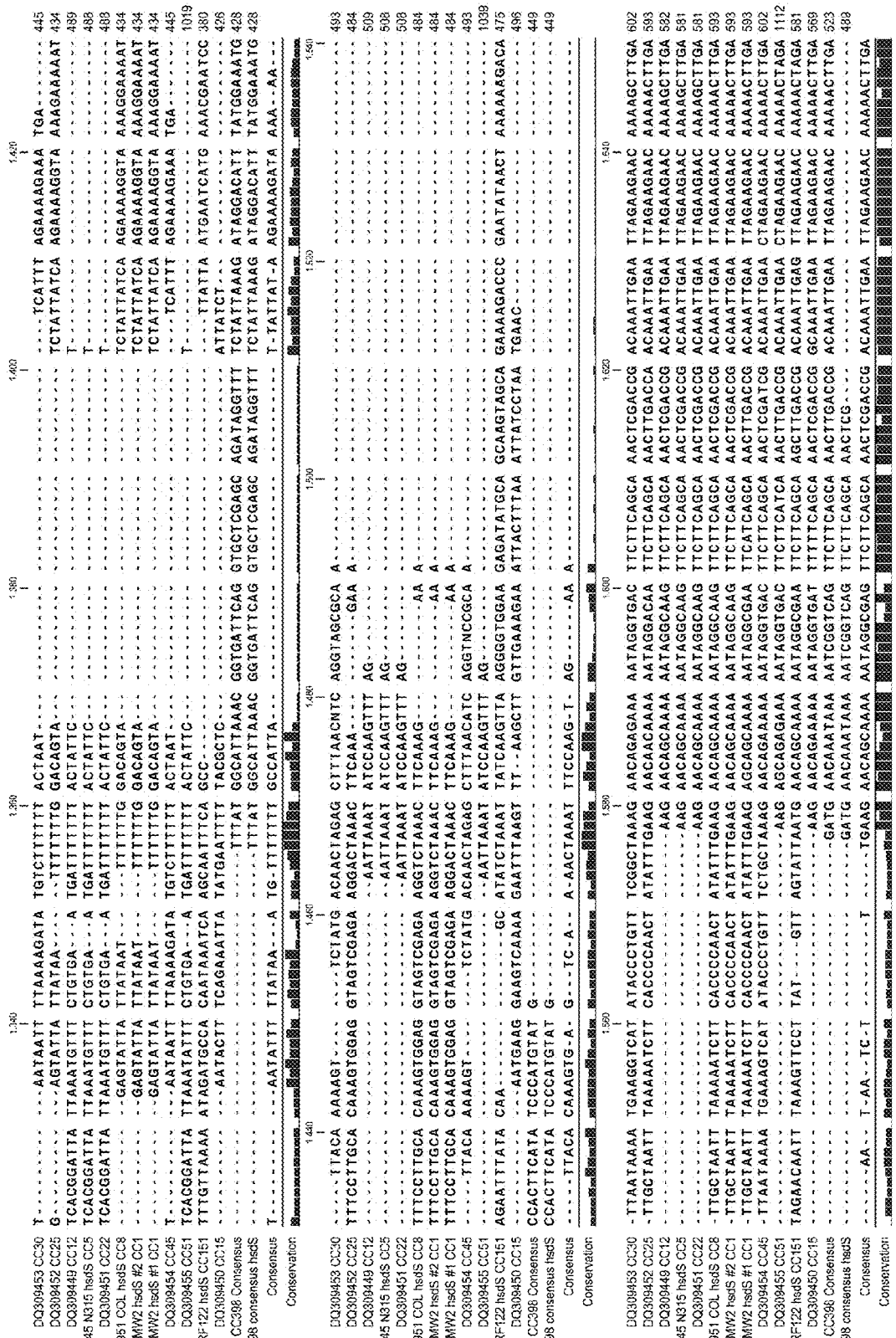
Figure 3F:
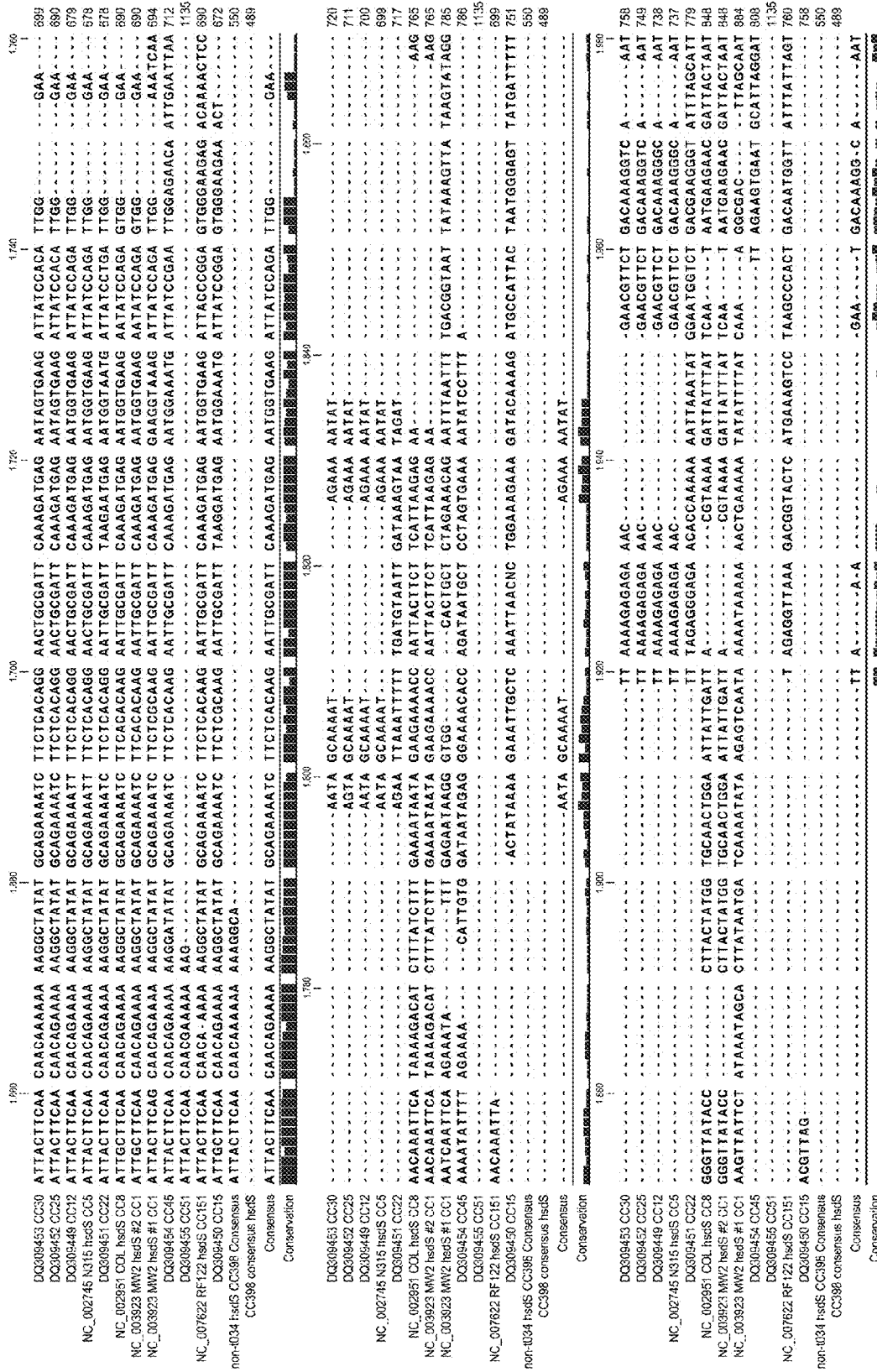
Figure 3G:
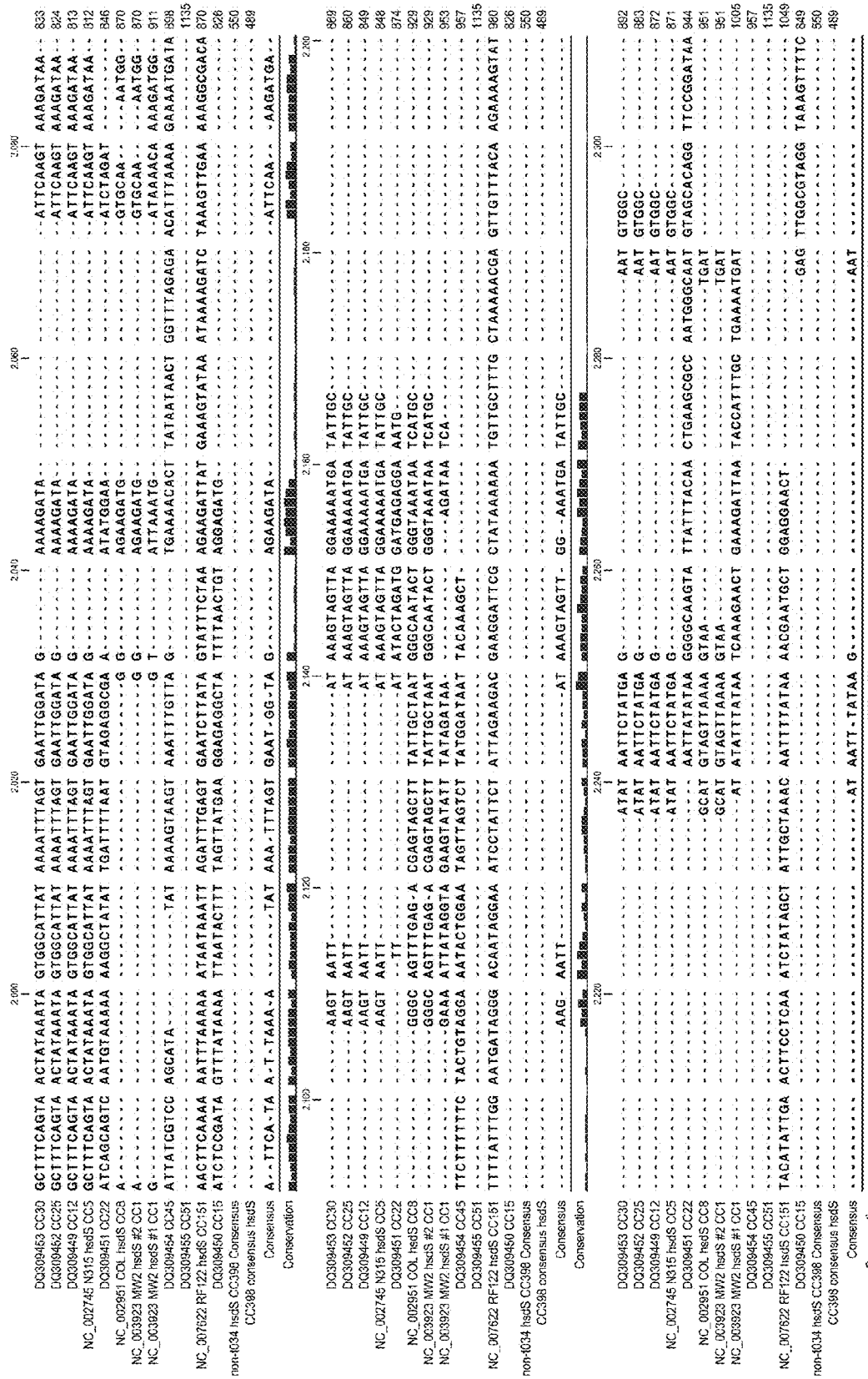
Figure 3H:
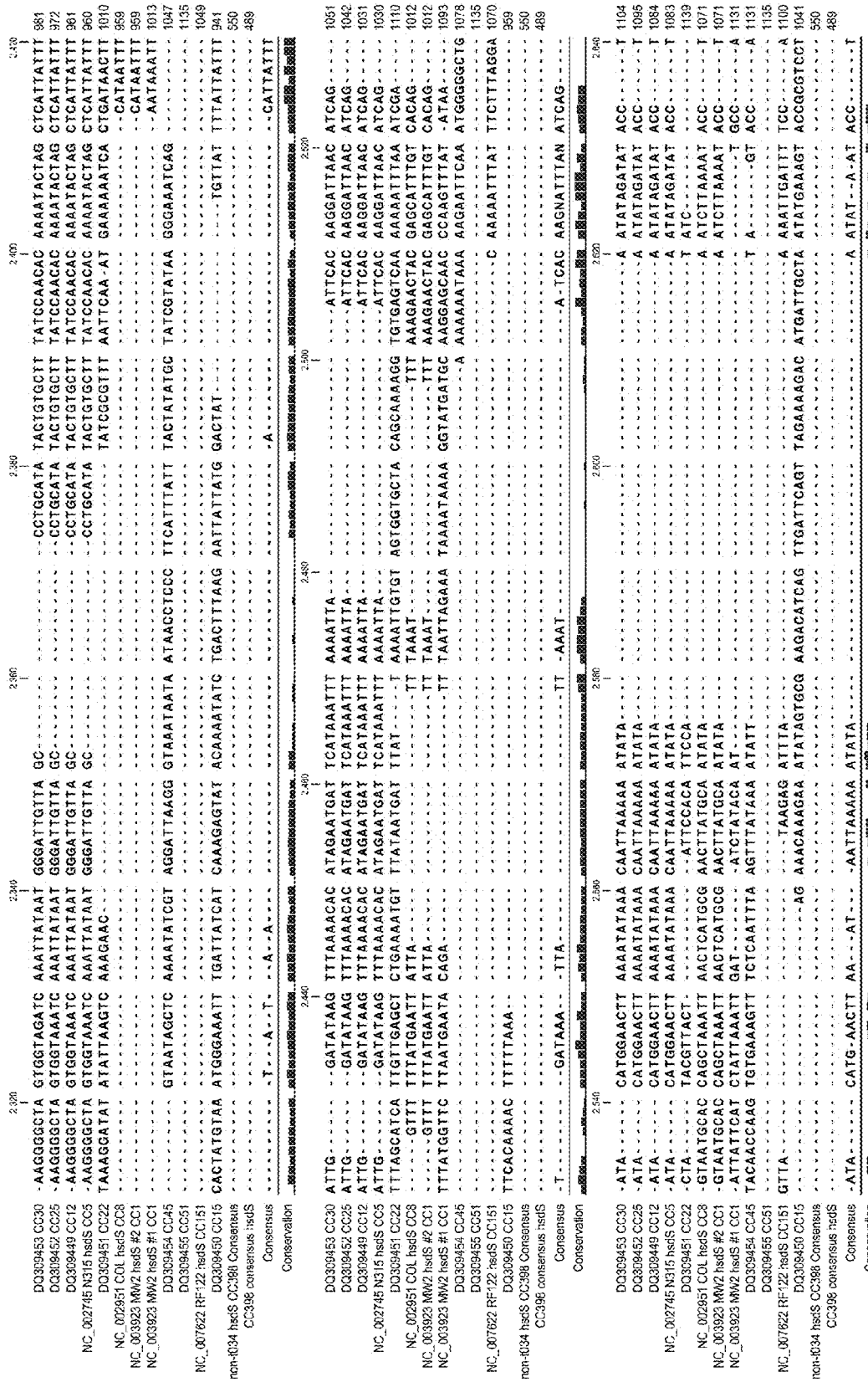
Figure 31:
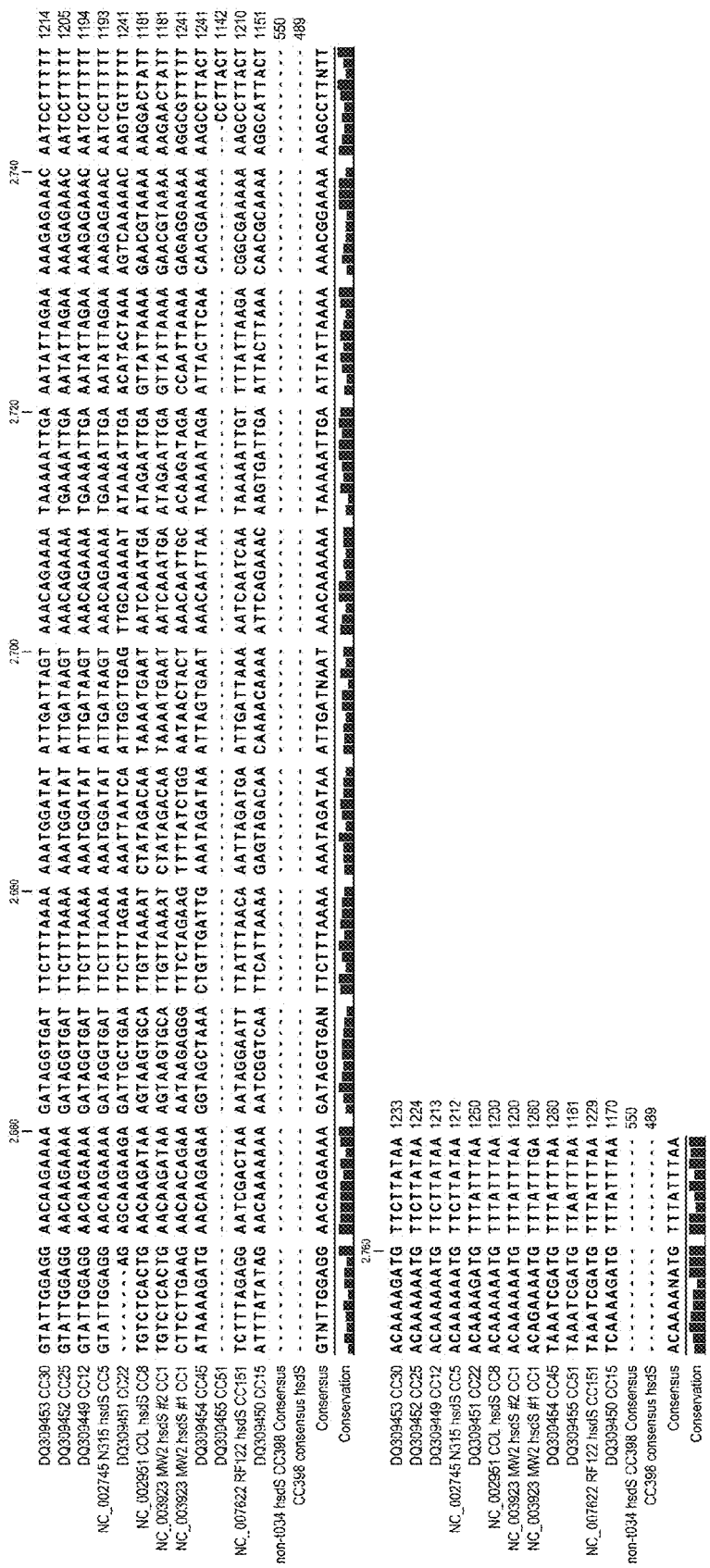

Preferably the CC398 strain of the present invention belongs to MLST type ST398 and variants of this MLST type including but not limited to ST291, ST621, ST752, ST753, ST804, ST813, ST1066, ST1067, ST1112, ST1232 and ST1277. It also quite possibly includes ST140, ST580, ST601, ST727, ST810 and ST1094 as double locus variants of CC398 identified sequence types. It includes but is not limited to S. aureus strains of spa type t011, t034, t108 t567, t899, t1197, t1451, t1939, t1793, t2876, t1255 and t571. but any CC398 related MLST types or spa types including as yet unidentified types are encompassed within the scope of the present invention. See FIG. 2 for a diagram of the CC398 related MLST and spa types.

Beta-Lactam Antibiotics

Beta-lactam antibiotics are a broad class of antibiotics that include penicillin derivatives, cephalosporins, monobactams, carbapenems, and β-lactamase inhibitors, that is, any antibiotic agent that contains a β-lactam nucleus in its molecular structure. They are the most widely-used group of antibiotics.

MRSA has evolved an ability to survive treatment with beta-lactamase resistant beta-lactam antibiotics, including but not limited to methicillin, dicloxacillin, nafcillin, and oxacillin.

Beta-lactam antibiotics include but are not limited to penicillins including narrow-spectrum penicillins, such as the Beta-lactamase sensitive penicillins including but not limited to benzathine penicillin, benzylpenicillin (penicillin G), phenoxymethylpenicillin (penicillin V), procaine penicillin and oxacillin; the Penicillinase-resistant penicillins including but not limited to methicillin, oxacillin, nafcillin, cloxacillin, dicloxacillin and flucloxacillin and the beta-lactamase-resistant penicillins such as temocillin. Moderate-spectrum penicillins such including but not limited to amoxycillin and ampicillin are also included as are any broad-spectrum penicillins including but not limited to co-amoxiclav (amoxicillin+clavulanic acid) as well as extended-spectrum penicillins including but not limited to azlocillin, carbenicillin, ticarcillin, mezlocillin and piperacillin.

Another class of Beta-lactam antibiotics is the cephalosporins, including first generation cephalosporins including but not limited to cephalexin, cephalothin and cefazolin as well as second generation cephalosporins including but not limited to moderate spectrum cephalosporins such as cefaclor, cefuroxime and cefamandole and second generation cephamycins including but not limited to cefotetan and cefoxitine. Third generation cephalosporins including but not limited to ceftriaxone, cefotaxime, cefpodoxime and ceftazidime are also included as are fourth generation cephalosporins including but not limited to cefepime and cefpirome.

Yet another class of Beta-lactam antibiotics is the carbapenems including but not limited to imipenem, meropenem, ertapenem, faropenem and doripenem.

Still another class of Beta-lactam antibiotics is the monobactams including but not limited to aztreonam (Azactam). The MRSA according to the present invention may be resistant to any one or more of the subgroups of betal-lactams described herein above.

Restriction Modification System (RM System)

In some embodiments of the invention the nucleic acid(s) from a *S. aureus* strain or lineage is a species specific restriction-modification (RM) gene, more preferably the nucleic acid(s) from a *S. aureus* strain or lineage is a clone specific restriction-modification (RM) gene. In a very preferred embodiment the nucleic acid(s) from a *S. aureus* clonal complex, strain or lineage is clone-specific nucleic acid(s) from the hsdS gene.

The restriction modification system (RM system) is used by bacteria, and perhaps other prokaryotic organisms to protect themselves from foreign DNA, such as bacteriophages. Certain bacteria strains were found to inhibit (restrict) the growth of viruses grown in previous strains. This effect was attributed to sequence-specific restriction enzymes.

Bacteria have restriction enzymes, also called restriction endonucleases, which cleave double stranded DNA at specific points into fragments, which are then degraded further by other endonucleases. This prevents infection by effectively destroying the foreign DNA introduced by an infectious agent (such as a bacteriophage). Approximately one quarter of known bacteria possess RM systems and of those about one half has more than one type of system.

Types of Restriction Modification Systems

There are three types of restriction modification systems: type I, type II and type III, all with restriction enzyme activity and a methylase activity.

Type I systems consist of three polypeptides: R (restriction), M (modification), and S (specificity). The resulting complex can both cleave and methylate DNA. The S subunit determines the specificity of both restriction and methylation. Cleavage occurs at variable distances from the recognition sequence, so discrete bands are not easily visualized by gel electrophoresis. In a preferred embodiment of the invention the RM system is a type I system.

Type II systems are the simplest and the most prevalent. Instead of working as a complex, the methyltransferase and endonuclease are encoded as two separate proteins and act independently (there is no specificity protein). Both proteins recognize the same recognition site, and therefore compete for activity. The methyltransferase acts as a monomer, methylating the duplex one strand at a time. The endonuclease acts as a homodimer, which facilitates the cleavage of both strands. Cleavage occurs at a defined position close to or within the recognition sequence, thus producing discrete fragments during gel electrophoresis. For this reason, Type II systems are used in labs for DNA analysis and gene cloning. In some embodiments of the invention the RM system is a type II system. In some embodiment of the invention the RM system may be a type I system.

Type III systems have R and M proteins that form a complex of modification and cleavage. The M protein, however, can methylate on its own. Methylation also only occurs on one strand of the DNA unlike most other known mechanisms. The heterodimer formed by the R and M proteins competes with itself by modifying and restricting the same reaction. In some embodiments of the invention the RM system is a type III system. In some embodiment of the invention the RM system may be a type III system.

Type I RM Systems

In preferred embodiments of the invention the nucleic acid(s) from a *S. aureus* strain or lineage is a species specific restriction-modification (RM) gene of the type I of RM systems, more preferably the nucleic acid(s) from a *S. aureus* strain or lineage is a clone specific type I restriction-modification (RM) gene.

There are three types of type I systems, namely type IA, type IB and type IC. Type I restriction enzymes comprises three subunits which are encoded by three closely linked genes hsdR, hsdM and hsdS. The HsdM and HsdS (also known as the specificity subunit) subunits are both necessary and sufficient for methyltransferase activity. The HsdR subunit (also known as the restriction subunit) is required for restriction. The type I RM system preferably used in the present invention prevents acquisition of DNA originated from genetically unrelated *S. aureus* clones and other foreign DNA.

In a preferred embodiment of the invention the nucleic acid(s) from a *S. aureus* clonal complex, strain or lineage is one or more clone-specific hsdS nucleic acid(s).

In a very preferred embodiment of the invention the nucleic acid(s) from a *S. aureus* clonal complex is clone-specific nucleic acid(s) from the hsdS gene, more preferably the clone-specific nucleic acid(s) are from the sau1hsdS1 or sau1hsdS2 genes. In a most preferred embodiment of the invention the nucleic acid(s) from a *S. aureus* clonal complex is sau1hsdS1 (SEQ ID NO: 1) or sau1hsdS2 from CC398.

It is understood, that some hsdS sequences are found in more than one lineage of *S. aureus*. Further, without being bound by theory, no lineage has two identical hsdS sequences. Therefore any combination of hsdS sequences can be used to identify any specific *S. aureus* lineage and this is thus an embodiment of the present invention.

Also, there may within a clonal complex and/or lineage be a small variation in the sequence of the hsdS gene(s) of that particular clonal complex/lineage. The sequence variation may be too minute to distinguish the particular bacteria from other bacteria belonging to the same clonal complex/lineage and thus in the present context a clone-specific nucleic acid may in fact be of more than one specific nucleotide sequence. Thus it is an object of the present invention to detect clone-specific nucleic acid(s) from the hsdS gene(s). The difference in sequence within a clonal complex/lineage in a single hsdS gene(s) may be 1, such as 2, such as 3, such as 4, such as 5, such as 6, such as 7, such as 8, such as 9, or such as 10 nucleotides whereby it is understood that the difference may reside in a replacement of one nucleotide for another or the deletion or insertion of any of the above number of nucleotides.

Detection

It is within the general scope of the present invention to provide methods for the detection of nucleic acid(s) from *S. aureus*, preferably nucleic acid(s) of the RM systems described herein above even more preferably clone-specific nucleic acid(s) from the hsdS gene and optionally nucleic acid(s) of an antibiotic gene, preferably mecA.

The detection of one or more nucleic acid molecules of the RM systems described herein above even more preferably clone-specific nucleic acid(s) from the hsdS gene allows for the identification, detection and/or typing of a *S. aureus* clonal complex, strain and/or lineage. The identification, detection and/or typing of a *S. aureus* clonal complex, strain and/or lineage is of relevance both medically and scientifically and may provide important information useful for example infection control.

Any method of detection of nucleic acid(s) from *S. aureus* falls within the general scope of the present invention. The detection methods may be generic for the detection of nucleic acids especially DNA and/or RNA. The detection methods may be directed towards the scoring of a presence or absence of one or more nucleic acid molecules or may be useful in the detection of expression levels.

The detection methods can be divided into two categories herein referred to as in situ methods or screening methods. The term in situ method refers to the detection of nucleic acid molecules in a sample wherein the structure of the sample has been preserved. This may thus be a biopsy wherein the structure of the tissue is preserved. In situ methods are generally histological i.e. microscopic in nature and include but are not limited to methods such as: in situ hybridization techniques and in situ PCR methods. Thus nucleic acid(s) of a clone-specific hsdS gene, preferably CC398 may be detected by any of the methods described herein.

Screening methods generally employ techniques of molecular biology and most often require the preparation of the sample material in order to access the nucleic acid molecules to be detected. Screening methods include, but are not limited to methods such as: Array systems, affinity matrices, Northern blotting and PCR techniques, such as real-time quantitative RT-PCR.

An aspect of the present invention regards the detection of nucleic acid molecules by any method known in the art. In the following are given examples of various detection methods that can be employed for this purpose, and the present invention includes all the mentioned methods, but is not limited to any of these.

Amplification Methods

In specific embodiments of the invention the nucleic acid(s) of *S. aureus*, specifically clone-specific nucleic acid(s) from the hsdS gene are amplified. The amplification method may be any method of amplifying nucleic acid(s) and may be selected from the group consisting of polymerase chain reaction (PCR), ligase chain reaction (LCR), nucleic acid sequence-based amplification (NASBA), self-sustained sequence replication (3SR), strand displacement amplification (SDA), branched DNA signal amplification (bDNA), transcription-mediated amplification (TMA), cycling probe technology (CPT), real-time PCR, quantitative PCR, nested PCR, and multiplex PCR.

PCR

The terms "PCR reaction", "PCR amplification", "PCR", "pre-PCR", "Q-PCR", "real-time quantitative PCR", "nested PCR", "multiplex PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence-based amplification (NASBA), self-sustained sequence replication (3SR), strand displacement amplification (SDA), branched DNA signal amplification (bDNA), transcription-mediated amplification (TMA), cycling probe technology (CPT), and Q Beta Replicase systems. The products formed by said amplification reaction may or may not be monitored in real time or only after the reaction as an end-point measurement.

Thus in one specific embodiment, the invention relates to a method for the detection, identification and/or typing of a *S. aureus* clonal complex, strain or lineage, in a test sample which comprises the following steps: a) treating said sample with an aqueous solution containing at least one pair of oligonucleotide primers, one of said primers being capable of hybridizing selectively with one of the two complementary strands of said *S. aureus* clone-specific hsdS gene that contains a target sequence, and the other of said primers being capable of hybridizing with the other of said strands so as to form an extension product which contains the target sequence as a template, said at least one pair of primers being chosen from a nucleotide sequence within the clone-specific hsdS gene respectively with regard to said *S. aureus* clonal complex, a sequence complementary thereof, and a variant thereof; b) synthesizing an extension product of each of said primers, said extension product containing the target sequence, and amplifying said target sequence, if any, to a detectable level; and c) detecting the presence and/or amount of said amplified target sequence as an indication of the presence and/or amount of said *S. aureus* clonal complex, in said test sample.

In one embodiment there is provided that the clonal complex is complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

Preferably, the primers are the primers specified in SEQ ID NO: 2 and SEQ ID NO: 6 for the detection and/or identification and/or typing of CC398 *S. aureus*.

Multiplex PCR

Multiplex PCR is a variant of PCR which enables simultaneous amplification of many targets of interest in one reaction by using more than one pair of primers. A Multiplex PCR assay is thus capable of screening for the presence of two or more nucleic acid(s) in a sample.

A preferred embodiment of the invention is a multiplex PCR reaction that allows the simultaneous detection of nucleic acid(s) of the RM systems described herein above and nucleic acid(s) of an antibiotic gene selected from the group consisting of mecA and vanA, preferably the antibiotic gene is mecA.

Another preferred embodiment of the invention is a multiplex PCR reaction that allows the simultaneous detection of nucleic acid(s) of the hsdS genes described herein above and nucleic acid(s) of an antibiotic gene selected from the group consisting of mecA and vanA, preferably the antibiotic gene is mecA.

A very preferred embodiment of the invention is a multiplex PCR reaction that allows the simultaneous detection of nucleic acid(s) of the hsdS genes of CC398 described herein above and nucleic acid(s) of an antibiotic gene selected from the group consisting of mecA and vanA, preferably the antibiotic gene is mecA.

Thus a very preferred embodiment of the invention the methods described herein further comprises amplification primers and/or probes which are specific and sensitive for determining the presence of nucleic acid(s) from the bacterial antibiotic resistance gene mecA in any sample suspected of containing said *S. aureus* nucleic acid(s) thereby determining MRSA, wherein each of said nucleic acid(s) or variant(s) or part(s) thereof comprises a selected target region hybridizable with said primers or probes; said method comprising the following steps: contacting said sample with said probes or primers and detecting the presence of amplified products or hybridized probes as an indication of the presence said specific *S. aureus* antibiotic resistance genes and thus MRSA.

Preferably, the primers are the primers specified in SEQ ID NO: 2 and SEQ ID NO: 6 for the identification, detection and/or typing of CC398 *S. aureus* and the primers specified in SEQ ID NO: 7 and SEQ ID NO: 8 for the detection of the mecA gene.

Real-Time Quantitative RT-PCR

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Ligase Chain Reaction (LCR)

An aspect of the present invention regards the detection of the nucleic acid molecules by means of using LCR. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA.

Primers

The PCR reactions described herein requires one or more pairs of amplification primers. The single-stranded DNA primer is from about 10 to about 50 nucleotide bases in length, more preferably from about 17 to about 40 nucleotide bases in length. It can be of any sequence. The primer can have sequence redundancies reducing the occurrence of mismatches.

In preferred embodiments of the invention the amplification primers are capable of hybridizing with any clone-specific nucleic acid(s) from the hsdS gene or a sequence complementary thereto. Thus in specific embodiments the amplification primers are capable of hybridizing with sau1hsdS1 of CC398 or sau1hsdS2 of CC398 or a sequence complementary thereto. Thus is one very preferred embodiment the amplification primers are capable of hybridizing the nucleotide sequence defined in: SEQ ID NO: 1 or a sequence complementary thereto.

In is contemplated that said primers may not necessarily be completely within the hsdS gene, but may also hybridize to adjacent regions to said hsdS gene.

PCR reactions require both forward and reverse primers for the amplification of nucleic acid(s). Thus in one embodiment of the invention the PCR reaction comprises one or more forward primers and one or more reverse primers. In a preferred embodiment the PCR reaction comprises one forward and one or more reverse primers.

In one embodiment the forward primer is a non-specific primer. In a more preferred embodiment the forward primer targets the upstream conserved region of the hsdS gene. In a very preferred embodiment the forward primer (AF primer) is AGGGTTTGAAGGCGAATGGG (SEQ ID NO: 6). The non-specific AF primer is not clone specific but general to the hsdS genes of many clonal complexes and is thus not encompassed to be within the scope of the clone specific primers of the invention.

By specific is meant that the primers/probes binds to regions of the hsdS gene that are clone specific i.e. the variable/unconserved regions of the hsdS gene.

In one embodiment the one or more reverse primers are *S. aureus* clonal complex, strain or lineage specific primers. In a more preferred embodiment the one or more reverse primers are specific for CC398 and may be selected from the group consisting of CAGTATTAAAGAGGTGACATGACCCCT (SEQ ID NO: 2), CACCTGAATCACCGTTTAATGCC (SEQ ID NO: 3), CGAGCACCTGAATCACCGTTT (SEQ ID NO: 4) and TGGGATATGAAGTGGCATTTCC (SEQ ID NO: 5).

In a very preferred embodiment the reverse primers is the CC398 specific primer is CAGTATTAAAGAGGTGACATGACCCCT (SEQ ID NO: 2).

In one embodiment the final concentration of the each primer is in a concentration range of 0.01 µM to 10 µM, for example 0.05 µM to 5 µM, such as 0.1 to 1 µM, for example 0.5 µM. In a very preferred embodiment the final concentration of each primer is 0.2 µM.

Analysis

The detection of PCR products may be by any method including but not limited to separation by agarose gel electrophoresis followed by ethidium bromide or DNA staining, hybridization assays performed in microtitration wells, capillary electrophoresis, flow cytometry for post-PCR detection of amplification products that are fluorescently labeled or have been subjected to an oligonucleotide ligation reaction and are captured on polystyrene beads.

Flow cytometry is suitable for the development of multiplex assays. Real-time PCR methods allows continuous monitoring of the amplified fragments during PCR by a homogeneous fluorometric hybridization assay and is used widely for quantification of the fusion transcripts.

Northern Blot Analysis

An aspect of the present invention regards the detection of the nucleic acid molecules herein disclosed by the classical and to the art well-known technique of Northern blot analysis. Many variations of the protocol exist and optimizations regarding the detection of nucleic acid molecules constitute preferred embodiment s of the present invention.

Thus nucleic acid(s) of a clone-specific hsdS gene, preferably CC398 may be detected by any of the methods described herein above.

Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid support, which can be a microchip, a glass slide or a microsphere-sized bead (see herein below).

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present invention regards the use of microarrays for the detection of nucleic acid(s) in a *S. aureus* strain or lineage, thereby identifying, detecting and/or typing said *S. aureus* strain and/or lineage. For this purpose, total nucleic acid(s) is extracted from a sample containing *S. aureus* and is used directly. The nucleic acid(s) may be 3'end labelled using T4 RNA ligase and either a Cy3- or Cy5-labeled short RNA linker (f. ex. 5'-PO4-rUrUrU-Cy3/dT-3' or 5'-PO4-rUrUrU-Cy5/dT-3'). The nucleic acid(s) samples may be labelled by incubation at 30° C. for 2 hours followed by heat inactivation of the T4 RNA ligase at 80° C. for 5 minutes. The fluorophore-labelled nucleic acid(s) complementary to the corresponding nucleic acid(s) capture probe sequences on the array will hybridize, via base pairing, to the spot at which the capture probes are affixed.

Several types of microarrays can be employed such as spotted oligonucleotide microarrays, pre-fabricated oligonucleotide microarrays or spotted long oligonucleotide arrays In spotted oligonucleotide microarrays the capture probes are oligonucleotides complementary to nucleic acid(s) sequences of *S. aureus*. This type of array is typically hybridized with amplified PCR products of nucleic acid(s) sequences of *S. aureus* from two samples to be compared (e.g. a CC398 containing sample and a CC5 containing sample or a mecA positive and a mecA negative sample) that are labelled with two different fluorophores. Nucleic acid(s) are extracted from the abovementioned two samples and used directly, and 3' end labeled using T4 RNA ligase and short RNA linkers labelled with two different fluorophores. The samples can be mixed and hybridized to one single microarray that is then scanned, allowing the visualization of up-regulated and down-regulated nucleic acid(s) genes in one go. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted nucleic acid(s). There are commercially available designs that cover complete genomes from companies such as Affymetrix, or Agilent. These microarrays give estimations of the absolute value of gene expression and therefore the comparison of two conditions requires the use of two separate microarrays.

Spotted long Oligonucleotide Arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

The clone specific probes may be any of the probes described herein below or any probes capable of hybridizing to the variable/nonconserved region of a *S. aureus* clonal complex; preferably the clonal complex is CC398.

In specific embodiments the clone specific probes may be any of the probes described herein below or any probes capable of hybridizing to the variable/nonconserved region of a *S. aureus* clonal complex; provided that the clonal complex is complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873 Preferably the clonal complex is CC398.

WO 2005056832 for example describes a microarray useful for *S. aureus* identification, detection and/or typing that may be useful in some embodiments of the present invention.

A preferred embodiment of the invention comprises labelling the *S. aureus* nucleic acid(s) in a sample or of a substantially homogeneous population of said *S. aureus* isolated from this sample and putting said labelled nucleic acid(s) into contact with a solid support coated with an array of probes in suitable conditions for hybridization, wherein at least one probe is able to specifically hybridize with clone-specific hsdS nucleic acid(s) or with a representative fragment thereof, susceptible to be present in said sample to be tested, so as to obtain a hybridization profile containing detectable signals characteristic for the presence or the absence of the clone-specific hsdS gene in said sample to be tested, and identification, detection and/or typing the *S. aureus* clonal complex relative to the characterization of the presence or absence of said clone-specific hsdS gene, wherein one or more probes optionally is able to specifically hybridize with nucleic acid(s) conferring antibiotic resistance.

In another preferred embodiment the method for determining the presence of hsdS nucleic acid(s) from a *S. aureus* clonal complex, strain or lineage in any sample further comprises a) depositing and fixing on an solid support or leaving in solution said *S. aureus* nucleic acid(s) of the sample or of a substantially homogeneous population of said *S. aureus* isolated from this sample, or inoculating said sample or said substantially homogeneous population of *S. aureus* isolated from this sample on an solid support, and lysing in situ said inoculated sample or said isolated *S. aureus* to release the said *S. aureus* hsdS nucleic acid(s), said *S. aureus* hsdS nucleic acid(s) being made in a substantially single-stranded form.

A preferred embodiment of the present invention thus regards the method of microarray use and analysis as described herein.

A more preferred embodiment of the present invention regards the use of a microarray method as described above for the detection of nucleic acid(s) in a *S. aureus* strain or lineage, thereby identifying, detecting and/or typing said *S. aureus* strain and/or lineage.

A most preferred embodiment of the present invention regards the use of microarrays methods as described above for the detection of nucleic acid(s) such as a hsdS gene, preferably a sau1hsdS1 or sau1hsdS2 gene from a *S. aureus* clonal complex.

In specific embodiments of the present invention which the clone specific probes regards the use of microarrays methods as described above for the detection of nucleic acid(s) such as a hsdS gene, preferably a sau1hsdS1 or sau1hsdS2 gene from a *S. aureus* clonal complex; provided that the clonal complex is complex is not CC1, CC5, CC8, CC22, CC30, or CC45. In some embodiments it is further provided that said clonal complex may not be any one or more of: CC12, CC15, CC25, CC51, CC151, CC97, CC771, CC130, CC188, and/or CC873 Preferably the clonal complex is CC398.

In a very preferred embodiment the invention regards the use of microarrays methods as described above for the detection of clone specific hsdS nucleic acid(s) such as any of sau1hsdS1 of CC398 or sau1hsdS2 of CC398 or a sequence complementary thereto. Thus is one very preferred embodiment the probes are capable of hybridizing the nucleotide sequence defined in: SEQ ID NO: 1 or a sequence complementary thereto.

In preferred embodiments of the invention the probes are capable of hybridizing with sau1hsdS1 of CC398 or sau1hsdS2 of CC398 or a sequence complementary thereto. Thus is one very preferred embodiment the probes are capable of hybridizing the nucleotide sequence defined in: SEQ ID NO: 1 or a sequence complementary thereto.

In some embodiments the probes are selected from the group consisting of CAGTATTAAAGAGGTGACATGAC-CCCT (SEQ ID NO: 2), CACCTGAATCACCGTTTAAT-GCC (SEQ ID NO: 3), CGAGCACCTGAATCACCGTTT (SEQ ID NO: 4) and TGGGATATGAAGTGGCATTTCC (SEQ ID NO: 5). Preferably, the probe is the CC398 specific primer CAGTATTAAAGAGGTGACATGACCCCT (SEQ ID NO: 2).

A specific embodiment of the invention further comprises labelling the *S. aureus* nucleic acid(s) in a sample or of a substantially homogeneous population of said *S. aureus* isolated from this sample and putting said labelled nucleic acid(s) into contact with a solid support coated with an array of probes in suitable conditions for hybridization, wherein at least one probe is able to specifically hybridize with clone-specific hsdS nucleic acid(s) or with a representative fragment thereof, susceptible to be present in said sample to be tested, so as to obtain a hybridization profile containing detectable signals characteristic for the presence or the absence of the clone-specific hsdS gene in said sample to be tested, and identifying, detecting and/or typing the *S. aureus* clonal complex relative to the characterization of the presence or absence of said clone-specific hsdS gene, wherein one or more probes optionally is able to specifically hybridize with nucleic acid(s) conferring antibiotic resistance.

Probe

It is an object of the present invention to provide a probe which can be used for the detection of a nucleic acid molecule as defined herein. A probe as defined herein is a specific sequence of a nucleic acid used to detect nucleic acids by hybridization. A nucleic acid is also here any nucleic acid, natural or synthetic such as DNA, RNA, LNA or PNA. A probe may be labelled, tagged or immobilized or otherwise modified according to the requirements of the detection method chosen. A label or a tag is an entity making it possible to identify a compound to which the probe is associated. It is within the scope of the present invention to employ probes that are labelled or tagged by any means known in the art such as but not limited to: radioactive labelling, fluorescent labelling and enzymatic labelling. Furthermore the probe, labelled or not, may be immobilized to facilitate detection according to the detection method of choice and this may be accomplished according to the preferred method of the particular detection method.

An aspect of the present invention relates to the use of a nucleic acid molecule as described herein as a probe, wherein the probe is a nucleotide sequence selected from the group consisting of SEQ ID NOS: 2, 3, 4, 5 and 6, and/or a nucleotide sequence which is complementary to a clone specific hsdS gene, more specifically to sau1hsdS1 of CC398 or sau1hsdS2 of CC398 and even more specifically SEQ ID NO: 1, or a fragment hereof, can hybridize under stringent condition and/or has an identity of at least 80% to any of these sequences. Most preferably the probe is either SEQ ID NO: 2 and/or a nucleotide sequence which is complementary to either sau1hsdS1 of CC398 (SEQ ID NO: 1) or sau1hsdS2 of CC398 or fragments hereof, and/or can hybridize under stringent condition and/or has an identity of at least 80% to any of these sequences. Any of the herein described probes may be modified by labelling or immobilization as mentioned above.

In Situ Hybridization

In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells.

Sample cells are treated to increase their permeability to allow the probe to enter the cells, the probe is added to the treated cells, allowed to hybridize at pertinent temperature, and then excess probe is washed away. A complementary probe is labelled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe mentioned herein.

An embodiment of the present invention regards the method of detection by in situ hybridization as described herein.

In Situ PCR

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labelled nucleotides (e.g. digoxigenin-11-dUTP, fluorescein-dUTP, 3H-CTP or biotin-16-dUTP) which have been incorporated into the PCR products during thermal cycling.

An embodiment of the present invention regards the method of in situ PCR as mentioned herein above for the detection of nucleic acid molecules as detailed herein.

The methods described herein above, may be carried out on any test sample. In preferred embodiments the test sample is a biological sample (see herein above).

In preferred embodiments of the invention is performed directly on a test sample, wherein said test sample may be a sample selected from the group consisting of swabs from mucosal tissues including but not limited to nasal swabs, throat swabs and mouth swabs. The sample may also be a sample selected from the group consisting of swabs from the skin surface especially from hands, feet, Perineum, face and any infectious tissue such as boils, sores and carbuncles. The sample may also be blood.

In some embodiments of the present invention the nucleic acid(s) are extracted from a test sample using a bacterial genomic DNA purification kit. Some embodiments further comprise culturing of the strains and/or lineages of S. aureus before the analysis.

In one embodiment of the present invention the nucleic acid(s) detection methods described herein above is performed directly from a test sample consisting of a bacterial culture or suspension.

Another aspect of the invention relates to an improved method of treatment for an infection by MRSA, using the methods described herein and performing a treatment of MRSA based, at least in part, on said identification, detection and/or typing of S. aureus.

Another aspect of the invention relates to s method of improving the hygiene in a hospital, using the methods described herein and performing hygiene measures in said hospital based, at least in part, on said identification, detection and/or typing of S. aureus.

The method described herein may also be used for obtaining hsdS sequences from any S. aureus clonal complex, strain or lineage directly from a test sample or a bacterial culture, which comprises the following steps: a) treating said sample with an aqueous solution containing at least one pair of primers having a sequence selected within the nucleotide sequences defined in SEQ ID NOS: 9, 10, 11 and 12, and a variant thereof, one of said primers being capable of hybridizing selectively with one of the two complementary strands of said S. aureus hsdS gene that contains a target sequence, and the other of said primers being capable of hybridizing with the other of said strands so as to form an extension product which contains the target sequence as a template; b) synthesizing an extension product of each of said primers, said extension product containing the target sequence, and amplifying said target sequence, if any, to a detectable level; and c) detecting the presence and/or amount of said amplified target sequence; and d) determining the nucleotide sequence of the said amplified target sequence by using any DNA sequencing method.

In one embodiment there is provided that the clonal complex is complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

The primers used to identify the unknown sau1hsdS1 gene region may be CAATTTGTCGGTCGAGTTTGCTG (SEQ ID NO: 9), TGTGAGAAGATTTTCTGCATATAGCC (SEQ ID NO: 10), GCCTTTTTTCTGTTGTTGAAGTAATTC (SEQ ID NO: 11) and GTCGGTCGAGTTTGCTGAAG (SEQ ID NO: 12).

TABLE 1

Sequences used

| SEQ ID No. | Description of sequence | Sequence |
|---|---|---|
| 1 | CC398 consensus sau1hsdS1 sequence | GCGAATGGGAAGAGAAGAAGCTAGGTGAGTTTGCTGGTAAAGTTAC CCAAAAAAATGTTGATAAAAAATATATTGAGACATTAACTAATTCAGC TGAGTTAGGTATCATATCTCAAAAGGATTATTTTGACAAAGAAATTTC GAATATAGATAATATTAAAAAGTACTATGTAGTTGAAGAGAATGATTT TGTTTATAACCCTAGAATGTCTAATTATGCTCCATTTGGACCAGTAAAT AGAAATAAGTTAGGGAAAAAAGGGGTCATGTCACCTCTTTATACTGTG TTTAAAATTCAAAACATTGATTTAAACTTTATTGAGTTTTATTTTAAATC TTCAAAATGGTATAGATTTATGGCATTAAACGGTGATTCAGGTGCTCG AGCAGATAGGTTTTCTATTAAAGATAGGACATTTATGGAAATGCCACT TCATATCCCATGTATGGATGAACAAATAAAAATCGGTCAGTTCTTCAGC AAACTCG |
| 2 | CC398-specific reverse primer ST398 r1 | CAGTATAAAGAGGTGACATGACCCCT |
| 3 | CC398-specific reverse primer ST398 r2 | CACCTGAATCACCGTTTAATGCC |
| 4 | CC398-specific reverse primer ST398 r3 | CGAGCACCTGAATCACCGTTT |
| 5 | CC398-specific reverse primer ST398 r4 | TGGGATATGAAGTGGCATTTCC |
| 6 | AF forward primer | AGGGTTTGAAGGCGAATGGG |
| 7 | mecup1 primer | GGGATCATAGCGTCATTATTC |
| 8 | mecup2 primer | AACGATTGTGACACGATAGCC |
| 9 | sau1hsdS1 identification primer 1 | CAATTTGTCGGTCGAGTTTGCTG |

TABLE 1-continued

Sequences used

| SEQ ID No. | Description of sequence | Sequence |
|---|---|---|
| 10 | sau1hsdS1 identification primer 2 | TGTGAGAAGATTTTCTGCATATAGCC |
| 11 | sau1hsdS1 identification primer 3 | GCCTTTTTTCTGTTGTTGAAGTAATTC |
| 12 | sau1hsdS1 identification primer 4 | GTCGGTCGAGTTTGCTGAAG |
| 13 | CC30 isolate 507 Sau1hsdS1 | ATGAGTAATACACAAACGAAAAATGTGCCAGAGTTGAGATTCCCAGGGT<br>TTGAAGGCGAATGGGAAGAGAAGAAGGTTGGCGAGTTATTAGAATTTAA<br>AAATGGTTTAAATAAAGGAAAAGAATATTTTGGCTCAGGATCGTCGATTG<br>TTAACTTCAAAGATGTATTTAATAACAGGAGCTTAAATACAAATAATCTG<br>ACTGGAAAAGTTAATGTGAATAGCAAAGAACTAAAAAATTATTCTGTTGA<br>AAAGGGTGATGTTTTTTTTACAAGGACTAGTGAGGTAATTGGTGAAATA<br>GGTTATCCGTCTGTAATTTTAAATGACCCTGAAAATACTGTGTTTAGTGG<br>ATTTGTATTAAGAGGGCGGCCTAAATCAGGAATTGATTTAATAAATAATA<br>ATTTTAAAAGATATGTCTTTTTTACTAATTCATTTAGAAAAGAAATGATTA<br>CAAAAAGTTCTATGACAACTAGAGCTTTAACNTCAGGTAGCGCAATTAAT<br>AAAATGAAGGTCATATACCCTGTTTCGGCTAAAGAACAGAGAAAAAATAG<br>GTGACTTCTTCAGCAAACTCGACCGACAAATTGAATTAGAAGAACAAAA<br>GCTTGAATTACTTCAACAACAAAAAAAAGGCTATATGCAGAAAATCTTCT<br>CACAGGAACTGCGATTCAAAGATGAGAATAGTGAAGATTATCCACATTG<br>GGAAAATAGCAAAATAGAAAAATATTTAAAAGAGAGAAACGAACGTTCT<br>GACAAAGGTCAAATGCTTTCAGTAACTATAAATAGTGGCATTATAAAATT<br>TAGTGAATTGGATAGAAAAGATAATTCAAGTAAAGATAAAGTAATTATA<br>AAGTAGTTAGGAAAAATGATATTGCATATAATTCTATGAGAATGTGGCAA<br>GGGGCTAGTGGTAGATCAAATTATAATGGGATTGTTAGCCCTGCATATA<br>CTGTGCTTTATCCAACACAAAATACTAGCTCATTATTTATTGGATATAAG<br>TTTAAAACACATAGAATGATTCATAAATTTAAAATTAATTCACAAGGATTA<br>ACATCAGATACATGGAACTTAAAATATAAACAATTAAAAAATATAAATATA<br>GATATACCTGTATTGGAGGAACAAGAAAAGATAGGTGATTTCTTTAAAAA<br>AATGGATATATTGATTAGTAAACAGAAAATAAAAATTGAAATATTAGAAAA<br>AGAGAAACAATCCTTTTTACAAAAGATGTTCTTATAA |
| 14 | CC45 isolate 3067 Sau1hsdS1 | ATGAGTAATACACAAAAGAAAAATGTGCCAGAGTTGAGATTCCCAGGGT<br>TTGAAGGCGAATGGGAAGAGAAGAAGGTTGGCGAGTTATTAGAATTTAA<br>AAATGGTTTAAATAAAGGAAAGGAATATTTTGGCTCAGGATCGTCGATT<br>GTTAACTTCAAAGATGTATTTAATAACCGGAGCATAAATACAAATAATCT<br>GACTGGAAAAGTTAATGTGAATAGCAAAGAACTGAAGAATTATTCCGTT<br>GAAAAGGGTGATGTTTTTTTTACAAGGACTAGTGAGGTGATTGGTGAAA<br>TAGGTTATCCGTCTGTAATTTTAAATGACCCTGAAAATACTGTGTTTAGT<br>GGATTTGTATTAAGAGGGCGGCCTAAATCAGGAATTGATTTAATAAATAA<br>TAATTTTAAAAGATATGTCTTTTTTACTAATTCATTTAGAAAAGAAATGAT<br>TACAAAAAGTTCTATGACAACTAGAGCTTTAACATCAGGTNCCGCAATTA<br>ATAAAATGAAAGTCATATACCCTGTTTCTGCTAAAGAACAGAAAAAAATA<br>GGTGACTTCTTCAGCAAACTCGATCGACAAATTGAACTAGAAGAACAAA<br>AACTTGAATTACTTCAACAACAGAAAAAAGGATATATGCAGAAAATCTTC<br>TCACAAGAATTGCGATTCAAAGATGAGAATGGAAATGATTATCCGAATT<br>GGAGAACAATTGAATTAAAAAATATTTTAGAAAACATTGTGGATAATAGA<br>GGGAAAACACCAGATAATGCTCCTAGTGAAAATATCCTTTATTAGAAGT<br>GAATGCATTAGGATATTATCGTCCAGCATATATAAAAGTAAGTAAATTTG<br>TTAGTGAAAACACTTATAATAACTGGTTTAGAGAACATTTAAAAGAAAAT<br>GATATTCTTTTTTCTACTGTAGGAAATACTGGAATAGTTAGTCTTATGGA<br>TAATTACAAAGCTGTAATAGCTCAAAATATCGTAGGATTAAGGGTAAATA<br>ATAATAACCTCCCTTCATTTATTTACTATATGCTATCGTATAAGGGAAATC<br>AGAAAAAAATAAAAAGAATTCAAATGGGGGCTGTACAACCAAGTGTGAA<br>AGTTTCTCAATTTAAGTTTATAAAATATTTAGTACCAATAAAAGATGAACA<br>AGAGAAGGTAGCTAAACTGTTGATTGAAATAGATAAATTAGTGAATAAAC<br>AATTAATAAAAATAGAATTACTTCAACAACGAAAAAAAGCCTTACTTAAAT<br>CGATGTTTATTTAA |
| 15 | CC51 isolate 3 Sau1hsdS1 | ATGAGTAATACACAAACGAAAAATGTGCCAGAGTTGAGATTCCCAGGGT<br>TTGAAGGCGAATGGGAAGAGAAGAAGGTTAGAAGATATTATAAAAGTTAA<br>TTCTGGAAAAGATTATAAACATTTGGATAAAGGCGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTTATATTAAGTTTATTTAGAAAAATAAATTGGA<br>AAGTATACGATGAATCAACAGGTGTGCCAAGCTTAAGTAAACAAACCAT<br>TAATAAAATAAATAGATTTGTCCCTACAAATAAAGAGCAGCAAAAAATAG |

TABLE 1-continued

Sequences used

| SEQ ID No. | Description of sequence | Sequence |
|---|---|---|
| | | GCAAGTTCTTCAGCAAACTTGACCGACAAATTGAATTAGAAGAACAAA<br>ACTTGAGTTATTTCAGCAACAGAAAAAAGGCTATATGCAGAAAATCTTTT<br>CGCAAGAATTGCGATTCAAAGATGAGAGTGGTAATGATTATCCAGATTG<br>GGAAGAGAAGGAATTAGGGGAAGTAGCTGATAGAGTAATAAGGAAAAA<br>TAAAAACTTTGAATCGAAAAAGCCTTTAACAATATCCGGACAGTTAGGTT<br>TAATTGATCAAACAGAATATTTTAGTAAATCAGTTTCGTCGAAAAATCTA<br>GAAAATTATACACTAATAAAGAATGGAGAATTCGCGTATAATAAAAGTTA<br>TTCTAATGGATACCCATTAGGGGCTATTAAAAGATTAACTAGATATGAT<br>AGTGGTGTATTGTCCTCTTTGTATATTTGCTTTTCTATTAAAAGTGAAATG<br>TCTAAAGACTTCATGGAAGCATATTTTGATTCGACACACTGGTATAGAGA<br>AGTTTCAGGAATTGCAGTTGAGGGTGCAAGAAATCACGGATTATTAAAT<br>ATTTCTGTGAATGATTTTTTTACTATTCTAATTAAATATCCAAGTTTAGAA<br>GAGCAGAGAAAATAGGTGACTTCTTCATCAAACTTGACCGACAAATTG<br>AACTAGAAGAACAAAAACTAGAATTACTTCAACAACGAAAAAAGCCTTA<br>CTTAAATCGATGTTAATTTAA |
| 16 | CC25 isolate 16 Sau1hsdS1 | ATGAGTAATACACAAAAGAAAAATTTGCCAGAGTTGAGATTCCCAGGGT<br>TTGAAGGCGAATGGGAAGAAAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTAAAAAAAGAGTATTATTATAATTTTTTTGG<br>ACAGTATCTATTATCAAGAAAAGGTAAAAGAAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAACAACAAAAAATAGGACAATTCT<br>TCAGCAAACTTGACCAACAAATTGAATTAGAAGAACAAAAACTTGAATTA<br>CTTCAACAACAGAAAAAGGCTATATGCAGAAAATCTTCTCACAGGAAC<br>TGCGATTCAAAGATGAGAATAGTGAAGATTATCCACATTGGGAAAGTAG<br>CAAAATAGAAAAATATTTAAAAGAGAGAAACGAACGTTCTGACAAAGGT<br>CAAATGCTTTCAGTAACTATAAATAGTGGCATTATAAAATTTAGTGAATT<br>GGATAGAAAAGATAATTCAAGTAAAGATAAAAGTAATTATAAAGTAGTTA<br>GGAAAAATGATATTGCATATAATTCTATGAGAATGTGGCAAGGGGCTAG<br>TGGTAAATCAAATTATAATGGGATTGTTAGCCCTGCATATACTGTGCTTT<br>ATCCAACACAAAATACTAGCTCATTATTTATTGGATATAAGTTTAAAACAC<br>ATAGAATGATTCATAAATTTAAAATTAATTCACAAGGATTAACATCAGATA<br>CATGGAACTTAAAATATAAACAATTAAAAAATATAAATATAGATATACCTG<br>TATTGGAGGAACAAGAAAAGATAGGTGATTTCTTTAAAAAAATGGATATA<br>TTGATAAGTAAACAGAAAATGAAAATTGAAATATTAGAAAAAGAGAAACA<br>ATCCTTTTTACAAAAAATGTTCTTATAA |
| 17 | CC22 isolate 720 Sau1hsdS1 | ATGAGTAATACACAAAAGAAAAATGTGCCAGAGTTGAGATTCCCAGGGT<br>TTGAAGGCGAATGGGAAGAAGAAGTTAGGGGATCTTACAGATAGAG<br>TAATTAGGAAAATAAAAACTTAGAATCGAAAAAGCCTTTAACAATATCC<br>GGACAGTTAGGTTTAATTGATCAAACAGAATACTTTAGTAAATCAGTTTC<br>GTCGAAAAATCTAGAAAATTATACACTAATAAAGAATGGAGAATTCGCGT<br>ATAACAAAAGTTATTCTAATGGATACCCATTAGGGGCTATTAAAAGATTA<br>ACTAGATATGATAGTGGTGTATTGTCCTCTTTGTATATTTGTTTTTCTATT<br>AAAAGTGAAATGTCTAAAGACTTCATGGAAGCATATTTTGATTCGACACA<br>CTGGTATAGAGAAGTTTCTGGAATTGCAGTTGAGGGTGCAAGAAATCAC<br>GGATTATTAAATGTTTCTGTGAATGATTTTTTTACTATTCTAATTAAATAT<br>CCAAGTTTAGAAGAACAGCAAAAATAGGCAAGTTCTTCAGCAAACTCG<br>ACCGACAAATTGAATTAGAAGAACAAAAGCTTGAATTACTTCAACAACAG<br>AAAAAAGGCTATATGCAGAAAATCTTCTCACAGGAATTGCGATTTAAGAA<br>TGAGAATGGTAATGATTATCCTGATTGGGAAAGAATTAAATTTTTTGATG<br>TAATTGATAAAGTAATAGATTTTAGAGGGAGAACACCAAAAAAATTAAAT<br>ATGGAATGGTCTGACGAAGGGTATTTAGCATTATCAGCAGTCAATGTAA<br>AAAAAGGCTATATTGATTTTAATGTAGAGGCGAAATATGGAAATCTAGAT<br>TTATATACTAGATGGATGAGAGGAAATGAATTATATAAGGGGCAAGTATT<br>ATTTACAACTGAAGCGCCAATGGGCAATGTAGCACAGGTTCCGGATAAT<br>AAAGGATATATATTAAGTCAAAGAACTATCGCGTTTAATTCAAATGAAAA<br>AATCACTGATAACTTTTTAGCATCATTGTTGAGCTCTGAAAATGTTTATAA<br>TGATTTATTAAAATTGTGTAGTGGTGCTACAGCAAAAGGTGTGAGTCAA<br>AAAAATTTAAATCGACTATACGTTACTATTCCACATTCCATATCAGAGCA<br>AGAAGAGATTGCTGAATTCTTTAGAAAAATTAATCAATTGGTTGAGTTGC<br>AAAAAATATAAAATTGAACATACTAAAGTCAAAAACAAGTGTTTTTACAAA<br>AGATGTTTATTTAA |
| 18 | CC15 isolate 3150 Sau1hsdS1 | ATGAGTAATAAACAAAAGAAAAATGTGCCAGAGTTGAGATTCCCAGGGT<br>TTGAAGGCGAATGGGAAGAGAAGAAGTTAGGGGAAGTAGGTACATTTA<br>CTTCAGGTGGGACACCCCTGAAATCAAAATCAGAGTATTGGAATGGAGA<br>TATTCCATGGATTACAACAGGTGATATTCATAACATAAAAGAGAAATA<br>TAACTAATTTTATAACAGAGAAAGGTTTAAATGAATCATCGGCAAAATTA |

TABLE 1-continued

Sequences used

| SEQ ID No. | Description of sequence | Sequence |
|---|---|---|
| | | ATAACTAATGAGGCGATTTTAATAGCTATGTATGGTCAAGGTAAAACTAG<br>AGGAATGTCAGCAATATTGAATTTTGAGGCAACAACTAACCAAGCATGT<br>GCTATATATCAAACCAATCAAAATATTAATTTTGTTTTTCAATACTTTCAG<br>AAATTATATGAATTTTTACGCTCATTATCTAATGAAGGAAGTCAAAAGAA<br>TTTAAGTTTAAGCTTGTTGAAAGAATTACTTTAAATTATCCTAATGAACA<br>AGAACAGAAAAAAATAGGTGATTTTTTCAGCAAACTCGACCGGCAAATT<br>GAATTAGAAGAACAAAAACTTGAATTGCTTCAACAACAGAAAAAAGGCT<br>ATATGCAGAAAATCTTCTCGCAAGAATTGCGATTTAAGGATGAGAATGG<br>AAATGATTATCCGGAGTGGGAAGAAACTACTATAAAGAAATTGCTCAA<br>ATTAACNCTGGAAAGAAAGATACAAAAGATGCCATTACTAATGGGAGTT<br>ATGATTTTTACGTTAGATCTCCGATAGTTTATAAAATTAATACTTTTAGTT<br>ATGAAGGAGAGGCTATTTTAACTGTAGGAGATGGAGTTGGCGTAGGTA<br>AAGTTTTCCACTATGTAAATGGGAAATTTGATTATCATCAAAGAGTATAC<br>AAAATATCTGACTTTAAGAATTATTATGGACTATTGTTATTTTATTATTTTT<br>CACAAAACTTTTTAAAAGAAACAAAGAAATATAGTGCGAAGACATCAGTT<br>GATTCAGTTAGAAAAGACATGATTGCTAATATGAAAGTACCGCGTCCTA<br>TTTATATAGAACAAAAAAAAATCGGTCAATTCATTAAAAGAGTAGACAAC<br>AAAACAAAAATTCAGAAACAAGTGATTGAATTACTTAAACAACGCAAAAA<br>GGCATTACTTCAAAAGATGTTTATTTAA |
| 19 | CC12 isolate 163 Sau1hsdS1 | ATGAGTAATACACAAAAGAAAAATGTGCCAGAGTTGAGATTCCCAGAGT<br>TTGAAGGCGAATGGGAAGAGAAGCAGTTAGGGGATCTTACAGATAGAG<br>TAATTAGGAAAAATAAAAACTTAGAATCGAAAAAAGCCTTTAACAATATC<br>CGGACAGTTAGGTTTAATTGATCAAACAGAATATTTTAGTAAATCAGTTT<br>CGTCGAAAAATCTAGAAAATTATACACTAATAAAGAATGGAGAATTCGC<br>GTATAACAAAAGTTATTCTAATGGATACCCATTAGGGGCTATTAAAAGAT<br>TAACTAGATATGATAGTGGTGTATTGTCCTCTTTGTATATTTGTTTTTCTA<br>TTAAAAGTGAAATGTCTAAAGACTTCATGGAAGCATATTTTGATTCGACA<br>CACTGGTATAGAGAAGTTTCTGGAATTGCAGTTGAGGGTGCAAGAAATC<br>ACGGATTATTAAATGTTTCTGTGAATGATTTTTTTACTATTCTAATTAAAT<br>ATCCAAGTTTAGAAGAACAGCAAAAAATAGGCAAGTTCTTCAGCAAACT<br>CGACCGACAAATTGAATTAGAAGAACAAAAGCTTGAATTACTTCAACAA<br>CAGAAAAAAGGCTATATGCAGAAAATTTTCTCACAGGAACTGCGATTCA<br>AAGATGAGAATGGTGAAGATTATCCAGATTGGGAAAATAGCAAAATAGA<br>AAAATATTTAAAAGAGAGAAACGAACGTTCTGACAAAGGGCAAATGCTT<br>TCAGTAACTATAAATAGTGGCATTATAAAATTTAGTGAATTGGATAGAAA<br>AGATAATTCAAGTAAAGATAAAAGTAATTATAAAGTAGTTAGGAAAAATG<br>ATATTGCATATAATTCTATGAGAATGTGGCAAGGGGCTAGTGGTAAATC<br>AAATTATAATGGGATTGTTAGCCCTGCATATACTGTGCTTTATCCAACAC<br>AAAATACTAGCTCATTATTTATTGGATATAAGTTTAAAACACATAGAATGA<br>TTCATAAATTTAAAATTAATTCACAAGGATTAACATCAGATACATGGAACT<br>TAAAATATAAACAATTAAAAAATATAAATATAGATATACCTGTATTGGAGG<br>AACAAGAAAAGATAGGTGATTTCTTTAAAAAAATGGATATATTGATAAGT<br>AAACAGAAAATGAAAATTGAAATATTAGAAAAAGAGAAACAATCCTTTTT<br>ACAAAAAATGTTCTTATAA |
| 20 | CC5 Mu50selection Sau1hsdS2 | ATGAGTAATACACAAACGAAAAATGTGCCAGAGTTGAGATTCCCAGGAT<br>TTGAGGGCGAATGGGAAGAGAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTAAAAAAGAGTATTATTATAATTTTTTGG<br>ACAGTATCTATTATCAAGAAAAGGTAAAAGAAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAACAACAAAAAATAGGACAATTCT<br>TCAGCAAACTTGACCAACAAATTGAATTAGAAGAACAAAAACTTGAATTA<br>CTTCAACAACAGAAAAATGCTATATACAGAAAATCTTCTCACAAGAATT<br>ACGATTCAAAGATGAAGAAGGTAATTACTATAAAGGATGGAACAAAAAG<br>CAATTAAAAGATGTATTAGAATTTAGTAATAAAAGAACTATTAATGAAAAT<br>GAATATCCTGTTTTAATATCGTCAAGACAAGGTTTAATACTTCAGTCAGA<br>CTACTATAAAGATAGGAAAACTTTTGCAGAGAGTAATATTGGGTATTTCA<br>TACTCCCTAAAAATCATATAACATACCGTTCAAGAAGCGACGATGGAATT<br>TTTAAGTTTAATTTAAATCTAATGATTGATGTAGGTATTATTAGTAAATAT<br>TACCCTGTCTTTAAAGGGATAGATGCAAATCAATATTATTTAACATTACA<br>CTTAAACTATCAACTGAAAAAGAATATATTAAATATGCAACTGGTACAT<br>CACAATTGGTACTCTCACAAAAAGACTTGCAAAACATAAAGACTAAATTG<br>CCATCTTATGAAGAACAACAAAAAATCGGTGATTTTTCAGTGAAATAGA<br>TAGATTGGTTGAAAACAATCTTCAAAGTCGGACGATTAAAAGTACGTA<br>AAAAAGAACTATTACAAAAAATGTTTGTTTAA |

TABLE 1-continued

Sequences used

| SEQ ID No. | Description of sequence | Sequence |
|---|---|---|
| 21 | CC8 Sau1hsdS2 | ATGAGTAATACACAAACGAAAAATGTGCCAGAGTTGAGATTCCCAGGAT<br>TTGAGGGCGAATGGGAAGAGAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTAAAAAAAGAGTATTATTATAATTTTTTTGG<br>ACAGTATCTATTATCAAGAAAAGGTAAAAGAAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAACAACAAAAAATAGGACAATTCT<br>TCAGCAAACTTGACCAACAAATTGAATTAGAAGAACAAAAACTTGAATTA<br>CTTCAACAACAGAAAAAATGCTATATACAGAAAATCTTCTCACAAGAATT<br>ACGATTCAAAGATGAAGAAGGTAATTACTATAAAGGATGGAACAAAAAG<br>CAATTAAAAGATGTATTAGAATTTAGTAATAAAAGAACTATTAATGAAAAT<br>GAATATCCTGTTTTAACATCGTCAAGACAAGGTTTAATACTTCAGTCAGA<br>CTACTATAAAGATAGGAAAACTTTTGCAGAGAGTAATATTGGGTATTTCA<br>TACTCCCTAAAAATCATATAACATACCGTTCAAGAAGCGACGATGGAATT<br>TTTAAGTTTAATTTAAATCTAATGATTGATGTAGGTATTATTAGTAAATAT<br>TACCCTGTCTTTAAAGGGATAGATGCAAATCAATATTATTTAACATTACA<br>CTTAAACTATCAACTGAAAAAGAATATATTAAATATGCAACTGGTACAT<br>CACAATTGGTACTCTCACAAAAAGACTTGCAAAACATAAAGACTAAATTG<br>CCATCTTATGAAGAACAACAAAAAATCGGTGATTTTTTCAGTGAAATAGA<br>TAGATTGGTTGAAAAACAATCTTCAAAAGTCGGACGATTAAAAGTACGTA<br>AAAAAGAACTATTACAAAAAATGTTTGTTTAA |
| 22 | BF primer | CCCAAAGGTGGAAGTGAAAA |
| 23 | CC1 strain MSSA476 SAS0395 | atgagtaatacacaaaagaaaaatgtgccagagttgaggttcccagggtttgaaggcgaa<br>tgggaagagaagaagttaggggaccttactaccaaaataggtagtggaaagactcccaaa<br>ggtggaagtgaaaactatacaaacaaaggcataccattttaaggagtcaaaatattaga<br>aatggtaaattaaatcttaatgacttagtttatattagtaaagatatagatgatgagatg<br>aaaaatagtagaacgtactatggtgatgttcttttaaatattacaggagcatcaataggt<br>agaacagccattaattcgatagttgaaacatgctaatttaaatcaacatgtatgtatt<br>attagattgaaaaagagtattattataattttttggacagtatctattatcaagaaaa<br>ggtaaaaggaaaattttccttgcacaaagtggaggtagtcgagaaggactaaacttcaaa<br>gaaattgctaatttaaaaatcttcaccccaaaatatttgaagagcagcaaaaaataggc<br>gaattcatcagcaaacttgaccgacaaattgaattagaagaacaaaaacttgaattactt<br>cagcaacagaaaaaaggctatatgcagaaaatcttctcgcaagaattgcgattcaaagat<br>gaggaaggtaaagattatccagatggggaaatcaattcaagaaatatttgaagat<br>aagggtggcactgctctagaaacagaatttaattttgacggtaattataaagtataagt<br>ataggaagttattctataaatagcacttataatgatcaaaatataagagtcaataaaaat<br>aaaaaaactgaaaaatatattttatcaaaaggcgacttagcaatggtatttaatgataaa<br>acaaaagatgggaaaattataggtagaagtatatttatagataaagataatcaatatatt<br>tataatcaaagaactgaaagattaataccatttgctgaaaatgataataaattttatggt<br>tcttaatgaatacagatttaattagaaataaaataaaggtatgatgcaaggagcaacc<br>caagtttatataaattattcatctattaaattgatatctatacaattgccacttcttgaa<br>gaacaacagaaaataagagggtttctagaagttttatctggaataactactaaacaattg<br>cacaagatagaccaattaaaagagaggaaaaaggcgtttttacagaaaatgtttatttga |
| 24 | CC771, isolate 32320 | atgagtaatacacaaacgaaaaatgtgccagagttgagattcccagggtttgaaggcgaa<br>tgggaagagaagaagttaggggatcttggcctgttcaaaaaagttattctttttcgaga<br>gctaaagaaggaaacggtaaaaaaaaacatattcattatggtgatattcattcaaaattt<br>aaaacagtcttagatagtgatggtaatatccctaatataattgagaaagctgtatttgag<br>ttgattcaaaaaggagacattgttttgcggatgcatcagaagattatagtgacctagga<br>aaagcagttatgatagatttcaaaccgaattcattgatttctggcttacatacacaccta<br>ttgattcaaaaaggagacattgtttttgcggatgcatcagaagattatagtgacctagga<br>tataaaaaattcattagacagcaaggtacaggaatatcagtacttggtatatcaaaaaaa<br>agtttattaaatttgaatgtattaataccacgaagtgaattagaacaacaaaaagtaggc<br>aagtcttcagcaaactcgaccgacaaattgaattagaagaacaaaaaatcgaattactt<br>caacaacagaaaaaaggctatatacagaaaatcttctcacaagaattgcgatttaaggat<br>gagaatggagatgattatccggagtgggaagaaactactataaaagaaattgctcaaatt<br>aacacaggaaaagaagatacaaaagatgccattactaatggggagttatgattttacgtt<br>agatctccgatagtttataaaattaatacttttagttataaggagaggctattttaact<br>gtaggagatggagttggcgtaggtaaagttttccactatgtaaatgggaaatttgattat<br>catcaaagagtatacaaaatatctgactttaagaattattatgattattgttattttat<br>tattttttcacaaaacttttaaaagaaacaaagaaatatagtgcgaagacatcagttgat<br>tcagttagaaaagacatggttgctaatatgaaagtaccacgtcctatttatatagaacag<br>gaaaaaatcggtcaattcattaaaaaagtagacaacaaaataaaaattcagaaacaagtg<br>attgaattacttaaacaacgcaaaaaggcattacttcaaaagatgtttatttaa |

TABLE 1-continued

Sequences used

| SEQ ID No. | Description of sequence | Sequence |
|---|---|---|
| 25 | CC97, strain C01791 | atgagtaatacacaaaagaaaaatgtgccagagttgagattcccaggatttgaaggcgaa tgggaagagaagcagttaggggatcttactaccaaaataggtagtggaaagactcccaaa ggtggaagtgaaaactatacaaacaaaggcataccattttttaaggagtcaaaatattaga aatggtaaattaaatcttaatgacttagtttatattagtaaagatatagatgatgagatg aaaaatagtagaacgtactatggtgatgttcttttaaatattacaggagcatcaataggt agaacagccattaattcgatagttgaaacgcatgctaatttaaatcaacatgtatgtatt attagattgaaaaaaagagtattattatattttttttggacagtatctattatcaagaaaa ggaaaaaggaaaattttccttgcacaaagtggaggtagtcgagaaggtctaaacttcaaa gaaattgctaatttaaaaatcttcaccccaactatatttgaagaacagcaaaaaatagc aagttcttcagcaaacttgaccgacaaattgaattagaagaacaaaaacttgaattactt caacaacagaaaaaggctatttgcagaaaatcttctcacaggaattgccgatttaaggat gagaatggaaatgattatccagagtggagatttgctagatttaaggactttatgtataaa ccaataaacatacgacctgcaataaatattagtaagtcagaattgctaactgtaaaatta cattgtaaaggatagagaaagctaatataaatcgagtattaaaactaggagctacgaat tattataagagatttgaaggtcaatttatttatgggaaacaaaacttttttcaatggagca tttgacatagtgccaaaaaaatttgatggactttattcatcaagtgatgtgccagcgttt gaaataaatccgaaaagattgaacctaactattttatcagctatatctctagaccaagc ttttataaaagtaaggaaaaatattctactggtacaggtagtaaaagaatacatgaaaat acggtgttaaatttctcttttacatttaccttgtttaaacgaacaattaaaaaattgcttct ttcgtttgttttctcaatagaaaaattgaattactagaaagaaaaatctatctaataaag aaacaaaagcaagctttgcttcaacaaatgttttatttaa |
| 26 | CC130, strain 459J | atgagtaatacacaaaagaaaaatgtgccagagttgagatttccagggtttgaaggcgaa tgggaagagaagaagttaggggaaattttttcaaataatttctggttcaacaccactaaaa tcaaataaaaagttttatgaaaatggtaatattaattgggtcaaaacgacagatttaaat aattctaaagttacgcatagtaaagaaaaaataactgaatatgctatgaatagtttgaaa ttaaaattagtgcctaaaaaattcagtacttatagctatgtatggtggttttaatcaaatt ggtcgaacaggtttgttaaaaatagatgccacaataaatcaagcaatttcagccttatta atgaatcatgaaacgaatccagaatttatacaagcatatctaaattatcaagttaaggggg tggaagagatatgcagcaagtagcagaaaagacccgaatataactaaaaagacatagaa caatttaaagttcctttatgttagtattaatgaacagcaaaaaataggcgaattcttcagc aagcttgaccgacaaattgagttagaagaacaaaaactagaattacttcaacaacaaaaa aaggctatatgcagaaaatcttctcacaagaattgcgattcaaagatgagaatggtgaag attacccggagtgggaagagaagcaacttggagaattgggagtaacatatgctggccttt ctggtaaagctaaagaagatttcggatttggtaaagatgtgtacgtaagttatgtgaatg ttttcaaaaacaacatagcaacattagaaactggtggaaaatgtaagtattaaacctggeg aaaaacaaaataatgtaaaatttggagatatttttatttacaacttcttcagaggttcctc atgaggtaggtatgtcctctgtatggttatatgagaaagataatgtatatttgaatagtt tttgttttggatttaggactacagttagttttataaaccctatattttggctagatatc taagaagctttgaaatgagaaaattaataacaatcttagctcagggatcaacgagattta atatttcaaaaaagaattgatgaaactgattgtgaaaatacctagattggatgagcaaa atagaataataaacctttttttcaattttagatggtggtattgaattacaatccatgaagg taaggaaadaaaaaagcgtaaacaaggattgcttcaaaaaatgttttatttaa |
| 27 | CC151, isolate 982BL | atgagtaatacacaaaagaaaaatgtgccagagttgagattcccagggtttgaaggcgaa tgggaagagaagaagttaggggaaattttttcaaataatttdggttcaacaccactaaaa tcaaataaaaagttttatgaaaatggtaatattaattgggtcaaaacgacagatttaaat aattctaaagttacgcatagtaaagaaaaaataactgaatatgctatgaatagtttgaaa ttaaaattagtgcctaaaaaattcagtacttatagctatgtatggtggttttaatcaaatt ggtcgaacaggtttgttaaaaatagatgccacaataaatcaagcaatttcagccttatta atgaatcatgaaacgaatccagaatttatacaagcatatctaaattatcaagttaaggggg tggaagagatatgcagcaagtagcagaaaagacccgaatataactaaaaagacatagaa caatttaaagttcctttatgttagtattaatgaacagcaaaaaataggcgaattcttcagc aagcttgaccgacaaattgagttagaagaacaaaaactagaattacttcaacaacaaaaa aaggctatatgcagaaaatcttctcacaagaattgcgattcaaagatgagaatggtgaag attacccggagtgggaagagacaaaactccaacaaattatagaggttaaagacggtactc atgaaagtcctaagcccactgacaaatgctatttattagtaacttcaaaaaatttaaaaa ataataaattagatttgagtgaatcttatagtatttctaaagaagattatgaaagtataa ataaaagatctaaagacgaaaaggcgcatttatttggaatgatagggacaataggaa atcctattctattagaagacgaaggattcgctataaaaaatgttgctttgctaaaaacga gttgtttacaagaaaagtattacatattgaacttcctcaaatctatagctattgctaaac aatttttataaaacgaatgctggaggaactcaaaaatttatttctttaggagttataagag atttaaaaatttgattttccatctttagaggaatcgactaaaataggaattttatttaaca aattagatgaattgattaaaaatcaatcaataaaaattgttttattaagacggcgaaaaa aagccttacttaaatcgatgtttatttaa |
| 28 | CC873, isolate 32326 | atgagtaatacacaaaagaaaaatgtgccagagttgagattcccagggtttgaaggcgaa tgggaagagaagtctattagtagttttttaaaggaaagtaaaataaaaggaagcaatgga agtcatgctaaaaagctaactgttaagctttgggggaaaaggagtagttcccaaaaaagag acatttaaaggaagtgacaatactcagtattataaaagaaaagcagggcaattgatgtat ggtaaadtgattttttaaattgtgctttttggtattgttcctgattcattaaataattat gaaagtactattgattccccaagttttgattttataaatggtgattctaaattcttacctt gaaagasttaaattaaagtcttttttataaaaaatttggagatattgcaaatggtagtaga aaagcaaaaacgtattaatcaagatacattcttatcattgccagttttttgcaccaaagtat |

TABLE 1-continued

Sequences used

| SEQ ID No. | Description of sequence | Sequence |
|---|---|---|
| | | gatgaacaattaagaataggcgaattctttagcaaactcgatcgacaaattgaactacaa<br>aaacaaaaacttgaattacttcaacaacagaaaaaaggctatatgcagaaaattttctca<br>caggaactgcgattcaaagatgagaatggtgaagattatccacattgggaaaatagcaaa<br>atagaaaaatatttaaagagagaaacgaacgttctgacaaaggtcaaatgctttcagta<br>actataaatagtggcattataaaatttagtgaattggatagaaaagataattcaagtaaa<br>aataaaagtaattataaagtagttaggaaaaatgatattgcatataattctatgagaatg<br>tggcaaggggctagtggtaaatcaaattataatgggattgttagccctgcatatactgtg<br>ctatatccaacacaaaataaagctcattatttattggatataagtttaaaacacataga<br>atgattcataaatttaaaattaattcacaaggattaacatcagatacatggaacttaaaa<br>tataaacaattaaaaaatataaatatagatatacctgtattggaggaacaagaaaagata<br>ggtgatttctttaaaaaaatggatatattgattagtaaacagaaaataaaaattgaaata<br>ttagaaaaagagaaacaatcctttttacaaaaaatgttcttataa |
| 29 | CC188, isolate 818 | atgagtaatacacaaaagaaaaatgtgccagagttgaggttcccagggtttgaaggcgaa<br>tgggaagagaagaagttagggggaccttactaccaaaataggtagtgaaagactcccaaa<br>ggtggaagtgaaaactatacaaacaaaggcataccatttttaaggagtcaaatattaga<br>aatggtaaattaaatcttaatgacttagtttatattagtaaagatatagatgatgagatg<br>aaaaatagtagaacgtactatggtgatgttctttaaatattacaggagcatcaataggt<br>agaacagccattaattcgatagttgaaatacatgctaatttaaatcaacatgtatgtatt<br>attagattgaaaaagagtattattataattttttttggacagtatctattatcaagaaaa<br>ggtaaaaggaaaattttccttgcacaaagtggaggtagtcgagaaggactaaacttcaaa<br>gaaattgctaatttaaaaatcttcaccccaactatatttgaagagcagcaaaaaataggc<br>gaattcatcagcaaacttgaccgacaaattgaattagaagaacaaaaacttgaattactt<br>cagcaacagaaaaaggctatatgcagaaatcttctcgcaagaattgcgattcaaagat<br>gaggaaggtaaagattatccagattggaaatcaaatcaattcaagaaatatttgagaat<br>aagggtggcactgctctagaaacagaattttaattttgacggtaattataaagttataagt<br>ataggaagttattctataaatagcacttataatgatcaaaatataagagtcaataaaaat<br>aaaaaaactgaaaatatattttatcaaaaggcgacttagcaatggtattaaatgataaa<br>acaaaagatgggaaaattataggtagaagtatatttatagataaagataatcaatatatt<br>tataatcaaagaactgaaagattaataccatttgctgaaaatgataataaattttatgg<br>ttcttaatgaatacagatttaattagaaataaaataaaaggtatgatgcaaggagcaacc<br>caagttatataaattatcatctattaaattgatatctatacaattgccacttcttgaa<br>gaacaacagaaaataagagggtttctagaagttttatctggaataactactaaacaattg<br>cacnagatagaccaattaaaagagaggaaaaaggcgttttttacagaaaatgtttatttga |
| 30 | CC72 hsds1 TCH130 | ATGAGTAATACACAAAAGAAAAATGTGCCAGAGTTGAGATTCCCAGGGT<br>TTGAAGGCGAATGGGAAGAGAAGAAGTTGGGGGAAGTAGCCAAAATAT<br>ATGATGGTACTCATCAAACTCCTAAATATACAAACGAAGGTATAAAATTT<br>TTGTCAGTAGAAAATATAAAAACGTTGAATTCAAGCAAGTATATTTCAGA<br>AGAAGCATTTGAAAAAGAGTTTAAAATCCGACCAGAATTCGGAGATATA<br>TTAATGACTCGAATTGGTGATATAGGTACACCAAACATAGTGAGTTCAAA<br>TGAAAAATTTGCTTACTATGTTAGCTTAGCATTATTAAAAACTAAGAATCT<br>TAATTCCTATTTTTTGAAAAATTTAATTTTATCATCATCTATCCAGAATGA<br>ACTATGGAGAAAAACTTTACATGTGGCATTTCCCAAAAAAATAAACAAAA<br>ATGAAATTGGAAAATTAAAATTAATTACCCTAAAAAGCAAGAACAACAA<br>AAAATTGGTCAGTTCTTCAGCAAACTCGACCGACAAATTGAATTAGAAG<br>AACAAAAACTCGAATTACTTCAACAACAGAAAAAAGGCTATATGCAGAAA<br>ATTTTCTCACAGGAACTGAGATTTAAAGATGAGAATGGTAATGATTATCC<br>GGAGTGGGAAGAGAGAAGATTTGCTGATATATTTAAATTTCATAATAAAC<br>TAAGAAAGCCAATTAAAGAAAATTTAAGAGTAAAGGGTTCTTATCCATAT<br>TATGGTGCTACAGGTATTATTGATTACGTTGACGACTTTATATTTGACGG<br>GAATTATTTACTTATTGGGAGAAGATGGTGCAAATATTATCACTAGAAGTG<br>CACCCCTAGTGTACTTAGTAAATGGAAAGTTTTGGGTAAATAATCATGCT<br>CATATATTATCTCCTTTAAATGGAAATATACAGTACTTGTATCAAGTTGCA<br>GAATTAGTTAATTATGAAAATACAATACTGGAACTGCTCAGCCTAAATT<br>AAACATTCAAAATTTAAAAATTATTAGTGTTGTAATTTCAACGAATTTAGA<br>AGAACAACAAAAATCGGAAGCTTTTTAAGTAAACTTGATCGTCAAATCG<br>ATTTAGAAGAACAAAAACTCGAATTACTTCAACAACGAAAAAAAGCCTTA<br>CTTAAATTGATGTTTGTTTAA |
| 31 | CC72 hsds2 TCH130 | ATGAGTAATACACAAAAGAAAAATGTGCCAGAGTTGAGATTCCCAGAGT<br>TTGAAGGCGAATGGGAAGAGAAGCAGTTAGGGAATATTATAAAAGTTAA<br>TTCTGGAAAAGATTATAAACATTTGGATAAAGGCGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAACTGGA<br>AAGTATACGATGAATCAACAGGTGTGCCAAGCTTAAGCAAACAAACCAT<br>TAATAAAATAAATAGATTTGTCCCTACAAATAAAGAGCACGAAAAAATAG<br>GCAAGTTCTTCAGCAAACTCGACCGGCAAATTGAATTAGAAGAACAAAA<br>ACTTGAATTACTTCAACAACAGAAAAAGGCTATATGCAGAAATCTTCT<br>CGCAAGAATTGCGATTCAAAGATGAGAATGGTAATGATTATCCAGATTG<br>GACAAATGAAAGATTGGGTGAAGTTCACAACTGTTACTATGGGACAAAGT<br>CCGAAAAGTGTAAATTATACTGATAACTCAAATGATACGGTATTAATCCA |

TABLE 1-continued

Sequences used

| SEQ ID No. | Description of sequence | Sequence |
|---|---|---|
| | | AGGAAATGCTGATATAGAGAATGGATTAATTAATCCCCGTATTTATACAA<br>GGGAAGTAACCAAATTAATTCAGAAGGACGAAATTATTTTAACTGTTAGA<br>GCACCTGTAGGCAAATTAGCTATGGCACAAATTAATGCGTGCATTGGTA<br>GAGGTGTATGCTCAATTAAAGGAGATAAATTTTATATTATTTTCTAGAAT<br>GGTTTGCCACTCAAATAAATGGATCCGTTTTTCACAGGGGAGTACATT<br>TGAATCTATTTCAGGGAATGACATAAGAAATATACACATTAAAATACCAG<br>TCGAAGATGAACGTACTAAAATTATAAAATTGTTAAATAGTTTAGATGTAT<br>TAAATTCAAAAACAGATTTAAAAATCCAAAACCTTAAACAGAGAAAACAA<br>TCGCTTCTACAAAAAATATTTGTTTAA |
| 32 | CC425 hsds1 | ATGAGTAATACACAAACGAAAATGTGCCAGAGTTGAGATTCCCAGGAT<br>TTGAAGGCGAATGGGAAGAAAAGCAGGTTGGCGAGTTATTAGAATTTAA<br>AAATGGTTTAAATAAAGGAAAAGAATATTTTGGCTCAGGATCGTCGATTG<br>TTAACTTCAAAGATGTATTTAATAACAGGAGCATAAATACAAATAATCTG<br>ACTGGAAAAGTTAATGTGAATAGCAAAGAACTGAAGAATTATTCCGTTG<br>AAAAGGGTGATGTTTTTTTTACAAGGACTAGTGAGGTAATTGGTGAAATA<br>GGTTATCCGTCTGTAATTTTAAATGACCCTGAAAATACTGTGTTTAGTGG<br>ATTTGTATTAAGAGGACGGCCTAAATCAGGAATTGATTTAATAAATAATA<br>ATTTTAAAAGATATGTCTTTTTTACTAATTCATTTAGAAAAGAAATGATTA<br>CAAAAAGTTCTATGACAACTAGAGCTTTAACATCAGGTACTGCAATTAAT<br>AAAATGAAGGTCATATACCCTGTTTCGGCTAAAGAACAGAAAAAAATAG<br>GTGACTTCTTCAGCAAACTCGATCGACAAATTGAATTAGAAGAACAAAA<br>ACTTGAATTGCTTCAACAACAGAAAAAAGGATATATGCAGAAAATCTTCA<br>CACAAGAATTGCGATTTAAGGACGAGAATGGAAATGATTATCCGGAGTG<br>GGAAGAAACTACTATAAAAGAAATTGCTCAAATTAACACAGGAAAGAAA<br>GATACAAAAGATGCCATTACTAATGGGAGTTATGATTTTTACGTTAGATC<br>TCCGATAGTTTATAAAATTAATACTTTTAGTTATGAAGGAGAGGCTATTTT<br>AACTGTAGGAGATGGAGTTGGCGTAGGTAAAGTTTTCCACTATGTAAAT<br>GGGAAATTTGATTATCATCAAAGAGTATACAAAATATCTGACTTTAAGAA<br>TTATTATGGATTATTGTTATTTTATTATTTTTACAAAACTTTTTAAAAGAA<br>ACAAAGAAATATAGTGCGAAGACATCAGTTGATTCAGTTAGAAAAGACA<br>TGGTTGCTAATATGAAAGTACCACGTCCTATTTATATAGAACAGGAAAAA<br>ATCGGTCAATTCATTAAAAAAGTAGACAACAAAATAAAAATTCAGAAACA<br>AGTGATTGAATTACTTAAACAACGCAAAAAGGCATTACTTCAAAAGATGT<br>TTATTTAA |
| 33 | MRSA9B | atgagtaatacacaaaagaaaaatgtgccagagttgagattcccagggtttgaaggcgaatgggaaga<br>gaagaagctaggtgagtttgctggtaaagttacccaaaaaaatgttgataaaaatatattgagacattaa<br>ctaattcagctgagttaggtatcatatctcaaaggattattttgacaaagaaatttcgaatatagataatatta<br>aaaagtactatgtagttgaagagaatgattttgtttataaccctagaatgctcaattatgctccatttggaccag<br>taaatagaaataagttagggaaaaaagggggtcatgtcacctcttttatactgtgttaaaattcaaaacattga<br>tttaaactttattgagttttattttaaatcttcaaaatggtatagatttatggcattaaacggtgattcaggtgctcg<br>agcagataggttttctattaaagataggacatttatggaaatgccacttcatatcccatgtatggatgaacaa<br>ataaaaatcggtcagttcttcagcaaacttgaccgacaaattgaattagaagaacaaaaacttgaattactt<br>caacaacagaaaaaaggctatatgcagaaaatcttctcgcaagaattgcgatttaaagatgagaatggt<br>aaagattatccggagtgggaagaaactactataaaagaaattgctcaaattaacactgaaagaaagat<br>acaaaagatgccattactaatgggagttatgattttacgttagatctccgatagtttataaaattaatacttttta<br>gttatgaaggagaggctattttaactgtaggagatggagttggcgtaggtaaagttttccactatgtaaatgg<br>gaaatttgattatcatcaaagagtatacaaaatatctgactttaagaattattatggattattgttatttattattttt<br>cacaaaacttttttaaaagaaacaaagaaatatagtgcgaagacatcagttgattcagttagaaaagacat<br>gattgctaatatgaaagtaccgcgtcctatttatatagaacaaaaaaaaatcggtcaattcattaaaagagt<br>agacaacaaaacaaaaattcagaaacaagtgattgaattacttaaacaacgcaaaaagtcattacttca<br>aaagatgtttatttaag |
| 34 | H1374 hsds2 | ATGAGTAATACACAAACGAAAATGTGCCAGAGTTGAGATTCCCAGGGT<br>TTGAAGGCGAATGGGAAGAGAAGAAGGTTGGCGAGTTATTAGAATTTAA<br>AAaTGGTTTAAATAAAGGAAAAGAATATTTTGGCTCAGGATCGTCGATTG<br>TTAACTTCAAAGATGTATTTAATAACAGGAGCTTAAATACAAATAATCTG<br>ACTGGAAAAGTTAATGTGAATAGCAAAGAACTAAAAAATTATTCTGTTGA<br>AAAGGGTGATGTTTTTTTTACAAGGACTAGTGAGGTAATTGGTGAAATA<br>GGTTATCCGTCTGTAATTTTAAATGACCCTGAAAATACTGTGTTTAGTGG<br>ATTTGTATTAAGAGGGCGGCCTAAATCAGGAATTGATTTAATAAATAATA<br>ATTTTAAAAGATATGTCTTTTTTACTAATTCATTTAGAAAAGAAATGATTA<br>CAAAAAGTTCTATGACAACTAGAGCTTTAACATCAGGTAGCGCAATTAAT<br>AAAATGAAGGTCATATACCCTGTTTCGGCTAAAGAACAGaGAAAAATAG<br>GTGACTTCTTCAGCAAACTCGACCGACAAATTGAATTAGAAGAACAAAA<br>GCTTGAATTACTTCAACAAAAAAAGGCTATATGCAGAAAATCTTCT<br>CACAGGAACTGCGATTCAAAGATGAGAATAGTGAAGATTATCCACATTG<br>GGAAGAAATAGCAAAATAGAAAAATTATTTAAAAGAGAAACGAACGTTCT<br>GACAAAGGTCAAATGCTTTCAGTAACTATAAATAGTGGCATTATAAAATT<br>TAGTGAATTGGATAGAAAAGATAATTCAAGTAAAGATAAAGTAATTATA<br>AAGTAGTTAGGAAAAATGATATTGCATATAATTCTATGAGAATGTGGCAA<br>GGGGCTAGTGGTAGATCAAATTATAATGGGATTGTTAGCCCTGCATATA<br>CTGTGCTTTATCCAACACAAAATACTAGCTCATTATTTATTGGATATAAG |

TABLE 1-continued

Sequences used

| SEQ ID No. | Description of sequence | Sequence |
|---|---|---|
| | | TTTAAAACACATAGAATGATTCATAAATTTAAAATTAATTCACAAGGATTA<br>ACATCAGATACATGGAACTTAAAATATAAACAATTAAAAAaTATAAATATA<br>GATATACCTGTATTGGAGGAACAAGAAAAGATAGGTGATTTCTTTAAAAA<br>AATGGATATATTGATTAGTAAACAGAAAATAAAAATTGAAATATTAGAAAA<br>aGAGAAACAATCCTTTTTACAAAaGATGTTCTTATAA |
| 35 | CC34 hsdS1 C160 | ATGAGTAATACACAAACGAAAAATGTGCCAGAGTTGAGATTCCCAGGGT<br>TTGAAGGCGAATGGGAAGAGAAGAAGGTTGGCGAGTTATTAGAATTTAA<br>AAATGGTTTAAATAAAGGAAAAGAATATTTTGGCTCAGGATCGTCGATTG<br>TTAACTTCAAAGATGTATTTAATAACAGGAGCTTAAATACAAATAATCTG<br>ACTGGAAAAGTTAATGTGAATAGCAAAGAACTAAAAAATTATTCTGTTGA<br>AAAGGGTGATGTTTTTTTTACAAGGACTAGTGAGGTAATTGGTGAAATA<br>GGTTATCCGTCTGTAATTTTAAATGACCCTGAAAATACTGTGTTTAGTGG<br>ATTTGTATTAAGAGGGCGGCCTAAATCAGGAATTGATTTAATAAATAATA<br>ATTTTAAAAGATATGTCTTTTTTACTAATTCATTTAGAAAAGAAATGATTA<br>CAAAAAGTTCTATGACAACTAGAGCTTTAACATCAGGTAGCGCAATTAAT<br>AAAATGAAGGTCATATACCCTGTTTCGGCTAAAGAACAGAGAAAAATAG<br>GTGACTTCTTCAGCAAACTCGACCGACAAATTGAATTAGAAGAACAAAA<br>GCTTGAATTACTTCAACAACAAAAAAAAGGCTATATGCAGAAAATCTTCT<br>CACAGGAACTGCGATTCAAAGATGAGAATAGTGAAGATTATCCACATTG<br>GGAAAATAGCAAAATAGAAAATATTTAAAAGAGAGAAACGAACGTTCT<br>GACAAAGGTCAAATGCTTTCAGTAACTATAAATAGTGGCATTATAAAATT<br>TAGTGAATTGGATAGAAAAGATAATTCAAGTAAAGATAAAAGTAATTATA<br>AAGTAGTTAGGAAAAATGATATTGCATATAATTCTATGAGAATGTGGCAA<br>GGGGCTAGTGGTAGATCAAATTATAATGGGATTGTTAGCCCTGCATATA<br>CTGTGCTTTATCCAACACAAAATACTAGCTCATTATTTATTGGATATAAG<br>TTTAAAACACATAGAATGATTCATAAATTTAAAATTAATTCACAAGGATTA<br>ACATCAGATACATGGAACTTAAAATATAAACAATTAAAAAATATAAATATA<br>GATATACCTGTATTGGAGGAACAAGAAAAGATAGGTGATTTCTTTAAAAA<br>AATGGATATATTGATTAGTAAACAGAAAATAAAAATTGAAATATTAGAAAA<br>AGAGAAACAATCCTTTTTACAAAGATGTTCTTATAA |
| 36 | t1333 hsds1 | ATGAGTAATACACAAACGAAAAATGTGCCAGAGTTGAGATTCCCAGGGT<br>TTGAAGGCGAATGGGAAGAGAAGAAGGTTGGCGAGTTATTAGAATTTAA<br>AAATGGTTTAAATAAAGGAAAAGAATATTTTGGCTCAGGATCGTCGATTG<br>TTAACTTCAAAGATGTATTTAATAACAGGAGCTTAAATACAAATAATCTG<br>ACTGGAAAAGTTAATGTGAATAGCAAAGAACTAAAAAATTATTCTGTTGA<br>AAAGGGTGATGTTTTTTTTACAAGGACTAGTGAGGTAATTGGTGAAATA<br>GGTTATCCGCCTGTAATTTTAAATGACCCTGAAAATACTGTGTTTAGTGG<br>ATTTGTATTAAGAGGGCGGCCTAAATCAGGAATTGATTTAATAAATAATA<br>ATTTTAAAAGATATGTCTTTTTTACTAATTCATTTAGAAAAGAAATGATTA<br>CAAAAAGTTCTATGACAACTAGAGCTTTAACATCAGGTAGCGCAATTAAT<br>AAAATGAAGGTCATATACCCTGTTTCGGCTAAAGAACAGAGAAAAATAG<br>GTGACTTCTTCAGCAAACTCGACCGACAAATTGAATTAGAAGAACAAAA<br>GCTTGAATTACTTCAACAACAAAAAAAAGGCTATATGCAGAAAATCTTCT<br>CACAGGAACTGCGATTCAAAGATGAGAATAGTGAAGATTATCCACATTG<br>GGAAAATAGCAAAATAGAAAATATTTAAAAGAGAGAAACGAACGTTCT<br>GACAAAGGTCAAATGCTTTCAGTAACTATAAATAGTGGCATTATAAAATT<br>TAGTGAATTGGATAGAAAAGATAATTCAAGTAAAGATAAAAGTAATTATA<br>AAGTAGTTAGGAAAAATGATATTGCATATAATTCTATGAGAATGTGGCAA<br>GGGGCTAGTGGTAGATCAAATTATAATGGGATTGTTAGCCCTGCATATA<br>CTGTGCTTTATCCAACACAAAATACTAGCTCATTATTTATTGGATATAAG<br>TTTAAAACACATAGAATGATTCATAAATTTAAAATTAATTCACAAGGATTA<br>ACATCAGATACATGGAACTTAAAATATAAACAATTAAAAAATATAAATATA<br>GATATACCTGTATTGGAGGAACAAGAAAAGATAGGTGATTTCTTTAAAAA<br>AATGGATATATTGATTAGTAAACAGAAAATAAAAATTGAAATATTAGAAAA<br>AGAGAAACAATCCTTTTTACAAAGATGTTCTTATAAG |
| 37 | CC30 hsdS2 MRSA252 | ATGAGTAATACACAAACGAAAAATGTGCCAGAGTTGAGATTCCCAGGGT<br>TTGAAGGCGAATGGGAAGAGAAAAAGTTAGGGGATCTTATAAAAGTTAA<br>TTCTGGAAAAGATTATAAACATTTGGAAAAAGGTGATATACCAGTCTATG<br>GTACTGGCGGTTATATGCAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAATTGGA<br>AAGTATACGATGAATCAACAGGTGTGCCAAGCTTAAGTAAACAAACCAT<br>TAATAAAATAAATAGATTTGTCCCTTCAAATAAAGAGCAGCAAAAAATAG<br>GCGAATTCTTCATCAAACTCGACCGACAAATTGAATTAGAAGAACAAAA<br>ACTTGAATTACTTCAACAACAGAAAAAGGCTATATGCAGAAAATCTTCT<br>CACAGGAATTGCGATTCAAGGATGAGAATGGAAACGATTATCCGAATTG<br>GGAAGAGAAGAAAATAGAAGATATAGCAAGCCAAGTATATGGAGGCGG<br>AACACCAAATACAAAGATTAAAGAATTTTGGAATGGAGATATTCCATGGA<br>TTCAAAGCTCTGACGTAAAAGTAAATGATTTGATTCTACGACAATGTAAT<br>AAATTTATTTCCAAGAATTCAATTGAGCTTTCTTCTGCAAAACTTATTCCT |

TABLE 1-continued

Sequences used

| SEQ ID No. | Description of sequence | Sequence |
|---|---|---|
| | | GCCAATTCAATTGCAATAGTTACAAGAGTCGGGGTTGGAAAACTGTGTT<br>TGGTAGAATTTGATTATGCTACAAGTCAAGATTTTTTATCATTAAGTAGT<br>CTTAAATATGACAAATTATACTCATTATATTCATTGCTATATACAATGAAA<br>AAAATTAGCGCTAATCTACAAGGAACTTCAATTAAAGGTATAACAAAAAA<br>AGAGTTGTTAGATAGTATAATAAAGATACCCCATAATCTAGAAGAACAGC<br>AAAAAATAGGTGATCTATTTTATAAAATTGATAAATATATCAGTTTTAATA<br>AATGTAAAATTGAGATACTTAAAAGTCTCAAACAAGGATTACTTCAAAAA<br>ATTTTTATATAA |
| 38 | CC34 hsdS2 C160 | ATGAGTAATACACAAACGAAAAATGTGCCAGAGTTGAGATTCCCAGGGT<br>TTGAAGGCGAATGGGAAGAGAAAAAGTTAGGGGATCTTATAAAAGTTAA<br>TTCTGGAAAAGATTATAAACATTTGGAAAAAGGTGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAATTGGA<br>AAGTATACGATGAATCAACAGGTGTGCCAAGCTTAAGTAAACAAACCAT<br>TAATAAAATAAATAGATTTGTCCCTTCAAATAAAGAGCAGCAAAAAATAG<br>GCGAATTCTTCATCAAACTCGACCGACAAATTGAATTAGAAGAACAAAA<br>ACTTGAATTACTTCAACAACAGAAAAAAGGCTATATGCAGAAAATCTTCT<br>CACAGGAATTGCGATTCAAGGATGAGAATGGAAACGATTATCCGAATTG<br>GGAAGAGAAGAAAATAGAAGATATAGCAAGCCAAGTATATGGAGGCGG<br>AACACCAAATACAAAGATTAAAGAATTTTGGAATGGAGATATTCCATGGA<br>TTCAAAGCTCTGACGTAAAAGTAAATGATTTGATTCTACGACAATGTAAT<br>AAATTTATTTCCAAGAATTCAATTGAGCTTTCTTCTGCAAAACTTATTCCT<br>GCCAATTCAATTGCAATAGTTACAAGAGTCGGGGTTGGAAAACTGTGTT<br>TGGTAGAATTTGATTATGCTACAAGTCAAGATTTTTTATCATTAAGTAGT<br>CTTAAATATGACAAATTATACTCATTATATTCATTGCTATATACAATGAAA<br>AAAATTAGCGCTAATCTACAAGGAACTTCAATTAAAGGTATAACAAAAAA<br>AGAGTTGTTAGATAGTATAATAAAGATACCCCATAATCTAGAAGAACAGC<br>AAAAAATAGGTGATCTATTTTATAAAATTGATAAATATATCAGTTTTAATA<br>AATGTAAAATTGAGATACTTAAAAGTCTCAAACAAGGATTACTTCAAAAA<br>ATTTTTATATAA |
| 39 | CC152 hsds2 | ATGAGTAATACACAAAGAAAAATGTGCCAGAGTTGAGATTCCCAGGGT<br>TTGAAGGCGAGTGGGAAGAAGAAGAAGCTAGAAGATATTATAAAAGTTAA<br>TTCTGGAAAAGATTATAAACATTTGGATAAAGGCGATATACCAGTCTATG<br>GTACTGGCGGTTATATGACAAGTGTTTCAGAACCACTGAGTGAAATTGA<br>TGCTGTTGGTATTGGGAGAAAAGGGACTATAAACAAACCATATGTACTT<br>GAGGCGCCGTTTTGGACGGTGGATACATTATTTTACTGTACACCTAAAA<br>AAGAAGTAGACATACTATTTATATTGAGTTTATTTAGAAAAATAAATTGGA<br>AGGTGTATGATGAATCAACAGGTGTGCCAAGCTTAAGTAAGCAAACCAT<br>TAATAAAATAATTAGATTTGTCCCTACAAATAAAGAACAACAAAAAATAG<br>GTAAGTTCTTCAGCAAACTTGACCGACAAATTGAATTAGAAGAACAAAA<br>CTTGAATTACTTCAACAACAGAAAAAAGGCTATATGCAGAAAATCTTCTC<br>GCAAGAATTGCGATTTAAAGATGAGAATGGTAATGATTATCCAGATTGG<br>GAAGAGAAGAAAATAGAAGATATAGCAAGCCAAGTATATGGAGGAGGA<br>ACACCAAATACAAAATTAAAGAATTTTGGAATGGAGATATTCCATGGAT<br>TCAAAGCTCTGACGTAAAAGTAAATGATTTGATTCTACAACAATGTAATA<br>AATTTATTTCCAAGAATTCAATTGAGCTTTCTTCTGCAAAACTTATTCCTG<br>CCAATTCAATTGCAATAGTTACAAGAGTCGGGGTTGGAAAACTGTGTTT<br>GGTAGAATTTGATTATGCTACAAGTCAAGATTTTTTATCATTAAGTAGTC<br>TTAAATATGACAAATTATACTCATTATATTCATTGCTATATACAATGAAAA<br>AAATTAGCGCTAATCTACAAGGAACTTCAATTAAAGGTATAACAAAAAA<br>GAGTTGTTAGATAGTATAATAAAGATACCCCATAATCTAGAAGAACAGCA<br>AAAAATAGGTGAGCTATTTTATAAAATAGATAAATATATCAGTTTTAATAA<br>ATGTAAAATTGAGATGCTTAAAAGTCTCAAACAAGGATTACTTCAAAAAA<br>TGTTTATATAA |
| 40 | H1374_hsds1 | ATGAGTAATACACAAACGAAAAATGTGCCAGAGTTGAGATTCCCAGGGt<br>TTGAAGGCGAATGGGAAGAGaAAAAGtTAGGGGATCTTATAAAAGTTAAT<br>TCTGGAAAAGATTATAAACATTTGGAAAAAGGTGATATACCAGTCTATGG<br>TACTGGCGGTTATATGACAAGTGTTTCAGAACCACTAAGTGAAATTGAT<br>GCTGTTGGTATTGGGAGAAAAGGGACTATAAACAAACCATATTTGCTTG<br>AGGCGCCGTTTTGGACGGTGGATACATTATTTTATTGTACACCTaAAAAA<br>GAAACAGACATACTATTTATATTAAGTTTAtTTAGaAAAATaAATTGGaAAG<br>TATACGATGAATCAACAGGTGTGCCAAGCTTAAGTAAACAAACCATTAAT<br>AAAATAAATAGATTTGTCCCTTCAAATAAAGAGCAGCAAAAAATAGGCGA<br>ATTCTTCATCAAACTCGACCGACAAATTGAATTAGAGAACAAAAACTTG<br>AATTACTTCAACAACAGAAAAAAGGCTATATGCAGAAAATCTTCTCACAG<br>GAATTGCGATTCAAGGATGAGAATGGAAACGATTATCCGAATTGGGAAG<br>AGAAGAAAATAGAAGATATAGCAAGCCAAGTATATGGAGGCGGAACAC<br>CAAATACAAAGATTAAAGaATTTTGGAATGGAGATATTCCATGGATTCAA<br>AGCTCTGACGTAAAAGTAAATGATTTGATTCTACGACAATGTAATAAATT |

TABLE 1-continued

Sequences used

| SEQ ID No. | Description of sequence | Sequence |
|---|---|---|
| | | TATTTCCAAGAATTCAATTGAGCTTTCTTCTGCaAAACTTATTCCTGCCAA<br>TTCAATTGCAATAGTTACAAGAGTCGGGGTTGGAAAACTGTGTTTGGTA<br>GAATTTGATTATGCTACAAGTCAAGATTTTTTATCATTAAGTAGTCTTAAA<br>TATGACAAATTATACTCATTATATTCATTGCTATATACAATGAAAAAAATT<br>AGCGCTAATCTACAAGGAACTTCAATTAAAGGTATAACaAAAAAAGAGTT<br>GTTAGATAGTATAATAAAGATACCCCATAATCTAGAAGAACAGCaAAAAA<br>TAGGTGATCTATTTTTATaAAATTGATAAATATATCAGTTTTAATAAATGTA<br>AAATTGAGATACTTAAAAGTCTCAAACAAGGATTACTTCAAAAAATTTTTA<br>TATAA |
| 41 | CC5 hsdS1 ED98 forward | atgagtaatacacaaaagaaaaatgtgccagagttgagattcccaggggtttgaaggcgaatgggaaga<br>gaagcagttgggggatcttacagatagagtaattaggaaaaataaaaacttagaatcgaaaaagccttta<br>acaatatccggacagttaggtttaattgatcaaacagaatattttagtaaatcagtttcgtcgaaaaatctag<br>aaaattatacactaataaagaatggagaattcgcgtataacaaaagttattctaatggatacccattaggg<br>gctattaaaagattaactagatatgatagtggtgtattgtcctcotttgtatatttgttttctattaaaagtgaaatgt<br>ctaaagacttcatgtgaagcatattttgattcgacacactggtatagagaagtttctggaattgcagttgaggg<br>tgcaagaaatcacggattattaaatgtttctgtgaatgattttttttactattctaattaaatatccaagtttagaag<br>aacagcaaaaaataggcaagttcttcagcaaactcgaccgacaaattgaattagaagaacaaaagctt<br>gaattacttcaacaacagaaaaaaggctatatgcagaaaattttctcacaggaactgcgattcaaagatg<br>agaatggtgaagattatccagattgggaaaatagcaaaatagaaaaatattttaaaagagagaaacgaa<br>cgttctgacaaagggcaaatgctttcagtaactataaatagtggcattataaaatttagtgaattggatagaa<br>aagataattcaagtaaagataaaagtaattataaagtagttaggaaaaatgatattgcatataattctatga<br>gaatgtggcaagggctagtggtaaatcaaattataatgggattgttagccctgcatatactgtgctttatcc<br>aacacaaaatactagctcattatttattggatataagtttaaaacacatagaatgattcataaattaaaatta<br>attcacaaggattaacatcagatacatggaacttaaaatataaacaattaaaaaatataaatatagatata<br>cctgtattggaggaacaagaaaagataggtgatttctttaaaaaaatggatatattgataagtaaacagaa<br>aatgaaaattgaaatattagaaaagagaaacaatcctttttacaaaaaatgttcttataa |
| 42 | CC5 hsdS1 | ATGAGTAATACACAAAAGAAAAATGTGCCAGAGTTGAGATTCCCAGGGT<br>TTGAAGGCGAATGGGAAGAGAAGCAGTTGGGGGATCTTACAGATAGAG<br>TAATTAGGAAAAATAAAAACTTAGAATCGAAAAAGCCTTTAACAATATCC<br>GGACAGTTAGGTTTAATTGATCAAACAGAATATTTTAGTAAATCAGTTTC<br>GTCGAAAAATCTAGAAAATTATACACTAATAAAGAATGGAGAATTCGCGT<br>ATAACAAAAGTTATTCTAATGGATACCCATTAGGGGCTATTAAAAGATTA<br>ACTAGATATGATAGTGGTGTATTGTCCTCTTTGTATATTTGTTTTTCTATT<br>AAAAGTGAAATGTCTAAAGACTTCATGGAAGCATATTTTGATTCGACACA<br>CTGGTATAGAGAAGTTTCTGGAATTGCAGTTGAGGGTGCAAGAAATCAC<br>GGATTATTAAATGTTTCTGTGAATGATTTTTTTACTATTCTAATTAAATAT<br>CCAAGTTTAGAAGAACAGCAAAAAATAGGCAAGTTCTTCAGCAAACTCG<br>ACCGACAAATTGAATTAGAAGAACAAAAGCTTGAATTACTTCAACAACAG<br>AAAAAAGGCTATATGCAGAAAATTTTCTCACAGGAACTGCGATTCAAAG<br>ATGAGAATGGTGAAGATTATCCAGATTGGGAAAATAGCAAAATAGAAAA<br>ATATTTAAAGAGAGAAACGAACGTTCTGACAAAGGGCAAATGCTTTCA<br>GTAACTATAAATAGTGGCATTATAAAATTTAGTGAATTGGATAGAAAGA<br>TAATTCAAGTAAAGATAAAAGTAATTATAAAGTAGTTAGGAAAAATGATA<br>TTGCATATAATTCTATGAGAATGTGGCAAGGGCTAGTGGTAAATCAAA<br>TTATAATGGGATTGTTAGCCCTGCATATACTGTGCTTTATCCAACACAAA<br>ATACTAGCTCATTATTTATTGGATATAAGTTTAAAACACATAGAATGATTC<br>ATAAATTTAAAATTAATTCACAAGGATTAACATCAGATACATGGAACTTAA<br>AATATAAACAATTAAAAAATATAAATATAGATATACCTGTATTGGAGGAA<br>CAAGAAAAGATAGGTGATTTCTTTAAAAAAATGGATATATTGATAAGTAA<br>ACAGAAAATGAAAATTGAAATATTAGAAAAGAGAAACAATCCTTTTTAC<br>AAAAAATGTTCTTATAA |
| 43 | CC5 hsdS2 | ATGAGTAATACACAAACGAAAAATGTGCCAGAGTTGAGATTCCCAGGAT<br>TTGAGGGCGAATGGGAAGAGAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTAAAAAAGAGTATTATTATAATTTTTTTGG<br>ACAGTATCTATTATCAAGAAAGGTAAAAGAAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAACAACAAAAAATAGGACAATTCT<br>TCAGCAAACTTGACCAACAAATTGAATTAGAAGAACAAAAACTTGAATTA<br>CTTCAACAACAGAAAAATGCTATATACAGAAATCTTCTCACAAGAATT<br>ACGATTCAAAGATGAAGAAGGTAATTACTATAAAGGATGGAACAAAAAG<br>CAATTAAAAGATGTATTAGAATTTAGTAATAAAAGAACTATTAATGAAAAT<br>GAATATCCTGTTTTAACATCGTCAAGACAAGGTTTAATACTTCAGTCAGA<br>CTACTATAAAGATAGGAAACTTTTGCAGAGAGTAATATTGGGTATTTCA<br>TACTCCCTAAAAATCATATAACATACCGTTCAAGAAGCGACGATGGAATT<br>TTTAAGTTTAATTTAAATCTAATGATTGATGTAGGTATTATTAGTAAATAT<br>TACCCTGTCTTTAAAGGGATAGATGCAAATCAATATTATTTAACATTACA |

TABLE 1-continued

Sequences used

| SEQ ID No. | Description of sequence | Sequence |
|---|---|---|
| | | CTTAAACTATCAACTGAAAAAGAATATATTAAATATGCAACTGGTACAT<br>CACAATTGGTACTCTCACAAAAAGACTTGCAAAACATAAAGACTAAATTG<br>CCATCTTATGAAGAACAACAAAAAATCGGTGATTTTTTCAGTGAAATAGA<br>TAGATTGGTTGAAAAACAATCTTCAAAAGTCGGACGATTAAAAGTACGTA<br>AAAAAGAACTATTACAAAAAATGTTTGTTTAA |
| 44 | CC5 hsdS2 ED98 | atgagtaatacacaaacgaaaaatgtgccagagttgagattcccaggatttgagggcgaatgggaaga<br>gaagaagttagggaatcttactaccaaaataggtagtggaaagactcccaaaggtggaagtgaaaact<br>atacaaacaaaggcataccatttttaaggagtcaaaatattagaaatggtaaattaaatcttaatgacttagt<br>ttatattagtaaagatatagatgatgagatgaaaaatagtagaacgtactatggtgatgttcttttaaatattac<br>aggagcatcaataggtagaacagccattaattcgatagttgaaacgcatgctaatttaaatcaacatgtat<br>gtattattagattaaaaaaagagtattattataatttttttggacagtatctattatcaagaaaaggtaaaagaa<br>aaattttccttgcacaaagtggaggtagtcgagaaggactaaacttcaaagaaattgctaatttaaaaatct<br>tcaccccaactatatttgaagaacaacaaaaaataggacaattcttcagcaaacttgaccaacaaattga<br>attagaagaacaaaaacttgaattacttcaacaacagaaaaaatgctatatacagaaatcttctcacaa<br>gaattacgattcaaagatgaagaaggtaattactataaaggatggaacaaaaagcaattaaaagatgta<br>ttagaatttagtaataaaagaactattaatgaaaatgaatatcctgttttaacatcgtcaagacaaggttttaat<br>acttcagtcagactactataaagataggaaaacttttttgcagagagtaatattgggtatttcatactccctaaa<br>aatcatataacataccgttcaagaagcgacgatggaatttttaagtttaatttaaatctaatgattgatgtaggt<br>attattagtaaatattaccctgtctttaaagggatagatgcaaatcaatattatttaacattacacttaaactatc<br>aactgaaaaagaatatattaaatatgcaactggtacatcacaattggtactctcacaaaaagacttgcaa<br>aacataaagactaaattgccatcttatgaagaacaacaaaaaatcggtgattttttcagtgaaatagatag<br>attggttgaaaaacaatcttcaaaagtcggacgattaaaagtacgtaaaaaagaactattacaaaaaatg<br>tttgtttaa |
| 45 | CC8 hsd1 USA300 | ATGAGTAATACACAAAAGAAAAATGTGCCAGAATTGAGGTTCCCAGGGT<br>TTGAAGGCGAATGGGAAGAGAAGCAGTTAGGGGATCTTACAGATAGAG<br>TAATTAGGAAAAATAAAAACTTAGAATCGAAAAAGCCTTTAACATATCC<br>GGACAGTTAGGTTTAATTGATCAAACAGAATATTTTAGTAAATCAGTTTC<br>GTCGAAAAATCTAGAAAATTATACACTAATAAAGAATGGAGAATTCGCGT<br>ATAACAAAGTTATTCTAATGGATACCCATTAGGGGCTATTAAAAGATTA<br>ACTAGATATGATAGTGGTGTATTGTCCTCTTTGTATATTTGTTTTTCTATT<br>AAAAGTGAAATGTCTAAAGACTTCATGGAAGCATATTTTGATTCGACACA<br>CTGGTATAGAAGTTTCTGGAATTGCAGTTGAGGGTGCAAGAAATCAC<br>GGATTATTAAATGTTTCTGTGAATGATTTTTTTACTATTCTAATTAAATAT<br>CCAAGTTTAGAAGAACAGCAAAAATAGGCAAGTTCTTCAGCAAACTCG<br>ACCGACAAATTGAATTAGAAGAACAAAAGCTTGAATTACTTCAACAACAG<br>AAAAAAGGCTATATGCAGAAAATTTTCTCACAGGAACTGCGATTCAAAG<br>ATGAGAATGGTGAAGATTATCCAGATTGGGAAAATAGCAAAATAGAAAA<br>ATATTTAAAAGAGAGAAACGAACGTTCTGACAAAGGGCAAATGCTTTCA<br>GTAACTATAAATAGTGGCATTATAAAATTTAGTGAATTGGATAGAAAAGA<br>TAATTCAAGTAAAGATAAAAGTAATTATAAAGTAGTTAGGAAAAATGATA<br>TTGCATATATAATTCTATGAGAATGTGGCAAGGGGCTAGTGGTAAATCAAA<br>TTATAATGGGATTGTTAGCCCTGCATATACTGTGCTTTATCCAACACAAA<br>ATACTAGCTCATTATTTATTGGATATAAGTTTAAAACACATAGAATGATTC<br>ATAAATTTAAAATTAATTCACAAGGATTAACATCAGATACATGGAACTTAA<br>AATATAAACAATTAAAAAATATAAATATAGATATACCTGTATTGGAGGAA<br>CAAGAAAAGATAGGTGATTTCTTTAAAAAAATGGATATATTGATAAGTAA<br>ACAGAAAATGAAAATTGAAATATTAGAAAAAGAGAAACAATCCTTTTTAC<br>AAAAAAATGTTCTTATAA |
| 46 | CC8 hsdS2 USA300 | ATGAGTAATACACAAAAGAAAAATGTGCCAGAATTGAGATTCCCAGGAT<br>TTGAAGGCGAATGGGAAGAGAAGAAGTTAGGGAATCTTACTACCAAAAT<br>AGGTAGTGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTGAAAAAAGAGTATTATTATAATTTTTTTGG<br>ACAGTATCTATTATCAAGAAAAGGTAAAGGAAAATTTTCCTTGCACAAA<br>GTGGAGGTAGTCGAGAAGGTCTAAACTTCAAAGAAATTGCTAATTTAAA<br>AATCTTCACCCCAACTATATTTGAAGAACAGCAAAAATAGGCAAGTTCT<br>TCAGCAAACTCGACCGACAAATTGAATTAGAAGAACAAAAACTTGAATT<br>GCTTCAACAACAGAAAAAGGCTATATGCAGAAAATCTTCACACAAGAA<br>TTGCGATTCAAAGATGAGAATGGTGAAGAATATCCAGAGTGGGAAAACA<br>AATTCATAAAAGACATCTTTATCTTTGAAAATAATAGAAGAAAACCAATTA<br>CTTCTTCATTAAGAGAAAGGGGTTATACCCTTACTATGGTGCAACTGG<br>AATTATTGATTACGTAAAAGATTATTTATTCAATAATGAAGAACGATTACT<br>AATAGGAGAAGATGGTGCAAAATGGGGGCAGTTTGAGACGAGTAGCTT<br>TATTGCTAATGGGCAATACTGGGTAAATAATCATGCGCATGTAGTTAAAA |

TABLE 1-continued

Sequences used

| SEQ ID No. | Description of sequence | Sequence |
|---|---|---|
| | | GTAATGATCATAATTTGTTTTTTATGAATTATTATTTAAATTTTAAAGAACT<br>ACGAGCATTTGTCACAGGTAATGCACCAGCTAAATTAACTCATGCGAAC<br>TTATGCAATATAAATCTTAAAATACCTTGTCTCACTGAACAAGATAAAGT<br>AAGTGCATTGTTAAAATCTATAGACAATAAAATGAATAATCAAATGAATA<br>GAATTGAGTTATTAAAAGAACGTAAAAAAGGACTATTACAAAAAATGTTT<br>ATTTAA |
| 47 | CC12 hsdS1 | ATGAGTAATACACAAAAGAAAAATGTGCCAGAGTTGAGATTCCCAGAGT<br>TTGAAGGCGAATGGGAAGAGAAGCAGTTAGGGGATCTTACAGATAGAG<br>TAATTAGGAAAATAAAAACTTAGAATCGAAAAAAGCCTTTAACAATATC<br>CGGACAGTTAGGTTTAATTGATCAAACAGAATATTTTAGTAAATCAGTTT<br>CGTCGAAAAATCTAGAAAATTATACACTAATAAAGAATGGAGAATTCGC<br>GTATAACAAAGTTATTCTAATGGATACCCATTAGGGGCTATTAAAAGAT<br>TAACTAGATATGATAGTGGTGTATTGTCCTCTTTGTATATTGTTTTTCTA<br>TTAAAAGTGAAATGTCTAAAGACTTCATGGAAGCATATTTTGATTCGACA<br>CACTGGTATAGAGAAGTTTCTGGAATTGCAGTTGAGGGTGCAAGAAATC<br>ACGGATTATTAAATGTTTCTGTGAATGATTTTTTTACTATTCTAATTAAAT<br>ATCCAAGTTTAGAAGAACAGCAAAAAATAGGCAAGTTCTTCAGCAAACT<br>CGACCGACAAATTGAATTAGAAGAACAAAAGCTTGAATTACTTCAACAA<br>CAGAAAAAAGGCTATATGCAGAAAATTTTCTCACAGGAACTGCGATTCA<br>AAGATGAGAATGGTGAAGATTATCCAGATTGGGAAAATAGCAAAATAGA<br>AAAATATTTAAAGAGAGAAACGAACGTTCTGACAAAGGGCAAATGCTT<br>TCAGTAACTATAAATAGTGGCATTATAAAATTTAGTGAATTGGATAGAAA<br>AGATAATTCAAGTAAAGATAAAAGTAATTATAAAGTAGTTAGGAAAAATG<br>ATATTGCATATAATTCTATGAGAATGTGGCAAGGGGCTAGTGGTAAATC<br>AAATTATAATGGGATTGTTAGCCCTGCATATACTGTGCTTTATCCAACAC<br>AAAATACTAGCTCATTATTTATTGGATATAAGTTTAAAACACATAGAATGA<br>TTCATAAATTTAAAATTAATTCACAAGGATTAACATCAGATACATGGAACT<br>TAAAATATAAACAATTAAAAAATATAAATATAGATATACCTGTATTGGAGG<br>AACAAGAAAAGATAGGTGATTTCTTTAAAAAAATGGATATATTGATAAGT<br>AAACAGAAAATGAAATTGAAATATTAGAAAAAGAGAAACAATCCTTTTT<br>ACAAAAAATGTTCTTATAA |
| 48 | CC1 hsdS1 MSSA476 | ATGAGTAATACACAAAAGAAAAATGTGCCAGAGTTGAGGTTCCCAGGGT<br>TTGAAGGCGAATGGGAAGAGAAGAAGTTAGGGGACCTTACTACCAAAA<br>TAGGTAGTGGAAAGACTCCCAAAGGTGGAAGTGAAAACTATACAAACAA<br>AGGCATACCATTTTTAAGGAGTCAAAATATTAGAAATGGTAAATTAAATC<br>TTAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAATACATGCTAATTTAAATCA<br>ACATGTATGTATTATTAGATTGAAAAAGAGTATTATTATAATTTTTTGG<br>ACAGTATCTATTATCAAGAAAGGTAAAAGGAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAGCAGCAAAAAATAGGCGAATTC<br>ATCAGCAAACTTGACCGACAAATTGAATTAGAAGAACAAAAACTTGAATT<br>ACTTCAGCAACAGAAAAAGGCTATATGCAGAAAATCTTCTCGCAAGAA<br>TTGCGATTCAAAGATGAGGAAGGTAAAGATTATCCAGATTGGAAATCAA<br>AATCAATTCAAGAAATATTTGAGAATAAGGGTGGCACTGCTCTAGAAAC<br>AGAATTTAATTTTGACGGTAATTATAAAGTTATAAGTATAGGAAGTTATTC<br>TATAAATAGCACTTATAATGATCAAAATATAAGAGTCAATAAAAATAAAA<br>AACTGAAAAATATATTTTATCAAAAGGCGACTTAGCAATGGTATTAAATG<br>ATAAAACAAAAGATGGGAAAATTATAGGTAGAAGTATATTTATAGATAAA<br>GATAATCAATATATTTATAATCAAAGAACTGAAAGATTAATACCATTTGCT<br>GAAAATGATAATAAATTTTTATGGTTCTTAATGAATACAGATTTAATTAGA<br>AATAAAATAAAGGTATGATGCAAGGAGCAACCCAAGTTTATATAAATTA<br>TTCATCCTATTAAATTGATATCTATACAATTGCCACTTCTTGAAGAACAACA<br>GAAAATAAGAGGGTTTCTAGAAGTTTTATCTGGAATAACTACTAAACAAT<br>TGCACAAGATAGACCAATTAAAAGAGAGGAAAAAGGCGTTTTTACAGAA<br>AATGTTTATTTGA |
| 49 | t337 hsdS1 | atgagtaatacacaaaagaaaaatgtgcctgagttgagattcccagggtttgaaggcgaatgggaagag<br>aagcaatttgctgatttactaaaataaatcaaggattgcagattgctattaatgaacgtaaaactgaatattc<br>tccagagttgtattttatataacaaatgaattttaagaccaaatagtcaaactaaatattttatcgaaaatcc<br>ccctcaatcagtaattgcaaataaagaagatattttaatgactagaacaggtaatactggaaaagtagtaa<br>ctaatgtatttggagcgtttcataataatttttttaaaattaaatttgataaaaatctgtatgatagattgttttttagta<br>gaggttttaaattcatctaagatacaaaataaaatactatctttagcaggatcttcgacgataccagatttaa<br>accatagtgattttatagtattagttcttcttatccgctgcttagagaacagcaaaaaataggtaaattcttcag<br>caaacttgaccgacaaattgaactagaagaacaaaaacttgaattactaaaacaacagaaaaaggct<br>atatgcagaaaatcttctcgcaagaattgcgattcaaagatgagaatggaaatgattatccagagtggga<br>atcaaaatcaattcaagaaatatttgagaataagggtggcactgctctagaaacagaatttaattttgacgg<br>taattataaagttataagtataggaagttattctataaatagcacttataatgatcaaaatataagagtcaata<br>aaaataaaaaaactgaaaaatatattttatcaaaaggcgacttagcaatggtattaaatgataaaacaaa<br>agatgggaaaattataggtagaagtatatttatagataaagataatcaatatatttataatcaaagaactga<br>aagattaataccatttgctgaaaatgataataaatttttatggttcttaatgaatacagatttaattagaaaataa |

TABLE 1-continued

Sequences used

| SEQ ID No. | Description of sequence | Sequence |
|---|---|---|
| | | aataaaaggtatgatgcaaggagcaacccaagtttatataaattattcatctattaaattgatatctatacaat tgccacttcttgaagaacaacagaaaataagaggttttctagaagtcttgtctggaataactactgaacaatt gcacaagatagaccaattaaaagagaggaaaaaggcgttttttacagaaaatgtttatttga |
| 50 | CC1 hsdS2 MSSA476 | ATGAGTAATACACAAACGAAAAATGTGCCAGAGTTGAGATTCCCAGGAT TTGAGGGCGAATGGGAAGAGAAGAAGTTAGGGAATCTTACTACCAAAAT AGGTAGTGGAAAGACTCCCAAAGGTGGAAGTGAAAACTATACAAACAAA GGCATACCATTTTTAAGGAGTCAAAATATTAGAAATGGTAAATTAAATCT TAATGACTTAGTTTATATTAGTAAAGATATAGATGATGAGATGAAAAATA GTAGAACGTACTATGGTGATGTTCTTTTAAATATTACAGGAGCATCAATA GGTAGAACAGCCATTAATTCGATAGTTGAAACGCATGCTAATTTAAATCA ACATGTATGTATTATTAGATTGAAAAAGAGTATTATTATAATTTTTTTGG ACAGTATCTATTATCAAGAAAAGGTAAAAGGAAAATTTTCCTTGCACAAA GTGGAGGTAGTCGAGAAGGTCTAAACTTCAAAGAAATTGCTAATTTAAA AATCTTCACCCCAACTATATTTGAAGAACAGCAAAAAATAGGCAAGTTCT TCAGCAAACTCGACCGACAAATTGAATTAGAAGAACAAAAACTTGAATT GCTTCAACAACAGAAAAAAGGCTATATGCAGAAAATCTTCACACAAGAA TTGCGATTCAAAGATGAGAATGGTGAAGAATATCCAGAGTGGGAAAACA AATTCATAAAAGACATCTTTATCTTTGAAAATAATAGAAGAAAACCAATTA CTTCTTCATTAAGAGAAAAGGGGTTATACCCTTACTATGGTGCAACTGG AATTATTGATTACGTAAAAGATTATTTATTCAATAATGAAGAACGATTACT AATAGGAGAAGATGGTGCAAAATGGGGGCAGTTTGAGACGAGTAGCTT TATTGCTAATGGGCAATACTGGGTAAATAATCATGCGCATGTAGTTAAAA GTAATGATCATAAATTTGTTTTTTATGAATTATTATTTAAATTTTAAAGAACT ACGAGCATTTGTCACAGGTAATGCACCAGCTAAATTAACTCATGCGAAC TTATGCAATATAAATCTTAAAATACCTTGTCTCACTGAACAAGATAAAGT AAGTGCATTGTTAAAATCTATAGACAATAAAATGAATAATCAAATGAATA GAATTGAGTTATTAAAAGAACGTAAAAAAGAACTATTACAAAAAATGTTT ATTTAA |
| 51 | CC22 hsdS1 EMRSA15 | ATGAGTAATACACAAAAGAAAAATGTGCCAGAGTTGAGATTCCCAGGGT TTGAAGGCGAATGGGAAGAGAAGAAGTTAGGGGATCTTACAGATAGAG TAATTAGGAAAAATAAAAACTTAGAATCGAAAAAGCCTTTAACAATATCC GGACAGTTAGGTTTAATTGATCAAACAGAATACTTTAGTAAATCAGTTTC GTCGAAAAATCTAGAAAATTATACACTAATAAAGAATGGAGAATTCGCGT ATAACAAAAGTTATTCTAATGGATACCCATTAGGGGCTATTAAAAGATTA ACTAGATATGATAGTGGTGTATTGTCCTCTTTGTATATTTGTTTTTCTATT AAAAGTGAAATGTCTAAAGACTTCATGGAAGCATATTTTGATTCGACACA CTGGTATAGAGAAGTTTCTGGAATTGCAGTTGAGGGTGCAAGAAATCAC GGATTATTAAATGTTTCTGTGAATGATTTTTTTACTATTCTAATTAAATAT CCAAGTTTAGAAGAACAGCAAAAAATAGGCAAGTTCTTCAGCAAACTCG ACCGACAAATTGAATTAGAAGAACAAAAGCTTGAATTACTTCAACAACAG AAAAAAGGCTATATGCAGAAAATCTTCTCACAGGAATTGCGATTTAAGAA TGAGAATGGTAATGATTATCCTGATTGGGAAAGAATTAAATTTTTTGATG TAATTGATAAAGTAATAGATTTTAGAGGGAGAACACCAAAAAAAATTAAAT ATGGAATGGTCTGACGAAGGGTATTTAGCATTATCAGCAGTCAATGTAA AAAAAGGCTATATTGATTTTAATGTAGAGGCGAAATATGGAAATCTAGAT TTATATACTAGATGGATGAGAGGAAATGAATTATATAAGGGGCAAGTATT ATTTACAACTGAAGCGCCAATGGGCAATGTAGCACAGGTTCCGGATAAT AAAGGATATATATTAAGTCAAAGAACTATCGCGTTTAATTCAAATGAAAA AATCACTGATAACTTTTTAGCATCATTGTTGAGCTCTGAAAATGTTTATAA TGATTTATTAAAATTGTGTAGTGGTGCTACAGCAAAAGGTGTGAGTCAA AAAAATTTAAATCGACTATACGTTACTATTCCACATTCCATATCAGAGCA AGAAGAGATTGCTGAATTCTTTAGAAAAATTAATCAATTGGTTGAGTTGC AAAAAATATAAAATTGAACATACTAAAAGTCAAAAACAAGTGTTTTTACAAA AGATGTTTATTTAA |
| 52 | NOH4 | ATGAGTAATACACAAAAGAAAAATGTGCCAGAGTTGAGATTCCCAGGGT TTGAAGGCGaATGGGAAGAGAAGAAGTTAGGGGATCTTACAGATAGAG TAATTAGGaAAAATaAAAACTTAGAATCGaAAAAGCCTTTAACAATATCCG GACAGTTAGGTTTAATTGATCAAACAGAATACTTTAGTAAATCAGTTTCG TCGAAAAATCTAGAAAATTATACACTAATAAAGAATGGAGAATTCGCGTA TAACAAAAGTTATTCTAATGGATACCCATTAGGGGCTATTAAAAGATTAA CTAGATATGATAGTGGTGTATTGTCCTCTTTGTATATTTGTTTTTCTATTA AAAGTGAAATGTCTAAAGACTTCATGGAAGCATATTTTGATTCGACACAC TGGTATAGAGAAGTTTCTGGAATTGCAGTTGAGGGTGCAAGAAATCACG GATTATTAAATGTTTCTGTGAATGATTTTTTTACTATTCTaATTAAATATCC aAGTTTAGAAGAACAGCAAAAAATAGGCAAGTTCTTCAGCAAACTCGAC CGACAAATTGAATTAGAAGAACAAAAGCTTGaATTACTTCAACAACAGA AAAAAGGCTATATGCAGAAAATCTTCTCACAGGAATTGCGATTTAAGAAT GAGAATGGTAATGATTATCCTGATTGGGaAAGAATTAAATTTTTTGATGT AATTGATAAAGTAATAGATTTTAGAGGGAGAACACCAAAAAAtAAATAT GGAATGGTCTGACGAAGGGTATTTAGCATTATCAGCAGTCAATGTAAAA AAAGGCTATATTGATTTTAATGTAGAGGCGAAATATGGAAATCTAGATTT |

TABLE 1-continued

Sequences used

| SEQ ID No. | Description of sequence | Sequence |
|---|---|---|
| | | ATATACTAGATGGATGAGAGGAAATGAATTATATAAGGGGCAAGTATTA<br>TTTACAACTGAAGCGCCAATGGGCAATGTAGCACAGGTTCCGGATAATA<br>AAGGATATATATTAAGTCAAAGAACTATCGCGTTTAATTCAAATGAAAAA<br>ATCACTGATAACTTTTTAGCATCATTGTTGAGCTCTGAAAATGTTTATAAT<br>GATTTATTAAAATTGTGTAGTGGTGCTACAGCAAAAGGTGTGAGTCAAA<br>AAAATTTAAATCGACTATACGTTACTATTCCACATTCCATATCAGAGCAA<br>GAAGAGATTGCTGAATTCTTTAGAAAAATTAATCAATTGGTTGAGTTGCA<br>AAAATATAAAATTGAACATACTAAAAGTCAAAAACAAGTGTTTTTACAAAA<br>GATGTTTATTTAA |
| 53 | CC239 hsdS1<br>TW20 | ATGAGTAATACACAAAAGAAAAATGTGCCAGAATTGAGATTCCCAGGAT<br>TTGAAGGCGAATGGGAAGAGAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTGAAAAAGAGTATTATTATAATTTTTTGG<br>ACAGTATCTATTATCAAGAAAAGGTAAAAGGAAAATTTTCCTTGCACAAA<br>GTGGAGGTAGTCGAGAAGGTCTAAACTTCAAAGAAATTGCTAATTTAAA<br>AATCTTCACCCCAACTATATTTGAAGAACAGCAAAAAATAGGCAAGTTCT<br>TCAGCAAACTCGACCGACAAATTGAATTAGAAGAACAAAAACTTGAATT<br>GCTTCAACAACAGAAAAAAGGCTATATGCAGAAAATCTTCACACAAGAA<br>TTGCGATTCAAAGATGAGAATGGTGAAGAATATCCAGAGTGGGAAAACA<br>AATTCATAAAAGACATCTTTATCTTTGAAAATAATAGAAGAAACCAATTA<br>CTTCTTCATTAAGAGAAAAGGGGTTATACCCTTACTATGGTGCAACTGG<br>AATTATTGATTACGTAAAAGATTATTTATTCAATAATGAAGAACGATTACT<br>AATAGGAGAAGATGGTGCAAAATGGGGGCAGTTTGAGACGAGTAGCTT<br>TATTGCTAATGGGCAATACTGGGTAAATAATCATGCGCATGTAGTTAAAA<br>GTAATGATCATAATTTGTTTTTTATGAATTATTATTTAAATTTTAAAGAACT<br>ACGAGCATTTGTCACAGGTAATGCACCAGCTAAATTAACTCATGCGAAC<br>TTATGCAATATAAATCTTAAAATACCTTGTCTCACTGAACAAGATAAAGT<br>AAGTGCATTGTTAAAATCTATAGACAATAAAATGAATAATCAAATGAATA<br>GAATTGAGTTATTAAAAGAACGTAAAAAAGGACTATTACAAAAAATGTTT<br>ATTTAA |
| 54 | CC239 hsdS2<br>TW20 | ATGAGTAATACACAAAAGAAAAATGTGCCAGAATTGAGATTCCCAGGAT<br>TTGAAGGCGAATGGGAAGAGAAGAAGTTAGGGAATCTTACTACCAAAAT<br>AGGTAGTGGAAAGACTCCCAAAGGTGGAAGTGAAAACTATACAAACAAA<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAGAACAGCCATTAATTCGATAGTTGAAACGCATGCTAATTTAAATCA<br>ACATGTATGTATTATTAGATTGAAAAAGAGTATTATTATAATTTTTTGG<br>ACAGTATCTATTATCAAGAAAAGGTAAAAGGAAAATTTTCCTTGCACAAA<br>GTGGAGGTAGTCGAGAAGGTCTAAACTTCAAAGAAATTGCTAATTTAAA<br>AATCTTCACCCCAACTATATTTGAAGAACAGCAAAAAATAGGCAAGTTCT<br>TCAGCAAACTCGACCGACAAATTGAATTAGAAGAACAAAAACTTGAATT<br>GCTTCAACAACAGAAAAAAGGCTATATGCAGAAAATCTTCACACAAGAA<br>TTGCGATTCAAAGATGAGAATGGTGAAGAATATCCAGAGTGGGAAAACA<br>AATTCATAAAAGACATCTTTATCTTTGAAAATAATAGAAGAAACCAATTA<br>CTTCTTCATTAAGAGAAAAGGGGTTATACCCTTACTATGGTGCAACTGG<br>AATTATTGATTACGTAAAAGATTATTTATTCAATAATGAAGAACGATTACT<br>AATAGGAGAAGATGGTGCAAAATGGGGGCAGTTTGAGACGAGTAGCTT<br>TATTGCTAATGGGCAATACTGGGTAAATAATCATGCGCATGTAGTTAAAA<br>GTAATGATCATAATTTGTTTTTTATGAATTATTATTTAAATTTTAAAGAACT<br>ACGAGCATTTGTCACAGGTAATGCACCAGCTAAATTAACTCATGCGAAC<br>TTATGCAATATAAATCTTAAAATACCTTGTCTCACTGAACAAGATAAAGT<br>AAGTGCATTGTTAAAATCTATAGACAATAAAATGAATAATCAAATGAATA<br>GAATTGAGTTATTAAAAGAACGTAAAAAAGGACTATTACAAAAAATGTTT<br>ATTTAA |
| 55 | CC151 hsdS2<br>RF122 | ATGAGTAATACACAAAGGAAAAATGTGCCAGAGTTGAGATTCCCAGGGT<br>TTGAAGGCGAATGGGAAGAGAAGAAGTTAGGGGATCTTACTACCAAAAT<br>AGGTAGTGGAAAGACTCCCAAAGGTGGAAGTGAAAACTATACAAACAAT<br>GGCATACCATTTTTAAGGAGTCAAAATATTAGAAATGGTAAATTAAATCT<br>TAATGACTTAGTTTATATTAGTAAAGATATAGATGATGAGATGAAAAATA<br>GTAGAACGTACTATGGTGATGTTCTTTTAAATATTACAGGAGCATCAATA<br>GGTAAAACAGCCATTAATTCGATAGTTGAAACGCATGCTAATTTAAATCA<br>ACATGTATGTATTATTAGATTGAAAAAGAGTATTATTATAATTTTTTGG<br>ACAGTAACTATTATCAAGAAAAGGAAAAGGAAAATTTTCCTTGCACAAA<br>GTGGAGGTAGTCGAGAAGGACTAAACTTCAAAGAAATTGCTAATTTAAA<br>AATCTTCACCCCAACTATATTTGAAGAACAGCAAAAAATAGGCAAGTTCT<br>TCAGCAAACTTGACCGACAAATTGAATTAGAAGAACAAAAACTTGAATTA |

TABLE 1-continued

Sequences used

| SEQ ID No. | Description of sequence | Sequence |
|---|---|---|
| | | CTTCAACAACAGAAAAAAGGCTATATGCAGAAAATCTTCTCACAGGAATT<br>ACGATTCAAAGACGAGAATGGTGAAGAATATCCAAATTGGGAAAACAAA<br>TTCATAAAAGACATCTTTATATTTGAAAATAATAGAAGAAAACCAATTACT<br>TCTTCATTAAGAGAAAAGGGGCTATACCCTTACTATGGCGCAACTGGAA<br>TTATTGATTACGTGAAAGAATATTTATTCAATAATGAGGAACGATTACTA<br>ATAGGAGAAGATGGTGCAAAATGGGGGCAGTTTGAGACGAGTAGCTTT<br>ATTGCTAATGGGCAATACTGGGTAAATAATCATGCGCATGTAGTTAAAA<br>GTAATGATCATAAATTTGTTTTTTATGAATTATTATTTAAATTTTAAAGAACT<br>ACGAGCATTTGTGATAGGTAATGCACCAGCTAAATTAACTCATGCGAAC<br>TTATGCAATATAAATCTTAAAATACCTTGTCTCACTGAACAAGATAAAGT<br>AAGTGCATTGTTAAAATCTATAGACAATAAAATGAATAATCAAATGAATA<br>GAATTGAGTTATTAAAAGAACGTAAAAAAGGACTATTACAAAAAATGTTT<br>ATTTAA |
| 56 | CC771 hsdS | atgagtaatacacaaacgaaaaatgtgccagagttgagattcccagggtttgaaggcgaatgggaaga<br>gaagaagttaggggatcttggcctgtttcaaaaaagttattcttttcgagagctaaagaaggaaacggtaa<br>aactaaacatattcattatggtgatattcattcaaaatttaaaacagtcttagatagtgatggtaatatccctaa<br>tataattgagaaagctgtatttgagttgattcaaaaaggagacattgttttgcggatgcatcagaagattata<br>gtgacctaggaaaagcagttatgatagatttcaaaccgaattcattgatttctggcttacatacacacctattt<br>agaccgcttaacaatgcaatttctaattttttgattttttacacaaaaactctgagttataaaaaattcattagac<br>agcaaggtacaggaatatcagtacttggtatatcaaaaaaaagtttattaaatttgaatgtattaataccacg<br>aagtgaattagaacaacaaaaagtaggcaagttcttcagcaaactcgaccgacaaattgaattagaag<br>aacaaaaaatcgaattacttcaacaacagaaaaaggctatatacagaaaatcttctcacaagaattgc<br>gatttaaggatgagaatggagatgattatccggagtgggaagaaactactataaaagaaattgctcaaat<br>taacacaggaaagaaagatacaaaagatgccattactaatgggagttatgattttacgttagatctccgat<br>agtttataaaattaatacttttagttatgaaggagaggctattttaactgtaggagatggagttggcgtaggta<br>aagttttccactatgtaaatgggaaatttgattatcatcaaagagtatacaaaatatctgactttaagaattatt<br>atggattattgttattttattattttcacaaaactttitaaagaaacaaagaaaatatagtgcgaagacatcagt<br>tgattcagttagaaaagacatggttgctaatatgaaagtaccacgtcctatttatatagaacaggaaaaaat<br>cggtcaattcattaaaaaagtagacaacaaaataaaaattcagaaacaagtgattgaattacttaaacaa<br>cgcaaaaaggcattacttcaaaagatgtttatttaa |
| 57 | CC133 hsdS1 | ATGAGTAATACACAAACGAAAAATGTGCCAGAGTTGAGATTCCCAGGGT<br>TTGAAGGCGAATGGGAAGAGAAGAAGTTAGGGGATCTTGGCCTGTTTC<br>AAAAAAGTTATTCTTTTTCGAGAGCTAAAGAAGGAAACGGTAAAACTAAA<br>CATATTCATTATGGTGATATTCATTCAAAATTTAAAACAGTCTTAGATAGT<br>GATGGTAATATCCCTAATATAATTGAGAAAGCTGTATTTGAGTTGATTCA<br>AAAAGGAGACATTGTTTTTGCGGATGCATCAGAAGATTATAGTGACCTA<br>GGAAAAGCAGTTATGATAGATTTCAAACCGAATTCATTGATTTCTGGCTT<br>ACATACACACCTATTTAGACCGCTTAACAATGCAATTTCTAATTTTTTGAT<br>TTTTTACACAAAAACTCTGAGTTATAAAAAATTCATTAGACAGCAAGGTA<br>CAGGAATATCAGTACTTGGTATATCAAAAAAAAGTTTATTAAATTTGAAT<br>GTATTAATACCACGAAGTGAATTAGAACAACAAAAAGTAGGCAAGTTCTT<br>CAGCAAACTCGACCGACAAATTGAATTAGAAGAACAAAAAATCGAATTA<br>CTTCAACAACAGAAAAAGGCTATATACAGAAAATCTTCTCACAAGAATT<br>GCGATTTAAGGATGAGAATGGAGATGATTATCCGGAGTGGGAAGAAAC<br>TACTATAAAAGAAATTGCTCAAATTAACACAGGAAAGAAAGATACAAAAG<br>ATGCCATTACTAATGGGAGTTATGATTTTTACGTTAGATCTCCGATAGTT<br>TATAAAATTAATACTTTTAGTTATGAAGGAGAGGCTATTTTAACTGTAGG<br>AGATGGAGTTGGCGTAGGTAAAGTTTTCCACTATGTAAATGGGAAATTT<br>GATTATCATCAAAGAGTATACAAAATATCTGACTTTAAGAATTATTATGG<br>ATTATTGTTATTTTATTATTTTTCACAAAACTTTTTAAAAGAAACAAAGAAA<br>TATAGTGCGAAGACATCAGTTGATTCAGTTAGAAAAGACATGGTTGCTA<br>ATATGAAAGTACCACGTCCTATTTATATAGAACAGGAAAAAATCGGTCAA<br>TTCATTAAAAAAGTAGACAACAAAATAAAAATTCAGAAACAAGTGATTGA<br>ATTACTTAAACAACGCAAAAAGGCATTACTTCAAAAGATGTTTATTTAA |
| 58 | CC151 hsdS1 RF122 | ATGAGTAATACACAAAAGAAAAATGTGCCAGAGTTGAGATTCCCAGGGT<br>TTGAAGGCGAATGGGAAGAGAAGAAGTTAGGGGAAATTTTTCAAATAAT<br>TTCTGGTTCAACACCACTAAAATCAAATAAAAAGTTTTATGAAAATGGTA<br>ATATTAATTGGGTCAAAACGACAGATTTAAATAATTCTAAAGTTACGCAT<br>AGTAAAGAAAAATAACTGAATATGCTATGAATAGTTTGAAATTAAAATTA<br>GTGCCTAAAAATTCAGTACTTATAGCTATGTATGGTGGTTTTAATCAAAT<br>TGGTCGAACAGGTTTGTTAAAAATAGATGCCACAATAAATCAAGCAATTT<br>CAGCCTTATTAATGAATCATGAAACGAATCCAGAATTTATACAAGATAAT<br>CTAAATTATCAAGTTAAGGGGTGGAAGAGATATGCAGCAAGTAGCAGAA<br>AAGACCCGAATATAACTAAAAAAGACATAGAACAATTTAAAGTTCCTTAT<br>GTTAGTATTAATGAACAGCAAAAAATAGGCGAATTCTTCAGCAAGCTTG<br>ACCGACAAATTGAGTTAGAAGAACAAAAACTAGAATTACTTCAACAACAA<br>AAAAAGGCTATATGCAGAAAATCTTCTCACAAGAATTGCGATTCAAAGAT<br>GAGAATGGTGAAGATTACCCGGAGTGGGAAGAGACAAAACTCCAACAA<br>ATTATAGGAGGTTAAAGACGGTACTCATGAAAGTCCTAAGCCCACTGAC<br>AATGGTTATTATTAGTAACTTCAAAAAATTTAAAAAATAATAAATTAGAT<br>TTGAGTGAATCTTATAGTATTTCTAAAGAAGATTATGAAAGTATAAATAAA |

TABLE 1-continued

Sequences used

| SEQ ID No. | Description of sequence | Sequence |
|---|---|---|
|  |  | AGATCTAAAGTTGAAAAAGGCGACATTTTATTTGGAATGATAGGGACAA<br>TAGGAAATCCTATTCTATTAGAAGACGAAGGATTCGCTATAAAAAATGTT<br>GCTTTGCTAAAAACGAGTTGTTTACAAGAAAAGTATTACATATTGAACTT<br>CCTCAAATCTATAGCTATTGCTAAACAATTTTATAAAACGAATGCTGGAG<br>GAACTCAAAAATTTATTTCTTTAGGAGTTATAAGAGATTTAAAAATTGATT<br>TTCCATCTTTAGAGGAATCGACTAAAATAGGAATTTTATTTAACAAATTA<br>GATGAATTGATTAAAAATCAATCAATAAAAATTGTTTTATTAAGACGGCG<br>AAAAAAAGCCTTACTTAAATCGATGTTTATTTAA |
| 59 | CC75 hsdS2 | ATGAGTAATACAGGAAAAATGAACGTGCCAGAGTTGAGATTCCCAGGAT<br>TTGAAGGCGAATGGGAAGAGAAGGAATTAAGAGAGTTAAGAAACCCTA<br>AGGATAAATATAGTTATACAGGTGGGCCTTTTGGCTCTGATTTAAAAAAA<br>TCTGACTATACAACTGATGGGATACAAATTATTCAACTTCAAAACATTGG<br>AGATGGATATTTCTATAATAGTAATAAGGTCTTTACATCTAATGAGAAAG<br>CAGAAGTACTTAAAAGTTGTAATGTATTTCCAGGAGATATAGTTATTGCT<br>AAAATGGCAGATCCTATAGCAAGAGCAGCGATTGTACCGGATAATAATA<br>TAGGGAAATATCTAATGGCCTCAGATGGGATAAGATTAAGTGTTGACAC<br>AGTACATTTCAATACAAAGTTTGTACTTGAGTGTATAAATAGAAAAGTT<br>TTAGAAAAAAAGTTGAGGATAATAGTTCGGGGTCAACTCGAATGAGAAT<br>AGGACTAAGTACATTAGGTAGTCTAACTTTAAAAACCACAACACTAAAAG<br>AACAACAAAAAATAGGACAATTCTTCAGCAAACTTGACCGACAAATTGTA<br>CTAGAAGAACAAAAACTTGAATTACTTCAACAACAGAAAAAAGGCTATAT<br>GCAGAAAATCTTTTCACAAGAATTGCGATTCAAAGATGAGAATGGTAAT<br>GATTATCCAGATTGGGAAGAGAAGCAATTAGGGGAATTATCACAAATTG<br>TACGAGGGGCTTCTCCTAGACCTATTAAAGATCCTAAATGGTTTAATAAA<br>GAATCAGATATAGGATGGCTAAGAATTTCTGATGTTACAAATCAAAACG<br>GGAAAATTTATCATTTGGAACAAAAATTATCAATTGAAGGTCAAGAAAAA<br>ACAAGGGTTTAGTAACAACACATTTATTATTAAGTATTGCGGCAAGTAT<br>TGGAAAACCTGTAATGAATTTTGTGAAAACGGGAGTTCATGATGGATTTT<br>TAATATTTTTAAAGCCTAAGTTTAATTTATTCTTTATGTACTATTGGCTTG<br>AATATTTCAAGGATAAATGGAGTAAATACGGTCAACCAGGTAGTCAGGT<br>TAATTTAAATTCAGAAATTGTCAAATCTCAGACACTGAATATGCCAAGCA<br>ATCACGAACAAGAAAAAGTGGGACAGTTTTTTAATAGAAATGAAAAACTA<br>ATTGAATTGCAGCAAGAAAAAATAATGTATATCAAGCGATGTAAGCAGG<br>TTTTACTTCAAAAAATGTTTATATAA |
| 60 | CC152 hsdS1 | ATGAGTAATACACAAAAGAAAAATGTGCCAGAGTTGAGATTCCCAGGGT<br>TTGAAGGCGAATGGGAAGAGAAGAAGTCTAGGGGATATTACAGATAGAT<br>TAATTAGGAAAAATAAAAACTTAGAATCGAAAAAGCCTTTAACAATATCC<br>GGACAGTTAGGTTTAATTGATCAAACAGAATATTTTAGTAAATCAGTTTC<br>GTCGAAAAATCTAGAAAATTATACACTAATAAAGAATGGAGAATTCGCGT<br>ATAACAAAAGTTATTCTAATGGATACCCATTAGGGGCTATTAAAAGATTA<br>ACTAGATATGATAGTGGTGTATTGTCCTCTTTGTATATTTGCTTTTCTATT<br>AAAAGTGAAATGTCTAAAGACTTCATGGAAGCATATTTTGATTCGACACA<br>CTGGTATAGAGAAGTTTCAGGAATTGCAGTTGAGGGTGCAAGAAATCAC<br>GGATTATTAAATATTTCTGTGAATGATTTTTTTTACTATTCTAATTAAATATC<br>CAAGTTTAGAAGAACAGAGAAAAATAGGTGACTTCTTCATCAAACTTGA<br>CCGGCAAATTGAATTAGAAGAACAAAAACTTGAATTACTTCAACAACAGA<br>AAAAAGGCTATATGCAGAAAATCTTCTCACAGGAACTGCGATTTAAGGA<br>TGAGAATGGTAATGATTATCCAGAGTGGGAAGAGAAAAAGTTAGGGGA<br>ACTTGGCCTATTTCAAAAAAGTTATTCTTTTTCGAGAGCTAAAGAAGGAA<br>ACGGTAAAACTAAGCATATTCATTATGGTGATATTCATTCAAAATTTAAAA<br>CAGTATTAGATAGTGACGGCAATATCCCTAATATAATTGAGGAAGCTGT<br>ATTTGAATTGGTTCAAAAAGGTGACATTATTTTTGCGGATGCATCAGAAG<br>ATTATAGTGACCTAGGAAAAGCAGTTATGATAGATTTCGAACCGAATTCA<br>TTGATTTCTGGATTACATACACACCTATTTAGACCGTTTAACAATGTAATT<br>TCTAATTTTTTGATCTTTTACACAAAAACTCTTAGTTATAAAAAATTCATTA<br>GACAGCAAGGTACAGGAATATCAGTACTTGGTATATCAAAAAAAAGTTT<br>ATTAAATTTGGATGTATTAATACCACAAAATGAATTAGAACAACAAAAAT<br>CGGTCAGTTCTTTAGCAAAATCGACCGACAAATTGAATTGGAACAACAA<br>AAGTTAGAATTACTTCAACAACAGAAAAAATCCTTACTTCAATCGATGTT<br>TATTTAA |
| 61 | CC75 hsds2 | ATGAGTAATACACAAACGAAAAATGTGCCAGAGTTGAGATTCCCAGGGT<br>TTGAAGGCGAATGGGAAGAGAAGGAATTGGGGAAATTTTTCAAATAAT<br>TTCTGGTTCAACACCACTAAAATCAAATAAAGAGTTTTATGAAAATGGTA<br>ATATTAATTGGGTCAAACGACAGATTTAAATAATTCTAAAGTTACGCAT<br>AGTAAAGAAAAATAACTGAATATGCTATGAAAAGTTTGAAATTAAAATT<br>AGTGCCTAAAAATTCAGTACTTATAGCTATGTATGGTGGTTTTAATCAAA<br>TTGGTAGAACAGGGTTTGTTAAAAAATAGATGCCACAATAAATCAAGCAATT<br>TCAGCCTTATTAATGAATCATGAAACGAATCCAGAATTTATACAAGCATT<br>TCTAAATTATCAAGTTAAGGGTTGGAAGCGATATGCAGCAAGTAGCAGA<br>AAAGACCCGAATATAACTAAAAAGACATAGAACAATTTAAAGTTCCTTA<br>TGTTAGTATTAATGAACAGCAAAAAATAGGCGAATTCTTCAGTAAAATTG |

TABLE 1-continued

Sequences used

| SEQ ID No. | Description of sequence | Sequence |
|---|---|---|
| | | ACCACCAAATCGAGTTAGAAGAACAAAAACTTGAATTACTTCAACAACA<br>GAAGAAAGGCTATATGCAGAAAATCTTCTCGCAGGAATTGCGATTCAAA<br>GATGAGAATGGTGAAGATTATCCGGATTGGGAAGTTACTACTATACAAA<br>ATATTACAAATATACCAGTTCGAAGAAGTCTTCTAATCAATATGCTGAC<br>AAGGATAATTCTAAAGGTTATCCAGTTTATGATGCCGTTCAAGAGATTG<br>GTAAAGATTCAAATTATGATATAGAAGAATCGTATATTTCTATTTTGAAG<br>GATGGAGCAGGAGTTGGTCGATTAAATTTAAGGCCAGGAAAATCATCC<br>GTAATTGGAACTATGGGCTACATACAGTCAAATAATGTAGATATTGAATT<br>CCTTTATTATCGAATGAAAGTAGTAGATTTTAAAAAGTATATAATTGGAA<br>GTACTATACCGCATTTGTACTTCAAAGACTATTCTAAAGAAACTTTATATA<br>TACCTTCAAGCATTCAAGAACAAGCAAAGATTGGTATGTTTATTTCAAAT<br>TTGGATAAGTTGATTGAAAATAAAAACCTTAAATTAAACTGTTTAAAACAA<br>TTAAAACAAGGATTGCTACAATCTATGTTTATTTAA |
| 62 | CC7 hsdS1<br>TCH959<br>(USA300) | ATGAGTAATACACAAAAGAAAATGTGCCAGAGTTGAGATTCCCAGGGT<br>TTGAAGGCGAATGGGAAGAGAAGCAGTTGGGGGAAGTAGGTACATTTA<br>CTTCAGGTGGGACACCCCTGAAATCAAAATCAGAGTATTGGAATGGAGA<br>TATTCCATGGATTACAACAGGTGATATTCATAACATAAAAGAGAAAATA<br>TAACTAATTTTATAACAGAGAAGGGTTTAAATGAATCATCGGCAAAATTA<br>ATAACTAATGAGGCGATTTTAATAGCTATGTATGGTCAAGGTAAAACTAG<br>AGGAATGTCAGCAATATTGAATTTTGAGGCAACAACTAACCAAGCATGT<br>GCTATATATCAAACTAATCAAAATATTAATTTTGTTTTCAATACTTTCAG<br>AAATTATATAAATTTTTACGCTCATTATCTAATGAGGGAAGTCAAAAGAA<br>TTTAAGTTTAAGTTTGTTGAAAGAAATTACTTTAAATTATCCTAATGAACA<br>AGAACAGAAAAAAATAGGTGTCTTCTTCAGCAAACTTGACCGACAAATT<br>GAATTAGAAGAACAAAAACTCGAATTACTTCAACAACAGAAAAAAGGCT<br>ATATGCAGAAAATTTTCTCACAGGAACTGCGATTCAAAGATGAGAATGG<br>TGAAGATTATCCAGATTGGAAAGAGAAGAAGTTAGGGGATATTACAGAA<br>CAATCTATGTATGGTATAGGTGCATCTGCAACAAGGTTTGATTCGAAAA<br>ATATATATATAAGAATTACTGATATTGATGAAAAATCAAGGAAATTAAATT<br>ATCAAAACTTAACTACACCTGATGAAGTTAATAATAAGTACAAGCTGAAA<br>AGAAATGATATTCTTTTTGCACGAACTGGTGCTAGCACGGGCAAAAGTT<br>ATATTCACAAAGAAGAAAAGGATATTTATAATTACTATTTCGCTGGATTTT<br>TAATAAAATTTGAAATAAACGAACAAAATAGTCCTTTGTTCATTTACCAAT<br>TTACACTAACATCAAAATTTAACAAATGGGTGAAGGTCATGTCTGTAAGA<br>TCTGGTCAACCGGGTATTAATAGTGAAGAATATGCAAAATTACCTTTAGT<br>TTTGCCCAATAAGTTAGAACAGCAAAAAATAGCAGAATTCTTAGATAGAT<br>TTGACCAACAAATTGAATTAGAAAACAAAAATAGAAATACTTCAACAA<br>CAGAAAAAAGGCTTACTTCAATCGATGTTTATTTAA |
| 63 | CC42 hsdS1<br>C427 | ATGAGTAATACACAAACGAAAATGTGCCAGAGTTGAGATTCCCAGGGT<br>TTGAAGGCGAATGGGAAGAGAAGAAGGTTGGCGAGTTATTAGAATTTAA<br>AAATGG1TTAAATAAAGGAAAAGAATATTTTGGCTCAGGATCGTCGATTG<br>TTAACTTCAAAGATGTATTTAATAACAGGAGCTTAAATACAAATAATCTG<br>ACTGGAAAAGTTAATGTGAATAGCAAAGAACTAAAAAATTATTCTGTTGA<br>AAAGGGTGATGTTTTTTTTACAAGGACTAGTGAGGTAATTGGTGAAATA<br>GGTTATCCGTCTGTAATTTTAAATGACCCTGAAAATACTGTGTTTAGTGG<br>ATTTGTATTAAGAGGGCGGCCTAAATCAGGAATTGATTTAATAAATAATA<br>ATTTTAAAAGATATGTCTTTTTTTACTAATTCATTTAGAAAAGAAATGATTA<br>CAAAAAGTTCTATGACAACTAGAGCTTTAACATCAGGTAGCGCAATTAAT<br>AAAATGAAGGTCATATACCCTGTTTCGGCTAAAGAACAGAGAAAAATAG<br>GTGACTTCTTCAGCAAACTCGACCGACAAATTGAATTAGAAGAACAAAA<br>GCTTGAATTACTTCAACAACAAAAAAAGGCTATATGCAGAAAATCTTCT<br>CACAGGAACTGCGATTCAAAGATGAGAATAGTGAAGATTATCCACATTG<br>GGAAAATAGCAAAATAGAAAAATATTTAAAAGAGAGAAACGAACGTTCT<br>GACAAAGGTCAAATGCTTTCAGTAACTATAAATAGTGGCATTATAAAATT<br>TAGTGAATTGGATAGAAAAGATAATTCAAGTAAAGATAAAAGTAATTATA<br>AAGTAGTTAGGAAAAATGATATTGCATATAATTCTATGAGAATGTGGCAA<br>GGGGCTAGTGGTAGATCAAATTATAATGGGATTGTTAGCCCTGCATATA<br>CTGTGCTTTATCCAACACAAAATACTAGCTCATTATTTATTGGATATAAG<br>TTTAAAACACATAGAATGATTCATAAATTTAAAATTAATTCACAAGGATTA<br>ACATCAGATACATGGAACTTAAAAATATAAACAATTAAAAAATATAAATATA<br>GATATACCTGTATTGGAGGAACAAGAAAAGATAGGTGATTTCTTTAAAAA<br>AATGGATATATTGATTAGTAAACAGAAATAAAAATTGAATATTAGAAAA<br>AGAGAAACAATCCTTTTTACAAAAGATGTTCTTATAA |
| 64 | CC42 hsdS2<br>C427 | ATGAGTAATACACAAACGAAAATGTGCCAGAGTTGAGATTCCCAGGGT<br>TTGAAGGCGAATGGGAAGAGAAAAAGTTAGGGGATCTTATAAAAGTTAA<br>TTCTGGAAAAGATTATAAACATTTGGAAAAAGGTGATATACCAGTCTATG<br>GTACTGGCGGTTATATGCAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAATTGGA<br>AAGTATACGATGAATCAACAGGTGTGCCAAGCTTAAGTAAACAAACCAT |

TABLE 1-continued

Sequences used

| SEQ ID No. | Description of sequence | Sequence |
|---|---|---|
| | | TAATAAAATAAATAGATTTGTCCCTTCAAATAAAGAGCAGCAAAAAATAG<br>GCGAATTCTTCATCAAACTCGACCGACAAATTGAATTAGAAGAACAAAA<br>ACTTGAATTACTTCAACAACAGAAAAAAGGCTATATGCAGAAAATCTTCT<br>CACAGGAATTGCGATTCAAGGATGAGAATGGAAACGATTATCCGAATTG<br>GGAAGAGAAGAAAATAGAAGATATAGCAAGCCAAGTATATGGAGGCGG<br>AACACCAAATACAAAGATTAAAGAATTTTGGAATGGAGATATTCCATGGA<br>TTCAAAGCTCTGACGTAAAAGTAAATGATTTGATTCTACGACAATGTAAT<br>AAATTTATTTCCAAGAATTCAATTGAGCTTTCTTCTGCAAAACTTATTCCT<br>GCCAATTCAATTGCAATAGTTACAAGAGTCGGGGTTGGAAAACTGTGTT<br>TGGTAGAATTTGATTATGCTACAAGTCAAGATTTTTTATCATTAAGTAGT<br>CTTAAATATGACAAATTATACTCATTATATTCATTGCTATATACAATGAAA<br>AAAATTAGCGCTAATCTACAAGGAACTTCAATTAAAGGTATAACAAAAAA<br>AGAGTTGTTAGATAGTATAATAAAGATACCCCATAATCTAGAAGAACAGC<br>AAAAAATAGGTGATCTATTTTATAAAATTGATAAATATATCAGTTTTAATA<br>AATGTAAAATTGAGATACTTAAAAGTCTCAAACAAGGATTACTTCAAAAA<br>ATTTTTATATAA |
| 65 | CC133 hsdS2 | ATGAGTAATACACAAAAGAAAAATGTGCCAGAATTGAGGTTCCCAGGGT<br>TTGAAGGCGAATGGGAAGAAAAAGAAGCTAGAAAGTATTATAAAAGTTAA<br>TTCTGGAAAAGATTATAAACATTTGGATAAAGGCGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAATTGGA<br>AAGTATACGATGAATCAACAGGTGTGCCAAGCTTAAGTAAACAAACCAT<br>TAATAAAATAAATAGATTTGTCCCTACAAATAAAGAGCAGCAAAAAATAG<br>GCAAGTTCTTCAGCAAACTTGACCGACAAATTGAACTACAAGAACAAAA<br>ACTTGAATTACTTCAACAACAGAAAAAAGGCTATATGCAGAAAATTTTCT<br>CACAGGAATTGCGATTCAAGGATGAGAATGGTAATGATTATCCGGAGTG<br>GGAAAATGTAATGCTTCAAAAAGTTTTGAAAGACAAAACTGAAGGTATAA<br>AGAGAGGACCTTTTGGAGGAGCATTAAAGAAAGATATATTTGTAGAAAG<br>CGGTTATGCAGTTTATGAACAAAGGAATGCAATTTATGATATAAGTAACT<br>TTAGATATTATATAAACGAAAATAAATATAAAGAAATGCAATCATTTTCGG<br>TTCAACCAAATGATATAATAATGAGTTGCTCAGGTACTATTGGAAGATTA<br>GCACTCATTCCTCATAATTATACAAAGGGAATTATAAACCAAGCGCTTAT<br>TAGATTTAGAACTAACCATAAAATTAGAAGTGAATTCTTTTTGATATTTAT<br>GAGGAGCAATCAAATGCAAAGAAAAATCCTAGAGGCAAATCCTGGGTC<br>GGCAATAACCAATTTAGTGCCTGTAAAAGAATTGAAATTAATCCCATTTC<br>CATTACCTGTAAAGTTTGAACAGGATAAAATTAGTCAATTTATACATATTA<br>TAAATCGACGTATTGAACAATCTGAAAAAAAGATTGAAAGTCTAAAAAAT<br>CGTAAACAAGGATTTCTTCAAAAGTTATTTGTTTAA |
| 66 | CC10 hsdS1 | ATGAGTAATACACAAAAGAAAAATGTGCCAGAGTTGAGATTCCCAGGGT<br>TTGAAGGCGAATGGGAAGAAAAAGAAGCTAGAAAGTATTATAAAAGTTAA<br>TTCTGGAAAAGATTATAAACATTTGGATAAAGGCGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTATTTTATTGTACACCTAAAA<br>AAGAAACAGACATACTATTTATATTAAGTTTATTTAGAAAAATAAATTGGA<br>AAGTATACGATGAATCAACAGGTGTGCCAAGCTTAAGTAAACAAACCAT<br>TAATAAAATAAATAGATTTGTCCCTACAAATAAAGAGCAGCAAAAAATAG<br>GCAAGTTCTTCAGCAAACTTGACCGACAAATTGAATTAGAAGAACAAAA<br>ACTTGAATTACTTCAACAACAGAAAAAAGGCTATATGCAGAAAATCTTCT<br>CGCAAGAATTGCGATTCAAAGATGAGAATGGTAATGATTATCCAGAGTG<br>GGAAAATGTAATGCTTCAAAAAGTTTTGAAAGACAAAACTGAAGGTATAA<br>AGAGAGGACCTTTTGGAGGAGCATTAAAGAAAGATATATTTGTAGAAAG<br>CGGTTATGCAGTTTATGAACAAAGGAATGCAATTTATGATATAAGTAACT<br>TTAGATATTATATAAACGAAAATAAATATAAAGAAATGCAATCATTTTCGG<br>TTCAACCAAATGATATAATAATGAGTTGCTCAGGTACTATTGGAAGATTA<br>GCACTCATTCCTCAGAATTATACAAAGGGAATTATAAACCAAGCGCTTAT<br>TAGATTTAGAACTAACCATAAAATTAGAAGTGAATTCTTTTTGATATTTAT<br>GAGGAGCAATCAAATGCAAAGAAAATTCTAGAGGCAAATCCTGGGTC<br>GGCAATAACCAATTTAGTGCCTGTAAAAGAATTGAAATTAATCCCATTTC<br>CATTACCTGTAAAGTTTGAACAGGATAAAATTAGTCAATTTATACTTATTA<br>TAAATCGACGTATTGAATAA |
| 67 | CC10hsdS2 D139 | ATGAGTAATACACAAACGAAAAATGTGCCAGAGTTGAGATTCCCAGGAT<br>TTGAAGGCGAATATTCTTTAGACATTTTTGGAAATCTAGCAACGAATAAG<br>AGTGATAAATTTAACCCTCAAAATGAGGATGCAAGTATTGATATAGAATT<br>GGATTGTATTGAACAAAATACGGGTCGATTAATTAAAATTTATAATTCAA<br>AAGAATTTTCAAGTCAAAAAATAAATTCAATCCACAAAATGTTTTGTATG<br>GGAAGCTCAGACCATATTTGAATAAGTATTATTTTACAAAAAAAGTGGA<br>GTGTGTTCATCAGAAATATGGGTTTTGAAATCAACGAAAGAAGATAAATT<br>ATTGAATTTATTTCTATATTATTTTATACAAACAAAACGATATTCTGATGTT |

TABLE 1-continued

Sequences used

| SEQ ID No. | Description of sequence | Sequence |
|---|---|---|
| | | GCTAGTAAATCGGCTGGTTCTAAGATGCCAAGGGCTGATTGGGGTTTA
GTAGAAAATATAAGAGTATATTTTCCAGAATTATGTGAACAGCAAAAAT
AGGCGAATTCTTCAGCAAACTCGACCGACAAATTGAACTAGAAGAACAA
AAACTTGAGTTACTTCAACAACAGAAAAAGGCTATATGCAGAAAATCTT
CTCACAGGAATTGCGATTTAAGGATGAGAATGGTAATGATTATCCTGAG
TGGGAGAAAAAGAAACTAAAAGAAATAGCTTATGTTTATACAGGAAACA
CGCCAAGTAAAAAAGAAATATATATTGGATTAAAGGTGAATACGTTTGG
GTTACACCTACTGATATTAATAATAGTAAAAATATTTATGAAAGTGAACAT
AAATTAACCCAAGAAGGTTATAAAAAGCAAGCAATTACCAGAAAATAC
ACTATTGGTTACGTGTATAGCTAGTATAGGAAAAACGCAATATTGAGAA
AACAGGGCTCGTGTAATCAACAAATAAATGCAGTAGTCCCATTTGAAAA
TATAAATATAGATTATCTTTATTATATTTCTGATTCATTATCAACGTTCATG
AAGTCTATTGCAGGAAAAACGGCTACACAAATAGTTAATAAAAACACTTT
CGAAAATTTGGAACTTTATTTAGCTTCTTTTGAAGAACAGAATAAAATAG
CAGATTTAATTAGCTCACTAGAAGAATTAATTGAAAAGCAAGCATCGAAG
TTAATTAAAATGAAGAGTCGTAAACAAGGATTGCTTCAAAAAATGTTTAT
TTAA>H19_hsdS1ATGAGTAATACACAAAAGAAAATGTGCCAGAGTTGA
GATTCCCAGGGTTTGAAGGCGAATGGGAAGAAAAGAAGCTAGAAAGTA
TTATAAAAGTTAATTCTGGAAAAGATTATAAACATTTGGATAAAGGCGAT
ATACCAGTCTATGGTACTGGCGGTTATATGACAAGTGTTTCAGAACCAC
TAAGTGAAATTGATGCTGTTGGTATTGGGAGAAAAGGGACTATAAACAA
ACCATATTTGCTTGAGGAGCCGTTTTGGACGGTGGATACATTATTTTATT
GTACACCTAAAAAAGAAACAGACATACTATTTATATTAAGTTTATTTAGAA
AAATAAATTGGAAAGTATACGATGAATCAACAGGTGTGCCAAGCTTAAG
TAAACAAACCATTAATAAAATAAATAGATTTGTCCCTACAAATAAAGAGC
AGCAAAAAATAGGCAAGTTCTTCAGCAAACTTGACCGACAAATTGAATT
AGAAGAACAAAAACTTGAATTACTTCAACAACAGAAAAAGGCTATATGC
AGAAAATCTTCTCGCAAGAATTGCGATTCAAAGATGAGAATGGTAATGA
TTATCCAGAGTGGGAAATGTAATGCTTCAAAAAGTTTTGAAAGACAAAA
CTGAAGGTATAAAGAGAGGACCTTTTGGAGGAGCATTAAAGAAAGATAT
ATTTGTAGAAAGCGGTTATGCAGTTTATGAACAAAGGAATGCAATTTATG
ATATAAGTAACTTTAGATATTATATAAACGAAAATAAATATAAAGAAATGC
AATCATTTTCGGTTCAACCAAATGATATAATAATGAGTTGCTCAGGTACT
ATTGGAAGATTAGCACTCATTCCTCAGAATTATACAAAGGGAATTATAAA
CCAAGCGCTTATTAGATTTAGAACTAACCATAAAATTAGAAGTGAATTCT
TTTTGATATTTATGAGGAGCAATCAAATGCAAAGAAAAATTCTAGAGGCA
AATCCTGGGTCGGCAATAACCAATTTAGTGCCTGTAAAAGAATTGAAAT
TAATCCCATTTCCATTACCTGTAAAGTTTGAACAGGATAAAATTAGTCAA
TTTATACTTATTATAAATCGACGTATTGAACAATCTGAAAAAAAGATTGAA
AGTCTAAAAAATCGTAAACAAGGATTTCTTCAAAAGTTATTTGTTTAA |
| 68 | H19 hsdS2 | ATGAGTAATACACAAACGAAAATGTGCCAGAGTTGAGATTCCCAGGAT
TTGAAGGCGAATATTCTTTAGACATTTTTGGAAATCTAGCAACGAATAAG
AGTGATAAATTTAACCCTCAAAATGAGGATGCAAGTATTGATATAGAATT
GGATTGTATTGAACAAAATACGGGTCGATTAATTAAAATTTATAATTCAA
AAGAATTTTCAAGTCAAAAAATAAATTCAATCCACAAAATGTTTTGTATG
GGAAGCTCAGACCATATTTGAATAAGTATTATTTTACAAAAAAAAGTGGA
GTGTGTTCATCAGAAATATGGGTTTTGAAATCAACGAAAGAAGATAAATT
ATTGAATTTATTTCTATATTATTTTATACAAACAAAACGATATTCTGATGTT
GCTAGTAAATCGGCTGGTTCTAAGATGCCAAGGGCTGATTGGGGTTTA
GTAGAAAATATAAGAGTATATTTTCCAGAATTATGTGAACAGCAAAAAT
AGGCGAATTCTTCAGCAAACTCGACCGACAAATTGAACTAGAAGAACAA
AAACTTGAGTTACTTCAACAACAGAAAAAGGCTATATGCAGAAAATCTT
CTCACAGGAATTGCGATTTAAGGATGAGAATGGTAATGATTATCCTGAG
TGGGAGAAAAAGAAACTAAAAGAAATAGCTTATGTTTATACAGGAAACA
CGCCAAGTAAAAAAGAAATATATATTGGATTAAAGGTGAATACGTTTGG
GTTACACCTACTGATATTAATAATAGTAAAAATATTTATGAAAGTGAACAT
AAATTAACCCAAGAAGGTTATAAAAAGCAAGCAATTACCAGAAAATAC
ACTATTGGTTACGTGTATAGCTAGTATAGGAAAAACGCAATATTGAGAA
AACAGGGCTCGTGTAATCAACAAATAAATGCAGTAGTCCCATTTGAAAA
TATAAATATAGATTATCTTTATTATATTTCTGATTCATTATCAACGTTCATG
AAGTCTATTGCAGGAAAAACGGCTACACAAATAGTTAATAAAAACACTTT
CGAAAATTTGGAACTTTATTTAGCTTCTTTTGAAGAACAGAATAAAATAG
CAGATTTAATTAGCTCACTAGAAGAATTAATTGAAAAGCAAGCATCGAAG
TTAATTAAAATGAAGAGTCGTAAACAAGGATTGCTTCAAAAAATGTTTAT
TTAA |
| 69 | IS256 | ATGAGTAATACACATATGAAAAATGTGCCAGAGTTGAGATTCCCAGAAT
TTGAAGGCGAGTGGGAAGAGAAGCAATTTGCTGATTTTACTAAAATAAA
TCAAGGATTACAGATTGCTATTAATGAACGTAAAACTGAATATTCTCCAG
AGTTGTATTTTTATATAACAAATGAATTTTTAAGACCAAATAGTCAAACTA
AATATTTTATCGAAAATCCCCCTCAATCAGTAATTGCAAATAAAGAAGAT
ATTTTAATGACTAGAACAGGTAATACTGGAAAAGTAGTAACTAATGTATT
TGGAGCGTTTCATAATAATTTTTTTAAAATTAAATTTGATAAAAATCTGTA |

TABLE 1-continued

Sequences used

| SEQ ID No. | Description of sequence | Sequence |
|---|---|---|
| | | TGATAGATTGTTTTTAGTAGAGGTTTTAAATTCATCTAAGATACAAAATAA<br>AATATTATCTTTAGCAGGATCTTCGACGATACCAGATTTAAACCATAGTG<br>ATTTTTATAGTATTAGTTCTTCTTATCCGCTGCTTAGAGAACAGCAAAAA<br>ATAGGTGATTTTTTCAGCAAAATCGATCGACAAATTGAACTACAAGAACA<br>AAAACTTGAATTACTTCAACAACAGAAAAAAGGCTATATGCAGAAAATTT<br>TCTCACAGGAACTGCGATTCAAAGATGAGAATGGTGAAGATTATCCAGA<br>TTGGAAAGAGAAGAAGTTAGGGGATATTACAGAACAATCTATGTATGGT<br>ATAGGTGCATCTGCAACAAGGTTTGATTCGAAAAATATATATATAAGAAT<br>TACTGATATTGATGAAAAATCAAGGAAATTAAATTATCAAAACTTAACTAC<br>ACCTGATGAACTTAATAATAAGTACAAGCTGAAAAGAAATGATATTCTTT<br>TTGCACGAACTGGTGCTAGCACGGGAAAAAGTTATATTCACAAAGAAGA<br>AAAGGATATTTATAATTACTATTTCGCTGGATTTTTAATAAAATTTGAAAT<br>AGACGAACAAAATAATCCTTTGTTCATTTACCAATTTACACTAACATCAA<br>AATTTAACAAATGGGTGAAGGTCATGTCTGTAAGATCTGGTCAACCGGG<br>CATTAATAGTGAAGAATATGCAAAATTACCTTTAGTTTTGCCCAATAAATT<br>AGAACAGCAAAAAATAGCAAAATTCTTAGATAGATTTGACCGACAAATTG<br>AATTAGAAAAACAAAAAATAGAAATACTTCAACAACAGAAAAAAGGCTTA<br>CTTCAATCGATGTTTATTTAA |
| 70 | CC80 hsdS<br>HT2005-175 | ATGAGTAATACACAAANGAAAAATGTGCCAGAGTTGAGATTCCCAGGGT<br>TTGAAGGCGAATGGGAAGAGAAGCAATTTGCTGATTTTACTAAAATAAA<br>TCAAGGATTACAGATTGCTATTAATGAACGTAAAACTGAATATTCTCCAG<br>AGTTGTATTTTTATATAACAAACGAATTTTTAAGACCAAATAGTCAAACTA<br>AATATTTTATCGAAATCCCCCTCAATCAGTAATTGCAAATAAAGAAGAT<br>ATTTTAATGACTAGAACAGGTAATACTGGAAAAGTAGTAACTAATGTATT<br>TGGAGCGTTTCATAATAATTTTTTTAAAATTAAATTTGATAAAAATCTGTA<br>TGATAGATTGTTTTTAGTAGAGGTTTTAAATTCATCTAAGATACAAAATAA<br>AATACTATCTTTAGCAGGATCTTCGACGATACCAGATTTAAACCATAGTG<br>ATTTTTATAGTATTAGTTCTTCTTATCCGCTGCTTAGAGAACAGCAAAAA<br>ATAGGTAAATTCTTCAGCAAACTCGACCGACAAATTGAATTAGAAGAAC<br>AAAAGCTTGAATTACTTCAACAACAGAAAAAAGGCTATATGCAGAAAATC<br>TTCTCACAGGAATTGCGATTTAAGGACGAGAATGGAAATGATTATCCGG<br>ATTGGGAGAAAAAGAAACTAAAAGAAATAGCTTGTGTTTATACAGGAAA<br>CACGCCAAGTAAAAAGAAAATATATATTGGAATAAGGGTGAATACGTTT<br>GGGTTACACCTACTGACATTAATAATAGTAAAAATATTTATGAAAGTGAA<br>AACAAATTAACCCAAGAAGGCTATAAAAAAGCAAGACAATTACCAGAAA<br>ATACACTATTGGTTACGTGTATAGCTAGTATAGGAAAAAACGCAATATTG<br>AGAAAACAGGGCTCGTGTAATCAACAAATAAATGCAGTAGTTCCATTTG<br>AAAATATAAATATAGATTATCTTTATTATATTTCTGATTCATTATCAACGTT<br>CATGAAATCTATTGCAGGAAAAACGGCTACACAAATAGTTAATAAAAACA<br>CTTTCGAAAATTTGGAAATTTATTTAGCTCCTTTTGAAGAACAGAATAAA<br>ATAGCAGATTTAATTAGCTCACTAGAAGAATTAATTGAAAAGCAAGCATC<br>GAAGTTAATTAAAATGAAGAGTCGTAAACAAGGAATGCTTCAAATAATGT<br>TTATTTAA |
| 71 | CC59 hsdS<br>HT2001-751 | ATGAGTAATACACAAAAGAAAAATGTGCCAGAGTTGAGGTTCCCAGAGT<br>TTGAAGGCGAGTGGGAAGAAAGGAAGTTAGGGGATCTTATAAAAGTTAA<br>TTCTGGAAAAGATTATAAACATTTGGATAAAGGCGATATACCAGTCTATG<br>GTACTGGCGGTTATATGACAAGTGTTTCAGAACCACTAAGTGAAATTGA<br>TGCTGTTGGTATTGGGAGAAAAGGGACTATAAACAAACCATATTTGCTT<br>GAGGCGCCGTTTTGGACGGTGGATACATTGTTTTATTGTACACCTGAAA<br>AAGAAGCAGACATACTATTTATATTAAGTTTATTTAGAAAAATAAATTGGA<br>AATTATACGATGAATCAACAGGTGTGCCAAGCTTAAGCAAGCAAACCAT<br>TAATAAAATAAATAGACTTGTCCCTACAAATAAAGAACAACAAAAAATAG<br>GCGAGTTCTTCAGCAAACTCGACCGACAAATTGAATTAGAAGAACAAA<br>ACTTGAATTACTTCAACAACAGAAAAAAGGCTATATGCAGAAAATTTTCT<br>CACAGGAACTGCGATTCAAAGATGAGAATGGTGAAGATTATTCGGAGTG<br>GGAAGAGAGAAGATTTGCTGATATATTTAAATTTCATAATAAACTAAGAA<br>AGCCAATTAAAGAAATTTAAGAGTAAAGGGTTCTTATCCATATTATGGT<br>GCTACAGGTATTATTGATTACGTTGACGACTTTATATTTGACGGGAATTA<br>TTTACTTATTGGAAGATGGTGCAAATATTATTACTAGAAGTGCACCCC<br>TAGTGTACTTAGTAAATGGAAAGTTTTGGGTAAATAATCATGCTCATATA<br>TTATCTCCTTTAAATGGAAATATACAGTACTTGTATCAAGTTGCAGAATT<br>AGTTAATTATGAAAAATACAATACTGGAACTGCTCAGCCTAAATTAAACA<br>TTCAAAATTTAAAAATTATTAATGTTGTAATTTCAACGAATTTAGAAGAAC<br>AACAAAAAATCGGAAGCTTTTTAAGTAAACTTGATCGTCAAATCGATTTA<br>GAAGAACAAAAACTCGAATTACTTCAACAACGAAAAAAGCCTTACTTAA<br>ATCGATGTTTGTTTAA |

Antibiotic Resistance

As mentioned herein above particular embodiments of the invention relates to the any of the methods described herein further comprising amplification primers and/or probes which are specific and sensitive for determining the presence of nucleic acid(s) from a bacterial antibiotic resistance gene selected from the group consisting of mecA and vanA in any sample suspected of containing said S. aureus nucleic acid(s) thereby determining MRSA, wherein each of said nucleic acid(s) or variant(s) or part(s) thereof comprises a selected target region hybridizable with said primers or probes; said method comprising the following steps: contacting said sample with said probes or primers and detecting the presence of amplified products or hybridized probes as an indication of the presence said specific S. aureus antibiotic resistance genes and thus MRSA.

In a particular embodiment the method above is a multiplex PCR as described herein above.

Thus, another embodiment of the invention relates to the any of the methods described herein further comprising the evaluation of MRSA mediated by a bacterial antibiotic resistance gene selected from the group consisting of mecA and vanA directly from a test sample or a S. aureus, which comprises the following steps: a) treating said sample with an aqueous solution containing at least one pair of, one of said primers being capable of hybridizing selectively with one of the two complementary strands of said bacterial antibiotic resistance gene that contains a target sequence, and the other of said primers being capable of hybridizing with the other of said strands so as to form an extension product which contains the target sequence as a template, said at least one pair of primers being chosen from a nucleotide sequence within the group consisting of SEQ ID NOS: 7 and 8, respectively with regard to said bacterial antibiotic resistance gene, a sequence complementary thereof, and a variant thereof; b) synthesizing an extension product of each of said primers, said extension product containing the target sequence, and amplifying said target sequence, if any, to a detectable level; and c) detecting the presence and/or amount of said amplified target sequence as an indication of a bacterial resistance mediated by one of said bacterial antibiotic resistance genes.

In a particular embodiment the method of the invention is a microarray method as described herein above.

Thus one embodiment of the invention relates to the any of the methods described herein further comprising the evaluation of MRSA mediated by a bacterial antibiotic resistance gene selected from the group consisting of mecA and vanA, directly from a test sample or a bacterial culture, which comprises the following steps: a) depositing and fixing on an solid support or leaving in solution the S. aureus nucleic acid(s) of the sample or of a substantially homogeneous population of S. aureus isolated from this sample, or inoculating said sample or said substantially homogeneous population of S. aureus isolated from this sample on an solid support, and lysing in situ said inoculated sample or isolated bacteria to release the S. aureus nucleic acid(s), said S. aureus nucleic acid(s) being made in a substantially single-stranded form; b) contacting said single-stranded nucleic acid(s) with a probe, said probe comprising at least one single-stranded nucleotide sequence complementary to sau1hsdS1 of CC398 or sau1hsdS2 of CC398 and a variant thereof, more specifically at least one single-stranded nucleotide sequence complementary to the nucleotide sequence defined in: SEQ ID NO: 1, which specifically hybridizes with said bacterial antibiotic resistance gene, respectively; and c) detecting the presence of a hybridization complex as an indication of a bacterial resistance mediated by said one of said bacterial antibiotic resistance genes.

In specific embodiment the antibiotic resistance gene is mecA.

Preferably the methods may be used for the distinction between MRSA and MSSA strains of S. aureus.

Thus methods may be used for the simultaneous detection of a bacterial antibiotic resistance gene and nucleic acid(s) of a clone-specific hsdS gene, preferably CC398.

In one embodiment where the methods further comprises the detection of a bacterial antibiotic resistance gene and/or evaluation of MRSA there is provided that the clonal complex is complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

Device

A further aspect of the present invention relates to a device for the detection of the presence of S. aureus nucleic acid(s), preferably for the detection, identification and/or typing of any S. aureus clonal complex, wherein the device comprises means for measuring the presence of clone-specific hsdS nucleic acid(s). and optionally for the presence of antibiotic resistance nucleic acid(s), preferably mecA nucleic acid(s), wherein the device comprises means for measuring the presence of S. aureus clone-specific hsdS nucleic acid(s). nucleic acid(s). The means for measuring the presence of S. aureus nucleic acid(s) in a sample may for example be a test system that applies any of the above mentioned systems, such as a PCR based assay or a microarray.

A device according to the present invention may for example comprise a rapid, qualitative and/or quantitative test system mounted on a solid support for the determination of S. aureus nucleic acid(s), preferably clone-specific nucleic acid(s) from the hsdS gene and optionally for the presence of antibiotic resistance nucleic acid(s), preferably mecA nucleic acid(s), in biological samples.

A solid support according to the present invention may comprise a material having a rigid or semi-rigid surface. Such materials will preferably take the form of plates or slides, small beads, pellets, disks, capillary tubes or other convenient forms, although other forms may be used. In some embodiments, at least one surface of the solid support will be substantially flat. In other embodiments, a roughly spherical shape is preferred. The solid support may be biological, non-biological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations. For example, the solid support may contain raised or depressed regions on which reactions including, but not limited to, hybridization, ligation, and cleavage takes place. In some embodiments, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinyliden-difluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—H functionalities, such as are found on silica surfaces. The solid support is preferably contacted by an array of ordered sets of molecules comprising or essentially consisting of dsDNA and/or ssDNA fragments that are preferably covalently attached to the solid support. In this way the DNA fragments are identified by their two dimensional position in the array.

The solid support can be used in any phase in performing any of the above assays, including dipsticks, membranes, absorptive pads, beads, microtiter wells, test tubes, and the like. Preferred are test devices which may be conveniently used by the testing personnel or the patient for self-testing, having minimal or no previous training. Such preferred test devices include dipsticks and membrane assay systems. The preparation and use of such conventional test systems is well described in the patent, medical, and scientific literature.

A particular aspect of the invention regards a solid support coated with a set of probes for identification, detection and/or typing of any S. aureus clonal complex from an extract of its genomic DNA, each probe being able to specifically hybridize with a relevant gene or with a representative fragment thereof susceptible to be present in said genomic DNA to be tested, characterized in that said relevant genes whose presence or absence is to be determined using the set of probes comprise the following genes: a) a clone-specific hsdS gene, for identification, detection and/or typing said S. aureus clonal complex, and b) at least one gene considered as a negative control, said gene being absent in the genome of said S. aureus species, and optionally c) a gene for antibiotic resistance.

Thus, in a particular embodiment the device comprises a solid support coated with a set of separated or compartmentalised probes for identification or typing of any S. aureus clonal complex from an extract of its genomic DNA, each probe being able to specifically hybridize with a relevant gene or with a representative fragment thereof susceptible to be present in said genomic DNA to be tested, characterized in that said relevant genes whose presence or absence is to be determined using the set of probes comprise the following genes: a) a clone-specific hsdS gene, for typing said S. aureus clonal complex, and b) at least one gene considered as a negative control, said gene being absent in the genome of said S. aureus species, and optionally c) a gene for antibiotic resistance.

Thus a very specific embodiment of the invention relates to DNA micro-array for identification, detection and/or typing of a S. aureus bacterial strain comprising the solid support described herein.

Another very specific embodiment of the invention relates to a device comprising a DNA micro-array for identification, detection and/or typing of a S. aureus bacterial strain comprising the solid support described herein In other embodiments of the invention the device may be a dipstick. Dipsticks may allow visual detection and confirmation of PCR-amplified S. aureus-specific transcripts by hybridization within minutes.

Dipsticks that can detect PCR products have for example recently been described by Deborggraeve et al. (2006) and Kalogianni et al. (2007). The PCR products may for example be biotinylated at the one end by using an upstream primer labelled with biotin at the 5' end.

Deborggraeve et al. (2006) describes a dry-reagent strip (4 mm×70 mm) consisting of an immersion pad, a conjugation pad, a laminated membrane and an absorbent pad assembled on a plastic adhesive backing that provides rigidity. The four parts are positioned in such a way that their ends overlapped in order to ensure continuous flow (by capillary action) of the developing solution from the wicking pad up to the absorbent pad. Gold nanoparticles (40 nm diameter) functionalized with poly(dT) strands, are placed on the conjugate pad and allowed to dry at room temperature. Streptavidin (27 pmol) is immobilized by physical adsorption on the test zone of the strip. Similarly, poly(dA) strands (1.2 pmol) are immobilized on the control zone of the strip.

The assay entails rapid hybridization of the amplified fragments (target DNA), in solution, with a dATP-tailed oligonucleotide probe, application to the sample loading area on the conjugate pad of the strip and immersion of the strip (via the immersion pad) in the developing solution. The developing solution migrates to the opposite end of the strip, by capillary forces, and causes rehydration of the poly(dT)-functionalized gold nanoparticles (Au NP), which are then connected to the probe via hybridization of the poly(dT) strands with the poly(dA) tail of the probe. As the solution passes through the test zone of the strip, the hybrids are captured by immobilized streptavidin, thus resulting in accumulation of Au NP which is detected visually as a characteristic red line. The red color of the Au NP is due to the plasmon resonance peak at 520 nm. The excess of poly(dT)-Au NP are captured by immobilized poly(dA) strands at the control zone of the strip, giving a second red line. In the absence of the translocation, no red line is observed at the test zone. A red line, however, is always formed at the control zone to confirm the proper functioning of the strip. Consequently, a sample is positive for a certain translocation when a red line is observed both in the test and the control zone.

Thus, biotinylated PCR products can then be mixed with a tailed oligonucleotide probe and allowed to hybridize. An aliquot of the solution may then be applied to the conjugate pad of the strip and the latter may be immersed into an appropriate developing solution (for example glycerol and SDS in phosphate-buffered saline). The formation of a red line in the test zone of the strip signifies the presence of a translocation-specific amplified sequence in the sample. A red line is always formed at the control zone of the strip to confirm the proper functioning of the test. Thus, a result is positive when a red line is observed both in the test zone and control zone, whereas in the absence of the translocation, a red line is formed only in the control zone.

Thus, some aspects of the invention regards, device for the detection of the presence of a specific S. aureus clonal complex, strain or lineage, wherein the device comprises means for measuring the presence of clonal complex, strain or lineage specific nucleic acid(s).

In specific embodiments the device is for the detection, identification and/or typing of any S. aureus clonal complex, wherein the device comprises means for measuring the presence of clone-specific hsdS nucleic acid(s). In one embodiment there is provided that the clonal complex is complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

In a particular embodiment the clonal complex, strain or lineage specific hsdS nucleic acid(s) are CC398 specific. In particular embodiments the primer of SEQ ID NO: 2 (CAG-TATTAAAGAGGTGACATGACCCCT) may be used as a means for detecting clonal complex, strain or lineage specific hsdS nucleic acid(s).

In a further embodiment of the device is a dipstick. The dipstick may be any dipstick including but not limited to the dipstick described herein above.

Another embodiment regards a device for the detection of the presence of a specific S. aureus strain or lineage and a bacterial resistance gene selected from the group consisting of mecA and vanA, preferably mecA for the detection of MRSA, wherein the device comprises means for measuring the presence of strain or lineage specific nucleic acid(s). In one embodiment there is provided that the clonal complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

In a preferred embodiment the strain or lineage specific nucleic acid(s) are CC398 specific and in an even more preferred embodiment the device is a dipstick.

Alternatively a dipstick may be used in the present aspect of the invention on any biological sample that is or may be converted to a fluid is preferred. Particularly biological samples that are obtainable from a body as a fluid are preferred; examples hereof include, and are not limited to: blood, serum, plasma, urine, cerebrospinal fluid, synovial fluid, ascites, semen, and saliva. Most preferable are serum and plasma samples.

Kit of Parts

All the materials and reagents required the detection of S. aureus clone-specific nucleic acid(s) according to the present invention can be assembled together in a kit, such kit includes at least elements in aid of assessing the presence of S. aureus clone-specific nucleic acid(s) in a biological sample obtained from an individual, and the instruction on how to do so. In specific embodiments the kit is for identification, detection and/or typing of any S. aureus clonal complex, comprising any suitable combination of clone-specific primers or probes. In an even more specific embodiment the kit is for identification, detection and/or typing CC398 S. aureus clonal complex, comprising any suitable combination of clone-specific primers or probes selected from the group consisting of SEQ ID NOS: 2, 3, 4, 5 and 6, sequences complementary thereof, and variants thereof. Preferably, the primers are the primers specified in SEQ ID NO: 2 and SEQ ID NO: 6.

The kit of parts may further comprise equipment for obtaining one or more biological samples, such equipment may for example be tools for taking swab samples such as sterile cotton buds, as well as syringes, vials or other. The kit of parts may be packed for single use or for repeated usage, and the elements therein may be disposable such as to be disposed of after a single use or may be of a quality that allows repeated usage.

Thus in one embodiment the invention relates to a kit for identification, detection and/or typing a S. aureus bacterial strain comprising the solid support described herein or the DNA micro-array described herein.

The kit may in some embodiment further comprise any suitable combination of primers selected from the group consisting of SEQ ID NOS: 7 and 8 sequences complementary thereof, and variants thereof for the simultaneous detection and/or quantification of the nucleic acid(s) of any combination of the bacterial resistance genes selected from the group consisting of mecA and vanA, preferably mecA for the detection of MRSA.

Preferably, the primers are the primers specified in SEQ ID NO: 2 and SEQ ID NO: 6 for the identification, detection and/or typing of CC398 S. aureus and the primers specified in SEQ ID NO: 7 and SEQ ID NO: 8 for the detection of the mecA gene.

In some embodiments the kit for identification, detection and/or typing a bacterial strain, comprises
a. means for taking a sample from a subject
b. means for mailing said sample to institution for the determining the presence of a specific S. aureus clonal complex, strain or lineage and optionally MRSA in a sample.

In other embodiments the kit for identification, detection and/or typing a bacterial strain, comprises
a. means for taking a sample from a subject
b. means for at the place where the sample is being taken, determining the presence of a specific S. aureus clonal complex, strain or lineage and optionally MRSA in a sample.

In one embodiment there is provided that the clonal complex is not CC1, CC5, CC8, CC22, CC30 or CC45. In some embodiments it is further provided that said clonal complex may not be any one or more of: CC12, CC15, CC25, CC51, CC151, CC97, CC771, CC130, CC188, and/or CC873

In a particular embodiment the specific S. aureus clonal complex, strain or lineage is CC398.

In the above test kit, the reagents may be supplied from storage bottles or one or more of the test tubes may be pre-filled with the reagents or controls.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the reagents such as vials or tubes in close confinement for commercial sale such as, e.g. injection or blow-molded plastic containers into which the desired vials are retained. The kits will also comprise a set of instructions on how to perform the assay.

The kit according to the present invention may furthermore comprise a device according to the invention as described above here in the section termed "device".

In a preferred embodiment there is provided a kit for identification, detection and/or typing of a S. aureus CC398 bacterial strain, comprising any suitable combination of primers selected from the group consisting of SEQ ID NOS: 2, 3, 4, 5 and 6, sequences complementary thereof, and variants thereof. Preferably, the primers are the primers specified in SEQ ID NO: 2 and SEQ ID NO: 6 for the identification, detection and/or typing of CC398 S. aureus.

In another preferred embodiment the kit further comprises any suitable combination of primers selected from the group consisting of SEQ ID NOS: 7 and 8, sequences complementary thereof, and variants thereof for the simultaneous detection and/or quantification of the nucleic acid(s) of the bacterial resistance gene MecA for the detection of MRSA. Preferably, the primers are the primers specified in SEQ ID NO: 2 and SEQ ID NO: 6 for the identification, detection and/or typing of CC398 S. aureus and the primers specified in SEQ ID NO: 7 and SEQ ID NO: 8 for the detection of the mecA gene.

Items

One embodiment of the invention relates to a method using amplification primers and/or probes which are specific and sensitive for determining the presence of nucleic acid(s) from a S. aureus strain or lineage in any sample suspected of containing said S. aureus nucleic acid(s) thereby identifying, detecting and/or typing said S. aureus strain or lineage, wherein each of said nucleic acid(s) or variant(s) or part(s) thereof comprises a selected target region hybridizable with said probes or primers; said method comprising the following steps: contacting said sample with said primers, or probes and detecting the presence of amplified products or hybridized probes as an indication of the presence of said specific S. aureus strain or lineage thereby identifying, detecting and/or typing said S. aureus strain or lineage.

In one embodiment there is provided that the clonal complex is complex is not CC1, CC5, CC8, CC22, CC30 or CC45.

In some embodiments it is further provided that said clonal complex may not be any one or more of: CC12, CC15, CC25, CC51, CC151, CC97, CC771, CC130, CC188, and/or CC873 In a preferred embodiment the clonal complex is CC398.

In another embodiment the nucleic acid(s) from a *S. aureus* strain or lineage is a species specific restriction-modification (RM) gene.

In another embodiment the nucleic acid(s) from a *S. aureus* strain or lineage is an hsdS gene.

In another embodiment the nucleic acid(s) from a *S. aureus* strain or lineage is sau1hsdS1 or sau1hsdS2.

In another embodiment the *S. aureus* strain or lineage is CC398.

Another embodiment of the invention relates to a method using amplification primers and/or probes which are specific and sensitive for determining the presence of nucleic acid(s) from *S. aureus* strain or lineage CC398 in any sample suspected of containing said *S. aureus* CC398 nucleic acid(s) thereby identifying, detecting and/or typing said *S. aureus* strain or lineage, wherein each of said nucleic acid(s) or variant(s) or part(s) thereof comprises a selected target region hybridizable with said probes or primers; said method comprising the following steps: contacting said sample with said primers or probes and detecting the presence of amplified products or hybridized probes as an indication of the presence of said specific *S. aureus* strain or lineage thereby identifying, detecting and/or typing said *S. aureus* strain or lineage.

In another embodiment said nucleic acid(s) are amplified d by a method selected from the group consisting of: polymerase chain reaction (PCR), ligase chain reaction (LCR), nucleic acid sequence-based amplification (NASBA), self-sustained sequence replication (3SR), strand displacement amplification (SDA), branched DNA signal amplification (bDNA), transcription-mediated amplification (TMA), cycling probe technology (CPT), real-time PCR, quantitative PCR, nested PCR, and multiplex PCR.

In a specific embodiment said nucleic acid(s) are amplified by PCR.

In another embodiment said amplification primers are capable of hybridizing with any hsdS sequence or a sequence complementary thereof, for the identification, detection and/or typing of a *S. aureus* clonal complex, strain or lineage.

In another embodiment said primers comprise a forward primer and one or more reverse primers.

In another embodiment said amplification primers or probes are capable of hybridizing with sau1hsdS1 of CC398 or sau1hsdS2 of CC398 or a sequence complementary thereto. Thus is one very preferred embodiment the amplification primers are capable of hybridizing the nucleotide sequence defined in: SEQ ID NO: 1 or a sequence complementary thereto.

In another embodiment said one or more primers or probes are selected from the group consisting of CAGTATTAAAGAGGTGACATGACCCCT (SEQ ID NO: 2), CACCTGAATCACCGTTTAATGCC (SEQ ID NO: 3), CGAGCACCTGAATCACCGTTT (SEQ ID NO: 4) and TGGGATATGAAGTGGCATTTCC (SEQ ID NO: 5).

In another embodiment said forward primer targets the upstream conserved region of the hsdS gene as defined by SEQ ID NO: 1 or SEQ ID NOS: 13-71.

In another embodiment said forward primer is AGGGTTTGAAGGCGAATGGG (SEQ ID NO: 6).

In another embodiment said one or more reverse primers are *S. aureus* strain or lineage specific primers.

In another embodiment said one or more reverse primers are selected from the group consisting of CAGTATTAAAGAGGTGACATGACCCCT (SEQ ID NO: 2), CACCTGAATCACCGTTTAATGCC (SEQ ID NO: 3), CGAGCACCTGAATCACCGTTT (SEQ ID NO: 4) and TGGGATATGAAGTGGCATTTCC (SEQ ID NO: 5).

In another embodiment said at least one of the one or more reverse primers is the CC398 specific primer CAGTATTAAAGAGGTGACATGACCCCT (SEQ ID NO: 2).

In another embodiment the final concentration of the each primer is in a concentration range of 0.01 µM to 10 µM, for example 0.05 µM to 5 µM, such as 0.1 to 1 µM, for example 0.2 µM.

In another embodiment the final concentration of each primer is 0.2 µM.

In another embodiment the method further comprises labelling the *S. aureus* nucleic acid(s) in a sample or of a substantially homogeneous population of said *S. aureus* isolated from this sample and putting said labelled *S. aureus* nucleic acid(s) into contact with a solid support coated with an array of probes in suitable conditions for hybridization, each probe being able to specifically hybridize with a relevant gene or with a representative fragment thereof, susceptible to be present in said sample to be tested, wherein said relevant genes whose presence or absence is to be determined using the set of probes comprise the following genes: a) at least one gene considered as a positive control whose presence in a genome is characteristic for the *S. aureus* strain or lineage, and b) at least one gene considered as a negative control, said gene being absent in the genome of the *S. aureus* strain or lineage, and optionally c) a gene for antibiotic resistance.

In another embodiment the method further comprises a) depositing and fixing on an solid support or leaving in solution the said *S. aureus* nucleic acid(s) of the sample or of a substantially homogeneous population of said *S. aureus* isolated from this sample, or inoculating said sample or said substantially homogeneous population of *S. aureus* isolated from this sample on an solid support, and lysing in situ said inoculated sample or said isolated *S. aureus* to release the said *S. aureus* DNA, said *S. aureus* DNA being made in a substantially single-stranded form.

In another embodiment the method further comprises labelling the *S. aureus* nucleic acid(s) in a sample and putting said labelled *S. aureus* nucleic acid(s) into contact with a solid support coated with an array of probes in suitable conditions for hybridization, each probe being able to specifically hybridize with a relevant gene or with a representative fragment thereof, susceptible to be present in said sample to be tested, wherein said relevant genes whose presence or absence is to be determined using the set of probe comprise the following genes: a) at least one gene considered as a positive control whose presence in a genome is characteristic for the *S. aureus* CC398 strain or lineage, and b) at least one gene considered as a negative control, said gene being absent in the genome of the *S. aureus* CC398 strain or lineage, and optionally c) a gene for antibiotic resistance.

In another embodiment the method is performed directly on a test sample.

In another embodiment the nucleic acid(s) are extracted from a test sample using a bacterial genomic DNA purification kit.

In another embodiment the test sample is derived from an animal.

In another embodiment the test sample is derived from poultry.

In another embodiment the test sample is derived from a mammal. In another embodiment the mammal is selected from the group consisting of humans, pigs, horses and cows.

In another embodiment the method is performed directly from a test sample consisting of a nasal swabs, throat swabs, mouth swabs, hand swabs and blood.

In another embodiment the method is performed directly from a test sample consisting of a bacterial culture or suspension.

In another embodiment the sample of nucleic acid(s) is is derived from strains and/or lineages of persons staying in a health care facility for an extended period of time, health care workers, farm workers, veterinarian staff, persons involved in sales to farms and any person involved in the handling of livestock and/or butchery.

In another embodiment the sample of nucleic acid(s) is derived from strains and/or lineages of one individual patient or hospital.

In another embodiment several lineages and/or hospital isolates are analysed.

In another embodiment the method further comprising a culturing of the strains and/or lineages of S. aureus before the analysis.

Yet another embodiment of the invention relates to a method for the detection, identification and/or typing of a S. aureus strain or lineage, in a test sample which comprises the following steps: a) treating said sample with an aqueous solution containing at least one pair of oligonucleotide primers, one of said primers being capable of hybridizing selectively with one of the two complementary strands of said S. aureus clone-specific hsdS gene that contains a target sequence, and the other of said primers being capable of hybridizing with the other of said strands so as to form an extension product which contains the target sequence as a template, said at least one pair of primers being chosen from a nucleotide sequence within the clone-specific hsdS gene respectively with regard to said S. aureus clonal complex, a sequence complementary thereof, and a variant thereof; b) synthesizing an extension product of each of said primers, said extension product containing the target sequence, and amplifying said target sequence, if any, to a detectable level; and c) detecting the presence and/or amount of said amplified target sequence as an indication of the presence and/or amount of said S. aureus clonal complex, in said test sample.

Yet another embodiment of the invention relates to a method for the detection, identification and/or typing of a S. aureus strain or lineage, directly from a test sample or from bacterial cultures, which comprises the following steps a) depositing and fixing on an solid support or leaving in solution the said S. aureus nucleic acid(s) of the sample or of a substantially homogeneous population of said S. aureus isolated from this sample, or inoculating said sample or said substantially homogeneous population of S. aureus isolated from this sample on an solid support, and lysing in situ said inoculated sample or said isolated S. aureus to release the said S. aureus DNA, said S. aureus DNA being made in a substantially single-stranded form; b) contacting said single-stranded DNA with a probe, said probe comprising at least one single-stranded nucleic acid which nucleotide sequence is sequence complementary to a sequence of SEQ ID NO: 1, and a variant thereof, which specifically and ubiquitously anneals with strains or lineages of S. aureus, under conditions such that the nucleic acid(s) of said probe can selectively hybridize with said S. aureus DNA, whereby a hybridization complex is formed; and c) detecting the presence of said hybridization complex on said solid support or in said solution as an indication of the presence and/or amount of said S. aureus, in said test sample.

Still another embodiment of the invention relates to a method for obtaining hsdS sequences from any S. aureus strain or lineage directly from a test sample or a bacterial culture, which comprises the following steps: a) treating said sample with an aqueous solution containing at least one pair of primers having a sequence selected within the nucleotide sequences defined in SEQ ID NOS: 9, 10, 11 and 12 and a variant thereof, one of said primers being capable of hybridizing selectively with one of the two complementary strands of said S. aureus hsdS gene that contains a target sequence, and the other of said primers being capable of hybridizing with the other of said strands so as to form an extension product which contains the target sequence as a template; b) synthesizing an extension product of each of said primers, said extension product containing the target sequence, and amplifying said target sequence, if any, to a detectable level; and c) detecting the presence and/or amount of said amplified target sequence; and d) determining the nucleotide sequence of the said amplified target sequence by using any DNA sequencing method.

In another embodiment the method further comprises amplification primers and/or probes which are specific and sensitive for determining the presence of nucleic acid(s) from a bacterial antibiotic resistance gene selected from the group consisting of MecA in any sample suspected of containing said antibiotic resistance gene, thereby determining MRSA, wherein each of said nucleic acid(s) or variant(s) or part(s) thereof comprises a selected target region hybridizable with said primers or probes; said method comprising the following steps: contacting said sample with said probes or primers and detecting the presence of amplified products or hybridized probes as an indication of the presence of said mecA.

Yet another embodiment of the invention relates to an improved method of treatment for an infection by MRSA, comprising a method described herein and performing a treatment of MRSA based, at least in part, on said identification, detection and/or typing of S. aureus.

Yet another embodiment of the invention relates to a method of improving the hygiene in hospital, comprising a method described herein and performing hygiene measures in said hospital based, at least in part, on said identification, detection and/or typing of S. aureus.

Yet another embodiment of the invention relates to a solid support coated with a set of probes for identification, detection and/or typing of a S. aureus bacterial strain from an extract of its genomic DNA, each probe being able to specifically hybridize with a relevant gene or with a representative fragment thereof susceptible to be present in said genomic DNA to be tested, characterized in that said relevant genes whose presence or absence is to be determined using the set of probes comprise the following genes: a) at least one gene considered as a positive control whose presence in a genome is characteristic for the S. aureus species, and b) at least one gene considered as a negative control, said gene being absent in the genome of said S. aureus species, and optionally d) a gene for antibiotic resistance.

Another embodiment relates to a solid support coated with a set of probes for identification, detection and/or typing of CC398 S. aureus bacterial strain from an extract of its genomic DNA, each probe being able to specifically hybridize with a relevant gene or with a representative fragment thereof susceptible to be present in said genomic DNA to be tested, characterized in that said relevant genes whose presence or absence is to be determined using the set of probes comprise the following genes: a) the sau1hsdS1 gene of SEQ ID NO: 1, which is considered as a positive control whose presence in a genome is characteristic for CC398 S. aureus, and b) at least one gene considered as a negative control, said gene being absent in the genome of said *S. aureus* species, and c) a restriction-modification (RM) gene and optionally d) a gene for antibiotic resistance.

Yet another embodiment of the invention relates to a DNA micro-array for identification, detection and/or typing of a *S. aureus* bacterial strain comprising the solid support of described herein. Still another embodiment relates to a micro-array for identification and typing of a *S. aureus* CC398 bacterial strain comprising the solid support described herein.

Yet another embodiment of the invention relates to a kit for identification, detection and/or typing of a *S. aureus* bacterial strain comprising the solid support described herein or the DNA micro-array described herein.

Yet another embodiment of the invention relates to a kit for identification, detection and/or typing of a *S. aureus* clonal complex, comprising any suitable combination of clone-specific primers. Still another embodiment relates to a kit for identification, detection and/or typing of a *S. aureus* CC398 clonal complex, comprising any suitable combination of primers selected from the group consisting of SEQ ID NOS: 2, 3, 4, 5 and 6, sequences complementary thereof, and variants thereof, more specifically the specific primers are selected from the group consisting of SEQ ID NOS: 2 and 6, sequences complementary thereof, and variants thereof.

In another embodiment of the invention the kit further comprises any suitable combination of primers selected from the group consisting of SEQ ID NOS: 7 and 8 sequences complementary thereof, and variants thereof for the simultaneous detection and/or quantification of the nucleic acid(s) of any combination of the bacterial resistance genes selected from the group consisting of mecA for the detection of MRSA.

Yet another embodiment of the invention relates to a kit for identification, detection and/or typing of a bacterial strain, comprising
a. means for taking a sample from a subject
b. means for mailing said sample to institution for identification, detection and/or typing of any *S. aureus* clonal complex and optionally for detection of MRSA in a sample.

Yet another embodiment of the invention relates to a kit for identification, detection and/or typing of a bacterial strain, comprising
a. means for taking a sample from a subject
b. means for at the place where the sample is being taken, identification, detection and/or typing of any *S. aureus* clonal complex and optionally for detection of MRSA in a sample.

Yet another embodiment of the invention relates to a device for the detection of the presence of a specific *S. aureus* strain or lineage, wherein the device comprises means for measuring the presence of strain or lineage specific nucleic acid(s).

Yet another embodiment of the invention relates to a device for the detection of the presence of a specific *S. aureus* strain or lineage and a bacterial resistance gene selected from the group consisting of MecA, for the detection of MRSA, wherein the device comprises means for measuring the presence of strain or lineage specific nucleic acid(s).

In another embodiment the strain or lineage specific nucleic acid(s) are CC398 specific In another embodiment the device is a dipstick.

EXAMPLES

Example 1

Design of Primers Specific for the sau1hsdS1 Gene in *S. aureus* CC398

A 489-bp region within the sau1hsdS1 gene was tentatively amplified in 8 *S. aureus* strains belonging to CC398-related spa types using the non-specific primers AF (SEQ ID NO: 6) and BF (SEQ ID NO: 22) published by Cockfield et al. (2008). However, this experiment yielded negative results. The experiment was repeated using the forward primer AF (SEQ ID NO: 6) and 4 novel reverse primers (SEQ ID NOS: 2-5) targeting two conserved regions in the 5'-end of the gene. By this approach PCR products of approximately 475-bp were obtained from all strains. Alignment of the sequences from the 8 strains revealed that they were 100% identical (see FIG. 3), indicating that this region is highly conserved within CC398 (SEQ ID NO: 1). interestingly, the sau1hsdS1 sequence in CC398 was distantly related (37% amino acid identity) to the sequence of the same gene in other *S. aureus* lineages. Four putative CC398-reverse primers (ST398 r1 to ST398 r4 (SEQ ID NOS: 2-5)) were designed and tested on the same 8 strains used in the previous experiment. The primer ST398 r1 (SEQ ID NO: 2) yielded an amplification product of approximately 320-bp in all strains. This primer was selected for further validation of the test on a large collection of *S. aureus* of animal and human origin. All PCR reactions were performed using Applied Biosystems Ampli-Taq Gold and associated buffers according to the manufacturer's directions. Primers were used at a concentration of 0.2 µM each. The PCR conditions were as follows: 12 min at 94° C., then 35 cycles of 30 sec at 95° C., 30 sec at 61° C. and 1 min at 72° C. The products were separated on 1.5% agarose gels.

Example 2

Validation of the PCR Test for Identification of *S. aureus* CC398

The primers AF (SEQ ID NO: 6) and ST398 r1 (SEQ ID NO: 2) were tested on a large strain collection composed by 65 CC398 strains previously identified by MLST and/or spa typing and representative of 8 spa types, and by 211 non-CC398 strains of human and animal origin, including CC5, CC8, CC15, CC20, CC22, CC30, CC45, CC80 and CC152 (Table 1). All CC398 strains were positive (100% sensitivity) whereas all non-CC398 strains were negative (100% specificity).

TABLE 2

List of strains used to validate the PCR test

| Strain code | Host | spa repeat succession | spa type | MLST/CC | mecA | CC398 PCR |
|---|---|---|---|---|---|---|
| DTU-70-95-9 | Swine | 08-16-02-25-02-25-24-25 | t2876 | CC398 | Negative | Positive |
| A-7 | Swine | 08-16-02-25-02-25-34-24-24-25 | t1793 | CC398 | Negative | Positive |
| A-6 | Swine | 08-16-02-25-02-25-34-24-24-25 | t1793 | CC398 | Negative | Positive |
| A-17 | Swine | 08-16-02-25-02-25-34-24-24-25 | t1793 | CC398 | Negative | Positive |
| A-3 | Swine | 08-16-02-25-02-25-34-24-24-25 | t1793 | CC398 | Negative | Positive |
| A-2 | Swine | 08-16-02-25-02-25-34-24-24-25 | t1793 | CC398 | Negative | Positive |

TABLE 2-continued

List of strains used to validate the PCR test

| Strain code | Host | spa repeat succession | spa type | MLST/CC | mecA | CC398 PCR |
|---|---|---|---|---|---|---|
| A-4 | Swine | 08-16-02-25-02-25-34-24-24-25 | t1793 | CC398 | Negative | Positive |
| A-12 | Swine | 08-16-02-25-02-25-34-24-24-25 | t1793 | CC398 | Negative | Positive |
| A-16 | Swine | 08-16-02-25-02-25-34-24-24-25 | t1793 | CC398 | Negative | Positive |
| 83 (P4) | Swine | 08-16-02-25-02-25-34-24-24-25 | t1793 | CC398 | Negative | Positive |
| P-99 | Swine | 08-16-02-25-02-25-34-24-25 | t034 | CC398 | Negative | Positive |
| P-77 | Swine | 08-16-02-25-02-25-34-24-25 | t034 | CC398 | Negative | Positive |
| P-60 | Swine | 08-16-02-25-02-25-34-24-25 | t034 | CC398 | Negative | Positive |
| P-88 | Swine | 08-16-02-25-02-25-34-24-25 | t034 | CC398 | Negative | Positive |
| B-11 | Swine | 08-16-02-25-02-25-34-24-25 | t034 | CC398 | Positive | Positive |
| B-7 | Swine | 08-16-02-25-02-25-34-24-25 | t034 | CC398 | Positive | Positive |
| B-6 | Swine | 08-16-02-25-02-25-34-24-25 | t034 | CC398 | Positive | Positive |
| B-10 | Swine | 08-16-02-25-02-25-34-24-25 | t034 | CC398 | Negative | Positive |
| 40315 | Human | 08-16-02-25-02-25-34-24-25 | t034 | CC398 | Positive | Positive |
| 40555 | Human | 08-16-02-25-02-25-34-24-25 | t034 | CC398 | Positive | Positive |
| 40850 | Human | 08-16-02-25-02-25-34-24-25 | t034 | CC398 | Positive | Positive |
| 42541 | Human | 08-16-02-25-02-25-34-24-25 | t034 | CC398 | Positive | Positive |
| 43511 | Human | 08-16-02-25-02-25-34-24-25 | t034 | CC398 | Positive | Positive |
| 43943 | Human | 08-16-02-25-02-25-34-24-25 | t034 | CC398 | Positive | Positive |
| 44184 | Human | 08-16-02-25-02-25-34-24-25 | t034 | CC398 | Positive | Positive |
| 44697 | Human | 08-16-02-25-02-25-34-24-25 | t034 | CC398 | Positive | Positive |
| 44738 | Human | 08-16-02-25-02-25-34-24-25 | t034 | CC398 | Positive | Positive |
| 45009 | Human | 08-16-02-25-02-25-34-24-25 | t034 | CC398 | Positive | Positive |
| 45145 | Human | 08-16-02-25-02-25-34-24-25 | t034 | CC398 | Positive | Positive |
| 45228 | Human | 08-16-02-25-02-25-34-24-25 | t034 | CC398 | Positive | Positive |
| 46428 | Human | 08-16-02-25-02-25-34-24-25 | t034 | CC398 | Positive | Positive |
| 47258 | Human | 08-16-02-25-02-25-34-24-25 | t034 | CC398 | Positive | Positive |
| 47432 | Human | 08-16-02-25-02-25-34-24-25 | t034 | CC398 | Positive | Positive |
| 47695 | Human | 08-16-02-25-02-25-34-24-25 | t034 | CC398 | Positive | Positive |
| 47769 | Human | 08-16-02-25-02-25-34-24-25 | t034 | CC398 | Positive | Positive |
| 47771 | Human | 08-16-02-25-02-25-34-24-25 | t034 | CC398 | Positive | Positive |
| 47772 | Human | 08-16-02-25-02-25-34-24-25 | t034 | CC398 | Positive | Positive |
| 47773 | Human | 08-16-02-25-02-25-34-24-25 | t034 | CC398 | Positive | Positive |
| 50148 | Human | 08-16-02-25-02-25-34-24-25 | t034 | CC398 | Positive | Positive |
| 51726 | Human | 08-16-02-25-02-25-34-24-25 | t034 | CC398 | Positive | Positive |
| 52290 | Human | 08-16-02-25-02-25-34-24-25 | t034 | CC398 | Positive | Positive |
| 52518 | Human | 08-16-02-25-02-25-34-24-25 | t034 | CC398 | Positive | Positive |
| 52944 | Human | 08-16-02-25-02-25-34-24-25 | t034 | CC398 | Positive | Positive |
| 53169 | Human | 08-16-02-25-02-25-34-24-25 | t034 | CC398 | Positive | Positive |
| 55488 | Human | 08-16-02-25-02-25-34-24-25 | t034 | CC398 | Positive | Positive |
| 55600 | Human | 08-16-02-25-02-25-34-24-25 | t034 | CC398 | Positive | Positive |
| 55729 | Human | 08-16-02-25-02-25-34-24-25 | t034 | CC398 | Positive | Positive |
| 55730 | Human | 08-16-02-25-02-25-34-24-25 | t034 | CC398 | Positive | Positive |
| 56755 | Human | 08-16-02-25-02-25-34-24-25 | t034 | CC398 | Positive | Positive |
| 56922 | Human | 08-16-02-25-02-25-34-24-25 | t034 | CC398 | Positive | Positive |
| A213 (H1) | Human | 08-16-02-25-02-25-34-24-25 | t034 | CC398 | Positive | Positive |
| K90 (H2) | Human | 08-16-02-25-02-25-34-24-25 | t034 | CC398 | Positive | Positive |
| A165 (H3) | Human | 08-16-02-25-02-25-34-24-25 | t034 | CC398 | Positive | Positive |
| 53 (P1) | Swine | 08-16-02-25-02-25-34-24-25 | t034 | CC398 | Positive | Positive |
| 62 (P2) | Swine | 08-16-02-25-02-25-34-24-25 | t034 | CC398 | Negative | Positive |
| 78 (P3) | Swine | 08-16-02-25-02-25-34-24-25 | t034 | CC398 | Negative | Positive |
| P-79 | Swine | 08-16-02-25-02-25-34-24-25 | t034 | CC398 | Negative | Positive |
| 288 | Human | 08-16-02-25-02-25-34-25 | t571 | CC398 | Positive | Positive |
| DTU-7 | Swine | 08-16-02-25-02-25-34-25 | t571 | CC398 | Negative | Positive |
| 51225 | Human | 08-16-02-25-24-25 | t108 | CC398 | Positive | Positive |
| DTU-34 | Swine | 08-16-02-25-24-25 | t108 | CC398 | positive | Positive |
| K101 (H4) | Human | 08-16-02-25-34-24-25 | t011 | CC398 | Positive | Positive |
| 7515 | Human | 08-16-02-25-34-24-25 | t011 | CC398 | Positive | Positive |
| P-100 | Swine | 08-16-20-25-02-25-39-24-25 | t034 | CC398 | Negative | Positive |
| P-93 sub hvid | Swine | 08-16-34-24-25 | t1255 | CC398 | Negative | Positive |
| D93 | Dog | 08-16-02-43-34-16-02-17-16 | t1651 | ND | Negative | Negative |
| S57 F8 | Cattle | 04-17 | t524 | ND | Negative | Negative |
| S57 F9 | Cattle | 04-17 | t524 | ND | Negative | Negative |
| DTU-A11 | Cattle | 04-17 | t524 | ND | Negative | Negative |
| C22496-2 | Sheep | 03-16-12-21-17-23-13-17-17-17-23-24 | t2678 | ND | Negative | Negative |
| C22511-1 | Sheep | 03-16-12-21-17-23-13-17-17-17-23-24 | t2678 | ND | Negative | Negative |
| C21336-1 | Cattle | 03-16-12-21-17-23-13-17-17-17-23-25 | t3046 | ND | Negative | Negative |
| CC2247 | Sheep | 03-16-12-21-17-23-13-17-17-23-24 | t3042 | ND | Negative | Negative |
| C22071 | Sheep | 03-16-12-21-17-23-24 | t3045 | ND | Negative | Negative |
| C22492 | Goat | 03-16-21-17-23-13-17-17-17-23-24 | t1166 | ND | Negative | Negative |
| L62 | Horse | 03-16-21-17-23-13-17-17-17-23-24 | t1166 | ND | Negative | Negative |
| C22559 | Sheep | 03-21-17-23-13-17-17-17-23-24 | t3047 | ND | Negative | Negative |
| C22528-3 | Cattle | 04-17 | t524 | ND | Negative | Negative |
| D91 | Dog | 04-12-12-17 | t227 | CC25 | Negative | Negative |
| L44 | Horse | 04-20-17-111-16-109-24-17 | t1294 | ND | Negative | Negative |
| L8-2 | Horse | 04-20-17-111-16-109-24-17 | t1294 | ND | Negative | Negative |
| C21875 | Horse | 04-20-17-111-16-109-24-17 | t1294 | ND | Negative | Negative |

TABLE 2-continued

List of strains used to validate the PCR test

| Strain code | Host | spa repeat succession | spa type | MLST/CC | mecA | CC398 PCR |
|---|---|---|---|---|---|---|
| L174 | Horse | 04-20-17-111-16-109-24-17 | t1294 | ND | Negative | Negative |
| C22365 | Horse | 04-20-17-25-16-16-109-24-50 | t3044 | ND | Negative | Negative |
| C22748-3 | Cattle | 04-20-17-31-24 | t2873 | ND | Negative | Negative |
| L134-1-2 | Horse | 04-20-69-31-70-13-17-16-16 | t2484 | ND | Negative | Negative |
| L147 sub 1 | Horse | 04-20-69-31-70-13-17-16-16-16-16 | t3043 | ND | Negative | Negative |
| L43 | Horse | 04-20-69-31-70-13-17-16-16-16-16 | t3043 | ND | Negative | Negative |
| L155 sub 1 | Horse | 04-20-69-31-70-13-17-16-16-16-16 | t3043 | ND | Negative | Negative |
| DTU-28 | Poultry | 04-44-33-31-12-16-34-17-25-22-34 | t2038 | ND | Negative | Negative |
| DTU-1B1 | Swine | 07-16-23-02-34 | t899 | CC9 | Negative | Negative |
| P-71 | Swine | 07-16-23-23-02-12-23-02-34 | t337 | CC9 | Negative | Negative |
| P-84 | Swine | 07-16-23-23-02-12-23-02-34 | t337 | CC9 | Negative | Negative |
| P-70 | Swine | 07-16-23-23-02-12-23-02-34 | t337 | CC9 | Negative | Negative |
| P-81 | Swine | 07-16-23-23-02-12-23-02-34 | t337 | CC9 | Negative | Negative |
| P-66 Yellow | Swine | 07-16-23-23-02-12-23-02-34 | t337 | CC9 | Negative | Negative |
| P-80 | Swine | 07-16-23-23-02-12-23-02-34 | t337 | CC9 | Negative | Negative |
| P-91 | Swine | 07-16-23-23-02-12-23-02-34 | t337 | CC9 | Negative | Negative |
| P-65 | Swine | 07-16-23-23-02-12-23-02-34 | t337 | CC9 | Negative | Negative |
| P-75 | Swine | 07-16-23-23-02-12-23-02-34 | t337 | CC9 | Negative | Negative |
| P-63 | Swine | 07-16-23-23-02-12-23-02-34 | t337 | CC9 | Negative | Negative |
| P-61 | Swine | 07-16-23-23-02-12-23-02-34 | t337 | CC9 | Negative | Negative |
| P-74 | Swine | 07-16-23-23-02-12-23-02-34 | t337 | CC9 | Negative | Negative |
| P-73 | Swine | 07-16-23-23-02-12-23-02-34 | t337 | CC9 | Negative | Negative |
| P-90 | Swine | 07-16-23-23-02-12-23-02-34 | t337 | CC9 | Negative | Negative |
| P-87 | Swine | 07-16-23-23-02-12-23-02-34 | t337 | CC9 | Negative | Negative |
| P-89 | Swine | 07-16-23-23-02-12-23-02-34 | t337 | CC9 | Negative | Negative |
| P-72 | Swine | 07-16-23-23-02-12-23-02-34 | t337 | CC9 | Negative | Negative |
| P93 | Swine | 07-16-23-23-02-12-23-02-34 | t337 | CC9 | Negative | Negative |
| C22928-2 | Swine | 07-16-23-23-02-12-23-02-34 | t337 | CC9 | Negative | Negative |
| P-98 | Swine | 07-16-23-23-02-12-23-02-34 | t337 | CC9 | Negative | Negative |
| DTU-12 | Swine | 07-16-23-23-02-12-23-02-34 | t337 | CC9 | Negative | Negative |
| S57 F3 | Cattle | 07-16-23-23-23-02-34 | t2839 | CC9 | Negative | Negative |
| DTU-9 | Swine | 07-16-23-23-23-02-34 | t2839 | CC9 | Negative | Negative |
| DTU-27 | Poultry | 07-23-12-12-34-34-33-34 | t203 | CC80 | Negative | Negative |
| DTU-A44 | Cattle | 07-23-12-21-17-34-34-34-34-34-33-34 | t527 | CC80 | Negative | Negative |
| D57 | Dog | 07-23-12-34-34-12-12-12-23-02-12-23 | t774 | CC15 | Negative | Negative |
| D56 | Dog | 07-23-12-34-34-12-12-23-02-12-23 | t084 | CC15 | Negative | Negative |
| C22917 sub | Horse | 07-23-12-34-34-12-12-23-02-12-23 | t084 | CC15 | Negative | Negative |
| 42394 | Human | 07-23-12-34-34-33-34 | t044 | CC80 | Positive | Negative |
| 42492 | Human | 07-23-12-34-34-33-34 | t044 | CC80 | Positive | Negative |
| 2710-2001 | Human | 07-23-12-34-34-33-34 | t044 | CC80 | Positive | Negative |
| 4003-2001 | Human | 07-23-12-34-34-33-34 | t044 | CC80 | Positive | Negative |
| 41722 | Human | 07-23-12-34-34-34-33-34 | t376 | CC80 | Positive | Negative |
| D35 | Dog | 07-23-21-17-34-12-23-02-12-23 | t091 | CC20 | Negative | Negative |
| 44886 | Human | 07-56-12-17-16-16-33-31-57-12 | t355 | ST152/377 | Positive | Negative |
| 53153 | Human | 07-56-12-17-16-16-33-31-57-12 | t355 | ST152/377 | Positive | Negative |
| 289 | Human | 08-02-25-24-25 | t567 | CC398 | Positive | Positive |
| 42481 | Human | 08-16-02-16-02-25-17-24 | t019 | CC30 | Positive | Negative |
| 42655 | Human | 08-16-02-16-02-25-17-24 | t019 | CC30 | Positive | Negative |
| 2294-2001 | Human | 08-16-02-16-02-25-17-24 | t019 | CC30 | Positive | Negative |
| 40323 | Human | 08-16-02-16-34 | t230 | CC45 | Positive | Negative |
| 45954 | Human | 08-16-02-16-34 | t230 | CC45 | Positive | Negative |
| 45955 | Human | 08-16-02-16-34 | t230 | CC45 | Positive | Negative |
| 41602 | Human | 08-16-02-16-34-13-17-34-16-34 | t015 | CC45 | Positive | Negative |
| 41623 | Human | 08-16-02-16-34-13-17-34-16-34 | t015 | CC45 | Positive | Negative |
| 52759 | Human | 08-16-02-16-34-13-17-34-16-34 | t015 | CC45 | Positive | Negative |
| 1781-2001 | Human | 09-02-16-34-13-17-34-16-34 | t065 | CC45 | Positive | Negative |
| C22823 | Poultry | 11-10-21-17-34-24-34-22-25 | t304 | CC8 | Negative | Negative |
| 40326 | Human | 11-12-21-17-34-24-34-22-25 | t024 | CC8 | Positive | Negative |
| 41047 | Human | 11-12-21-17-34-24-34-22-25 | t024 | CC8 | Positive | Negative |
| 41103 | Human | 11-12-21-17-34-24-34-22-25 | t024 | CC8 | Positive | Negative |
| 42474 | Human | 11-12-21-17-34-24-34-22-25 | t024 | CC8 | Positive | Negative |
| 42738 | Human | 11-12-21-17-34-24-34-22-25 | t024 | CC8 | Positive | Negative |
| 44611 | Human | 11-12-21-17-34-24-34-22-25 | t024 | CC8 | Positive | Negative |
| 47894 | Human | 11-12-21-17-34-24-34-22-25 | t024 | CC8 | Positive | Negative |
| 53148 | Human | 11-12-21-17-34-24-34-22-25 | t024 | CC8 | Positive | Negative |
| 51414 | Human | 11-19-12-05-17-34-24-34-22-25 | t064 | CC8 | Positive | Negative |
| 43484 | Human | 11-19-12-21-17-34-24-34-22-25 | t008 | CC8 | Positive | Negative |
| 43596 | Human | 11-19-12-21-17-34-24-34-22-25 | t008 | CC8 | Positive | Negative |
| 44065 | Human | 11-19-12-21-17-34-24-34-22-25 | t008 | CC8 | Positive | Negative |
| 44329 | Human | 11-19-12-21-17-34-24-34-22-25 | t008 | CC8 | Positive | Negative |
| 44628 | Human | 11-19-12-21-17-34-24-34-22-25 | t008 | CC8 | Positive | Negative |
| 45544 | Human | 11-19-12-21-17-34-24-34-22-25 | t008 | CC8 | Positive | Negative |
| 46744 | Human | 11-19-12-21-17-34-24-34-22-25 | t008 | CC8 | Positive | Negative |
| 46763 | Human | 11-19-12-21-17-34-24-34-22-25 | t008 | CC8 | Positive | Negative |
| 43332 | Human | 15-12-16-02-16-02-25-17-24-24 | t012 | CC30 | Positive | Negative |
| 53463 | Human | 15-12-16-02-16-02-25-17-24-24 | t012 | CC30 | Positive | Negative |

TABLE 2-continued

List of strains used to validate the PCR test

| Strain code | Host | spa repeat succession | spa type | MLST/CC | mecA | CC398 PCR |
|---|---|---|---|---|---|---|
| D42 | Dog | 15-12-16-02-24-24 | t030 | CC8 | Negative | Negative |
| 50587 | Human | 15-12-16-02-25-17-24 | t037 | CC8 | Positive | Negative |
| 51772 | Human | 15-12-16-02-25-17-24 | t037 | CC8 | Positive | Negative |
| 52294 | Human | 15-12-16-02-25-17-24 | t037 | CC8 | Positive | Negative |
| 2769-2001 | Human | 15-12-16-02-25-17-24 | t037 | CC8 | Positive | Negative |
| 45141 | Human | 15-12-16-16-02-16-02-25-17-24 | t318 | CC30 | Positive | Negative |
| 47500 | Human | 15-12-16-16-02-16-02-25-17-24 | t318 | CC30 | Positive | Negative |
| 50293 | Human | 15-12-16-16-02-16-02-25-17-24 | t318 | CC30 | Positive | Negative |
| 53318 | Human | 15-12-16-16-02-16-02-25-17-24 | t318 | CC30 | Positive | Negative |
| D90 | Dog | 15-12-16-17-25-17-24 | t3055 | CC30 | Negative | Negative |
| C21209-6 | Swine | 15-12-16-34-02-25-17-24 | t1333 | CC30 | Negative | Negative |
| C21209-5 | Swine | 15-12-16-34-02-25-17-24 | t1333 | CC30 | Negative | Negative |
| C22348 | Swine | 15-12-16-34-02-25-17-24 | t1333 | CC30 | Negative | Negative |
| C22356-2 | Swine | 15-12-16-34-02-25-17-24 | t1333 | CC30 | Negative | Negative |
| C21209-1 | Swine | 15-12-16-34-02-25-17-24 | t1333 | CC30 | Negative | Negative |
| C212094 | Swine | 15-12-16-34-02-25-17-24 | t1333 | CC30 | Negative | Negative |
| DTU-13 | Swine | 15-12-16-34-02-25-17-24 | t1333 | CC30 | Negative | Negative |
| DTU-15 | Swine | 15-12-16-34-02-25-17-24-17-24 | t2840 | CC30 | Negative | Negative |
| 3715-2001 | Human | 26-17-20-17-12-17-16 | t045 | CC5 | Positive | Negative |
| 51302 | Human | 26-17-20-17-12-17-16? | t045 | CC5 | Positive | Negative |
| 3081-03 | Human | 26-17-20-17-12-17-17-16 | t003 | CC5 | Positive | Negative |
| 40012 | Human | 26-17-20-17-12-17-17-16 | t003 | CC5 | Positive | Negative |
| 41348 | Human | 26-17-20-17-12-17-17-16 | t003 | CC5 | Positive | Negative |
| 41389 | Human | 26-17-20-17-12-17-17-16 | t003 | CC5 | Positive | Negative |
| 43102 | Human | 26-17-20-17-12-17-17-16 | t003 | CC5 | Positive | Negative |
| 43209 | Human | 26-17-20-17-12-17-17-16 | t003 | CC5 | Positive | Negative |
| 43519 | Human | 26-17-20-17-12-17-17-16 | t003 | CC5 | Positive | Negative |
| 44607 | Human | 26-17-20-17-12-17-17-16 | t003 | CC5 | Positive | Negative |
| 4563-2001 | Human | 26-17-20-17-12-17-17-16 | t003 | CC5 | Positive | Negative |
| 43052 | Human | 26-17-25-17-25-16-28 | t541 | CC22 | Positive | Negative |
| D66 | Dog | 26-17-34-17-12-17-17-16 | t1335 | ND | Negative | Negative |
| L31-3-2 | Horse | 26-23-12-21-17-34-34-34-34-33-34 | t2112 | ND. | Negative | Negative |
| L31-1 | Horse | 26-23-12-21-17-34-34-34-33-34 | t2112 | ND. | Negative | Negative |
| 42295 | Human | 26-23-13-23-05-17-25-17-25-16-28 | t223 | CC22 | Positive | Negative |
| 2244-2001 | Human | 26-23-13-23-31-05-17-25-16-16-28 | t016 | CC30 | Positive | Negative |
| 40322 | Human | 26-23-13-23-31-05-17-25-17-25-16-28 | t005 | CC22 | Positive | Negative |
| 43514 | Human | 26-23-13-23-31-05-17-25-17-25-16-28 | t005 | CC22 | Positive | Negative |
| 40135 | Human | 26-23-13-23-31-29-17-31-29-17-25-16-28 | t022 | CC22 | Positive | Negative |
| 42223 | Human | 26-23-13-23-31-29-17-31-29-17-25-17-25-16-28 | t022 | CC22 | Positive | Negative |
| 45193 | Human | 26-23-13-23-31-29-17-31-29-17-25-17-25-16-28 | t022 | CC22 | Positive | Negative |
| DTU-72 | Poultry | 26-23-17-17-16 | t2049 | CC5 | Negative | Negative |
| D16 | Dog | 26-23-17-34-17-20-17-12-16 | t548 | CC5 | Negative | Negative |
| C13167 | Poultry | 26-23-17-34-17-20-17-12-17-16 | t002 | CC5 | Negative | Negative |
| C13060 | Poultry | 26-23-17-34-17-20-17-12-17-16 | t002 | CC5 | Negative | Negative |
| C13197 | Poultry | 26-23-17-34-17-20-17-12-17-16 | t002 | CC5 | Negative | Negative |
| C13197 | Poultry | 26-23-17-34-17-20-17-12-17-16 | t002 | CC5 | Negative | Negative |
| C13167 | Poultry | 26-23-17-34-17-20-17-12-17-16 | t002 | CC5 | Negative | Negative |
| C13167 | Poultry | 26-23-17-34-17-20-17-12-17-16 | t002 | CC5 | Negative | Negative |
| C13156 | Poultry | 26-23-17-34-17-20-17-12-17-16 | t002 | CC5 | Negative | Negative |
| C13156 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13212 | Poultry | 26-23-17-34-17-20-17-12-17-16 | t002 | CC5 | Negative | Negative |
| C13212 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13060 | Poultry | 26-23-17-34-17-20-17-12-17-16 | t002 | CC5 | Negative | Negative |
| C13351 | Poultry | 26-23-17-34-17-20-17-12-17-16 | t002 | CC5 | Negative | Negative |
| C13212 | Poultry | 26-23-17-34-17-20-17-12-17-16 | t002 | CC5 | Negative | Negative |
| C13115 | Poultry | 26-23-17-34-17-20-17-12-17-16 | t002 | CC5 | Negative | Negative |
| C13262 | Poultry | 26-23-17-34-17-20-17-12-17-16 | t002 | CC5 | Negative | Negative |
| C13167 | Poultry | 26-23-17-34-17-20-17-12-17-16 | t002 | CC5 | Negative | Negative |
| C13033 | Poultry | 26-23-17-34-17-20-17-12-17-16 | t002 | CC5 | Negative | Negative |
| C13033 | Poultry | 26-23-17-34-17-20-17-12-17-16 | t002 | CC5 | Negative | Negative |
| C13033 | Poultry | 26-23-17-34-17-20-17-12-17-16 | t002 | CC5 | Negative | Negative |
| C13262 | Poultry | 26-23-17-34-17-20-17-12-17-16 | t002 | CC5 | Negative | Negative |
| C13131 | Poultry | 26-23-17-34-17-20-17-12-17-16 | t002 | CC5 | Negative | Negative |
| C13041 | Poultry | 26-23-17-34-17-20-17-12-17-16 | t002 | CC5 | Negative | Negative |
| C13041 | Poultry | 26-23-17-34-17-20-17-12-17-16 | t002 | CC5 | Negative | Negative |
| C13041 | Poultry | 26-23-17-34-17-20-17-12-17-16 | t002 | CC5 | Negative | Negative |
| C13212 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13167 | Poultry | 26-23-17-34-17-20-17-12-17-16 | t002 | CC5 | Negative | Negative |
| C13167 | Poultry | 26-23-17-34-17-20-17-12-17-16 | t002 | CC5 | Negative | Negative |

TABLE 2-continued

List of strains used to validate the PCR test

| Strain code | Host | spa repeat succession | spa type | MLST/CC | mecA | CC398 PCR |
|---|---|---|---|---|---|---|
| C13262 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13156 | Poultry | 26-23-17-34-17-20-17-12-17-16 | t002 | CC5 | Negative | Negative |
| C13212 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13060 | Poultry | 26-23-17-34-17-20-17-12-17-16 | t002 | CC5 | Negative | Negative |
| C13131 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| C13131 | Poultry | 26-23-17-34-17-20-17-12-17-16 | t002 | CC5 | Negative | Negative |
| C13197 | Poultry | 26-23-17-34-17-20-17-12-17-16 | t002 | CC5 | Negative | Negative |
| C13197 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352 | Poultry | 26-23-17-34-17-20-17-12-17-16 | t002 | CC5 | Negative | Negative |
| 22352-Poul | Poultry | 26-23-17-34-17-20-17-12-17-16 | t002 | CC5 | Negative | Negative |
| C21898 | Poultry | 26-23-17-34-17-20-17-12-17-16 | t002 | CC5 | Negative | Negative |
| C21898 | Poultry | 26-23-17-34-17-20-17-12-17-16 | t002 | CC5 | Negative | Negative |
| C21898 | Poultry | 26-23-17-34-17-20-17-12-17-16 | t002 | CC5 | Negative | Negative |
| C21899 | Poultry | 26-23-17-34-17-20-17-12-17-16 | t002 | CC5 | Negative | Negative |
| C21899 | Poultry | 26-23-17-34-17-20-17-12-17-16 | t002 | CC5 | Negative | Negative |
| C22352 | Poultry | 26-23-17-34-17-20-17-12-17-16 | t002 | CC5 | Negative | Negative |
| C22428 | Poultry | 26-23-17-34-17-20-17-12-17-16 | t002 | CC5 | Negative | Negative |
| C22438 | Poultry | 26-23-17-34-17-20-17-12-17-16 | t002 | CC5 | Negative | Negative |
| C22505 | Poultry | 26-23-17-34-17-20-17-12-17-16 | t002 | CC5 | Negative | Negative |
| C13262 | Poultry | 26-23-17-34-17-20-17-12-17-16 | t002 | CC5 | Negative | Negative |
| C21899 | Poultry | 26-23-17-34-17-20-17-12-17-16 | t002 | CC5 | Negative | Negative |
| DTU-21 | Poultry | 26-23-17-34-17-20-17-12-17-16 | t002 | CC5 | Negative | Negative |
| 42584 | Human | 26-23-17-34-17-20-17-12-17-16 | t002 | CC5 | Positive | Negative |
| 42965 | Human | 26-23-17-34-17-20-17-12-17-16 | t002 | CC5 | Positive | Negative |
| 44634 | Human | 26-23-17-34-17-20-17-12-17-16 | t002 | CC5 | Positive | Negative |
| 45542 | Human | 26-23-17-34-17-20-17-12-17-16 | t002 | CC5 | Positive | Negative |
| 47901 | Human | 26-23-17-34-17-20-17-12-17-16 | t002 | CC5 | Positive | Negative |
| 51412 | Human | 26-23-17-34-17-20-17-12-17-16 | t002 | CC5 | Positive | Negative |
| C13292 | Poultry | 26-23-17-34-17-20-17-12-17-17 | t002 | CC5 | Negative | Negative |
| C13292 | Poultry | 26-23-17-34-17-20-17-12-17-17 | t002 | CC5 | Negative | Negative |
| DTU-71 | Poultry | 26-23-17-34-17-20-17-12-17-17-16 | t306 | CC5 | Negative | Negative |
| 47143 | Human | 26-23-23-13-23-31-29-17-31-29-17-25-17-25-16-28 | t032 | CC22 | Positive | Negative |
| 47908 | Human | 26-23-23-13-23-31-29-17-31-29-17-25-17-25-16-28 | t032 | CC22 | Positive | Negative |
| 53349 | Human | 26-23-23-13-23-31-29-17-31-29-17-25-17-25-16-28 | t032 | CC22 | Positive | Negative |
| 1983-2000 | Human | 26-30-17-34-17-20-17-12-17-16 | t001 | CC5 | Positive | Negative |
| 23757-1999 | Human | 26-30-17-34-17-20-17-12-17-16 | t001 | CC5 | Positive | Negative |
| 40638 | Human | 26-30-17-34-17-34-17-20-17-12-17-16 | t041 | CC5 | Positive | Negative |

ND, not determined.

Example 3

Development of the Multiplex PCR for Discrimination Between MRSA and MSSA CC398 Strains In order to allow differentiation between MRSA and MSSA variants of CC398, the CC398-specific primer set AF (SEQ ID NO: 6) ST398 r1 (SEQ ID NO: 2) was combined with primers mecup1 (SEQ ID NO: 7)-mecup2 (SEQ ID NO: 8) targeting the methicillin resistance mecA gene. Such primers have been designed in a previous study to develop a diagnostic kit (EVIGENE MRSA) produced by Statens Serum Institut for rapid MRSA identification (Poulsen et al. 2003). The multiplex PCR was tested on 4 S. aureus strains representing MSSA non-CC398 (strain ATCC 6538), MRSA non-CC398 (strain ATCC 33591), MSSA CC398 (SSI 52615) and MRSA (KVL 288). The results of this experiment are shown in FIG. 1.

REFERENCES

Bannerman T L. 2003. Staphylococcus, Micrococcus and other catalase-positive cocci that grow aerobically. In Manual of Clinical Microbiology, 8th edition. Eds. Murray P R, Baron E J, Jorgensen J H, Pfaller M A, Yolken R H. Pp. 384-404. American Society for Microbiology, Washington, D.C.

Chambers 1997. Methicillin resistance in staphylococci: molecular and biochemical basis and clinical implications. Clin. Microbiol. Rev. 10: 781-791.

Cockfield J D, Pathak S, Edgeworth J D, and Lindsay J A. 2008. Rapid determination of hospital-acquired meticillin-resistant S. aureus lineages. J. Med. Microbiol. 56: 614-619.

Deborggraeve S, Claes F, Laurent T, Mertens P, Leclipteux T, Dujardin J C, Herdewijn P, and Buscher P. 2006 Molecular dipstick test for diagnosis of sleeping sickness, J. Clin. Microbiol. 44: 2884-2889.

Enright, M C, Day N P J, Davies C E, Peacock S J, and Spratt B G. 2000. Multilocus sequence typing for characterization of methicillin-resistant and methicillin-susceptible clones of S. aureus. J. Clin. Microbiol. 38: 1008-1015.

European Commission 2007. Commission decision of 20 Dec. 2007 concerning a financial contribution from the Community towards a survey on the prevalence of Salmonella spp. and Methicillin-resistant S. aureus in herds of breeding pigs to be carried out in the Member States (2008/55/EC). Official Journal of The European Union 17 Jan. 2008.

Kalogianni D P, Bravous V, Christopoulos T K, Ioannou P C, and Zoumbos N C. 2007. Dry-reagent disposable dipstick test for visual screening of seven leukemia-related chromosomal translocations. Nucleic Acids Res. 35: e23.

Koreen L, Ramaswamy S V, Graviss E A, Naidich S, Musser J M, and Kreiswirth B N. 2004. spa typing method for discriminating among S. aureus isolates: implications for use of a single marker to detect genetic micro- and macro-variation. J. Clin. Microbiol. 42: 792-799.

Lewis H C, Molbak K, Reese C, Aarestrup F M, Selchau M, Sarum M, et al. Pigs as source of methicillin-resistant S. aureus CC398 in humans, Denmark. Emerg. Inf. Dis. 2008; 14: 1383-1389

Moodley, A., Nightingale, E. C., Stegger, M., Nielsen, S. S, Skov, R., Guardabassi, L. 2008. High risk of nasal carriage of methicillin resistant S. aureus among Danish veterinary practitioners. Scand. J. Work Environ. Health 34: 151-157.

Murchan S, Kaufmann M E, Deplano A, de Ryck R, Struelens M, Zinn C E, Fussing V, Salmenlinna S, Vuopio-Varkila J, El Solh N, Cuny C, Witte W, Tassios P T, Legakis N, van Leeuwen W, van Belkum A, Vindel A, Laconcha I, Garaizar J, Haeggman S, Olsson-Liljequist B, Ransjo U, Coombes G, Cookson B. 2003. Harmonization of pulsed-field gel electrophoresis protocols for epidemiological typing of strains of methicillin-resistant S. aureus: a single approach developed by consensus in 10 European laboratories and its application for tracing the spread of related strains. J Clin Microbiol. 41:1574-85

Poulsen A B, Skov R, and Pallesen L V. 2003. Detection of methicillin resistance in coagulase-negative staphylococci and in staphylococci directly from simulated blood cultures using the EVIGENE MRSA Detection Kit, J. Antimicrob. Chemother. 51: 419-421.

Vannuffel P, Gigi J, Ezzedine H, Vandercam B, Delmee M, Wauters G, Gala J L. 1996. Specific detection of methicillin-resistant Staphylococcus species by multiplex PCR. J. Clin. Microbiol. 34:1599.

van Loo I, Huijsdens X, Tiemersma E, de Neeling A, van de Sande-Bruinsma N, Beaujean D, Voss A, Kluytmans J. Emergence of methicillin-resistant S. aureus of animal origin in humans. Emerg Infect Dis. 2007; 13:1834-1839

Voss A, Loeffen F, Bakker J, Klaassen C, and Wulf M. 2005. Methicillin-resistant Staphylcoccus aureus in pig farming. Emerg. Infect. Dis. 11:1965-6.

Waldron D E and Lindsay J A. 2006. Saul: a novel lineage-specific type I restriction-modification system that blocks horizontal gene transfer into S. aureus and between S. aureus isolates of different lineages. J. Bacteriol. 188: 5578-5585

Wulf M W, Sørum M, van Nes A, Skov R, Melchers W J, Klaassen C H et al. Prevalence of methicillin-resistant S. aureus among veterinarians: an international study. Clin Microbiol Infect. 2008; 14:29-34.

All patent and non-patent references cited in the application, or in the present application, are also hereby incorporated by reference in their entirety.

The invention claimed is:

1. A method for differentiating between Methicillin-resistant S. aureus (MRSA) and Methicillin-susceptible S. aureus (MSSA) variants of S. aureus clonal complex 398 (CC398) in a sample from an animal subject, comprising:
contacting the S. aureus nucleic acid in said sample or in a substantially homogeneous population of said S. aureus nucleic acid isolated from said sample with first forward primer SEQ ID NO: 6 and first reverse primer sequence selected from the group consisting of SEQ ID NO: 2 through 5, synthesizing a first extension product of said first forward primer and said first reverse primer, amplifying said first extension product, and detecting the presence of said first extension product; and
contacting said S. aureus nucleic acid in said sample with primers SEQ ID NO: 7 and SEQ ID NO: 8, synthesizing a second extension product of primers SEQ ID NO: 7 and SEQ ID NO: 8, amplifying said second extension product, and detecting the presence of said second extension product;
wherein the presence of said first extension product in combination with the absence of said second extension product indicates the presence of MSSA in said sample, and wherein the presence of said first extension product in combination with the presence of said second extension product indicates the presence of MRSA in said sample.

2. The method according to claim 1, wherein said first reverse primer is SEQ ID NO: 2.

3. The method according to claim 1, wherein if the presence of MRSA in said sample is indicated, the method further comprises treatment of said subject for MRSA.

4. The method according to claim 1, wherein said subject is a mammal.

5. A method for differentiating between Methicillin-resistant S. aureus (MRSA) and Methicillin-susceptible S. aureus (MSSA) variants of S. aureus clonal complex 398 (CC398) in a sample from an animal subject, comprising:
labelling the S. aureus nucleic acid in said sample or in a substantially homogeneous population of said S. aureus isolated from said sample;
hybridizing the labelled nucleic acid with at least one first probe selected from the group consisting of SEQ ID NOS: 2-6 coated on a solid support and at least one second probe selected from SEQ ID NO: 7 and 8 coated on a solid support; and
detecting the presence of said labelled nucleic acid in association with said at least one first probe and/or said at least one second probe;
wherein the presence of said labelled nucleic acid in association with said at least one first probe in combination with the absence of said labelled nucleic acid in association with at least one second probe indicates the presence of MSSA in said sample, and
wherein the presence of said labelled nucleic acid in association with said at least one first probe in combination with the presence of said labelled nucleic acid in association with at least one second probe indicates the presence of MRSA in said sample.

6. The method according to claim 5, wherein said at least one first probe is SEQ ID NO: 2 or SEQ ID NO: 6.

7. The method according to claim 5, wherein if the presence of MRSA in said sample is indicated, the method further comprises treatment of said subject for MRSA.

8. The method according to claim 7, wherein said subject is a mammal.

9. A method for differentiating between Methicillin-resistant S. aureus (MRSA) and Methicillin-susceptible S. aureus (MSSA) variants of S. aureus clonal complex 398 (CC398) in a sample from an animal subject, comprising:
labelling at least one first probe selected from the group consisting of SEQ ID NOS: 2-6 and labelling at least one second probe selected from SEQ ID NO: 7 and 8;
hybridizing said at least one first probe and said at least one second probe with said sample coated on a solid support or with a substantially homogeneous population of said S. aureus isolated from said sample coated on a solid support; and
detecting the presence of said at least one first probe and/or said at least one second probe;
wherein the presence of said at least one first probe in combination with the absence of said at least one second probe indicates the presence of MSSA in said sample, and
wherein the presence of said at least one first probe in combination with the presence of said at least one second probe indicates the presence of MRSA in said sample.

10. The method according to claim 9, wherein said at least one first probe is SEQ ID NO: 2 or SEQ ID NO: 6.

11. The method according to claim 9, wherein if the presence of MRSA in said sample is indicated, the method further comprises treatment of said subject for MRSA.

12. The method according to claim 11, wherein said subject is a mammal.

* * * * *

SEQUENCE LISTING

```
<160> NUMBER OF SEQ ID NOS: 71

<210> SEQ ID NO 1
<211> LENGTH: 489
<212> TYPE: DNA
<213> ORGANISM: Staphylococcus aureus

<400> SEQUENCE: 1
gcgaatggga agagaagaag ctaggtgagt ttgctggtaa agttacccaa aaaaatgttg      60
ataaaaaata tattgagaca ttaactaatt cagctgagtt aggtatcata tctcaaaagg     120
attattttga caaagaaatt tcgaatatag ataatattaa aaagtactat gtagttgaag     180
agaatgattt tgtttataac cctagaatgt ctaattatgc tccatttgga ccagtaaata     240
gaaataagtt agggaaaaaa ggggtcatgt cacctcttta tactgtgttt aaaattcaaa     300
acattgattt aaactttatt gagtttttatt ttaaatcttc aaaatggtat agatttatgg     360
cattaaacgg tgattcaggt gctcgagcag ataggttttc tattaaagat aggacattta     420
tggaaatgcc acttcatatc ccatgtatgg atgaacaaat aaaaatcggt cagttcttca     480
gcaaactcg                                                            489

<210> SEQ ID NO 2
<211> LENGTH: 27
<212> TYPE: DNA
<213> ORGANISM: Staphylococcus aureus

<400> SEQUENCE: 2
cagtattaaa gaggtgacat gacccct                                         27

<210> SEQ ID NO 3
<211> LENGTH: 23
<212> TYPE: DNA
<213> ORGANISM: Staphylococcus aureus
```

```
<400> SEQUENCE: 3
cacctgaatc accgtttaat gcc                                          23

<210> SEQ ID NO 4
<211> LENGTH: 21
<212> TYPE: DNA
<213> ORGANISM: Staphylococcus aureus

<400> SEQUENCE: 4
cgagcacctg aatcaccgtt t                                            21

<210> SEQ ID NO 5
<211> LENGTH: 22
<212> TYPE: DNA
<213> ORGANISM: Staphylococcus aureus

<400> SEQUENCE: 5
tgggatatga agtggcattt cc                                           22

<210> SEQ ID NO 6
<211> LENGTH: 20
<212> TYPE: DNA
<213> ORGANISM: Staphylococcus aureus

<400> SEQUENCE: 6
agggtttgaa ggcgaatggg                                              20

<210> SEQ ID NO 7
<211> LENGTH: 21
<212> TYPE: DNA
<213> ORGANISM: Staphylococcus aureus

<400> SEQUENCE: 7
gggatcatag cgtcattatt c                                            21

<210> SEQ ID NO 8
<211> LENGTH: 21
<212> TYPE: DNA
<213> ORGANISM: Staphylococcus aureus

<400> SEQUENCE: 8
aacgattgtg acacgatagc c                                            21

<210> SEQ ID NO 9
<211> LENGTH: 23
<212> TYPE: DNA
<213> ORGANISM: Staphylococcus aureus

<400> SEQUENCE: 9
caatttgtcg gtcgagtttg ctg                                          23

<210> SEQ ID NO 10
<211> LENGTH: 26
<212> TYPE: DNA
<213> ORGANISM: Staphylococcus aureus

<400> SEQUENCE: 10
tgtgagaaga ttttctgcat atagcc                                       26

<210> SEQ ID NO 11
<211> LENGTH: 27
<212> TYPE: DNA
```

<213> ORGANISM: Staphylococcus aureus

<400> SEQUENCE: 11 gcctttttc tgttgttgaa gtaattc    27

<210> SEQ ID NO 12
<211> LENGTH: 20
<212> TYPE: DNA
<213> ORGANISM: Staphylococcus aureus

<400> SEQUENCE: 12
gtcggtcgag tttgctgaag    20

<210> SEQ ID NO 13
<211> LENGTH: 1233
<212> TYPE: DNA
<213> ORGANISM: Staphylococcus aureus
<220> FEATURE:
<221> NAME/KEY: misc_feature
<222> LOCATION: (480)..(480)
<223> OTHER INFORMATION: n is a, c, g, or t

<400> SEQUENCE: 13

| | | |
|---|---|---|
| atgagtaata cacaaacgaa aaatgtgcca gagttgagat tcccagggtt tgaaggcgaa | 60 |
| tgggaagaga agaaggttgg cgagttatta gaatttaaaa atggtttaaa taaaggaaaa | 120 |
| gaatattttg gctcaggatc gtcgattgtt aacttcaaag atgtatttaa taacaggagc | 180 |
| ttaaatacaa ataatctgac tggaaaagtt aatgtgaata gcaagaaact aaaaaattat | 240 |
| tctgttgaaa agggtgatgt ttttttttaca aggactagtg aggtaattgg tgaaataggt | 300 |
| tatccgtctg taattttaaa tgaccctgaa aatactgtgt tagtggatt tgtattaaga | 360 |
| gggcggccta aatcaggaat tgatttaata aataataatt ttaaaagata tgtctttttt | 420 |
| actaattcat ttagaaaaga aatgattaca aaaagttcta tgacaactag agctttaacn | 480 |
| tcaggtagcg caattaataa aatgaaggtc atatacctg tttcggctaa agaacagaga | 540 |
| aaaataggtg acttcttcag caaactcgac cgacaaattg aattagaaga caaaagctt | 600 |
| gaattacttc aacaacaaaa aaaaggctat atgcagaaaa tcttctcaca ggaactgcga | 660 |
| ttcaaagatg agaatagtga agattatcca cattgggaaa atagcaaaat agaaaaatat | 720 |
| ttaaaagaga gaaacgaacg ttctgacaaa ggtcaaatgc tttcagtaac tataaatagt | 780 |
| ggcattataa aatttagtga attggataga aaagataatt caagtaaaga taaaagtaat | 840 |
| tataaagtag ttaggaaaaa tgatattgca tataattcta tgagaatgtg caagggggct | 900 |
| agtggtagat caaattataa tgggattgtt agccctgcat atactgtgct ttatccaaca | 960 |
| caaaatacta gctcattatt tattggatat aagtttaaaa cacatagaat gattcataaa | 1020 |
| tttaaaatta attcacaagg attaacatca gatacatgga acttaaaata taacaatta | 1080 |
| aaaaatataa atatagatat acctgtattg gaggaacaag aaaagatagg tgatttcttt | 1140 |
| aaaaaaatgg atatattgat tagtaaacag aaaataaaaa ttgaaatatt agaaaaagag | 1200 |
| aaacaatcct ttttacaaaa gatgttctta taa | 1233 |

<210> SEQ ID NO 14
<211> LENGTH: 1260
<212> TYPE: DNA
<213> ORGANISM: Staphylococcus aureus
<220> FEATURE:
<221> NAME/KEY: misc_feature
<222> LOCATION: (487)..(487)
<223> OTHER INFORMATION: n is a, c, g, or t

<400> SEQUENCE: 14

```
atgagtaata cacaaaagaa aaatgtgcca gagttgagat tcccagggtt tgaaggcgaa      60
tgggaagaga agaaggttgg cgagttatta gaatttaaaa atggtttaaa taaaggaaag     120
gaatattttg gctcaggatc gtcgattgtt aacttcaaag atgtatttaa taaccggagc     180
ataaatacaa ataatctgac tggaaaagtt aatgtgaata gcaagaaact gaagaattat     240
tccgttgaaa agggtgatgt ttttttaca aggactagtg aggtgattgg tgaaataggt      300
tatccgtctg taattttaaa tgaccctgaa atactgtgt ttagtggatt tgtattaaga      360
gggcggccta atcaggaat tgatttaata aataataatt ttaaaagata tgtctttttt       420
actaattcat ttagaaaaga aatgattaca aaagttcta tgacaactag agctttaaca      480
tcaggtnccg caattaataa aatgaaagtc atataccctg tttctgctaa agaacagaaa     540
aaaataggtg acttcttcag caaactcgat cgacaaattg aactagaaga caaaaacactt   600
gaattacttc aacaacagaa aaaaggatat atgcagaaaa tcttctcaca gaattgcga     660
ttcaaagatg agaatggaaa tgattatccg aattggagaa caattgaatt aaaaaatatt    720
ttagaaaaca ttgtggataa tagagggaaa acaccagata tgctcctag tgaaaaatat     780
cctttattag aagtgaatgc attaggatat tatcgtccag catatataaa agtaagtaaa    840
tttgttagtg aaaacactta taataactgg tttagagaac attaaaaga aaatgatatt      900
cttttttcta ctgtaggaaa tactggaata gttagtctta tggataatta caaagctgta    960
atagctcaaa atatcgtagg attaagggta ataataata acctcccttc atttatttac    1020
tatatgctat cgtataaggg aaatcagaaa aaaataaaaa gaattcaaat gggggctgta   1080
caaccaagtg tgaaagtttc tcaatttaag tttataaaat atttagtacc aataaaagat   1140
gaacaagaga aggtagctaa actgttgatt gaaatagata aattagtgaa taaacaatta   1200
ataaaaatag aattacttca acaacgaaaa aaagccttac ttaaatcgat gtttatttaa   1260
```

<210> SEQ ID NO 15
<211> LENGTH: 1161
<212> TYPE: DNA
<213> ORGANISM: Staphylococcus aureus

<400> SEQUENCE: 15

```
atgagtaata cacaaacgaa aaatgtgcca gagttgagat tcccagggtt tgaaggcgaa      60
tgggaagaga agaagttaga agatattata aaagttaatt ctggaaaaga ttataaacat     120
ttggataaag gcgatatacc agtctatggt actggcggtt atatgacaag tgtttcagaa     180
ccactaagtg aaattgatgc tgttggtatt gggagaaaag ggactataaa caaaccatat     240
ttgcttgagg cgccgttttg gacggtggat acattatttt attgtacacc taaaaaagaa     300
acagacatac tatttatatt aagtttattt agaaaaataa attggaaagt atacgatgaa    360
tcaacaggtg tgccaagctt aagtaaacaa accattaata aaataaatag atttgtccct    420
acaaataaag agcagcaaaa aataggcaag ttcttcagca aacttgaccg acaaattgaa    480
ttagaagaac aaaaacttga gttatttcag caacagaaaa aaggctatat gcagaaaatc   540
ttttcgcaag aattgcgatt caagatgag agtggtaatg attatccaga ttgggaagag    600
aaggaattag gggaagtagc tgatagagta ataaggaaaa ataaaaactt gaatcgaaa     660
aagcctttaa caatatccgg acagttaggt ttaattgatc aaacagaata ttttagtaaa   720
tcagtttcgt cgaaaaatct agaaaattat acactaataa agaatggaga attcgcgtat   780
```

```
aataaaagtt attctaatgg atacccatta ggggctatta aaagattaac tagatatgat    840
agtggtgtat tgtcctcttt gtatatttgc ttttctatta aaagtgaaat gtctaaagac    900
ttcatggaag catattttga ttcgacacac tggtatagag aagtttcagg aattgcagtt    960
gagggtgcaa gaaatcacgg attattaaat atttctgtga atgatttttt tactattcta   1020
attaaatatc caagtttaga agagcagaga aaaataggtg acttcttcat caaacttgac   1080
cgacaaattg aactagaaga acaaaaaacta gaattacttc aacaacgaaa aaaagcctta   1140
cttaaatcga tgttaattta a                                             1161
```

```
<210> SEQ ID NO 16
<211> LENGTH: 1224
<212> TYPE: DNA
<213> ORGANISM: Staphylococcus aureus

<400> SEQUENCE: 16
atgagtaata cacaaaagaa aaatttgcca gagttgagat tcccagggtt tgaaggcgaa     60
tgggaagaaa agaagttagg gaatcttact accaaaatag gtagtggaaa gactcccaaa    120
ggtggaagtg aaaactatac aaacaaaggc ataccatttt taaggagtca aaatattaga    180
aatggtaaat taaatcttaa tgacttagtt tatattagta aagatataga tgatgagatg    240
aaaaatagta gaacgtacta tggtgatgtt cttttaaata ttacaggagc atcaataggt    300
agaacagcca ttaattcgat agttgaaacg catgctaatt taaatcaaca tgtatgtatt    360
attagattaa aaaagagta ttattataat ttttttggac agtatctatt atcaagaaaa    420
ggtaaaagaa aattttcct tgcacaaagt ggaggtagtc gagaaggact aaacttcaaa    480
gaaattgcta atttaaaaat cttcaccca actatatttg aagaacaaca aaaaatagga    540
caattcttca gcaaacttga ccaacaaatt gaattagaag aacaaaaact tgaattactt    600
caacaacaga aaaaggcta tgcagaaaa atcttctcac aggaactgcg attcaaagat    660
gagaatagtg aagattatcc acattgggaa gtagcaaaa tagaaaaata tttaaaagag    720
agaaacgaac gttctgacaa aggtcaaatg ctttcagtaa ctataaatag tggcattata    780
aaatttagtg aattggatag aaaagataat tcaagtaaag ataaaagtaa ttataaagta    840
gttaggaaaa atgatattgc atataattct atgagaatgt ggcaaggggc tagtggtaaa    900
tcaaattata tgggattgt tagccctgca tatactgtgc tttatccaac acaaaatact    960
agctcattat ttattggata aagtttaaa acacatagaa tgattcataa atttaaaatt   1020
aattcacaag gattaacatc agatacatgg aacttaaat ataacaatt aaaaatata    1080 aatatagata tacctgtatt ggaggaacaa gaaaagatag gtgatttctt taaaaaaatg   1140
gatatattga taagtaaaca gaaaatgaaa attgaaatat tagaaaaaga gaaacaatcc   1200
tttttacaaa aaatgttctt ataa                                          1224
```

```
<210> SEQ ID NO 17
<211> LENGTH: 1260
<212> TYPE: DNA
<213> ORGANISM: Staphylococcus aureus

<400> SEQUENCE: 17
atgagtaata cacaaaagaa aaatgtgcca gagttgagat tcccagggtt tgaaggcgaa     60
tgggaagaga agaagttagg ggatcttaca gatagagtaa ttaggaaaaa taaaaactta    120
gaatcgaaaa agcctttaac aatatccgga cagttaggtt taattgatca acagaatac    180 tttagtaaat cagtttcgtc gaaaaatcta gaaaattata cactaataaa gaatggagaa    240
```

```
ttcgcgtata acaaaagtta ttctaatgga tacccattag gggctattaa aagattaact    300
agatatgata gtggtgtatt gtcctctttg tatatttgtt tttctattaa aagtgaaatg    360
tctaaagact tcatggaagc atattttgat tcgacacact ggtatagaga agtttctgga    420
attgcagttg agggtgcaag aaatcacgga ttattaaatg tttctgtgaa tgattttttt    480
actattctaa ttaaatatcc aagtttagaa gaacagcaaa aaataggcaa gttcttcagc    540
aaactcgacc gacaaattga attagaagaa caaaagcttg aattacttca acaacagaaa    600
aaaggctata tgcagaaaat cttctcacag gaattgcgat ttaagaatga gaatggtaat    660
gattatcctg attgggaaag aattaaattt tttgatgtaa ttgataaagt aatagatttt    720
agagggagaa caccaaaaaa attaaatatg gaatggtctg acgaagggta tttagcatta    780
tcagcagtca atgtaaaaaa aggctatatt gattttaatg tagaggcgaa atatggaaat    840
ctagatttat atactagatg gatgagagga aatgaattat ataaggggca agtattattt    900
acaactgaag cgccaatggg caatgtagca caggttccgg ataataaagg atatatatta    960
agtcaaagaa ctatcgcgtt taattcaaat gaaaaaatca ctgataactt tttagcatca   1020
ttgttgagct ctgaaaatgt ttataatgat ttattaaaat tgtgtagtgg tgctacagca   1080
aaaggtgtga gtcaaaaaaa tttaaatcga ctatacgtta ctattccaca ttccatatca   1140
gagcaagaag agattgctga attcttttaga aaaattaatc aattggttga gttgcaaaaa   1200
tataaaattg aacatactaa aagtcaaaaa caagtgtttt tacaaaagat gtttatttaa   1260

<210> SEQ ID NO 18
<211> LENGTH: 1170
<212> TYPE: DNA
<213> ORGANISM: Staphylococcus aureus
<220> FEATURE:
<221> NAME/KEY: misc_feature
<222> LOCATION: (700)..(700)
<223> OTHER INFORMATION: n is a, c, g, or t

<400> SEQUENCE: 18
atgagtaata acaaaagaa aaatgtgcca gagttgagat tcccagggtt tgaaggcgaa     60
tgggaagaga agaagttagg ggaagtaggt acatttactt caggtgggac acccctgaaa    120
tcaaaatcag agtattggaa tggagatatt ccatggatta caacaggtga tattcataac    180 ataaaagag aaaatataac taattttata acagagaaag gtttaaatga atcatcggca    240
aaattaataa ctaatgaggc gattttaata gctatgtatg gtcaaggtaa aactagagga    300
atgtcagcaa tattgaattt tgaggcaaca actaaccaag catgtgctat atatcaaacc    360
aatcaaaata ttaattttgt ttttcaatac tttcagaaat tatatgaatt tttacgctca    420
ttatctaatg aaggaagtca aaagaattta agtttaagct tgttgaaaga aattacttta    480
aattatccta atgaacaaga acagaaaaaa ataggtgatt ttttcagcaa actcgaccgg    540
caaattgaat tagaagaaca aaaacttgaa ttgcttcaac aacagaaaaa aggctatatg    600
cagaaaatct tctcgcaaga attgcgattt aaggatgaga atggaaatga ttatccggag    660
tgggaagaaa ctactataaa agaaattgct caaattaacn ctggaaagaa agatacaaaa    720
gatgccatta ctaatgggag ttatgatttt tacgttagat ctccgatagt ttataaaatt    780
aatactttta gttatgaagg agaggctatt ttaactgtag gagatggagt tggcgtaggt    840
aaagttttcc actatgtaaa tgggaaattt gattatcatc aaagagtata caaaatatct    900
gactttaaga attattatgg actattgtta tttattatt tttcacaaaa ctttttaaaa    960
```

| | |
|---|---|
| gaaacaaaga aatatagtgc gaagacatca gttgattcag ttagaaaaga catgattgct | 1020 |
| aatatgaaag taccgcgtcc tatttatata gaacaaaaaa aaatcggtca attcattaaa | 1080 |
| agagtagaca acaaaacaaa aattcagaaa caagtgattg aattacttaa acaacgcaaa | 1140 |
| aaggcattac ttcaaaagat gtttatttaa | 1170 |

<210> SEQ ID NO 19
<211> LENGTH: 1213
<212> TYPE: DNA
<213> ORGANISM: Staphylococcus aureus

<400> SEQUENCE: 19

| | |
|---|---|
| atgagtaata cacaaaagaa aaatgtgcca gagttgagat tcccagagtt tgaaggcgaa | 60 |
| tgggaagaga agcagttagg ggatcttaca gatagagtaa ttaggaaaaa taaaaactta | 120 |
| gaatcgaaaa aagcctttaa caatatccgg acagttaggt ttaattgatc aaacagaata | 180 |
| tttttagtaaa tcagtttcgt cgaaaaatct agaaaattat acactaataa gaatggaga | 240 |
| attcgcgtat aacaaaagtt attctaatgg atacccatta ggggctatta aaagattaac | 300 |
| tagatatgat agtggtgtat tgtcctcttt gtatatttgt ttttctatta aaagtgaaat | 360 |
| gtctaaagac ttcatggaag catatttga ttcgacacac tggtatagag aagtttctgg | 420 |
| aattgcagtt gagggtgcaa gaaatcacgg attattaaat gtttctgtga atgatttttt | 480 |
| tactattcta attaaatatc caagtttaga agaacagcaa aaaataggca gttcttcag | 540 |
| caaactcgac cgacaaattg aattagaaga acaaaagctt gaattacttc aacaacagaa | 600 |
| aaaaggctat atgcagaaaa ttttctcaca ggaactgcga ttcaaagatg agaatggtga | 660 |
| agattatcca gattgggaaa atagcaaaat agaaaatat ttaaaagaga gaaacgaacg | 720 |
| ttctgacaaa gggcaaatgc tttcagtaac tataaatagt ggcattataa aatttagtga | 780 |
| attggataga aaagataatt caagtaaaga taaagtaat tataaagtag ttaggaaaaa | 840 |
| tgatattgca tataattcta tgagaatgtg gcaaggggc agtggtaaat caaattataa | 900 |
| tgggattgtt agccctgcat atactgtgct ttatccaaca caaatacta gctcattatt | 960 |
| tattggatat aagtttaaaa cacatagaat gattcataaa tttaaaatta attcacaagg | 1020 |
| attaacatca gatacatgga acttaaaata taaacaatta aaaaatataa atatagatat | 1080 |
| acctgtattg gaggaacaag aaaagatagg tgatttcttt aaaaaaatgg atatattgat | 1140 |
| aagtaaacag aaaatgaaaa ttgaaatatt agaaaaagag aaacaatcct ttttacaaaa | 1200 |
| aatgttctta taa | 1213 |

<210> SEQ ID NO 20
<211> LENGTH: 1230
<212> TYPE: DNA
<213> ORGANISM: Staphylococcus aureus Mu50

<400> SEQUENCE: 20

| | |
|---|---|
| atgagtaata cacaaacgaa aaatgtgcca gagttgagat tcccaggatt tgagggcgaa | 60 |
| tgggaagaga agaagttagg gaatcttact accaaaatag gtagtggaaa gactcccaaa | 120 |
| ggtggaagtg aaaactatac aaacaaaggc ataccatttt taaggagtca aaatattaga | 180 |
| aatggtaaat taaatcttaa tgacttagtt tatattagta agatataga tgatgagatg | 240 |
| aaaaatagta gaacgtacta tggtgatgtt cttttaaata ttacaggagc atcaataggt | 300 |
| agaacagcca ttaattcgat agttgaaacg catgctaatt taaatcaaca tgtatgtatt | 360 |
| attagattaa aaaagagta ttattataat tttttttggac agtatctatt atcaagaaaa | 420 |

```
ggtaaaagaa aaattttcct tgcacaaagt ggaggtagtc gagaaggact aaacttcaaa        480
gaaattgcta atttaaaaat cttcacccca actatatttg aagaacaaca aaaaatagga        540
caattcttca gcaaacttga ccaacaaatt gaattagaag aacaaaaact tgaattactt        600
caacaacaga aaaaatgcta tatacagaaa atcttctcac aagaattacg attcaaagat        660
gaagaaggta attactataa aggatggaac aaaaagcaat taaaagatgt attagaattt        720
agtaataaaa gaactattaa tgaaaatgaa tatcctgttt taatatcgtc aagacaaggt        780
ttaatacttc agtcagacta ctataaagat aggaaaactt ttgcagagag taatattggg        840
tatttcatac tccctaaaaa tcatataaca taccgttcaa gaagcgacga tggaattttt        900
aagtttaatt taaatctaat gattgatgta ggtattatta gtaaatatta ccctgtcttt        960
aaagggatag atgcaaatca atattattta acattacact taaactatca actgaaaaaa       1020
gaatatatta aatatgcaac tggtacatca caattggtac tctcacaaaa agacttgcaa       1080
aacataaaga ctaaattgcc atcttatgaa gaacaacaaa aaatcggtga tttttttcagt     1140 gaaatagata gattggttga aaaacaatct tcaaaagtcg gacgattaaa agtacgtaaa       1200
aaagaactat tacaaaaaat gtttgtttaa                                       1230

<210> SEQ ID NO 21
<211> LENGTH: 1230
<212> TYPE: DNA
<213> ORGANISM: Staphylococcus aureus N315

<400> SEQUENCE: 21
atgagtaata cacaaacgaa aaatgtgcca gagttgagat tcccaggatt tgagggcgaa         60
tgggaagaga agaagttagg gaatcttact accaaaatag gtagtggaaa gactcccaaa        120
ggtggaagtg aaaactatac aaacaaaggc ataccatttt taaggagtca aaatattaga        180
aatggtaaat taaatcttaa tgacttagtt tatattagta agatatagta tgatgagatg        240
aaaaatagta gaacgtacta tggtgatgtt cttttaaata ttacaggagc atcaataggt        300
agaacagcca ttaattcgat agttgaaacg catgctaatt taaatcaaca tgtatgtatt        360
attagattaa aaaaagagta ttattataat ttttttggac agtatctatt atcaagaaaa        420
ggtaaaagaa aaattttcct tgcacaaagt ggaggtagtc gagaaggact aaacttcaaa        480
gaaattgcta atttaaaaat cttcacccca actatatttg aagaacaaca aaaaatagga        540
caattcttca gcaaacttga ccaacaaatt gaattagaag aacaaaaact tgaattactt        600
caacaacaga aaaaatgcta tatacagaaa atcttctcac aagaattacg attcaaagat        660
gaagaaggta attactataa aggatggaac aaaaagcaat taaaagatgt attagaattt        720
agtaataaaa gaactattaa tgaaaatgaa tatcctgttt taacatcgtc aagacaaggt        780
ttaatacttc agtcagacta ctataaagat aggaaaactt ttgcagagag taatattggg        840
tatttcatac tccctaaaaa tcatataaca taccgttcaa gaagcgacga tggaattttt        900
aagtttaatt taaatctaat gattgatgta ggtattatta gtaaatatta ccctgtcttt        960
aaagggatag atgcaaatca atattattta acattacact taaactatca actgaaaaaa       1020
gaatatatta aatatgcaac tggtacatca caattggtac tctcacaaaa agacttgcaa       1080
aacataaaga ctaaattgcc atcttatgaa gaacaacaaa aaatcggtga tttttttcagt     1140 gaaatagata gattggttga aaaacaatct tcaaaagtcg gacgattaaa agtacgtaaa       1200
aaagaactat tacaaaaaat gtttgtttaa                                       1230
```

<210> SEQ ID NO 22
<211> LENGTH: 20
<212> TYPE: DNA
<213> ORGANISM: Staphylococcus aureus

<400> SEQUENCE: 22
cccaaaggtg gaagtgaaaa                                                   20

<210> SEQ ID NO 23
<211> LENGTH: 1260
<212> TYPE: DNA
<213> ORGANISM: Staphylococcus aureus

<400> SEQUENCE: 23

| | | | | | |
|---|---|---|---|---|---|
| atgagtaata | cacaaaagaa | aaatgtgcca | gagttgaggt | tcccagggtt | tgaaggcgaa | 60 |
| tgggaagaga | agaagttagg | ggaccttact | accaaaatag | gtagtggaaa | gactcccaaa | 120 |
| ggtggaagtg | aaaactatac | aaacaaaggc | ataccatttt | taaggagtca | aaatattaga | 180 |
| aatggtaaat | taaatcttaa | tgacttagtt | tatattagta | agatataga | tgatgagatg | 240 |
| aaaaatagta | gaacgtacta | tggtgatgtt | cttttaaata | ttacaggagc | atcaataggt | 300 |
| agaacagcca | ttaattcgat | agttgaaata | catgctaatt | taaatcaaca | tgtatgtatt | 360 |
| attagattga | aaaagagta | ttattataat | ttttttggac | agtatctatt | atcaagaaaa | 420 |
| ggtaaaagga | aaattttcct | tgcacaaagt | ggaggtagtc | gagaaggact | aaacttcaaa | 480 |
| gaaattgcta | atttaaaaat | cttcaccccca | actatatttg | aagagcagca | aaaaatagggc | 540 |
| gaattcatca | gcaaacttga | ccgacaaatt | gaattagaag | aacaaaaact | tgaattactt | 600 |
| cagcaacaga | aaaaggcta | tatgcagaaa | atcttctcgc | aagaattgcg | attcaaagat | 660 |
| gaggaaggta | aagattatcc | agattggaaa | tcaaaatcaa | ttcaagaaat | atttgagaat | 720 |
| aagggtggca | ctgctctaga | aacagaattt | aattttgacg | gtaattataa | agttataagt | 780 |
| ataggaagtt | attctataaa | tagcacttat | aatgatcaaa | ataagagt | caataaaaat | 840 |
| aaaaaaactg | aaaatatat | tttatcaaaa | ggcgacttag | caatggtatt | aaatgataaa | 900 |
| acaaaagatg | ggaaaattat | aggtagaagt | atatttatg | ataaagataa | tcaatatatt | 960 |
| tataatcaaa | gaactgaaag | attaatacca | tttgctgaaa | atgataataa | attttatgg | 1020 |
| ttcttaatga | atacagattt | aattagaaat | aaaataaaag | gtatgatgca | aggagcaacc | 1080 |
| caagtttata | taaattattc | atctattaaa | ttgatatcta | tacaattgcc | acttcttgaa | 1140 |
| gaacaacaga | aaataagagg | gtttctagaa | gttttatctg | gaataactac | taaacaattg | 1200 |
| cacaagatag | accaattaaa | agagaggaaa | aaggcgtttt | tacagaaaat | gtttatttga | 1260 |

<210> SEQ ID NO 24
<211> LENGTH: 1194
<212> TYPE: DNA
<213> ORGANISM: Staphylococcus aureus

<400> SEQUENCE: 24

| | | | | | |
|---|---|---|---|---|---|
| atgagtaata | cacaaacgaa | aaatgtgcca | gagttgagat | tcccagggtt | tgaaggcgaa | 60 |
| tgggaagaga | agaagttagg | ggatcttggc | ctgtttcaaa | aaagttattc | ttttcgaga | 120 |
| gctaaagaag | gaaacggtaa | aactaaacat | attcattatg | gtgatattca | ttcaaaattt | 180 |
| aaaacagtct | tagatagtga | tggtaatatc | cctaatataa | ttgagaaagc | tgtatttgag | 240 |
| ttgattcaaa | aaggagacat | tgttttttgcg | gatgcatcag | aagattatag | tgacctagga | 300 |
| aaagcagtta | tgatagattt | caaaccgaat | tcattgattt | ctggcttaca | tacacaccta | 360 |

```
tttagaccgc ttaacaatgc aatttctaat ttttttgattt tttacacaaa aactctgagt      420
tataaaaaat tcattagaca gcaaggtaca ggaatatcag tacttggtat atcaaaaaaa      480
agtttattaa atttgaatgt attaatacca cgaagtgaat tagaacaaca aaaagtaggc      540
aagttcttca gcaaactcga ccgacaaatt gaattagaag aacaaaaaat cgaattactt      600
caacaacaga aaaaggcta tatacagaaa atcttctcac aagaattgcg atttaaggat       660
gagaatggag atgattatcc ggagtgggaa gaaactacta aaaagaaat tgctcaaatt      720 aacacaggaa agaaagatac aaaagatgcc attactaatg ggagttatga ttttttacgtt   780 agatctccga tagtttataa aattaatact tttagttatg aaggagaggc tattttaact     840
gtaggagatg gagttggcgt aggtaaagtt ttccactatg taaatgggaa atttgattat     900
catcaaagag tatacaaaat atctgacttt aagaattatt atggattatt gttattttat    960 tattttttcac aaaacttttt aaaagaaaca agaaatata gtgcgaagac atcagttgat   1020
tcagttagaa aagacatggt tgctaatatg aaagtaccac gtcctattta tatagaacag     1080
gaaaaaatcg gtcaattcat taaaaaagta gacaacaaaa taaaaattca gaaacaagtg    1140
attgaattac ttaaacaacg caaaaaggca ttacttcaaa agatgtttat ttaa           1194

<210> SEQ ID NO 25
<211> LENGTH: 1239
<212> TYPE: DNA
<213> ORGANISM: Staphylococcus aureus

<400> SEQUENCE: 25
atgagtaata cacaaaagaa aaatgtgcca gagttgagat tcccaggatt tgaaggcgaa     60
tgggaagaga agcagttagg ggatcttact accaaaatag gtagtggaaa gactcccaaa    120
ggtggaagtg aaaactatac aaacaaaggc ataccatttt taaggagtca aaatattaga    180
aatggtaaat taaatcttaa tgacttagtt tatattagta agatataga tgatgagatg      240 aaaaatagta gaacgtacta tggtgatgtt ctttttaaata ttacaggagc atcaataggt     300
agaacagcca ttaattcgat agttgaaacg catgctaatt taaatcaaca tgtatgtatt     360
attagattga aaaagagta ttattatatt ttttttggac agtatctatt atcaagaaaa    420
ggaaaaagga aattttcct tgcacaaagt ggaggtagtc gagaaggtct aaacttcaaa     480
gaaattgcta atttaaaaat cttcaccccca actatatttg aagaacagca aaaaatagac    540
aagttcttca gcaaacttga ccgacaaatt gaattagaag aacaaaaact tgaattactt    600
caacaacaga aaaaggcta tttgcagaaa atcttctcac aggaattgcg atttaaggat     660
gagaatggaa atgattatcc agagtggaga tttgctagat ttaaggactt tatgtataaa    720
ccaataaaca tacgacctgc aataaatatt agtaagtcag aattgctaac tgtaaaatta    780
cattgtaaag ggatagagaa agctaatata aatcgagtat taaaactagg agctacgaat   840
tattataaga gatttgaagg tcaatttatt tatgggaaac aaaactttt caatggagca     900 tttgacatag tgccaaaaaa atttgatgga ctttattcat caagtgatgt gccagcgttt    960
gaaataaata ccgaaaagat tgaacctaac tatttttatca gctatatctc tagaccaagc  1020
ttttataaaa gtaaggaaaa atattctact ggtacaggta gtaaaagaat acatgaaaat    1080
acggtgttaa atttctcttt acatttacct tgtttaaacg aacaattaaa aattgcttct   1140
ttcgtttgtt ttctcaatag aaaaattgaa ttactagaaa gaaaaatcta tctaataaag   1200
aaacaaaagc aagctttgct tcaacaaatg tttatttaa                            1239
```

<210> SEQ ID NO 26
<211> LENGTH: 1253
<212> TYPE: DNA
<213> ORGANISM: Staphylococcus aureus

<400> SEQUENCE: 26

```
atgagtaata cacaaaagaa aaatgtgcca gagttgagat ttccagggtt tgaaggcgaa      60
tgggaagaga agaagttagg ggaaattttt caaataattt ctggttcaac accactaaaa     120
tcaaataaaa agttttatga aatggtaat attaattggg tcaaaacgac agatttaaat      180
aattctaaag ttacgcatag taaagaaaaa ataactgaat atgctatgaa agtttgaaa      240
ttaaaattag tgcctaaaaa ttcagtactt atagctatgt atggtggttt taatcaaatt     300
ggtcgaacag gtttgttaaa aatagatgcc acaataaatc aagcaatttc agccttatta     360
atgaatcatg aaacgaatcc agaatttata caagcatatc taaattatca agttaagggg     420
tggaagagat atgcagcaag tagcagaaaa gacccgaata taactaaaaa agacatagaa     480
caatttaaag ttccttatgt tagtattaat gaacagcaaa aaataggcga attcttcagc     540
aagcttgacc gacaaattga gttagaagaa caaaaactag aattacttca acaacaaaaa     600
aaggctatat gcagaaaatc ttctcacaag aattgcgatt caaagatgag aatggtgaag     660
attcccgga gtgggaagag aagcaacttg gagaattggg agtaacatat gctggccttt      720
ctggtaaagc taaagaagat ttcggatttg gtaaagatgt gtacgtaagt tatgtgaatg     780
ttttcaaaaa caacatagca acattagaaa tggtggaaaa tgtaagtatt aaacctggcg     840
aaaaacaaaa taatgtaaaa tttggagata ttttattac aacttcttca gaggttcctc      900
atgaggtagg tatgtcctct gtatggttat atgagaaaga taatgtatat ttgaatagtt     960
tttgttttgg atttaggact acagttagtt ttataaaccc tatattttg gctagatatc     1020
taagaagctt tgaaatgaga aaattaataa caatcttagc tcagggatca acgagattta     1080
atatttcaaa aaaagaattg atgaaactga ttgtgaaaat acctagattg gatgagcaaa     1140
atagaataat aaaccttttt tcaatttag atggtggtat tgaattacaa tccatgaagg     1200
taaggaaact aaaaaagcgt aaacaaggat tgcttcaaaa aatgtttatt taa           1253
```

<210> SEQ ID NO 27
<211> LENGTH: 1229
<212> TYPE: DNA
<213> ORGANISM: Staphylococcus aureus

<400> SEQUENCE: 27

```
atgagtaata cacaaaagaa aaatgtgcca gagttgagat tcccagggtt tgaaggcgaa      60
tgggaagaga agaagttagg ggaaattttt caaataattt ctggttcaac accactaaaa     120
tcaaataaaa agttttatga aatggtaat attaattggg tcaaaacgac agatttaaat      180
aattctaaag ttacgcatag taaagaaaaa ataactgaat atgctatgaa agtttgaaa      240
ttaaaattag tgcctaaaaa ttcagtactt atagctatgt atggtggttt taatcaaatt     300
ggtcgaacag gtttgttaaa aatagatgcc acaataaatc aagcaatttc agccttatta     360
atgaatcatg aaacgaatcc agaatttata caagcatatc taaattatca agttaagggg     420
tggaagagat atgcagcaag tagcagaaaa gacccgaata taactaaaaa agacatagaa     480
caatttaaag ttccttatgt tagtattaat gaacagcaaa aaataggcga attcttcagc     540
aagcttgacc gacaaattga gttagaagaa caaaaactag aattacttca acaacaaaaa     600
aaggctatat gcagaaaatc ttctcacaag aattgcgatt caaagatgag aatggtgaag     660
```

```
attacccgga gtgggaagag acaaaactcc aacaaattat agaggttaaa gacggtactc    720
atgaaagtcc taagcccact gacaatggtt atttattagt aacttcaaaa aatttaaaaa    780
ataataaatt agatttgagt gaatcttata gtatttctaa agaagattat gaaagtataa    840
ataaaagatc taaagttgaa aaaggcgaca ttttatttgg aatgataggg acaataggaa    900
atcctattct attagaagac gaaggattcg ctataaaaaa tgttgctttg ctaaaaacga    960
gttgtttaca agaaaagtat tacatattga acttcctcaa atctatagct attgctaaac   1020
aattttataa aacgaatgct ggaggaactc aaaaatttat ttctttagga gttataagag   1080
atttaaaaat tgattttcca tctttagagg aatcgactaa aataggaatt ttatttaaca   1140
aattagatga attgattaaa aatcaatcaa taaaaattgt tttattaaga cggcgaaaaa   1200
aagccttact taaatcgatg tttatttaa                                     1229
```

<210> SEQ ID NO 28
<211> LENGTH: 1185
<212> TYPE: DNA
<213> ORGANISM: Staphylococcus aureus

<400> SEQUENCE: 28

```
atgagtaata cacaaaagaa aaatgtgcca gagttgagat tcccagggtt tgaaggcgaa     60
tgggaagaga agtctattag tagtttttta aaggaaagta aaataaaagg aagcaatgga    120
agtcatgcta aaaagctaac tgttaagctt tggggaaaag gagtagttcc caaaaaagag    180
acatttaaag gaagtgacaa tactcagtat tataaaagaa aagcagggca attgatgtat    240
ggtaaacttg atttttttaaa ttgtgctttt ggtattgttc ctgattcatt aaataattat    300
gaaagtacta ttgattcccc aagttttgat tttataaatg gtgattctaa attcttactt    360
gaaagaatta aattaaagtc tttttataaa aaatttggag atattgcaaa tggtagtaga    420
aaagcaaaac gtattaatca agatacattc ttatcattgc cagttttttgc accaaagtat    480 gatgaacaat taagaatagg cgaattcttt agcaaactcg atcgacaaat tgaactacaa    540
aaacaaaaac ttgaattact tcaacaacag aaaaaaggct atatgcagaa attttttctca    600 caggaactgc gattcaaaga tgagaatggt gaagattatc cacattggga aaatagcaaa    660
atagaaaaat attttaaaga gagaaacgaa cgttctgaca aaggtcaaat gctttcagta    720
actataaata gtggcattat aaaatttagt gaattggata gaaaagataa ttcaagtaaa    780
aataaaagta attataaagt agttaggaaa aatgatattg catataattc tatgagaatg    840
tggcaagggg ctagtggtaa atcaaattat aatgggattg ttagccctgc atatactgtg    900
ctatatccaa cacaaaatac tagctcatta tttattggat ataagtttaa aacacataga    960
atgattcata aatttaaaat taattcacaa ggattaacat cagatacatg gaacttaaaa   1020
tataaacaat taaaaaatat aaatatagat ataccctgtat tggaggaaca agaaaagata   1080
ggtgatttct ttaaaaaaat ggatatattg attagtaaac agaaaataaa aattgaaata   1140
ttagaaaaag agaaacaatc cttttttacaa aaaatgttct tataa                   1185
```

<210> SEQ ID NO 29
<211> LENGTH: 1260
<212> TYPE: DNA
<213> ORGANISM: Staphylococcus aureus
<220> FEATURE:
<221> NAME/KEY: misc_feature
<222> LOCATION: (1204)..(1204)
<223> OTHER INFORMATION: n is a, c, g, or t

<400> SEQUENCE: 29

```
atgagtaata cacaaaagaa aaatgtgcca gagttgaggt tcccagggtt tgaaggcgaa      60
tgggaagaga agaagttagg ggaccttact accaaaatag gtagtggaaa gactcccaaa     120
ggtggaagtg aaaactatac aaacaaaggc ataccatttt taaggagtca aaatattaga     180
aatggtaaat taaatcttaa tgacttagtt tatattagta agatatagag tgatgagatg     240
aaaaatagta gaacgtacta tggtgatgtt cttttaaata ttacaggagc atcaataggt     300
agaacagcca ttaattcgat agttgaaata catgctaatt taaatcaaca tgtatgtatt     360
attagattga aaaagagta ttattataat ttttttggac agtatctatt atcaagaaaa     420
ggtaaaagga aattttcct tgcacaaagt ggaggtagtc gagaaggact aaacttcaaa     480
gaaattgcta atttaaaaat cttcacccca actatatttg aagagcagca aaaaataggc     540
gaattcatca gcaaacttga ccgacaaatt gaattagaag aacaaaaact tgaattactt     600
cagcaacaga aaaaaggcta tatgcagaaa atcttctcgc aagaattgcg attcaaagat     660
gaggaaggta aagattatcc agattggaaa tcaaaatcaa ttcaagaaat atttgagaat     720
aagggtggca ctgctctaga aacagaattt aatttttgacg gtaattataa agttataagt     780
ataggaagtt attctataaa tagcacttat aatgatcaaa atataagagt caataaaaat     840
aaaaaaactg aaaatatatt tttatcaaaa ggcgacttag caatggtatt aaatgataaa     900
acaaaagatg gaaaattat aggtagaagt atatttatag ataaagataa tcaatatatt     960
tataatcaaa gaactgaaag attaatacca tttgctgaaa atgataataa atttttatgg    1020
ttcttaatga atacagatttt aattagaaat aaaataaaag gtatgatgca aggagcaacc    1080
caagtttata taaattattc atctattaaa ttgatatcta taaattgcc acttcttgaa    1140
gaacaacaga aaataagagg gtttctagaa gttttatctg gaataactac taaacaattg    1200
cacnagatag accaattaaa agagaggaaa aaggcgtttt tacagaaaat gtttatttga    1260
```

<210> SEQ ID NO 30
<211> LENGTH: 1170
<212> TYPE: DNA
<213> ORGANISM: Staphylococcus aureus

<400> SEQUENCE: 30

```
atgagtaata cacaaaagaa aaatgtgcca gagttgagat tcccagggtt tgaaggcgaa      60
tgggaagaga agaagttggg ggaagtagcc aaaatatatg atggtactca tcaaactcct     120
aaatatacaa acgaaggtat aaaatttttg tcagtagaaa atataaaaac gttgaattca     180
agcaagtata tttcagaaga agcatttgaa aaagagttta aatccgacc agaattcgga     240
gatatattaa tgactcgaat tggtgatata ggtacaccaa acatagtgag ttcaaatgaa     300
aaatttgctt actatgttag cttagcatta ttaaaaacta gaatcttaa ttcctatttt     360
ttgaaaaatt taattttatc atcatctatc cagaatgaac tatggagaaa aactttacat     420
gtggcatttc ccaaaaaaat aaacaaaaat gaaattggaa aaattaaaat taattaccct     480
aaaaagcaag aacaacaaaa aattggtcag ttcttcagca aactcgaccg acaaattgaa     540
ttagaagaac aaaaactcga attacttcaa caacagaaaa aaggctatat gcagaaaatt     600
ttctcacagg aactgagatt aaagatgag aatggtaatg attatccgga gtgggaagag     660
agaagatttg ctgatatatt taaatttcat aataaactaa gaaagccaat taagaaaat     720
ttaagagtaa agggttctta tccatattat ggtgctacag gtattattga ttacgttgac     780
gactttatat ttgacgggaa ttatttactt attggagaag atggtgcaaa tattatcact     840
```

| | | |
|---|---|---|
| agaagtgcac ccctagtgta cttagtaaat ggaaagtttt gggtaaataa tcatgctcat | 900 | |
| atattatctc ctttaaatgg aaatatacag tacttgtatc aagttgcaga attagttaat | 960 | |
| tatgaaaaat acaatactgg aactgctcag cctaaattaa acattcaaaa tttaaaaatt | 1020 | |
| attagtgttg taatttcaac gaatttagaa gaacaacaaa aaatcggaag cttttttaagt | 1080 | |
| aaacttgatc gtcaaatcga tttagaagaa caaaaactcg aattacttca acaacgaaaa | 1140 | |
| aaagccttac ttaaattgat gtttgtttaa | 1170 | |

<210> SEQ ID NO 31
<211> LENGTH: 1119
<212> TYPE: DNA
<213> ORGANISM: Staphylococcus aureus

<400> SEQUENCE: 31

| | | |
|---|---|---|
| atgagtaata cacaaaagaa aaatgtgcca gagttgagat tcccagagtt tgaaggcgaa | 60 | |
| tgggaagaga agcagttagg gaatattata aaagttaatt ctggaaaaga ttataaacat | 120 | |
| ttggataaag gcgatatacc agtctatggt actggcggtt atatgacaag tgtttcagaa | 180 | |
| ccactaagtg aaattgatgc tgttggtatt gggagaaaag ggactataaa caaaccatat | 240 | |
| ttgcttgagg cgccgttttg gacggtggat acattatttt attgtacacc taaaaaagaa | 300 | |
| acagacatac tatttatatt aagtttattt agaaaaataa actggaaagt atacgatgaa | 360 | |
| tcaacaggtg tgccaagctt aagcaaacaa accattaata aaataaatag atttgtccct | 420 | |
| acaaataaag agcagcaaaa aataggcaag ttcttcagca aactcgaccg gcaaattgaa | 480 | |
| ttagaagaac aaaaacttga attacttcaa caacagaaaa aaggctatat gcagaaaatc | 540 | |
| ttctcgcaag aattgcgatt caaagatgag aatggtaatg attatccaga ttggacaaat | 600 | |
| gaaagattgg gtgaagttac aactgttact atgggacaaa gtccgaaaag tgtaaattat | 660 | |
| actgataact caaatgatac ggtattaatc caaggaaatg ctgatataga gaatggatta | 720 | |
| attaatcccc gtatttatac aagggaagta accaaattaa ttcagaagga cgaaattatt | 780 | |
| ttaactgtta gagcacctgt aggcaaatta gctatggcac aaattaatgc gtgcattggt | 840 | |
| agaggtgtat gctcaattaa aggagataaa tttttatatt attttctaga atggtttgcc | 900 | |
| actcaaaata aatggatccg tttttcacag gggagtacat tgaatctat ttcagggaat | 960 | |
| gacataagaa atatacacat taaaatacca gtcgaagata acgtactaa aattataaaa | 1020 | |
| ttgttaaata gtttagatgt attaaattca aaaacagatt taaaaatcca aaaccttaaa | 1080 | |
| cagagaaaac aatcgcttct acaaaaaata tttgtttaa | 1119 | |

<210> SEQ ID NO 32
<211> LENGTH: 1203
<212> TYPE: DNA
<213> ORGANISM: Staphylococcus aureus

<400> SEQUENCE: 32

| | | |
|---|---|---|
| atgagtaata cacaaacgaa aaatgtgcca gagttgagat tcccaggatt tgaaggcgaa | 60 | |
| tgggaagaaa agcaggttgg cgagttatta gaatttaaaa atggtttaaa taaggaaaa | 120 | |
| gaatattttg gctcaggatc gtcgattgtt aacttcaaag atgtatttaa taacaggagc | 180 | |
| ataaatacaa ataatctgac tggaaaagtt aatgtgaata gcaaagaact gaagaattat | 240 | |
| tccgttgaaa agggtgatgt tttttttaca aggactagtg aggtaattgg tgaaataggt | 300 | |
| tatccgtctg taatttttaaa tgaccctgaa aatactgtgt ttagtggatt tgtattaaga | 360 | |

```
ggacggccta aatcaggaat tgatttaata aataataatt ttaaaagata tgtcttttt    420 actaattcat ttagaaaaga aatgattaca aaaagttcta tgacaactag agctttaaca    480
tcaggtactg caattaataa aatgaaggtc atatacgctg tttcggctaa agaacagaaa    540
aaaataggtg acttcttcag caaactcgat cgacaaattg aattagaaga acaaaaactt    600
gaattgcttc aacaacagaa aaaggatat atgcagaaaa tcttcacaca agaattgcga     660
tttaaggacg agaatggaaa tgattatccg gagtgggaag aaactactat aaaagaaatt    720
gctcaaatta acacaggaaa gaaagataca aaagatgcca ttactaatgg gagttatgat    780
ttttacgtta gatctccgat agtttataaa attaatactt ttagttatga aggagaggct    840
attttaactg taggagatgg agttggcgta ggtaaagttt tccactatgt aaatgggaaa    900
tttgattatc atcaaagagt atacaaaata tctgacttta agaattatta tggattattg    960 ttatttatt attttttcaca aacttttta aagaaacaa agaaatatag tgcgaagaca     1020
tcagttgatt cagttagaaa agacatggtt gctaatatga agtaccacg tcctattat      1080 atagaacagg aaaaaatcgg tcaattcatt aaaaagtag acaacaaat aaaaattcag     1140 aaacaagtga ttgaattact taaacaacgc aaaaggcat tacttcaaaa gatgtttatt    1200
taa                                                                 1203

<210> SEQ ID NO 33
<211> LENGTH: 1180
<212> TYPE: DNA
<213> ORGANISM: Staphylococcus aureus

<400> SEQUENCE: 33
atgagtaata cacaaaagaa aaatgtgcca gagttgagat tcccagggtt tgaaggcgaa    60
tgggaagaga agaagctagg tgagtttgct ggtaaagtta cccaaaaaaa tgttgataaa    120
aaatatattg agacattaac taattcagct gagttaggta tcatatctca aaaggattat    180
tttgacaaag aaatttcgaa tatagataat attaaaaagt actatgtagt tgaagagaat    240
gattttgttt ataaccctag aatgtctaat tatgctccat ttggaccagt aaatagaaat    300
aagttaggga aaaagggggt catgtcacct ctttatactg tgtttaaaat tcaaaacatt    360
gatttaaact ttattgagtt ttatttaaa tcttcaaaat ggtatagatt tatggcatta    420
aacggtgatt caggtgctcg agcagatagg ttttctatta agataggac atttatggaa    480 atgccacttc atatcccatg tatggatgaa caaataaaaa tcggtcagtt cttcagcaaa    540
cttgaccgac aaattgaatt agaagaacaa aaacttgaat tacttcaaca acagaaaaaa    600
ggctatatgc agaaaatctt ctcgcaagaa ttgcgattta agatgagaa tggtaaagat    660 tatccggagt gggaagaaac tactataaaa gaattgctc aaattaacac tggaaagaaa    720
gatacaaaag atgccattac taatgggagt tatgattttt acgttagatc tccgatagtt    780
tataaaatta atactttag ttatgaagga gaggctattt taactgtagg agatggagtt    840
ggcgtaggta agtttttcca ctatgtaaat gggaaatttg attatcatca agagtatac     900 aaaatatctg actttaagaa ttattatgga ttattgttat tttattattt tcacaaaac    960 ttttaaaag aaacaagaa atatagtgcg aagacatcag ttgattcagt tagaaaagac     1020
atgattgcta atatgaaagt accgcgtcct atttatatag aacaaaaaaa aatcggtcaa    1080
ttcattaaaa gagtagacaa caaaacaaaa attcagaaac aagtgattga attacttaaa    1140
caacgcaaaa agtcattact tcaaaagatg tttatttaag                         1180
```

<210> SEQ ID NO 34
<211> LENGTH: 1233
<212> TYPE: DNA
<213> ORGANISM: Staphylococcus aureus

<400> SEQUENCE: 34

| | | | | | | |
|---|---|---|---|---|---|---|
| atgagtaata | cacaaacgaa | aaatgtgcca | gagttgagat | tcccagggtt | tgaaggcgaa | 60 |
| tgggaagaga | agaaggttgg | cgagttatta | gaatttaaaa | atggtttaaa | taaggaaaa | 120 |
| gaatattttg | gctcaggatc | gtcgattgtt | aacttcaaag | atgtatttaa | taacaggagc | 180 |
| ttaaatacaa | ataatctgac | tggaaaagtt | aatgtgaata | gcaagaact | aaaaaattat | 240 |
| tctgttgaaa | agggtgatgt | ttttttaca | aggactagtg | aggtaattgg | tgaaataggt | 300 |
| tatccgtctg | taattttaaa | tgaccctgaa | atactgtgt | ttagtggatt | tgtattaaga | 360 |
| gggcggccta | aatcaggaat | tgatttaata | aataataatt | ttaaaagata | tgtctttttt | 420 |
| actaattcat | ttagaaaaga | aatgattaca | aaagttcta | tgacaactag | agctttaaca | 480 |
| tcaggtagcg | caattaataa | aatgaaggtc | atatacctg | tttcggctaa | agaacagaga | 540 |
| aaaataggtg | acttcttcag | caaactcgac | cgacaaattg | aattagaaga | acaaaagctt | 600 |
| gaattacttc | aacaacaaaa | aaaaggctat | atgcagaaaa | tcttctcaca | ggaactgcga | 660 |
| ttcaaagatg | agaatagtga | agattatcca | cattgggaaa | atagcaaaat | agaaaaatat | 720 |
| ttaaaagaga | gaaacgaacg | ttctgacaaa | ggtcaaatgc | tttcagtaac | tataaatagt | 780 |
| ggcattataa | aatttagtga | attggataga | aaagataatt | caagtaaaga | taaaagtaat | 840 |
| tataaagtag | ttaggaaaaa | tgatattgca | tataattcta | tgagaatgtg | gcaagggct | 900 |
| agtggtagat | caaattataa | tgggattgtt | agccctgcat | atactgtgct | ttatccaaca | 960 |
| caaaatacta | gctcattatt | tattggatat | aagtttaaaa | cacatagaat | gattcataaa | 1020 |
| tttaaaatta | attcacaagg | attaacatca | gatacatgga | acttaaaata | taacaatta | 1080 |
| aaaaatataa | atatagatat | acctgtattg | gaggaacaag | aaaagatagg | tgatttcttt | 1140 |
| aaaaaaatgg | atatattgat | tagtaaacag | aaaataaaaa | ttgaaatatt | agaaaaagag | 1200 |
| aaacaatcct | ttttacaaaa | gatgttctta | taa | | | 1233 |

<210> SEQ ID NO 35
<211> LENGTH: 1233
<212> TYPE: DNA
<213> ORGANISM: Staphylococcus aureus

<400> SEQUENCE: 35

| | | | | | | |
|---|---|---|---|---|---|---|
| atgagtaata | cacaaacgaa | aaatgtgcca | gagttgagat | tcccagggtt | tgaaggcgaa | 60 |
| tgggaagaga | agaaggttgg | cgagttatta | gaatttaaaa | atggtttaaa | taaggaaaa | 120 |
| gaatattttg | gctcaggatc | gtcgattgtt | aacttcaaag | atgtatttaa | taacaggagc | 180 |
| ttaaatacaa | ataatctgac | tggaaaagtt | aatgtgaata | gcaagaact | aaaaaattat | 240 |
| tctgttgaaa | agggtgatgt | ttttttaca | aggactagtg | aggtaattgg | tgaaataggt | 300 |
| tatccgtctg | taattttaaa | tgaccctgaa | atactgtgt | ttagtggatt | tgtattaaga | 360 |
| gggcggccta | aatcaggaat | tgatttaata | aataataatt | ttaaaagata | tgtctttttt | 420 |
| actaattcat | ttagaaaaga | aatgattaca | aaagttcta | tgacaactag | agctttaaca | 480 |
| tcaggtagcg | caattaataa | aatgaaggtc | atatacctg | tttcggctaa | agaacagaga | 540 |
| aaaataggtg | acttcttcag | caaactcgac | cgacaaattg | aattagaaga | acaaaagctt | 600 |
| gaattacttc | aacaacaaaa | aaaaggctat | atgcagaaaa | tcttctcaca | ggaactgcga | 660 |

```
ttcaaagatg agaatagtga agattatcca cattgggaaa atagcaaaat agaaaaatat    720
ttaaaagaga gaaacgaacg ttctgacaaa ggtcaaatgc tttcagtaac tataaatagt    780
ggcattataa aatttagtga attggataga aaagataatt caagtaaaga taaaagtaat    840
tataaagtag ttaggaaaaa tgatattgca tataattcta tgagaatgtg caaggggct    900 agtggtagat caaattataa tgggattgtt agccctgcat atactgtgct ttatccaaca    960
caaaatacta gctcattatt tattggatat aagtttaaaa cacatagaat gattcataaa   1020
tttaaaatta attcacaagg attaacatca gatacatgga acttaaaata taaacaatta   1080
aaaaatataa atatagatat acctgtattg gaggaacaag aaaagatagg tgatttcttt   1140
aaaaaaatgg atatattgat tagtaaacag aaaataaaaa ttgaaatatt agaaaaagag   1200
aaacaatcct ttttacaaaa gatgttctta taa                                1233

<210> SEQ ID NO 36
<211> LENGTH: 1234
<212> TYPE: DNA
<213> ORGANISM: Staphylococcus aureus

<400> SEQUENCE: 36
atgagtaata cacaaacgaa aaatgtgcca gagttgagat tcccagggtt tgaaggcgaa     60
tgggaagaga agaaggttgg cgagttatta gaatttaaaa atggtttaaa taaggaaaa    120 gaatattttg gctcaggatc gtcgattgtt aacttcaaag atgtatttaa taacaggagc    180
ttaaatacaa ataatctgac tggaaaagtt aatgtgaata gcaagaact aaaaaattat    240 tctgttgaaa agggtgatgt ttttttttaca aggactagtg aggtaattgg tgaaataggt    300
tatccgcctg taatttttaaa tgaccctgaa aatactgtgt ttagtggatt tgtattaaga    360
gggcggccta aatcaggaat tgatttaata aataataatt ttaaaagata tgtctttttt    420
actaattcat ttagaaaaga aatgattaca aaaagttcta tgacaactag gctttaaca    480 tcaggtagcg caattaataa aatgaaggtc atataccctg tttcggctaa agaacgagaa    540
aaaataggtg acttcttcag caaactcgac cgacaaattg aattagaaga acaaaagctt    600
gaattacttc aacaacaaaa aaaaggctat atgcagaaaa tcttctcaca ggaactgcga    660
ttcaaagatg agaatagtga agattatcca cattgggaaa atagcaaaat agaaaaatat    720
ttaaaagaga gaaacgaacg ttctgacaaa ggtcaaatgc tttcagtaac tataaatagt    780
ggcattataa aatttagtga attggataga aaagataatt caagtaaaga taaaagtaat    840
tataaagtag ttaggaaaaa tgatattgca tataattcta tgagaatgtg caaggggct    900 agtggtagat caaattataa tgggattgtt agccctgcat atactgtgct ttatccaaca    960
caaaatacta gctcattatt tattggatat aagtttaaaa cacatagaat gattcataaa   1020
tttaaaatta attcacaagg attaacatca gatacatgga acttaaaata taaacaatta   1080
aaaaatataa atatagatat acctgtattg gaggaacaag aaaagatagg tgatttcttt   1140
aaaaaaatgg atatattgat tagtaaacag aaaataaaaa ttgaaatatt agaaaaagag   1200
aaacaatcct ttttacaaaa gatgttctta taag                               1234

<210> SEQ ID NO 37
<211> LENGTH: 1155
<212> TYPE: DNA
<213> ORGANISM: Staphylococcus aureus

<400> SEQUENCE: 37
atgagtaata cacaaacgaa aaatgtgcca gagttgagat tcccagggtt tgaaggcgaa     60
```

```
tgggaagaga aaaagttagg ggatcttata aaagttaatt ctggaaaaga ttataaacat    120
ttggaaaaag gtgatatacc agtctatggt actggcggtt atatgacaag tgtttcagaa    180
ccactaagtg aaattgatgc tgttggtatt gggagaaaag ggactataaa caaaccatat    240
ttgcttgagg cgccgttttg dacggtggat acattatttt attgtacacc taaaaaagaa    300
acagacatac tatttatatt aagtttattt agaaaaataa attggaaagt atacgatgaa    360
tcaacaggtg tgccaagctt aagtaaacaa accattaata aaataaatag atttgtccct    420
tcaaataaag agcagcaaaa aataggcgaa ttcttcatca aactcgaccg acaaattgaa    480
ttagaagaac aaaaacttga attacttcaa caacagaaaa aaggctatat gcagaaaatc    540
ttctcacagg aattgcgatt caaggatgag aatggaaacg attatccgaa ttgggaagag    600
aagaaaatag aagatatagc aagccaagta tatggaggcg aacaccaaaa tacaaagatt    660
aaagaatttt ggaatggaga tattccatgg attcaaagct ctgacgtaaa agtaaatgat    720
ttgattctac gacaatgtaa taaatttatt tccaagaatt caattgagct ttcttctgca    780
aaacttattc ctgccaattc aattgcaata gttacaagag tcggggttgg aaaactgtgt    840
ttggtagaat ttgattatgc tacaagtcaa gatttttttat cattaagtag tcttaaaatat   900 gacaaattat actcattata ttcattgcta tatacaatga aaaaaattag cgctaatcta    960
caaggaactt caattaaagg tataacaaaa aaagagttgt tagatagtat aataaagata   1020
ccccataatc tagaagaaca gcaaaaaata ggtgatctat tttataaaat tgataaatat   1080
atcagtttta ataatgtaa aattgagata cttaaaagtc tcaaacaagg attacttcaa   1140
aaaattttta tataa                                                    1155

<210> SEQ ID NO 38
<211> LENGTH: 1155
<212> TYPE: DNA
<213> ORGANISM: Staphylococcus aureus

<400> SEQUENCE: 38
atgagtaata cacaaacgaa aaatgtgcca gagttgagat tcccagggtt tgaaggcgaa     60
tgggaagaga aaaagttagg ggatcttata aaagttaatt ctggaaaaga ttataaacat    120
ttggaaaaag gtgatatacc agtctatggt actggcggtt atatgacaag tgtttcagaa    180
ccactaagtg aaattgatgc tgttggtatt gggagaaaag ggactataaa caaaccatat    240
ttgcttgagg cgccgttttg dacggtggat acattatttt attgtacacc taaaaaagaa    300
acagacatac tatttatatt aagtttattt agaaaaataa attggaaagt atacgatgaa    360
tcaacaggtg tgccaagctt aagtaaacaa accattaata aaataaatag atttgtccct    420
tcaaataaag agcagcaaaa aataggcgaa ttcttcatca aactcgaccg acaaattgaa    480
ttagaagaac aaaaacttga attacttcaa caacagaaaa aaggctatat gcagaaaatc    540
ttctcacagg aattgcgatt caaggatgag aatggaaacg attatccgaa ttgggaagag    600
aagaaaatag aagatatagc aagccaagta tatggaggcg aacaccaaaa tacaaagatt    660
aaagaatttt ggaatggaga tattccatgg attcaaagct ctgacgtaaa agtaaatgat    720
ttgattctac gacaatgtaa taaatttatt tccaagaatt caattgagct ttcttctgca    780
aaacttattc ctgccaattc aattgcaata gttacaagag tcggggttgg aaaactgtgt    840
ttggtagaat ttgattatgc tacaagtcaa gatttttttat cattaagtag tcttaaaatat   900 gacaaattat actcattata ttcattgcta tatacaatga aaaaaattag cgctaatcta    960
```

```
caaggaactt caattaaagg tataacaaaa aaagagttgt tagatagtat aataaagata   1020
ccccataatc tagaagaaca gcaaaaaata ggtgatctat tttataaaat tgataaatat   1080 atcagttta ataaatgtaa aattgagata cttaaaagtc tcaaacaagg attacttcaa    1140
aaaattttta tataa                                                    1155

<210> SEQ ID NO 39
<211> LENGTH: 1155
<212> TYPE: DNA
<213> ORGANISM: Staphylococcus aureus

<400> SEQUENCE: 39
atgagtaata cacaaaagaa aaatgtgcca gagttgagat tcccagggtt tgaaggcgag    60
tgggaagaga agaagctaga agatattata aagttaatt ctggaaaaga ttataaacat    120
ttggataaag gcgatatacc agtctatggt actggcggtt atatgacaag tgtttcagaa   180
ccactgagtg aaattgatgc tgttggtatt gggagaaaag ggactataaa caaaccatat   240
gtacttgagg cgccgttttg gacggtggat acattattt actgtacacc taaaaaagaa   300
gtagacatac tatttatatt gagttttattt agaaaaataa attggaaggt gtatgatgaa   360
tcaacaggtg tgccaagctt aagtaagcaa accattaata aataattag atttgtccct    420 acaaataaag aacaacaaaa aataggtaag ttcttcagca aacttgaccg acaaattgaa    480
ttagaagaac aaaaacttga attacttcaa caacagaaaa aaggctatat gcagaaaatc   540
ttctcgcaag aattgcgatt taaagatgag aatggtaatg attatccaga ttgggaagag   600
aagaaaatag aagatatagc aagccaagta tatggaggag gaacaccaaa tacaaaaatt   660
aaagaatttt ggaatggaga tattccatgg attcaaagct ctgacgtaaa agtaaatgat   720
ttgattctac aacaatgtaa taaatttat tccaagaatt caattgagct ttcttctgca    780
aaacttattc ctgccaattc aattgcaata gttacaagag tcggggttgg aaaactgtgt   840
ttggtagaat tgattatgc tacaagtcaa gatttttttat cattaagtag tcttaaatat    900
gacaaattat actcattata ttcattgcta tatacaatga aaaaaattag cgctaatcta    960
caaggaactt caattaaagg tataacaaaa aaagagttgt tagatagtat aataaagata   1020
ccccataatc tagaagaaca gcaaaaaata ggtgagctat tttataaaat agataaatat   1080 atcagttta ataaatgtaa aattgagatg cttaaaagtc tcaaacaagg attacttcaa    1140
aaaatgttta tataa                                                    1155

<210> SEQ ID NO 40
<211> LENGTH: 1155
<212> TYPE: DNA
<213> ORGANISM: Staphylococcus aureus

<400> SEQUENCE: 40
atgagtaata cacaaacgaa aaatgtgcca gagttgagat tcccagggtt tgaaggcgaa    60
tgggaagaga aaaagttagg ggatcttata aagttaatt ctggaaaaga ttataaacat    120
ttggaaaaag gtgatatacc agtctatggt actggcggtt atatgacaag tgtttcagaa   180
ccactaagtg aaattgatgc tgttggtatt gggagaaaag ggactataaa caaaccatat   240
ttgcttgagg cgccgttttg gacggtggat acattattt attgtacacc taaaaaagaa   300
acagacatac tatttatatt aagtttattt agaaaaataa attggaaagt atacgatgaa   360
tcaacaggtg tgccaagctt aagtaaacaa accattaata aataaatag atttgtccct    420 tcaaataaag agcagcaaaa aataggcgaa ttcttcatca aactcgaccg acaaattgaa   480
```

```
ttagaagaac aaaaacttga attacttcaa caacagaaaa aaggctatat gcagaaaatc      540
ttctcacagg aattgcgatt caaggatgag aatggaaacg attatccgaa ttgggaagag      600
aagaaaatag aagatatagc aagccaagta tatggaggcg aacaccaaa tacaaagatt      660 aaagaattt ggaatggaga tattccatgg attcaaagct ctgacgtaaa agtaaatgat      720
ttgattctac gacaatgtaa taaatttatt ccaagaatt caattgagct ttcttctgca      780
aaacttattc ctgccaattc aattgcaata gttacaagac tcggggttgg aaaactgtgt      840
ttggtagaat ttgattatgc tacaagtcaa gattttttat cattaagtag tcttaaatat      900
gacaaattat actcattata ttcattgcta tatacaatga aaaaaattag cgctaatcta      960
caaggaactt caattaaagg tataacaaaa aaagagttgt tagatagtat aataaagata     1020
ccccataatc tagaagaaca gcaaaaaata ggtgatctat tttataaaat tgataaatat     1080 atcagttttta ataaatgtaa aattgagata cttaaaagtc tcaaacaagg attacttcaa     1140 aaaatttta tataa                                                       1155

<210> SEQ ID NO 41
<211> LENGTH: 1212
<212> TYPE: DNA
<213> ORGANISM: Staphylococcus aureus

<400> SEQUENCE: 41
atgagtaata cacaaagaa aaatgtgcca gagttgagat tcccagggtt tgaaggcgaa       60
tgggaagaga agcagttggg ggatcttaca gatagagtaa ttaggaaaaa taaaaactta      120
gaatcgaaaa agccttttaac aatatccgga cagttaggtt taattgatca aacagaatat      180
tttagtaaat cagtttcgtc gaaaaatcta gaaaattata cactaataaa gaatggagaa      240
ttcgcgtata acaaaagtta ttctaatgga tacccattag gggctattaa aagattaact      300
agatatgata gtggtgtatt gtcctctttg tatatttgtt tttctattaa agtgaaatg      360 tctaaagact tcatggaagc atattttgat tcgacacact ggtatagaga agtttctgga      420
attgcagttg agggtgcaag aaatcacgga ttattaaatg tttctgtgaa tgattttttt      480
actattctaa ttaaatatcc aagtttagaa gaacagcaaa aaataggcaa gttcttcagc      540
aaactcgacc gacaaattga attagaagaa caaaagcttg aattacttca acaacagaaa      600
aaaggctata tgcagaaaat ttctcacag gaactgcgat tcaaagatga gaatggtgaa      660
gattatccag attgggaaaa tagcaaaata gaaaaatatt taaaagagag aaacgaacgt      720
tctgacaaag ggcaaatgct ttcagtaact ataaatagtg gcattataaa atttagtgaa      780
ttggatagaa aagataattc aagtaaagat aaaagtaatt ataaagtagt taggaaaaat      840
gatattgcat ataattctat gagaatgtgg caagggctag tggtaaatc aaattataat      900 gggattgtta gccctgcata tactgtgctt tatccaacac aaaatactag ctcattattt      960
attggatata agtttaaaac acatagaatg attcataaat ttaaaattaa ttcacaagga     1020
ttaacatcag atacatggaa cttaaaatat aaacaattaa aaatataaa tatagatata     1080 cctgtattgg aggaacaaga aaagataggt gatttcttta aaaaaatgga tatattgata     1140
agtaaacaga aaatgaaaat tgaaatatta gaaaagaga acaatccctt tttacaaaaa     1200
atgttcttat aa                                                        1212

<210> SEQ ID NO 42
<211> LENGTH: 1212
<212> TYPE: DNA
```

<213> ORGANISM: Staphylococcus aureus

<400> SEQUENCE: 42

```
atgagtaata cacaaaagaa aaatgtgcca gagttgagat tcccagggtt tgaaggcgaa      60
tgggaagaga agcagttggg ggatcttaca gatagagtaa ttaggaaaaa taaaaactta     120
gaatcgaaaa agcctttaac aatatccgga cagttaggtt taattgatca aacagaatat     180
tttagtaaat cagtttcgtc gaaaaatcta gaaaattata cactaataaa gaatggagaa     240
ttcgcgtata acaaaagtta ttctaatgga tacccattag gggctattaa aagattaact     300
agatatgata gtggtgtatt gtcctctttg tatatttgtt tttctattaa aagtgaaatg     360
tctaaagact tcatggaagc atattttgat tcgacacact ggtatagaga agtttctgga     420
attgcagttg agggtgcaag aaatcacgga ttattaaatg tttctgtgaa tgattttttt     480
actattctaa ttaaatatcc aagtttagaa gaacagcaaa aaataggcaa gttcttcagc     540
aaactcgacc gacaaattga attagaagaa caaaagcttg aattacttca acaacagaaa     600
aaaggctata tgcagaaaat tttctcacag gaactgcgat tcaaagatga aatggtgaa      660
gattatccag attgggaaaa tagcaaaata gaaaaatatt taaaagagag aaacgaacgt     720
tctgacaaag gcaaatgct ttcagtaact ataaatagtg gcattataaa atttagtgaa      780
ttggatagaa aagataattc aagtaaagat aaaagtaatt ataaagtagt taggaaaaat     840
gatattgcat ataattctat gagaatgtgg caaggggcta gtggtaaatc aaattataat     900
gggattgtta gccctgcata tactgtgctt tatccaacac aaaatactag ctcattattt     960
attggatata agtttaaaac acatagaatg attcataaat ttaaaattaa ttcacaagga    1020
ttaacatcag atacatggaa cttaaaatat aaacaattaa aaaatataaa tatagatata    1080
cctgtattgg aggaacaaga aaagataggt gatttcttta aaaaaatgga tatattgata    1140
agtaaacaga aaatgaaaat tgaaatatta gaaaagagaa aacaatcctt tttacaaaaa    1200
atgttcttat aa                                                       1212
```

<210> SEQ ID NO 43
<211> LENGTH: 1230
<212> TYPE: DNA
<213> ORGANISM: Staphylococcus aureus

<400> SEQUENCE: 43

```
atgagtaata cacaaacgaa aaatgtgcca gagttgagat tcccaggatt tgagggcgaa      60
tgggaagaga agaagttagg gaatcttact accaaaatag gtagtggaaa gactcccaaa     120
ggtggaagtg aaaactatac aaacaaaggc ataccatttt taaggagtca aatattaga      180
aatggtaaat taaatcttaa tgacttagtt tatattagta agatataga tgatgagatg      240
aaaaatagta gaacgtacta tggtgatgtt cttttaaata ttacaggagc atcaataggt     300
agaacagcca ttaattcgat agttgaaacg catgctaatt taaatcaaca tgtatgtatt     360
attagattaa aaaagagta ttattataat ttttttggac agtatctatt atcaagaaaa     420
ggtaaaagaa aaatttttcct tgcacaaagt ggaggtagtc gagaaggact aaacttcaaa     480
gaaattgcta atttaaaaat cttcaccca actatatttg aagaacaaca aaaaatagga     540
caattcttca gcaaacttga ccaacaaatt gaattagaag aacaaaaact tgaattactt     600
caacaacaga aaaatgcta tatacagaaa atcttctcac aagaattacg attcaaagat     660
gaagaaggta attactataa aggatggaac aaaagcaat taaagatgt attagaattt      720
agtaataaaa gaactattaa tgaaaatgaa tatcctgttt taacatcgtc aagacaaggt     780
```

```
ttaatacttc agtcagacta ctataaagat aggaaaactt ttgcagagag taatattggg      840
tatttcatac tccctaaaaa tcatataaca taccgttcaa gaagcgacga tggaattttt      900
aagtttaatt taaatctaat gattgatgta ggtattatta gtaaatatta ccctgtcttt      960
aaagggatag atgcaaatca atattattta acattacact taaactatca actgaaaaaa     1020
gaatatatta aatatgcaac tggtacatca caattggtac tctcacaaaa agacttgcaa     1080
aacataaaga ctaaattgcc atcttatgaa gaacaacaaa aaatcggtga ttttttcagt     1140
gaaatagata gattggttga aaaacaatct tcaaaagtcg gacgattaaa agtacgtaaa     1200
aaagaactat tacaaaaaat gtttgtttaa                                      1230

<210> SEQ ID NO 44
<211> LENGTH: 1230
<212> TYPE: DNA
<213> ORGANISM: Staphylococcus aureus

<400> SEQUENCE: 44
atgagtaata cacaaacgaa aaatgtgcca gagttgagat tcccaggatt tgagggcgaa       60
tgggaagaga agaagttagg gaatcttact accaaaatag gtagtggaaa gactcccaaa      120
ggtggaagtg aaaactatac aaacaaaggc ataccatttt taaggagtca aaatattaga      180
aatggtaaat taaatcttaa tgacttagtt tatattagta aagatataga tgatgagatg      240
aaaaatagta gaacgtacta tggtgatgtt cttttaaata ttacaggagc atcaataggt      300
agaacagcca ttaattcgat agttgaaacg catgctaatt taaatcaaca tgtatgtatt      360
attagattaa aaaagagta ttattataat tttttggac agtatctatt atcaagaaaa      420
ggtaaaagaa aaattttcct tgcacaaagt ggaggtagtc gagaaggact aaacttcaaa      480
gaaattgcta atttaaaaat cttcaccca actatatttg aagaacaaca aaaaatagga      540
caattcttca gcaaacttga ccaacaaatt gaattagaag aacaaaaact tgaattactt      600
caacaacaga aaaaatgcta tatacagaaa atcttctcac aagaattacg attcaaagat      660
gaagaaggta attactataa aggatggaac aaaaagcaat taaagatgt attagaattt      720 agtaataaaa gaactattaa tgaaaatgaa atcctgtttt aacatcgtc aagacaaggt      780 ttaatacttc agtcagacta ctataaagat aggaaaactt ttgcagagag taatattggg      840
tatttcatac tccctaaaaa tcatataaca taccgttcaa gaagcgacga tggaattttt      900
aagtttaatt taaatctaat gattgatgta ggtattatta gtaaatatta ccctgtcttt      960
aaagggatag atgcaaatca atattattta acattacact taaactatca actgaaaaaa     1020
gaatatatta aatatgcaac tggtacatca caattggtac tctcacaaaa agacttgcaa     1080
aacataaaga ctaaattgcc atcttatgaa gaacaacaaa aaatcggtga ttttttcagt     1140
gaaatagata gattggttga aaaacaatct tcaaaagtcg gacgattaaa agtacgtaaa     1200
aaagaactat tacaaaaaat gtttgtttaa                                      1230

<210> SEQ ID NO 45
<211> LENGTH: 1212
<212> TYPE: DNA
<213> ORGANISM: Staphylococcus aureus

<400> SEQUENCE: 45
atgagtaata cacaaaagaa aaatgtgcca gaattgaggt tcccagggtt tgaaggcgaa       60
tgggaagaga agcagttagg ggatcttaca gatagagtaa ttaggaaaaa taaaaactta      120
```

```
gaatcgaaaa agcctttaac aatatccgga cagttaggtt taattgatca aacagaatat      180
tttagtaaat cagtttcgtc gaaaaatcta gaaaattata cactaataaa gaatggagaa      240
ttcgcgtata acaaaagtta ttctaatgga tacccattag gggctattaa aagattaact      300
agatatgata gtggtgtatt gtcctctttg tatatttgtt tttctattaa aagtgaaatg      360
tctaaagact tcatggaagc atattttgat tcgacacact ggtatagaga agtttctgga      420
attgcagttg agggtgcaag aaatcacgga ttattaaatg tttctgtgaa tgattttttt      480
actattctaa ttaaatatcc aagtttagaa gaacagcaaa aaataggcaa gttcttcagc      540
aaactcgacc gacaaattga attagaagaa caaaagcttg aattacttca acaacgaaaa      600
aaaggctata tgcagaaaat tttctcacag gaactgcgat tcaaagatga gaatggtgaa      660
gattatccag attgggaaaa tagcaaaata gaaaaatatt taaaagagag aaacgaacgt      720
tctgacaaag ggcaaatgct ttcagtaact ataaatagtg gcattataaa atttagtgaa      780
ttggatagaa aagataattc aagtaaagat aaaagtaatt ataaagtagt taggaaaaat      840
gatattgcat ataattctat gagaatgtgg caaggggcta gtggtaaatc aaattataat      900
gggattgtta gccctgcata tactgtgctt tatccaacac aaaatactag ctcattattt      960
attggatata agtttaaaac acatagaatg attcataaat ttaaaattaa ttcacaagga     1020
ttaacatcag atacatggaa cttaaaatat aaacaattaa aaaatataaa tatagatata     1080
cctgtattgg aggaacaaga aaagataggt gatttcttta aaaaaatgga tatattgata     1140
agtaaacaga aaatgaaaat tgaaatatta gaaaagagaa acaatccttt tttacaaaaa     1200
atgttcttat aa                                                        1212

<210> SEQ ID NO 46
<211> LENGTH: 1200
<212> TYPE: DNA
<213> ORGANISM: Staphylococcus aureus

<400> SEQUENCE: 46
atgagtaata cacaaaagaa aaatgtgcca gaattgagat tcccaggatt tgaaggcgaa       60
tgggaagaga agaagttagg gaatcttact accaaaatag gtagtggaaa gactcccaaa      120
ggtggaagtg aaaactatac aaacaaaggc ataccatttt taaggagtca aaatattaga      180
aatggtaaat taaatcttaa tgacttagtt tatattagta agatataga tgatgagatg      240 aaaaatagta gaacgtacta tggtgatgtt cttttaaata ttacaggagc atcaataggt      300
agaacagcca ttaattcgat agttgaaacg catgctaatt taaatcaaca tgtatgtatt      360
attagattga aaaagagta ttattataat tttttttggac agtatctatt atcaagaaaa      420
ggtaaaagga aaattttcct tgcacaaagt ggaggtagtc gagaaggtct aaacttcaaa      480
gaaattgcta atttaaaaat cttcaccccca actatatttg aagaacagca aaaaataggc      540
aagttcttca gcaaactcga ccgacaaatt gaattagaag aacaaaaact tgaattgctt      600
caacaacaga aaaaggcta tgcagaaaa tcttcacac aagaattgcg attcaaagat      660
gagaatggtg aagaatatcc agagtgggaa aacaaattca taaaagacat ctttatcttt      720
gaaaataata aagaaaacc aattacttct tcattaagag aaaaggggtt ataccttac      780 tatggtgcaa ctggaattat tgattacgta aaagattatt tattcaataa tgaagaacga      840
ttactaatag gagaagatgg tgcaaaatgg gggcagtttg agacgagtag cttattgct      900 aatgggcaat actgggtaaa taatcatgcg catgtagtta aaagtaatga tcataatttg      960
ttttttatga attattattt aaatttttaaa gaactacgag catttgtcac aggtaatgca     1020
```

```
ccagctaaat taactcatgc gaacttatgc aatataaatc ttaaaatacc ttgtctcact   1080
gaacaagata aagtaagtgc attgttaaaa tctatagaca ataaaatgaa taatcaaatg   1140
aatagaattg agttattaaa agaacgtaaa aaaggactat tacaaaaaat gtttatttaa   1200
```

<210> SEQ ID NO 47
<211> LENGTH: 1213
<212> TYPE: DNA
<213> ORGANISM: Staphylococcus aureus

<400> SEQUENCE: 47

```
atgagtaata cacaaaagaa aaatgtgcca gagttgagat tcccagagtt tgaaggcgaa     60
tgggaagaga agcagttagg ggatcttaca gatagagtaa ttaggaaaaa taaaaactta    120
gaatcgaaaa aagcctttaa caatatccgg acagttaggt ttaattgatc aaacagaata    180
ttttagtaaa tcagtttcgt cgaaaaatct agaaaattat acactaataa agaatggaga    240
attcgcgtat aacaaaagtt attctaatgg atacccatta ggggctatta aaagattaac    300
tagatatgat agtggtgtat tgtcctcttt gtatatttgt ttttctatta aaagtgaaat    360
gtctaaagac ttcatggaag catattttga ttcgacacac tggtatagag aagtttctgg    420
aattgcagtt gagggtgcaa gaaatcacgg attattaaat gtttctgtga atgatttttt    480
tactattcta attaaatatc caagtttaga agaacagcaa aaaataggca agttcttcag    540
caaactcgac cgacaaattg aattagaaga acaaaagctt gaattacttc aacaacagaa    600
aaaaggctat atgcagaaaa ttttctcaca ggaactgcga ttcaaagatg agaatggtga    660
agattatcca gattgggaaa atagcaaaat agaaaaatat ttaaaagaga gaaacgaacg    720
ttctgacaaa gggcaaatgc tttcagtaac tataaatagt ggcattataa aatttagtga    780
attggataga aaagataatt caagtaaaga taaagtaatt tataaagtag ttaggaaaaa    840
tgatattgca tataattcta tgagaatgtg gcaaggggct agtggtaaat caaattataa    900
tgggattgtt agccctgcat atactgtgct ttatccaaca caaaatacta gctcattatt    960
tattggatat aagttaaaaa cacatagaat gattcataaa tttaaattta attcacaagg   1020
attaacatca gatacatgga acttaaaata taaacaatta aaaaatataa atatagatat   1080
acctgtattg gaggaacaag aaaagatagg tgatttcttt aaaaaaatgg atatattgat   1140
aagtaaacag aaaatgaaaa ttgaaatatt agaaaagag aaacaatcct ttttacaaaa   1200
aatgttctta taa                                                       1213
```

<210> SEQ ID NO 48
<211> LENGTH: 1260
<212> TYPE: DNA
<213> ORGANISM: Staphylococcus aureus

<400> SEQUENCE: 48

```
atgagtaata cacaaaagaa aaatgtgcca gagttgaggt tcccagggtt tgaaggcgaa     60
tgggaagaga agaagttagg ggaccttact accaaaatag gtagtggaaa gactcccaaa    120
ggtggaagtg aaaactatac aaacaaaggc ataccatttt taaggagtca aatattaga    180 aatggtaaat taaatcttaa tgacttagtt tatattagta aagatataga tgatgagatg    240
aaaaatagta gaacgtacta tggtgatgtt cttttaaata ttacaggagc atcaataggt    300
agaacagcca ttaattcgat agttgaaata catgctaatt taaatcaaca tgtatgtatt    360
attagattga aaaaagagta ttattataat tttttttggac agtatctatt atcaagaaaa    420
```

```
ggtaaaagga aaattttcct tgcacaaagt ggaggtagtc gagaaggact aaacttcaaa      480
gaaattgcta atttaaaaat cttcacccca actatatttg aagagcagca aaaaataggc      540
gaattcatca gcaaacttga ccgacaaatt gaattagaag aacaaaaact tgaattactt      600
cagcaacaga aaaaggcta tatgcagaaa atcttctcgc aagaattgcg attcaaagat       660
```

```
gaggaaggta aagattatcc agattggaaa tcaaaatcaa ttcaagaaat atttgagaat      720
aagggtggca ctgctctaga aacagaattt aattttgacg gtaattataa agttataagt      780
ataggaagtt attctataaa tagcacttat aatgatcaaa atataagagt caataaaaat      840
aaaaaaactg aaaatatat tttatcaaaa ggcgacttag caatggtatt aaatgataaa       900 acaaagatg ggaaaattat aggtagaagt atatttatag ataaagataa tcaatatatt       960
tataatcaaa gaactgaaag attaatacca tttgctgaaa atgataataa atttttatgg     1020
ttcttaatga atacagattt aattagaaat aaaataaaag gtatgatgca aggagcaacc     1080
caagtttata taaattattc atctattaaa ttgatatcta tacaattgcc acttcttgaa     1140
gaacaacaga aaataagagg gttctagaa gtttttatctg gaataactac taaacaattg     1200
cacaagatag accaattaaa agagaggaaa aaggcgtttt tacagaaaat gtttatttga    1260
```

<210> SEQ ID NO 49
<211> LENGTH: 1227
<212> TYPE: DNA
<213> ORGANISM: Staphylococcus aureus

<400> SEQUENCE: 49

```
atgagtaata cacaaaagaa aaatgtgcct gagttgagat tcccagggtt tgaaggcgaa       60
tgggaagaga agcaatttgc tgattttact aaaataaatc aaggattgca gattgctatt      120
aatgaacgta aaactgaata ttctccagag ttgtattttt atataacaaa tgaattttta      180
agaccaaata gtcaaactaa atattttatc gaaaatcccc ctcaatcagt aattgcaaat      240
aaagaagata ttttaatgac tagaacaggt aatactggaa aagtagtaac taatgtattt      300
ggagcgtttc ataataattt ttttaaaatt aaatttgata aaaatctgta tgatagattg      360 ttttagtag aggttttaaa ttcatctaag atacaaaata aaatactatc tttagcagga      420
tcttcgacga taccagattt aaaccatagt gattttata gtattagttc ttcttatccg       480
ctgcttagag aacagcaaaa aataggtaaa ttcttcagca aacttgaccg acaaattgaa      540
ctagaagaac aaaaacttga attactaaaa caacagaaaa aaggctatat gcagaaaatc      600
ttctcgcaag aattgcgatt caaagatgag aatggaaatg attatccaga gtgggaatca      660
aaatcaattc aagaaatatt tgagaataag ggtggcactg ctctagaaac agaatttaat      720
tttgacggta attataaagt tataagtata ggaagttatt ctataaatag cacttataat      780
gatcaaaata taagagtcaa taaaataaa aaaactgaaa atatatttt atcaaaaggc       840 gacttagcaa tggtattaaa tgataaaaca aagatgggga aaattatagg tagaagtata      900
tttatagata aagataatca atatatttat aatcaaagaa ctgaaagatt aataccattt      960
gctgaaaatg ataataaatt tttatggttc ttaatgaata cagatttaat tagaaataaa     1020
ataaaaggta tgatgcaagg agcaacccaa gtttatataa attattcatc tattaaattg     1080
atatctatac aattgccact tcttgaagaa caacagaaaa taagaggttt ctagaagtc      1140 ttgtctggaa taactactga acaattgcac aagatagacc aattaaaaga gaggaaaaag    1200 gcgttttta cagaaaatgtt tatttga                                        1227
```

```
<210> SEQ ID NO 50
<211> LENGTH: 1200
<212> TYPE: DNA
<213> ORGANISM: Staphylococcus aureus

<400> SEQUENCE: 50
atgagtaata cacaaacgaa aaatgtgcca gagttgagat tcccaggatt tgagggcgaa      60
tgggaagaga agaagttagg gaatcttact accaaaatag gtagtggaaa gactcccaaa     120
ggtggaagtg aaaactatac aaacaaaggc ataccatttt taaggagtca aaatattaga     180
aatggtaaat taaatcttaa tgacttagtt tatattagta agatataga tgatgagatg      240 aaaaatagta aacgtacta tggtgatgtt cttttaaata ttacaggagc atcaataggt      300
agaacagcca ttaattcgat agttgaaacg catgctaatt taaatcaaca tgtatgtatt     360
attagattga aaaagagta ttattataat ttttttggac agtatctatt atcaagaaaa      420
ggtaaaagga aattttcct tgcacaaagt ggaggtagtc gagaaggtct aaacttcaaa      480
gaaattgcta atttaaaaat cttcaccca actatatttg aagaacagca aaaaataggc      540
aagttcttca gcaaactcga ccgacaaatt gaattagaag aacaaaaact tgaattgctt     600
caacaacaga aaaaaggcta tatgcagaaa atcttcacac aagaattgcg attcaaagat     660
gagaatggtg aagaatatcc agagtgggaa aacaaattca taaaagacat ctttatcttt     720
gaaaataata aagaaaaacc aattacttct tcattaagag aaaagggttt atacccttac     780
tatggtgcaa ctggaattat tgattacgta aaagattatt tattcaataa tgaagaacga     840
ttactaatag gaagagatgg tgcaaaatgg gggcagtttg agacgagtag ctttattgct     900
aatgggcaat actgggtaaa taatcatgcg catgtagtta aaagtaatga tcataatttg     960 tttttatga attattattt aaatttttaaa gaactacgag catttgtcac aggtaatgca    1020
ccagctaaat taactcatgc gaacttatgc aatataaatc ttaaaatacc ttgtctcact    1080
gaacaagata agtaagtgc attgttaaaa tctatagaca ataaaatgaa taatcaaatg    1140
aatagaattg agttattaaa agaacgtaaa aaagaactat tacaaaaaat gtttatttaa    1200

<210> SEQ ID NO 51
<211> LENGTH: 1260
<212> TYPE: DNA
<213> ORGANISM: Staphylococcus aureus

<400> SEQUENCE: 51
atgagtaata cacaaaagaa aaatgtgcca gagttgagat tcccagggtt tgaaggcgaa      60
tgggaagaga agaagttagg ggatcttaca gatagagtaa ttaggaaaaa taaaaactta     120
gaatcgaaaa agcctttaac aatatccgga cagttaggtt taattgatca aacagaatac     180
tttagtaaat cagtttcgtc gaaaaatcta gaaaattata cactaataaa gatggagaa      240 ttcgcgtata acaaaagtta ttctaatgga tacccattag gggctattaa aagattaact     300
agatatgata gtggtgtatt gtcctctttg tatatttgtt tttctattaa agtgaaatg      360 tctaaagact tcatggaagc atattttgat tcgacacact ggtatagaga gtttctgga     420 attgcagttg agggtgcaag aaatcacgga ttattaaatg tttctgtgaa tgattttttt     480
actattctaa ttaaatatcc aagtttagaa gaacagcaaa aaataggcaa gttcttcagc     540
aaactcgacc gacaaattga attagaagaa caaaagcttg aattacttca acaacagaaa     600
aaaggctata tgcagaaaat cttctcacag gaattgcgat taagaatga gaatggtaat     660 gattatcctg attgggaaag aattaaattt tttgatgtaa ttgataaagt aatagatttt     720
```

| | |
|---|---|
| agagggagaa caccaaaaaa attaaatatg gaatggtctg acgaagggta tttagcatta | 780 |
| tcagcagtca atgtaaaaaa aggctatatt gattttaatg tagaggcgaa atatggaaat | 840 |
| ctagatttat atactagatg gatgagagga aatgaattat ataagggca agtattattt | 900 |
| acaactgaag cgccaatggg caatgtagca caggttccgg ataataaagg atatatatta | 960 |
| agtcaaagaa ctatcgcgtt taattcaaat gaaaaaatca ctgataactt tttagcatca | 1020 |
| ttgttgagct ctgaaaatgt ttataatgat ttattaaaat tgtgtagtgg tgctacagca | 1080 |
| aaaggtgtga gtcaaaaaaa tttaaatcga ctatacgtta ctattccaca ttccatatca | 1140 |
| gagcaagaag agattgctga attctttaga aaaattaatc aattggttga gttgcaaaaa | 1200 |
| tataaaattg aacatactaa aagtcaaaaa caagtgtttt tacaaaagat gtttatttaa | 1260 |

<210> SEQ ID NO 52
<211> LENGTH: 1259
<212> TYPE: DNA
<213> ORGANISM: Staphylococcus aureus

<400> SEQUENCE: 52

| | |
|---|---|
| atgagtaata cacaaaagaa aaatgtgcca gagttgagat tcccagggtt tgaaggcgaa | 60 |
| tgggaagaga agaagttagg ggatcttaca gatagagtaa ttaggaaaaa taaaaactta | 120 |
| gaatcgaaaa agcctttaac aatatccgga cagttaggtt taattgatca aacagaatac | 180 |
| tttagtaaat cagtttcgtc gaaaaatcta gaaaattata cactaataaa gatggagaa | 240 |
| ttcgcgtata acaaaagtta ttctaatgga tacccattag gggctattaa agattaact | 300 |
| agatatgata gtggtgtatt gtcctctttg tatatttgtt tttctattaa aagtgaaatg | 360 |
| tctaaagact tcatggaagc atattttgat tcgacacact ggtatagaga agtttctgga | 420 |
| attgcagttg agggtgcaag aaatcacgga ttattaaatg tttctgtgaa tgattttttt | 480 |
| actattctaa ttaaatatcc aagtttagaa gaacagcaaa aaataggcaa gttcttcagc | 540 |
| aaactcgacc gacaaattga attagaagaa caaaagcttg aattacttca acaacagaaa | 600 |
| aaaggctata tgcagaaaat cttctcacag gaattgcgat ttaagaatga aatggtaat | 660 |
| gattatcctg attgggaaag aattaaattt tttgatgtaa ttgataaagt aatagatttt | 720 |
| agagggagaa caccaaaaaa ttaaatatgg aatggtctga cgaagggtat ttagcattat | 780 |
| cagcagtcaa tgtaaaaaaa ggctatattg attttaatgt agaggcgaaa tatggaaatc | 840 |
| tagatttata tactagatgg atgagaggaa atgaattata taagggcaa gtattattta | 900 |
| caactgaagc gccaatgggc aatgtagcac aggttccgga taataaagga tatatattaa | 960 |
| gtcaaagaac tatcgcgttt aattcaaatg aaaaaatcac tgataacttt ttagcatcat | 1020 |
| tgttgagctc tgaaaatgtt tataatgatt tattaaaatt gtgtagtggt gctacagcaa | 1080 |
| aaggtgtgag tcaaaaaaat ttaaatcgac tatacgttac tattccacat tccatatcag | 1140 |
| agcaagaaga gattgctgaa ttctttagaa aaattaatca attggttgag ttgcaaaaat | 1200 |
| ataaaattga acatactaaa agtcaaaaac aagtgttttt acaaaagatg tttatttaa | 1259 |

<210> SEQ ID NO 53
<211> LENGTH: 1200
<212> TYPE: DNA
<213> ORGANISM: Staphylococcus aureus

<400> SEQUENCE: 53

| | |
|---|---|
| atgagtaata cacaaaagaa aaatgtgcca gaattgagat tcccaggatt tgaaggcgaa | 60 |
| tgggaagaga agaagttagg gaatcttact accaaaatag gtagtggaaa gactcccaaa | 120 |

```
ggtggaagtg aaaactatac aaacaaaggc ataccatttt taaggagtca aatattaga      180 aatggtaaat taaatcttaa tgacttagtt tatattagta aagatataga tgatgagatg      240
aaaaatagta gaacgtacta tggtgatgtt cttttaaata ttacaggagc atcaataggt      300
agaacagcca ttaattcgat agttgaaacg catgctaatt taaatcaaca tgtatgtatt      360
attagattga aaaagagta ttattataat tttttggac agtatctatt atcaagaaaa        420
```



```
ggtggaagtg aaaactatac aaacaaaggc ataccatttt taaggagtca aatattaga      180 aatggtaaat taaatcttaa tgacttagtt tatattagta aagatataga tgatgagatg      240
aaaaatagta gaacgtacta tggtgatgtt cttttaaata ttacaggagc atcaataggt      300
agaacagcca ttaattcgat agttgaaacg catgctaatt taaatcaaca tgtatgtatt      360
attagattga aaaagagta ttattataat tttttggac agtatctatt atcaagaaaa        420
ggtaaaagga aaattttcct tgcacaaagt ggaggtagtc gagaaggtct aaacttcaaa      480
gaaattgcta atttaaaaat cttcaccccca actatatttg aagaacagca aaaaataggc    540
aagttcttca gcaaactcga ccgacaaatt gaattagaag aacaaaaact tgaattgctt      600
caacaacaga aaaaggcta tgcagaaaa atcttcacac aagaattgcg attcaaagat        660
gagaatggtg aagaatatcc agagtgggaa acaaattca taaagacat ctttatcttt       720 gaaaataata aagaaaacc aattacttct tcattaagag aaagggggtt ataccctcac       780
tatggtgcaa ctggaattat tgattacgta aaagattatt tattcaataa tgaagaacga      840
ttactaatag gagaagatgg tgcaaaatgg gggcagtttg agacgagtag ctttattgct      900
aatgggcaat actgggtaaa taatcatgcg catgtagtta aaagtaatga tcataatttg      960
ttttttatga attattattt aaattttaaa gaactacgag catttgtcac aggtaatgca     1020
ccagctaaat taactcatgc gaacttatgc aatataaatc ttaaaatacc ttgtctcact    1080
gaacaagata agtaagtgc attgttaaaa tctatagaca ataaaatgaa taatcaaatg      1140
aatagaattg agttattaaa agaacgtaaa aaaggactat acaaaaaaat gtttattttaa    1200
```

<210> SEQ ID NO 54
<211> LENGTH: 1200
<212> TYPE: DNA
<213> ORGANISM: Staphylococcus aureus

<400> SEQUENCE: 54

```
atgagtaata cacaaaagaa aaatgtgcca gaattgagat tcccaggatt tgaaggcgaa       60
tgggaagaga agaagtagg gaatcttact accaaaatag gtagtggaaa gactcccaaa      120
ggtggaagtg aaaactatac aaacaaaggc ataccatttt taaggagtca aatattaga      180 aatggtaaat taaatcttaa tgacttagtt tatattagta aagatataga tgatgagatg      240
aaaaatagta gaacgtacta tggtgatgtt cttttaaata ttacaggagc atcaataggt      300
agaacagcca ttaattcgat agttgaaacg catgctaatt taaatcaaca tgtatgtatt      360
attagattga aaaagagta ttattataat tttttggac agtatctatt atcaagaaaa        420
ggtaaaagga aaattttcct tgcacaaagt ggaggtagtc gagaaggtct aaacttcaaa      480
gaaattgcta atttaaaaat cttcaccccca actatatttg aagaacagca aaaaataggc    540
aagttcttca gcaaactcga ccgacaaatt gaattagaag aacaaaaact tgaattgctt      600
caacaacaga aaaaggcta tgcagaaaa atcttcacac aagaattgcg attcaaagat        660
gagaatggtg aagaatatcc agagtgggaa acaaattca taaagacat ctttatcttt       720 gaaaataata aagaaaacc aattacttct tcattaagag aaagggggtt ataccctcac       780
tatggtgcaa ctggaattat tgattacgta aaagattatt tattcaataa tgaagaacga      840
ttactaatag gagaagatgg tgcaaaatgg gggcagtttg agacgagtag ctttattgct      900
aatgggcaat actgggtaaa taatcatgcg catgtagtta aaagtaatga tcataatttg      960
ttttttatga attattattt aaattttaaa gaactacgag catttgtcac aggtaatgca     1020
```

| ccagctaaat taactcatgc gaacttatgc aatataaatc ttaaaatacc ttgtctcact | 1080 |
| gaacaagata agtaagtgc attgttaaaa tctatagaca ataaaatgaa taatcaaatg | 1140 |
| aatagaattg agttattaaa agaacgtaaa aaaggactat tacaaaaaat gtttatttaa | 1200 |

<210> SEQ ID NO 55
<211> LENGTH: 1200
<212> TYPE: DNA
<213> ORGANISM: Staphylococcus aureus

<400> SEQUENCE: 55

| atgagtaata cacaaaggaa aaatgtgcca gagttgagat tcccagggtt tgaaggcgaa | 60 |
| tgggaagaga agaagttagg ggatcttact accaaaatag gtagtggaaa gactcccaaa | 120 |
| ggtggaagtg aaaactatac aaacaatggc ataccatttt taaggagtca aaatattaga | 180 |
| aatggtaaat taaatcttaa tgacttagtt tatattagta agatataga tgatgagatg | 240 |
| aaaaatagta gaacgtacta tggtgatgtt cttttaaata ttacaggagc atcaataggt | 300 |
| aaaacagcca ttaattcgat agttgaaacg catgctaatt taaatcaaca tgtatgtatt | 360 |
| attagattga aaaagagta ttattataat ttttttggac agtaactatt atcaagaaaa | 420 |
| ggaaaaagga aaattttcct tgcacaaagt ggaggtagtc gagaaggact aaacttcaaa | 480 |
| gaaattgcta atttaaaaat cttcaccccca actatatttg aagaacagca aaaaataggc | 540 |
| aagttcttca gcaaacttga ccgacaaatt gaattagaag aacaaaaact tgaattactt | 600 |
| caacaacaga aaaaggcta tgcagaaaa atcttctcac aggaattacg attcaaagac | 660 |
| gagaatggtg aagaatatcc aaattgggaa acaaattca taaagacat ctttatattt | 720 |
| gaaaataata aagaaaaccc aattacttct tcattaagag aaaagggct atacccttac | 780 |
| tatggcgcaa ctggaattat tgattacgtg aaagaatatt tattcaataa tgaggaacga | 840 |
| ttactaatag gagaagatgg tgcaaaatgg gggcagtttg agacgagtag ctttattgct | 900 |
| aatgggcaat actgggtaaa taatcatgcg catgtagtta aaagtaatga tcataatttg | 960 |
| tttttttatga attattattt aaattttaaa gaactacgag catttgtgat aggtaatgca | 1020 |
| ccagctaaat taactcatgc gaacttatgc aatataaatc ttaaaatacc ttgtctcact | 1080 |
| gaacaagata agtaagtgc attgttaaaa tctatagaca ataaaatgaa taatcaaatg | 1140 |
| aatagaattg agttattaaa agaacgtaaa aaaggactat tacaaaaaat gtttatttaa | 1200 |

<210> SEQ ID NO 56
<211> LENGTH: 1194
<212> TYPE: DNA
<213> ORGANISM: Staphylococcus aureus

<400> SEQUENCE: 56

| atgagtaata cacaaacgaa aaatgtgcca gagttgagat tcccagggtt tgaaggcgaa | 60 |
| tgggaagaga agaagttagg ggatcttggc ctgtttcaaa aaagttattc tttttcgaga | 120 |
| gctaaagaag gaaacggtaa aactaaacat attcattatg gtgatattca ttcaaaattt | 180 |
| aaaacagtct tagatagtga tggtaatatc cctaatataa ttgagaaagc tgtatttgag | 240 |
| ttgattcaaa aaggagacat tgttttttgcg gatgcatcag aagattatag tgacctagga | 300 |
| aaagcagtta tgatagattt caaaccgaat tcattgattt ctggcttaca tacacaccta | 360 |
| tttagaccgc ttaacaatgc aatttctaat ttttttgattt tttacacaaa aactctgagt | 420 |
| tataaaaaat tcattagaca gcaaggtaca ggaatatcag tacttggtat atcaaaaaaa | 480 |
| agtttattaa atttgaatgt attaatacca cgaagtgaat tagaacaaca aaaagtaggc | 540 |

```
aagttcttca gcaaactcga ccgacaaatt gaattagaag aacaaaaaat cgaattactt    600
caacaacaga aaaaaggcta tatacagaaa atcttctcac aagaattgcg atttaaggat    660
gagaatggag atgattatcc ggagtgggaa gaaactacta taaaagaaat tgctcaaatt    720
aacacaggaa agaaagatac aaaagatgcc attactaatg ggagttatga tttttacgtt    780
agatctccga tagtttataa aattaatact tttagttatg aaggagaggc tattttaact    840
gtaggagatg gagttggcgt aggtaaagtt ttccactatg taaatgggaa atttgattat    900
catcaaagag tatacaaaat atctgacttt aagaattatt atggattatt gttattttat    960 tattttttcac aaaacttttt aaaagaaaca agaaatata gtgcgaagac atcagttgat   1020
tcagttagaa aagacatggt tgctaatatg aaagtaccac gtcctattta tatagaacag   1080
gaaaaaatcg gtcaattcat taaaaaagta gacaacaaaa taaaaattca gaaacaagtg   1140
attgaattac ttaaacaacg caaaaaggca ttacttcaaa agatgtttat ttaa          1194
```

<210> SEQ ID NO 57  
<211> LENGTH: 1194  
<212> TYPE: DNA  
<213> ORGANISM: Staphylococcus aureus

<400> SEQUENCE: 57

```
atgagtaata cacaaacgaa aaatgtgcca gagttgagat tcccagggtt tgaaggcgaa     60
tgggaagaga agaagttagg ggatcttggc ctgtttcaaa aaagttattc ttttttcgaga    120 gctaaagaag gaaacggtaa aactaaacat attcattatg gtgatattca ttcaaaattt    180
aaaacagtct tagatagtga tggtaatatc cctaatataa ttgagaaagc tgtatttgag    240
ttgattcaaa aaggagacat tgttttttgcg gatgcatcag aagattatag tgacctagga    300
aaagcagtta tgatagattt caaaccgaat tcattgattt ctggcttaca tacacaccta    360
tttagaccgc ttaacaatgc aatttctaat tttttgattt tttacacaaa aactctgagt    420
tataaaaaat tcattagaca gcaaggtaca ggaatatcag tacttggtat atcaaaaaaa    480
agtttattaa atttgaatgt attaataccga cgaagtgaat tagaacaaca aaaagtaggc    540
aagttcttca gcaaactcga ccgacaaatt gaattagaag aacaaaaaat cgaattactt    600
caacaacaga aaaaaggcta tatacagaaa atcttctcac aagaattgcg atttaaggat    660
gagaatggag atgattatcc ggagtgggaa gaaactacta taaaagaaat tgctcaaatt    720
aacacaggaa agaaagatac aaaagatgcc attactaatg ggagttatga tttttacgtt    780
agatctccga tagtttataa aattaatact tttagttatg aaggagaggc tattttaact    840
gtaggagatg gagttggcgt aggtaaagtt ttccactatg taaatgggaa atttgattat    900
catcaaagag tatacaaaat atctgacttt aagaattatt atggattatt gttattttat    960 tattttttcac aaaacttttt aaaagaaaca agaaatata gtgcgaagac atcagttgat   1020
tcagttagaa aagacatggt tgctaatatg aaagtaccac gtcctattta tatagaacag   1080
gaaaaaatcg gtcaattcat taaaaaagta gacaacaaaa taaaaattca gaaacaagtg   1140
attgaattac ttaaacaacg caaaaaggca ttacttcaaa agatgtttat ttaa          1194
```

<210> SEQ ID NO 58  
<211> LENGTH: 1230  
<212> TYPE: DNA  
<213> ORGANISM: Staphylococcus aureus

<400> SEQUENCE: 58

```
atgagtaata cacaaaagaa aaatgtgcca gagttgagat tcccagggtt tgaaggcgaa    60
tgggaagaga agaagttagg ggaaatttt caaataattt ctggttcaac accactaaaa   120
tcaaataaaa agttttatga aatggtaat attaattggg tcaaaacgac agatttaaat   180
aattctaaag ttacgcatag taagaaaaa ataactgaat atgctatgaa tagtttgaaa   240
ttaaaattag tgcctaaaaa ttcagtactt atagctatgt atggtggttt taatcaaatt   300
ggtcgaacag gtttgttaaa aatagatgcc acaataaatc aagcaatttc agccttatta   360
atgaatcatg aaacgaatcc agaatttata caagcatatc taaattatca agttaagggg   420
tggaagagat atgcagcaag tagcagaaaa gacccgaata taactaaaaa agacatagaa   480
caatttaaag ttccttatgt tagtattaat gaacagcaaa aaataggcga attcttcagc   540
aagcttgacc gacaaattga gttagaagaa caaaaactag aattacttca acaacaaaaa   600
aaggctatat gcagaaaatc ttctcacaag aattgcgatt caaagatgag aatggtgaag   660
attacccgga gtgggaagag acaaaactcc aacaaattat aggaggttaa agacggtact   720
catgaaagtc ctaagcccac tgacaatggt tatttattag taacttcaaa aaatttaaaa   780
aataataaat tagatttgag tgaatcttat agtatttcta aagaagatta tgaaagtata   840
aataaaagat ctaaagttga aaaaggcgac attttatttg gaatgatagg gacaatagga   900
aatcctattc tattagaaga cgaaggattc gctataaaaa atgttgcttt gctaaaaacg   960
agttgtttac aagaaaagta ttacatattg aacttcctca aatctatagc tattgctaaa  1020
caatttata aaacgaatgc tggaggaact caaaaattta tttctttagg agttataaga  1080
gatttaaaaa ttgattttcc atctttagag gaatcgacta aaataggaat tttatttaac  1140
aaattagatg aattgattaa aaatcaatca ataaaaattg ttttattaag acggcgaaaa  1200
aaagccttac ttaaatcgat gttatttaa                                     1230

<210> SEQ ID NO 59
<211> LENGTH: 1266
<212> TYPE: DNA
<213> ORGANISM: Staphylococcus aureus

<400> SEQUENCE: 59
atgagtaata caggaaaaat gaacgtgcca gagttgagat tcccaggatt tgaaggcgaa    60
tgggaagaga aggaattaag agagttaaga aaccctaagg ataaatatag ttatacaggt   120
gggccttttg gctctgattt aaaaaaatct gactatacaa ctgatgggat acaaattatt   180
caacttcaaa acattggaga tggatatttc tataatagta ataaggtctt tacatctaat   240
gagaaagcag aagtacttaa agttgtaat gtatttccag agatatagt tattgctaaa    300
atggcagatc ctatagcaag agcagcgatt gtaccggata taatatagg gaaatatcta   360
atggcctcag atgggataag attaagtgtt gacacagtac atttcaatac aaagtttgta   420
cttgagtgta taaatagaaa aagttttaga aaaaagttg aggataatag ttcggggtca   480
actcgaatga gaataggact aagtacatta ggtagtctaa ctttaaaaac cacaacacta   540
aaagaacaac aaaaatagg acaattcttc agcaaacttg accgacaaat tgtactagaa   600
gaacaaaaac ttgaattact tcaacaacag aaaaaaggct atatgcagaa atctttttca   660
caagaattgc gattcaaaga tgagaatggt aatgattatc agattggga agagaagcaa   720
ttaggggaat atcacaaat tgtacgaggg gcttctccta gacctattaa agatcctaaa   780
tggtttaata agaatcaga tataggatgg ctaagaattt ctgatgttac aaatcaaaac   840
gggaaaattt atcatttgga acaaaaatta tcaattgaag gtcaagaaaa aacaagggtt   900
```

-continued

| | |
|---|---|
| ttagtaacaa cacatttatt attaagtatt gcggcaagta ttggaaaacc tgtaatgaat | 960 |
| tttgtgaaaa cgggagttca tgatggattt ttaatatttt taaagcctaa gtttaattta | 1020 |
| ttctttatgt actattggct tgaatatttc aaggataaat ggagtaaata cggtcaacca | 1080 |
| ggtagtcagg ttaatttaaa ttcagaaatt gtcaaatctc agacactgaa tatgccaagc | 1140 |
| aatcacgaac aagaaaaagt gggacagttt tttaatagaa atgaaaaact aattgaattg | 1200 |
| cagcaagaaa aataatgta tatcaagcga tgtaagcagg ttttacttca aaaaatgttt | 1260 |
| atataa | 1266 |

<210> SEQ ID NO 60
<211> LENGTH: 1254
<212> TYPE: DNA
<213> ORGANISM: Staphylococcus aureus

<400> SEQUENCE: 60

| | |
|---|---|
| atgagtaata cacaaaagaa aaatgtgcca gagttgagat tcccagggtt tgaaggcgaa | 60 |
| tgggaagaga agaagctagg ggatattaca gatagattaa ttaggaaaaa taaaaactta | 120 |
| gaatcgaaaa agcctttaac aatatccgga cagttaggtt taattgatca aacagaatat | 180 |
| tttagtaaat cagtttcgtc gaaaaatcta gaaaattata cactaataaa gaatggagaa | 240 |
| ttcgcgtata acaaaagtta ttctaatgga tacccattag gggctattaa aagattaact | 300 |
| agatatgata gtggtgtatt gtcctctttg tatatttgct tttctattaa aagtgaaatg | 360 |
| tctaaagact tcatggaagc atattttgat tcgacacact ggtatagaga gtttcagga | 420 |
| attgcagttg agggtgcaag aaatcacgga ttattaaata tttctgtgaa tgattttttt | 480 |
| actattctaa ttaaatatcc aagtttagaa gaacagagaa aaataggtga cttcttcatc | 540 |
| aaacttgacc ggcaaattga attagaagaa caaaaacttg aattacttca acaacagaaa | 600 |
| aaaggctata tgcagaaaat cttctcacag gaactgcgat ttaaggatga gaatggtaat | 660 |
| gattatccag agtgggaaga gaaaaagtta ggggaacttg gcctatttca aaaaagttat | 720 |
| tcttttcga gagctaaaga aggaaacggt aaaactaagc atattcatta tggtgatatt | 780 |
| cattcaaaat ttaaaacagt attagatagt gacggcaata tccctaatat aattgaggaa | 840 |
| gctgtatttg aattggttca aaaaggtgac attattttg cggatgcatc agaagattat | 900 |
| agtgacctag aaaagcagt tatgatagat ttcgaaccga attcattgat ttctggatta | 960 |
| catacacacc tatttagacc gtttaacaat gtaatttcta attttttgat cttttacaca | 1020 |
| aaaactctta gttataaaaa attcattaga cagcaaggta caggaatatc agtacttggt | 1080 |
| atatcaaaaa aaagtttatt aaatttggat gtattaatac cacaaaatga attagaacaa | 1140 |
| caaaaaatcg gtcagttctt tagcaaaatc gaccgacaaa ttgaattgga caacaaaag | 1200 |
| ttagaattac ttcaacaaca gaaaaaatcc ttacttcaat cgatgtttat ttaa | 1254 |

<210> SEQ ID NO 61
<211> LENGTH: 1179
<212> TYPE: DNA
<213> ORGANISM: Staphylococcus aureus

<400> SEQUENCE: 61

| | |
|---|---|
| atgagtaata cacaaacgaa aaatgtgcca gagttgagat tcccagggtt tgaaggcgaa | 60 |
| tgggaagaga aggaattagg ggaaattttt caaataattt ctggttcaac accactaaaa | 120 |
| tcaaataaag agtttatga aatggtaat attaattggg tcaaaacgac agatttaaat | 180 |

```
aattctaaag ttacgcatag taaagaaaaa ataactgaat atgctatgaa agtttgaaa       240 ttaaaattag tgcctaaaaa ttcagtactt atagctatgt atggtggttt taatcaaatt      300
ggtagaacag gtttgttaaa aatagatgcc acaataaatc aagcaatttc agccttatta     360
atgaatcatg aaacgaatcc agaatttata caagcatttc taaattatca agttaagggt     420
tggaagcgat atgcagcaag tagcagaaaa gacccgaata taactaaaaa agacatagaa     480
caatttaaag ttccttatgt tagtattaat gaacagcaaa aaataggcga attcttcagt     540
aaaattgacc accaaatcga gttagaagaa caaaaacttg aattacttca acaacagaag     600
aaaggctata tgcagaaaat cttctcgcag gaattgcgat tcaaagatga gaatggtgaa     660
gattatccgg attgggaagt tactactata caaaatatta caaaatatac cagttcgaag     720
aagtcttcta atcaatatgc tgacaaggat aattctaaag gttatccagt ttatgatgcc     780
gttcaagaga ttggtaaaga ttcaaattat gatatagaag aatcgtatat ttctattttg     840
aaggatggag caggagttgg tcgattaaat ttaaggccag gaaaatcatc cgtaattgga     900
actatgggct acatacagtc aaataatgta gatattgaat tcctttatta tcgaatgaaa     960
gtagtagatt ttaaaaagta tataattgga agtactatac cgcatttgta cttcaaagac    1020
tattctaaag aaactttata tataccttca agcattcaag aacaagcaaa gattggtatg    1080
tttatttcaa atttggataa gttgattgaa aataaaaacc ttaaattaaa ctgtttaaaa    1140
caattaaaac aaggattgct acaatctatg tttatttaa                           1179

<210> SEQ ID NO 62
<211> LENGTH: 1230
<212> TYPE: DNA
<213> ORGANISM: Staphylococcus aureus

<400> SEQUENCE: 62
atgagtaata cacaaaagaa aaatgtgcca gagttgagat tcccagggtt tgaaggcgaa        60
tgggaagaga agcagttggg ggaagtaggt acatttactt caggtgggac accccctgaaa     120 tcaaaatcag agtattggaa tggagatatt ccatggatta caacaggtga tattcataac       180
ataaaaagag aaaatataac taattttata acagagaagg gtttaaatga atcatcggca       240
aaattaataa ctaatgaggc gatttaaata gctatgtatg gtcaaggtaa aactagagga       300
atgtcagcaa tattgaattt tgaggcaaca actaaccaag catgtgctat atatcaaact       360
aatcaaaata ttaattttgt ttttcaatac tttcagaaat tatataaatt tttacgctca       420
ttatctaatg agggaagtca aaagaattta agtttaagtt tgttgaaaga aattacttta       480
aattatccta tgaacaagga acagaaaaaa ataggtgtct tcttcagcaa acttgaccga       540
caaattgaat tagaagaaca aaaactcgaa ttacttcaac aacagaaaaa aggctatatg       600
cagaaaattt tctcacagga actgcgattc aaagatgaga atggtgaaga ttatccagat       660
tggaaagaga agaagttagg ggatattaca gaacaatcta tgtatggtat aggtgcatct       720
gcaacaaggt ttgattcgaa aaatatatat ataagaatta ctgatattga tgaaaaatca       780
aggaaattaa attatcaaaa cttaactaca cctgatgaag ttaataataa gtacaagctg       840
aaaagaaatg atattctttt tgcacgaact ggtgctagca cgggcaaaag ttatattcac       900
aaagaagaaa aggatattta taattactat ttcgctggat ttttaataaa atttgaaata       960
aacgaacaaa atagtccttt gttcatttac caatttacac taacatcaaa atttaacaaa    1020
tgggtgaagg tcatgtctgt aagatctggt caaccgggta ttaatagtga agaatatgca    1080
aaattacctt tagttttgcc caataagtta gaacagcaaa aaatagcaga attcttagat    1140
```

| | |
|---|---|
| agatttgacc aacaaattga attagaaaaa caaaaaatag aaatacttca acaacagaaa | 1200 |
| aaaggcttac ttcaatcgat gtttatttaa | 1230 |

<210> SEQ ID NO 63
<211> LENGTH: 1233
<212> TYPE: DNA
<213> ORGANISM: Staphylococcus aureus

<400> SEQUENCE: 63

| | |
|---|---|
| atgagtaata cacaaacgaa aaatgtgcca gagttgagat tcccagggtt tgaaggcgaa | 60 |
| tgggaagaga agaaggttgg cgagttatta gaatttaaaa atggtttaaa taaggaaaa | 120 |
| gaatattttg gctcaggatc gtcgattgtt aacttcaaag atgtatttaa taacaggagc | 180 |
| ttaaatacaa ataatctgac tggaaaagtt aatgtgaata gcaaagaact aaaaaattat | 240 |
| tctgttgaaa agggtgatgt ttttttttaca aggactagtg aggtaattgg tgaaataggt | 300 |
| tatccgtctg taattttaaa tgaccctgaa aatactgtgt ttagtggatt tgtattaaga | 360 |
| gggcggccta atcaggaat tgatttaata aataataatt ttaaaagata tgtctttttt | 420 |
| actaattcat ttagaaaaga aatgattaca aaaagttcta tgacaactag agctttaaca | 480 |
| tcaggtagcg caattaataa aatgaaggtc atataccctg tttcggctaa agaacagaga | 540 |
| aaataggtg acttcttcag caaactcgac cgacaaattg aattagaaga acaaaagctt | 600 |
| gaattacttc aacaacaaaa aaaggctat atgcagaaaa tcttctcaca ggaactgcga | 660 |
| ttcaaagatg agaatagtga agattatcca cattgggaaa atagcaaaat agaaaaatat | 720 |
| ttaaaagaga gaaacgaacg ttctgacaaa ggtcaaatgc tttcagtaac tataaatagt | 780 |
| ggcattataa aatttagtga attggataga aagataatt caagtaaaga taaaagtaat | 840 |
| tataaagtag ttaggaaaaa tgatattgca tataattcta tgagaatgtg gcaaggggct | 900 |
| agtggtagat caaattataa tgggattgtt agccctgcat atactgtgct ttatccaaca | 960 |
| caaaatacta gctcattatt tattggatat aagtttaaaa cacatagaat gattcataaa | 1020 |
| tttaaaatta attcacaagg attaacatca gatacatgga acttaaaata taaacaatta | 1080 |
| aaaaatataa atatagatat acctgtattg gaggaacaag aaaagatagg tgatttctttt | 1140 |
| aaaaaaatgg atatattgat tagtaaacag aaaataaaaa ttgaaatatt agaaaaagag | 1200 |
| aaacaatcct tttacaaaa gatgttctta taa | 1233 |

<210> SEQ ID NO 64
<211> LENGTH: 1155
<212> TYPE: DNA
<213> ORGANISM: Staphylococcus aureus

<400> SEQUENCE: 64

| | |
|---|---|
| atgagtaata cacaaacgaa aaatgtgcca gagttgagat tcccagggtt tgaaggcgaa | 60 |
| tgggaagaga aaaagttagg ggatcttata aagttaatt ctggaaaaga ttataaacat | 120 |
| ttggaaaaag gtgatatacc agtctatggt actggcggtt atatgacaag tgtttcagaa | 180 |
| ccactaagtg aaattgatgc tgttggtatt gggagaaaag ggactataaa caaccatat | 240 |
| ttgcttgagg cgccgttttg gacggtggat acattatttt attgtacacc taaaaagaa | 300 |
| acagacatac tatttatatt aagtttatt agaaaaataa attggaaagt atacgatgaa | 360 |
| tcaacaggtg tgccaagctt aagtaaacaa accattaata aaataaatag atttgtccct | 420 |
| tcaaataaag agcagcaaaa aataggcgaa ttcttcatca aactcgaccg acaaattgaa | 480 |

```
ttagaagaac aaaaacttga attacttcaa caacagaaaa aaggctatat gcagaaaatc        540
ttctcacagg aattgcgatt caaggatgag aatggaaacg attatccgaa ttgggaagag        600
aagaaaatag aagatatagc aagccaagta tatggaggcg aacaccaaa tacaaagatt         660 aaagaatttt ggaatggaga tattccatgg attcaaagct ctgacgtaaa agtaaatgat        720
ttgattctac gacaatgtaa taaatttatt tccaagaatt caattgagct ttcttctgca       780
aaacttattc ctgccaattc aattgcaata gttacaagag tcggggttgg aaaactgtgt        840
ttggtagaat ttgattatgc tacaagtcaa gattttttat cattaagtag tcttaaatat       900
gacaaattat actcattata ttcattgcta tatacaatga aaaaaattag cgctaatcta       960
caaggaactt caattaaagg tataacaaaa aaagagttgt tagatagtat aataaagata      1020 cccataatc tagaagaaca gcaaaaaata ggtgatctat tttataaaat tgataaatat       1080
atcagtttta ataaatgtaa aattgagata cttaaaagtc tcaaacaagg attacttcaa      1140
aaaattttta tataa                                                       1155

<210> SEQ ID NO 65
<211> LENGTH: 1179
<212> TYPE: DNA
<213> ORGANISM: Staphylococcus aureus

<400> SEQUENCE: 65
atgagtaata cacaaaagaa aaatgtgcca gaattgaggt tcccagggtt tgaaggcgaa        60
tgggaagaaa agaagctaga agtattata aaagttaatt ctggaaaaga ttataaacat       120
ttggataaag gcgatatacc agtctatggt actggcggtt atatgacaag tgtttcagaa       180
ccactaagtg aaattgatgc tgttggtatt gggagaaaag ggactataaa caaaccatat       240
ttgcttgagg cgccgttttg gacggtggat acattatttt attgtacacc taaaaagaa        300 acagacatac tatttatatt aagtttattt agaaaaataa attggaaagt atacgatgaa       360
tcaacaggtg tgccaagctt aagtaaacaa accattaata aaataaatag atttgtccct       420
acaaataaag agcagcaaaa aataggcaag ttcttcagca aacttgaccg acaaattgaa       480
ctacaagaac aaaaacttga attacttcaa caacagaaaa aaggctatat gcagaaaatt       540
ttctcacagg aattgcgatt caaggatgag aatggtaatg attatccgga gtgggaaaat       600
gtaatgcttc aaaaagtttt gaaagacaaa actgaaggta taaagagagg accttttgga       660
ggagcattaa agaaagatat atttgtagaa agcggttatg cagtttatga acaaaggaat       720
gcaatttatg atataagtaa cttagatat tatataaacg aaaataaata taagaaatg         780 caatcatttt cggttcaacc aaatgatata ataatgagtt gctcaggtac tattggaaga       840
ttagcactca ttcctcataa ttatacaaag ggaattataa accaagcgct tattagattt       900
agaactaacc ataaaattag aagtgaattc ttttgatat ttatgaggag caatcaaatg         960
caaagaaaaa tcctagaggc aaatcctggg tcggcaataa ccaatttagt gcctgtaaaa      1020
gaattgaaat taatcccatt tccattacct gtaaagtttg aacaggataa aattagtcaa      1080
tttatacata ttataaatcg acgtattgaa caatctgaaa aaagattga agtctaaaa        1140 aatcgtaaac aaggatttct tcaaaagtta tttgttttaa                            1179

<210> SEQ ID NO 66
<211> LENGTH: 1113
<212> TYPE: DNA
<213> ORGANISM: Staphylococcus aureus

<400> SEQUENCE: 66
```

```
atgagtaata cacaaaagaa aaatgtgcca gagttgagat tcccagggtt tgaaggcgaa      60
tgggaagaaa agaagctaga aagtattata aagttaatt  ctggaaaaga ttataaacat     120
ttggataaag gcgatatacc agtctatggt actggcggtt atatgacaag tgtttcagaa     180
ccactaagtg aaattgatgc tgttggtatt gggagaaaag ggactataaa caaccatat     240
ttgcttgagg cgccgttttg acggtggat  acattatttt attgtacacc taaaaaagaa    300
acagacatac tatttatatt aagtttattt agaaaaataa attggaaagt atacgatgaa    360
tcaacaggtg tgccaagctt aagtaaacaa accattaata aaataaatag atttgtccct    420
acaaataaag agcagcaaaa aataggcaag ttcttcagca aacttgaccg acaaattgaa    480
ttagaagaac aaaaacttga attacttcaa caacagaaaa aaggctatat gcagaaaatc    540
ttctcgcaag aattgcgatt caaagatgag aatggtaatg attatccaga gtgggaaaat    600
gtaatgcttc aaaaagtttt gaaagacaaa actgaaggta taagagagg  acctttgga    660
ggagcattaa agaaagatat atttgtgaaa gcggttatg  cagtttatga acaaaggaat    720
gcaattatg  atataagtaa ctttagatat tatataaacg aaaataaata taagaaatg    780
caatcatttt cggttcaacc aaatgatata ataatgagtt gctcaggtac tattggaaga    840
ttagcactca ttcctcagaa ttatacaaag ggaattataa accaagcgct tattagattt    900
agaactaacc ataaaattag aagtgaattc ttttgatat  ttatgaggag caatcaaatg    960
caaagaaaaa ttctagaggc aaatcctggg tcggcaataa ccaatttagt gcctgtaaaa   1020
gaattgaaat taatcccatt tccattacct gtaaagtttg aacaggataa aattagtcaa   1080
tttatactta ttataaatcg acgtattgaa taa                                1113
```

<210> SEQ ID NO 67
<211> LENGTH: 2387
<212> TYPE: DNA
<213> ORGANISM: Staphylococcus aureus
<400> SEQUENCE: 67

```
atgagtaata cacaaacgaa aaatgtgcca gagttgagat tcccaggatt tgaaggcgaa      60
tattctttag acattttgg  aaatctagca acgaataaga gtgataaatt taaccctcaa    120
aatgaggatg caagtattga tatagaattg gattgtattg aacaaaatac gggtcgatta    180
attaaaattt ataattcaaa agaattttca agtcaaaaaa ataaattcaa tccacaaaat    240
gttttgtatg ggaagctcag accatatttg aataagtatt attttacaaa aaaaagtgga    300
gtgtgttcat cagaaatatg ggttttgaaa tcaacgaaag aagataaatt attgaattta    360
tttctatatt attttataca aacaaaacga tattctgatg ttgctagtaa atcggctggt    420
tctaagatgc caagggctga ttggggttta gtagaaaata taagagtata ttttccagaa    480
ttatgtgaac agcaaaaaat aggcgaattc ttcagcaaac tcgaccgaca aattgaacta    540
gaagaacaaa aacttgagtt acttcaacaa cagaaaaaag ctatatgca  gaaaatcttc    600
tcacaggaat tgcgatttaa ggatgagaat ggtaatgatt atcctgagtg ggagaaaaag    660
aaactaaaag aaatagctta tgtttataca ggaaacacgc caagtaaaaa agaaaatata    720
tattggatta aggtgaata  cgtttgggtt acacctactg atattaataa tagtaaaaat    780
atttatgaaa gtgaacataa attaacccaa gaaggttata aaaaagcaag acaattacca    840
gaaaatacac tattggttac gtgtatagct agtataggaa aaaacgcaat attgagaaaa    900
cagggctcgt gtaatcaaca aataaatgca gtagtcccat ttgaaaatat aaatatagat    960
```

```
tatctttatt atatttctga ttcattatca acgttcatga agtctattgc aggaaaaacg   1020
gctacacaaa tagttaataa aaacactttc gaaaatttgg aactttattt agcttctttt   1080
gaagaacaga ataaaatagc agatttaatt agctcactag aagaattaat tgaaaagcaa   1140
gcatcgaagt taattaaaat gaagagtcgt aaacaaggat tgcttcaaaa aatgtttatt   1200
taahhsdsat gagtaataca caaaagaaaa atgtgccaga gttgagattc ccagggtttg   1260
aaggcgaatg ggaagaaaag aagctagaaa gtattataaa agttaattct ggaaaagatt   1320
ataaacattt ggataaaggc gatataccag tctatggtac tggcggttat atgacaagtg   1380
tttcagaacc actaagtgaa attgatgctg ttggtattgg gagaaaaggg actataaaca   1440
aaccatattt gcttgaggag ccgttttgga cggtggatac attattttat tgtacaccta   1500
aaaaagaaac agacatacta tttatattaa gtttatttag aaaaataaat tggaaagtat   1560
acgatgaatc aacaggtgtg ccaagcttaa gtaaacaaac cattaataaa ataaatagat   1620
ttgtccctac aaataaagag cagcaaaaaa taggcaagtt cttcagcaaa cttgaccgac   1680
aaattgaatt agaagaacaa aaacttgaat tacttcaaca acagaaaaaa ggctatatgc   1740
agaaaatctt ctcgcaagaa ttgcgattca agatgagaa tggtaatgat tatccagagt   1800
gggaaaatgt aatgcttcaa aaagttttga agacaaaac tgaaggtata aagagaggac   1860
cttttggagg agcattaaag aaagatatat ttgtagaaag cggttatgca gtttatgaac   1920
aaaggaatgc aatttatgat ataagtaact ttagatatta tataaacgaa ataaatata    1980 aagaaatgca atcattttcg gttcaaccaa atgatataat aatgagttgc tcaggtacta   2040
ttggaagatt agcactcatt cctcagaatt atacaaaggg aattataaac caagcgctta   2100
ttagatttag aactaaccat aaaattagaa gtgaattctt tttgatattt atgaggagca   2160
atcaaatgca agaaaaatt ctagaggcaa atcctgggtc ggcaataacc aatttagtgc   2220
ctgtaaaaga attgaaatta atcccatttc cattacctgt aaagtttgaa caggataaaa   2280
ttagtcaatt tatacttatt ataaatcgac gtattgaaca atctgaaaaa agattgaaa    2340 gtctaaaaaa tcgtaaacaa ggatttcttc aaaagttatt tgtttaa                 2387

<210> SEQ ID NO 68
<211> LENGTH: 1203
<212> TYPE: DNA
<213> ORGANISM: Staphylococcus aureus

<400> SEQUENCE: 68
atgagtaata cacaaacgaa aaatgtgcca gagttgagat cccaggatt tgaaggcgaa     60 tattctttag acatttttgg aaatctagca acgaataaga gtgataaatt taaccctcaa    120
aatgaggatg caagtattga tatagaattg gattgtattg aacaaaatac gggtcgatta    180
attaaaattt ataattcaaa agaattttca agtcaaaaaa ataaattcaa tccacaaaat    240
gttttgtatg ggaagctcag accatatttg aataagtatt attttacaaa aaaagtggaa    300
gtgtgttcat cagaaatatg ggttttgaaa tcaacgaaag aagataaatt attgaattta    360
tttctatatt atttatacaa aacaaaacga tattctgatg ttgctagtaa atcggctggt    420
tctaagatgc caagggctga ttggggttta gtagaaaata taagagtata ttttccagaa    480
ttatgtgaac agcaaaaaat aggcgaattc ttcagcaaac tcgaccgaca aattgaacta    540
gaagaacaaa aacttgagtt acttcaacaa cagaaaaaag gctatatgca gaaaatcttc    600
tcacaggaat tgcgatttaa ggatgagaat ggtaatgatt atcctgagtg ggagaaaaag    660
aaactaaaag aaatagctta tgtttataca ggaaacacgc caagtaaaaa agaaaatata    720
```

```
tattggatta aaggtgaata cgtttgggtt acacctactg atattaataa tagtaaaaat    780
atttatgaaa gtgaacataa attaacccaa gaaggttata aaaaagcaag acaattacca    840
gaaaatacac tattggttac gtgtatagct agtataggaa aaaacgcaat attgagaaaa    900
cagggctcgt gtaatcaaca aataaatgca gtagtcccat ttgaaaatat aaatatagat    960
tatctttatt atatttctga ttcattatca acgttcatga agtctattgc aggaaaaacg   1020
gctacacaaa tagttaataa aaacactttc gaaaatttgg aactttattt agcttctttt   1080
gaagaacaga ataaaatagc agatttaatt agctcactag aagaattaat tgaaaagcaa   1140
gcatcgaagt taattaaaat gaagagtcgt aaacaaggat tgcttcaaaa aatgtttatt   1200
taa                                                                 1203

<210> SEQ ID NO 69
<211> LENGTH: 1221
<212> TYPE: DNA
<213> ORGANISM: Staphylococcus aureus

<400> SEQUENCE: 69
atgagtaata cacatatgaa aaatgtgcca gagttgagat tcccagaatt tgaaggcgag     60
tgggaagaga agcaatttgc tgattttact aaaataaatc aaggattaca gattgctatt    120
aatgaacgta aaactgaata ttctccagag ttgtattttt atataacaaa tgaatttta    180 agaccaaata gtcaaactaa atattttatc gaaaatcccc ctcaatcagt aattgcaaat    240
aaagaagata tttaatgac tagaacaggt aatactggaa aagtagtaac taatgtattt    300
ggagcgtttc ataataattt ttttaaaatt aaatttgata aaaatctgta tgatagattg    360
tttttagtag aggttttaaa ttcatctaag atacaaaata aatattatc tttagcagga    420 tcttcgacga taccagattt aaaccatagt gatttttata gtattagttc ttcttatccg    480
ctgcttagag aacagcaaaa aataggtgat ttttttcagca aaatcgatcg acaaattgaa    540
ctacaagaac aaaaacttga attacttcaa caacagaaaa aaggctatat gcagaaaatt    600
ttctcacagg aactgcgatt caaagatgag aatggtgaag attatccaga ttggaaagag    660
aagaagttag gggatattac agaacaatct atgtatggta taggtgcatc tgcaacaagg    720
tttgattcga aaaatatata tataagaatt actgatattg atgaaaaatc aaggaaatta    780
aattatcaaa acttaactac acctgatgaa cttaataata agtacaagct gaaaagaaat    840
gatattcttt ttgcacgaac tggtgctagc acgggaaaaa gttatattca caagaagaa    900 aaggatattt ataattacta tttcgctgga ttttttaataa aatttgaaat agacgaacaa    960
aataatcctt tgttcatta ccaatttaca ctaacatcaa aatttaacaa atgggtgaag   1020
gtcatgtctg taagatctgg tcaaccgggc attaatagtg aagaatatgc aaaattacct   1080
ttagttttgc ccaataaatt agaacagcaa aaaatagcaa aattcttaga tagatttgac   1140
cgacaaattg aattagaaaa acaaaaaata gaaatacttc aacaacagaa aaaaggctta   1200
cttcaatcga tgtttattta a                                            1221

<210> SEQ ID NO 70
<211> LENGTH: 1206
<212> TYPE: DNA
<213> ORGANISM: Staphylococcus aureus
<220> FEATURE:
<221> NAME/KEY: misc_feature
<222> LOCATION: (17)..(17)
<223> OTHER INFORMATION: n is a, c, g, or t
```

<400> SEQUENCE: 70

```
atgagtaata cacaaangaa aaatgtgcca gagttgagat tcccagggtt tgaaggcgaa      60
tgggaagaga agcaatttgc tgattttact aaaataaatc aaggattaca gattgctatt     120
aatgaacgta aaactgaata ttctccagag ttgtattttt atataacaaa cgaattttta     180
agaccaaata gtcaaactaa atattttatc gaaaatcccc ctcaatcagt aattgcaaat     240
aaagaagata ttttaatgac tagaacaggt aatactggaa aagtagtaac taatgtatt      300
ggagcgtttc ataataattt ttttaaaatt aaatttgata aaaatctgta tgatagattg     360
ttttagtag aggttttaaa ttcatctaag atacaaaata aaatactatc tttagcagga      420
tcttcgacga taccagattt aaaccatagt gatttttata gtattagttc ttcttatccg     480
ctgcttagag aacagcaaaa aataggtaaa ttcttcagca aactcgaccg acaaattgaa     540
ttagaagaac aaaagcttga attacttcaa caacagaaaa aaggctatat gcagaaaatc     600
ttctcacagg aattgcgatt taaggacgag aatggaaatg attatccgga ttgggagaaa     660
aagaaactaa aagaaatagc ttgtgtttat acaggaaaca cgccaagtaa aaagaaaat      720
atatattgga ataagggtga atacgtttgg gttacaccta ctgacattaa taatagtaaa     780
aatatttatg aaagtgaaaa caaattaacc caagaaggct ataaaaaagc aagacaatta     840
ccagaaaata cactattggt tacgtgtata gctagtatag gaaaaaacgc aatattgaga     900
aaacagggct cgtgtaatca acaaataaat gcagtagttc catttgaaaa ataaaatata     960
gattatcttt attatatttc tgattcatta tcaacgttca tgaaatctat gcaggaaaa     1020
acggctacac aaatagttaa taaaaacact ttcgaaaatt tggaaattta tttagctcct    1080
tttgaagaac agaataaaat agcagattta attagctcac tagaagaatt aattgaaaag    1140
caagcatcga agttaattaa aatgaagagt cgtaaacaag gaatgcttca aataatgttt    1200
atttaa                                                               1206
```

<210> SEQ ID NO 71
<211> LENGTH: 1110
<212> TYPE: DNA
<213> ORGANISM: Staphylococcus aureus

<400> SEQUENCE: 71

```
atgagtaata cacaaaagaa aaatgtgcca gagttgaggt tcccagagtt tgaaggcgag      60
tgggaagaaa ggaagttagg ggatcttata aaagttaatt ctggaaaaga ttataaacat     120
ttggataaag gcgatatacc agtctatggt actggcggtt atatgacaag tgtttcagaa     180
ccactaagtg aaattgatgc tgttggtatt gggagaaaag ggactataaa caaaccatat     240
ttgcttgagg cgccgttttg gacggtggat acattgtttt attgtacacc tgaaaaagaa     300
gcagacatac tatttatatt aagtttattt agaaaaataa attggaaatt atacgatgaa     360
tcaacaggtg tgccaagctt aagcaagcaa accattaata aaataaatag acttgtccct     420
acaaataaag aacaacaaaa aataggcgag ttcttcagca aactcgaccg acaaattgaa     480
ttagaagaac aaaaacttga attacttcaa caacagaaaa aaggctatat gcagaaaatt     540
ttctcacagg aactgcgatt caaagatgag aatggtgaag attattcgga gtgggaagag    600
agaagatttg ctgatatatt taaatttcat aataaactaa gaaagccaat taagaaaat     660
ttaagagtaa agggttctta tccatattat ggtgctacag gtattattga ttacgttgac     720
gactttatat ttgacgggaa ttatttactt attggagaag atggtgcaaa tattattact     780
agaagtgcac ccctagtgta cttagtaaat ggaaagtttt gggtaaataa tcatgctcat     840
```

```
atattatctc ctttaaatgg aaatatacag tacttgtatc aagttgcaga attagttaat      900
tatgaaaaat acaatactgg aactgctcag cctaaattaa acattcaaaa tttaaaaatt      960
attaatgttg taatttcaac gaatttagaa gaacaacaaa aaatcggaag cttttttaagt   1020 aaacttgatc gtcaaatcga tttagaagaa caaaaactcg aattacttca acaacgaaaa    1080
aaagccttac ttaaatcgat gtttgtttaa                                     1110
```